United States Patent
Marzabadi et al.

(10) Patent No.: US 7,189,720 B2
(45) Date of Patent: *Mar. 13, 2007

(54) SELECTIVE NPY (Y5) ANTAGONISTS

(75) Inventors: Mohammad R. Marzabadi, Ridgewood, NJ (US); Stewart A. Noble, San Diego, CA (US); Mahesh N. Desai, Nutley, NJ (US)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 11/099,960

(22) Filed: Apr. 6, 2005

(65) Prior Publication Data

US 2005/0176709 A1    Aug. 11, 2005

Related U.S. Application Data

(63) Continuation of application No. 10/009,849, filed as application No. PCT/US00/10784 on Apr. 21, 2000, now Pat. No. 6,989,379, and a continuation-in-part of application No. 09/296,332, filed on Apr. 22, 1999, now Pat. No. 6,340,683, and a continuation-in-part of application No. 09/343,762, filed on Jun. 30, 1999, now Pat. No. 6,218,408, and a continuation-in-part of application No. 09/343,994, filed on Jun. 30, 1999, now Pat. No. 6,124,331.

(51) Int. Cl.
C07D 251/50    (2006.01)
C07D 251/70    (2006.01)
A61K 31/53     (2006.01)
A61P 3/04      (2006.01)

(52) U.S. Cl. .................. 514/245; 544/197; 544/198; 544/208; 544/209

(58) Field of Classification Search .......... 544/197, 544/198, 208, 209, 245; 514/245
See application file for complete search history.

(56) References Cited

U.S. PATENT DOCUMENTS

| | | | |
|---|---|---|---|
| 3,128,272 A * | 4/1964 | Wear et al. ............. 544/199 |
| 4,383,113 A | 5/1983 | Levitt et al. |
| 5,166,214 A | 11/1992 | Billheimer et al. |
| 5,232,921 A | 8/1993 | Biziere et al. |
| 5,238,936 A | 8/1993 | Regnier et al. |
| 5,536,722 A | 7/1996 | Coe et al. |
| 5,550,138 A | 8/1996 | Sohda et al. |
| 6,124,331 A | 9/2000 | Marzabadi et al. |
| 6,214,853 B1 | 4/2001 | Marzabadi et al. |
| 6,218,408 B1 | 4/2001 | Marzabadi et al. |
| 6,222,040 B1 | 4/2001 | Marzabadi et al. |
| 6,225,330 B1 | 5/2001 | Marzabadi et al. |
| 6,340,683 B1 | 1/2002 | Marzabadi et al. |
| 6,569,856 B2 | 5/2003 | Marzabadi et al. |

FOREIGN PATENT DOCUMENTS

| | | |
|---|---|---|
| DE | 19824175 | 12/1999 |
| EP | 0 283 390 | 9/1988 |
| EP | 0 448 078 | 9/1991 |
| EP | 0 432 040 | 12/1991 |
| EP | 0 775 487 | 5/1997 |
| JP | 57151653 | 9/1982 |
| WO | WO 93/23381 | 11/1993 |
| WO | WO 94/18212 | 8/1994 |
| WO | WO 96/19457 | 6/1996 |
| WO | WO 97/19682 | 6/1997 |
| WO | WO 97/20823 | 6/1997 |
| WO | WO 98/35944 | 8/1998 |
| WO | WO 98/35957 | 8/1998 |
| WO | WO 99/001128 | 1/1999 |
| WO | WO 99/05138 | 2/1999 |
| WO | WO 99/32466 | 7/1999 |
| WO | WO 99/62892 | 12/1999 |
| WO | WO 00/68197 | 11/2000 |
| WO | WO 01/23389 | 4/2001 |
| WO | WO 01/44201 | 6/2001 |
| WO | WO 01/64675 | 9/2001 |

OTHER PUBLICATIONS

Betancur, et al., TIPS vol. 18 (1997), 372-386.
Berlin, et al., Proc. Okla. Acad. Sci. 71 (1991): 29-33.
Brown, et al., Aust. J. Chem. 34 (1981): 2423-2429.
Khazi, et al., J. Hetereocyclic Chem., 4 (1995): 243-248.

(Continued)

*Primary Examiner*—Venkataraman Balasubramanian
(74) *Attorney, Agent, or Firm*—Stephen G. Kalinchak

(57) ABSTRACT

This invention is directed to triazine derivatives, bicyclic compounds and tricyclic compounds which are selective antagonists for a NPY (Y5) receptor. The invention provides a pharmaceutical composition comprising a therapeutically effective amount of a compound of the invention and a pharmaceutically acceptable carrier. This invention provides a pharmaceutical composition made by combining a therapeutically effective amount of a compound of this invention and a pharmaceutically acceptable carrier. This invention provides a process for making a pharmaceutical composition comprising combining a therapeutically effective amount of a compound of the invention and a pharmaceutically acceptable carrier. The invention further provides the use of a compound of the invention for the preparation of a pharmaceutical composition for treating an abnormality, wherein the abnormality is alleviated by decreasing the activity of a human Y5 receptor.

16 Claims, 6 Drawing Sheets

OTHER PUBLICATIONS

McNally, et al., Bio. Med. Chem. Lett., 10 (2002): 212-216.
Ohkubo, et al., Chem. Pharm. Bull., 43(9) (1995): 1479-1504.
Peesapati, et al., OPPI Briefs, 25(5) (1993): 602-606.
Wettstein, et al., Pharmac. Ther. 65 (1995): 397-414.
Wieland, et al. Expert Opin. Investig. Drugs; 9(6)(2000): 1327-1346.
Xia, et al., Bioorg. Med. Chem. Lett. 6(7)(1996): 919-922.
Yamane, Kameji, Nippon Kagaku Zasshi 91(4)(1970): 395-399.
Yamane, et al., Nippon Kagaku Zasshi 90(6)(1969): 569-571.
Yamane, et al., Nippon Kagaku Zasshi 89(6)(1968): 612-614.

* cited by examiner

Example 23

Example 24

Example 25

Example 26

Example 27

Example 28

Example 29

Example 30

Example 31

Example 32

Example 33

Example 34

Example 35

Example 36

Example 37

Example 38

Example 39

Example 40

Example 41

Example 42

Example 43

Example 44

Example 45

Example 46

Example 47

Example 48

Example 49

Example 50

Example 51

Example 52

Example 53

Example 54

Example 55

Example 56

Example 57

Example 58

SELECTIVE NPY (Y5) ANTAGONISTS

This application is a continuation of U.S. Ser. No. 10/009,849. filed Apr. 11, 2002, now U.S. Pat. No. 6,989,379, issued Jan. 24, 2006, which is a §371 national stage of PCT International Application No. PCT/US00/10784, filed Apr. 21, 2000 on behalf of Synaptic Pharmaceutical Corporation, which claims priority of and is a continuation-in-part of U.S. Ser. No. 09/296,332, filed Apr. 22, 1999, now U.S. Pat. No. 6,340,683, issued Jan. 22, 2002, U.S. Ser. No. 09/343,762, filed Jun. 30, 1999, now U.S. Pat. No. 6,218,408, issued. Apr. 17, 2001, and U.S. Ser. No. 09/343,994, filed Jun. 30, 1999, now U.S. Pat. No. 6,124,331, issued Sep. 26, 2000, the contents of all of which are hereby incorporated by reference into the subject application.

BACKGROUND OF THE INVENTION

Throughout this application, various references are referred to within parentheses. Disclosures of these publications in their entireties are hereby incorporated by reference into this application to more fully describe the state of the art to which this invention pertains. Full bibliographic citations for these references may be found at the end of this application, preceding the claims.

The peptide neurotransmitter neuropeptide Y (NPY) is a 36 amino acid member of the pancreatic polypeptide family with widespread distribution throughout the mammalian nervous system (Dumont et al., 1992). The family includes the pancreatic polypeptide (PP), synthesized primarily by endocrine cells in the pancreas; peptide YY (PYY), synthesized primarily by endocrine cells in the gut; and NPY, synthesized primarily in neurons (Michel, 1991; Dumont et al., 1992; Wahlestedt and Reis, 1993). All pancreatic polypeptide family members share a compact structure involving a "PP-fold" and a conserved C-terminal hexapeptide ending in $Tyr^{36}$ (or $Y^{36}$ in the single letter code). The striking conservation of $Y^{36}$ has prompted the reference to the pancreatic polypeptides' receptors as "Y-type" receptors (Wahlestedt et al., 1987), all of which are proposed to function as seven transmembrane-spanning G protein-coupled receptors (Dumont et al., 1992).

NPY and its relatives elicit a broad range of physiological effects through activation of at least five G protein-coupled receptor subtypes known as Y1, Y2, Y3, Y4 (or PP), and the "atypical Y1". While the Y1, Y2, Y3, and Y4 (or PP) receptors were each described previously in both radioligand binding and functional assays, the "atypical Y1" receptor is unique in that its classification is based solely on feeding behavior induced by various peptides including NPY.

The role of NPY in normal and abnormal eating behavior, and the ability to interfere with NPY-dependent pathways as a means to appetite and weight control, are areas of great interest in pharmacological and pharmaceutical research (Sahu and Kalra, 1993; Dryden et al., 1994). NPY is considered to be the most powerful stimulant of feeding behavior yet described (Clark et al., 1984; Levine and Morley, 1984; Stanley and Leibowitz, 1984). The stimulation of feeding behavior by NPY is thought to occur primarily through activation of the hypothalamic "atypical Y1" receptor. For example, direct injection of NPY into the hypothalamus of satiated rats can increase food intake up to 10-fold over a 4-hour period (Stanley et al., 1992). Similar studies using other peptides has resulted in a pharmacologic profile for the "atypical Y1" receptor according to the rank order of potencies of peptides in stimulating feeding behavior as follows: $NPY_{2-36}$ NPY~PYY~$[Leu^{31},Pro^{34}]$ NPY>$NPY_{13-36}$ (Kalra et al., 1991; Stanley et al., 1992). The profile is similar to that of a Y1-like receptor except for the anomalous ability of $NPY_{2-36}$ to stimulate food intake with potency equivalent or better than that of NPY. A subsequent report in *J. Med. Chem.* by Balasubramaniam and coworkers (1994) showed that feeding can be regulated by $[D-Trp^{32}]$ NPY. While this peptide was presented as an NPY antagonist, the published data at least in part support a stimulatory effect of $[D-Trp^{32}]$NPY on feeding. In contrast to other NPY receptor subtypes, the "feeding" receptor has never been characterized for peptide binding affinity in radioligand binding assays.

This problem has been addressed by cloning rat and human cDNAs which encode a single receptor protein, referred to herein as Y5, whose pharmacologic profile links it to the "atypical Y1" receptor. The identification and characterization of a single molecular entity which explains the "atypical Y1" receptor allows the design of selective drugs which modulate feeding behavior (WO 96/16542). It is important to note, though, that any credible means of studying or modifying NPY-dependent feeding behavior must necessarily be highly selective, as NPY interacts with multiple receptor subtypes, as noted above (Dumont et al., 1992).

As used in this invention, the term "antagonist" refers to a compound which binds to, and decreases the activity of, a receptor in the presence of an agonist. In the case of a G-protein coupled receptor, activation may be measured using any appropriate second messenger system which is coupled to the receptor in a cell or tissue in which the receptor is expressed. Some specific but by no means limiting examples of well-known second messenger systems are adenylate cyclase, intracellular calcium mobilization, ion channel activation, guanylate cyclase, and inositol phospholipid hydrolysis. Conversely, the term "agonist" refers to a compound which binds to, and increases the activity of, a receptor as compared with the activity of the receptor in the absence of any agonist.

In order to test compounds for selective binding to the human Y5 receptor the cloned cDNAs encoding both the human and rat Y2 and Y4 (or PP) receptors have been used. The human and rat Y5 receptors are described in coassigned U.S. Pat. No. 5,602,024 and in PCT International Application US95/15646, published Jun. 6, 1996, as WO 96/16542, the contents of which are hereby incorporated by reference into this application. The human and rat Y2 receptors are described in coassigned U.S. Pat. No. 5,545,549 and in PCT International Application US95/01469, published Aug. 10, 1995, as WO 95/21245, the contents of which are hereby incorporated by reference into this application. The human and rat Y4 receptors are described in coassigned U.S. Pat. No. 5,516,653 and in PCT International Application PCT/US94/14436, published Jul. 6, 1995, as WO 95/17906, the contents of which are hereby incorporated by reference into this application. The Y1 receptor has been cloned from a variety of species including human, rat and mouse (Larhammar et al., 1992; Herzog et al., 1992; Eva et al., 1990; Eva et al., 1992).

Using the NPY-Y5-selective antagonist CGP 71683A, it was demonstrated recently that food intake in free-feeding and energy-derived lean rats is mediated by the Y5 receptor (Criscione et al., 1998). CGP 71683A has high affinity for the cloned rat NPY-Y5 receptor subtype, but 1,000-fold lower affinity for the cloned rat NPY-Y1, Y2, and Y4 receptors. Examples of additional NPY-Y5-selective compounds are disclosed in WO 97/20823, WO 98/35957, and WO 98/35944.

In different embodiments of this invention the synthesis of novel triazine compounds, bicyclic compounds and tricyclic compounds which bind selectively to the cloned human Y5 receptor, compared to the other cloned human NPY receptors, and inhibit the activation of the cloned human Y5 receptor as measured in in vitro assays is disclosed. The in vitro receptor binding and activation assays described hereinafter were performed using various cultured cell lines, each transfected with and expressing only a single Y-type receptor.

In addition, the compounds of the present invention may be used to treat abnormal conditions such as feeding disorders (obesity and bulimia nervosa), sexual/reproductive disorders, depression, epileptic seizure, hypertension, cerebral hemorrhage, congestive heart failure, sleep disturbances, or any condition in which antagonism of a Y5 receptor may be beneficial.

SUMMARY OF THE INVENTION

This invention provides a compound having the structure

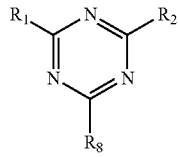

wherein $R_1$ is F; Cl; Br; I; $NR_3R_4$; or phenyl or heteroaryl; wherein the phenyl or heteroaryl may be substituted with one or more of F, Cl, Br, I, —CN, —$NO_2$, —$NR_5R_6$, —$SO_2R_5$, —$(CH_2)_nC(Y)R_7$, —$(CH_2)_nYR_5$, —$(CH_2)_nC(Y)NR_5R_6$, —$(CH_2)_nNR_5C(Y)R_5$, —$(CH_2)_nCO_2R_5$, —$(CH_2)_nSO_2NR_5R_6$, a straight chained or branched $C_1$–$C_7$ alkyl, monofluoroalkyl, polyfluoroalkyl, aminoalkyl, $C_2$–$C_7$ alkenyl or $C_2$–$C_7$ alkynyl, or a $C_3$–$C_7$ cycloalkyl or cycloalkenyl;

wherein $R_2$ is $NR_3R_4$;

wherein $R_3$ is independently H; —$(CH_2)_uYR_5$; —$(CH_2)_tC(Y)NR_5R_6$; —$(CH_2)_uNR_5C(Y)R_5$; —$(CH_2)_tC(Y)R_7$; —$(CH_2)_tCO_2R_5$; —$(CH_2)_uNR_5R_6$; —$(CH_2)_uCN$; —C(Y)$R_5$; —C(Y)$NR_5R_6$; —$CO_2R_5$; straight chained or branched $C_1$–$C_7$ alkyl, $C_2$–$C_7$ alkenyl, or $C_2$–$C_7$ alkynyl; $C_3$–$C_7$ cycloalkyl or cycloalkenyl; phenyl; $C_1$–$C_6$ phenylalkyl; or $C_1$–$C_6$ heteroarylalkyl; wherein the phenyl, $C_1$–$C_6$ phenylalkyl, or $C_1$–$C_6$ heteroarylalkyl may be substituted with one or more of F, Cl, Br, I, —CN, —$NO_2$, —$NR_5R_6$, —$SO_2R_5$, —$(CH_2)_nC(Y)R_7$, —$(CH_2)_nYR_5$, —$(CH_2)_nC(Y)NR_5R_6$, —$(CH_2)_nNR_5C(Y)R_5$, —$(CH_2)_nCO_2R_5$, —$(CH_2)_nSO_2NR_5R_6$, a straight chained or branched $C_1$–$C_7$ alkyl, monofluoroalkyl, polyfluoroalkyl, aminoalkyl, $C_2$–$C_7$ alkenyl or $C_2$–$C_7$ alkynyl, or a $C_3$–$C_7$ cycloalkyl or cycloalkenyl;

wherein $R_4$ is independently H; —$(CH_2)_uYR_5$; —$(CH_2)_tC(Y)NR_5R_6$; —$(CH_2)_uNR_5C(Y)R_5$; —$(CH_2)_tC(Y)R_7$; —$(CH_2)_tCO_2R_5$; —$(CH_2)_uNR_5R_6$; —$(CH_2)_uCN$; straight chained or branched $C_1$–$C_7$ alkyl; straight chained or branched $C_2$–$C_7$ alkenyl or $C_2$–$C_7$ alkynyl; $C_3$–$C_7$ cycloalkyl or cycloalkenyl; phenyl; or $C_1$–$C_6$ phenylalkyl; wherein the phenyl or $C_1$–$C_6$ phenylalkyl may be substituted with one or more of F, Cl, Br, I, —CN, —$NO_2$, —$NR_5R_6$, —$SO_2R_5$, —$(CH_2)_nC(Y)R_7$, —$(CH_2)_nYR_5$, —$(CH_2)_nC(Y)NR_5R_6$, —$(CH_2)_nNR_5C(Y)R_5$, —$(CH_2)_nCO_2R_5$, —$(CH_2)_nSO_2NR_5R_6$, a straight chained or branched $C_1$–$C_7$ alkyl, monofluoroalkyl, polyfluoroalkyl, aminoalkyl, $C_2$–$C_7$ alkenyl or $C_2$–$C_7$ alkynyl, or a $C_3$–$C_7$ cycloalkyl or cycloalkenyl;

or $R_3$ and $R_4$ taken together with the nitrogen atom to which they are attached are 1-azetidinyl, 1-pyrrolidinyl, 1-piperidinyl, or 1H-azepanyl, wherein the 1-azetidinyl, 1-pyrrolidinyl, 1-piperidinyl, or 1H-azepanyl is substituted with one or more of F, —CN, —$(CH_2)_nNR_5R_6$, —$SO_2R_5$, —$(CH_2)_nC(Y)R_7$, —$(CH_2)_nYR_5$, —$(CH_2)_nC(Y)NR_5R_6$, —$(CH_2)_nNR_5C(Y)R_5$, —$(CH_2)_nCO_2R_5$, a straight chained or branched $C_1$–$C_7$ alkyl, monofluoroalkyl, polyfluoroalkyl, aminoalkyl, a $C_2$–$C_7$ alkenyl or $C_2$–$C_7$ alkynyl, a $C_3$–$C_7$ cycloalkyl or cycloalkenyl, or phenyl or heteroaryl; wherein if —$(CH_2)_nNR_5R_6$, —$(CH_2)_nYR_5$, or —$(CH_2)_nNR_5C(Y)R_5$ are in the 2-position, then n is not 0; wherein the phenyl or heteroaryl may be substituted with one or more of F, Cl, Br, I, —CN, —$NO_2$, —$NR_5R_6$, —$SO_2R_5$, —$(CH_2)_nC(Y)R_7$, —$(CH_2)_nYR_5$, —$(CH_2)_nC(Y)NR_5R_6$, —$(CH_2)_nNR_5C(Y)R_5$, —$(CH_2)_nCO_2R_5$, —$(CH_2)_nSO_2NR_5R_6$, a straight chained or branched $C_1$–$C_7$ alkyl, monofluoroalkyl, polyfluoroalkyl, aminoalkyl, a $C_2$–$C_7$ alkenyl or $C_2$–$C_7$ alkynyl, or a $C_3$–$C_7$ cycloalkyl or cycloalkenyl;

or $R_3$ and $R_4$ taken together with the nitrogen atom to which they are attached are morpholinyl, thiomorpholinyl, [1,4]oxazepanyl, [1,4]thiazepanyl, piperazinyl, or [1,4]diazepanyl, wherein the morpholinyl, thiomorpholinyl, [1,4]oxazepanyl, [1,4]thiazepanyl, piperazinyl, or [1,4]diazepanyl is substituted with one or more straight chained or branched $C_1$–$C_7$ alkyl or $C_1$–$C_7$ phenylalkyl; and wherein the nitrogen atom of the piperazinyl or [1,4]diazepanyl ring is substituted with —$(CH_2)_uYR_5$; —$(CH_2)_tC(Y)NR_5R_6$; —$(CH_2)_uNR_5C(Y)R_5$; —$(CH_2)_tC(Y)R_7$; —$(CH_2)_tCO_2R_5$; —$(CH_2)_uNR_5R_6$; —$(CH_2)_uCN$; —C(Y)$R_5$; —C(Y)$NR_5R_6$; —$CO_2R_5$; straight chained or branched $C_1$–$C_7$ alkyl, $C_2$–$C_7$ alkenyl, or $C_2$–$C_7$ alkynyl; or $C_3$–$C_7$ cycloalkyl or cycloalkenyl; phenyl; $C_1$–$C_6$ phenylalkyl; or $C_1$–$C_6$ heteroarylalkyl; wherein the phenyl, $C_1$–$C_6$ phenylalkyl, or $C_1$–$C_6$ heteroarylalkyl may be substituted with one or more of F, Cl, Br, I, —CN, —$NO_2$, —$NR_5R_6$, —$SO_2R_5$, —$(CH_2)_nC(Y)R_7$, —$(CH_2)_nYR_5$, —$(CH_2)_nC(Y)NR_5R_6$, —$(CH_2)_nNR_5C(Y)R_5$, —$(CH_2)_nCO_2R_5$, —$(CH_2)_nSO_2NR_5R_6$, a straight chained or branched $C_1$–$C_7$ alkyl, monofluoroalkyl, polyfluoroalkyl, aminoalkyl, a $C_2$–$C_7$ alkenyl or $C_2$–$C_7$ alkynyl, or a $C_3$–$C_7$ cycloalkyl or cycloalkenyl;

wherein each of $R_5$, $R_6$ and $R_7$ is independently H; or straight chained or branched $C_1$–$C_7$ alkyl;

wherein each n is independently an integer from 0 to 6 inclusive;

wherein each t is independently an integer from 1 to 4 inclusive;

wherein each u is independently an integer from 2 to 4 inclusive;

wherein Y is O or S;

wherein $R_8$ is

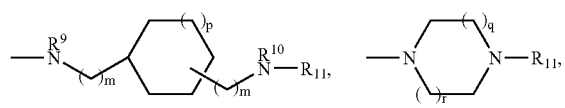

-continued

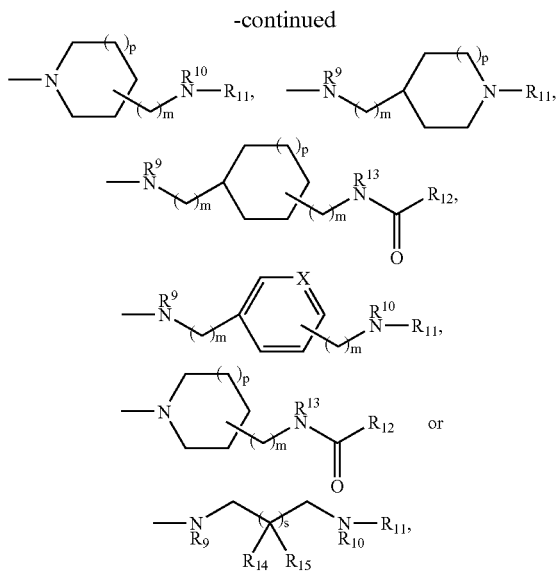

provided that if $R_8$ contains a piperidinyl group and m is O, then the compound is not an -aminal-containing compound;

wherein each of $R_9$ and $R_{10}$ is independently H; straight chained or branched $C_1$–$C_4$ alkyl;

wherein $R_{11}$ is H or

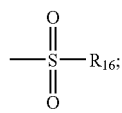

wherein $R_{12}$ is H;

wherein $R_{13}$ is independently H; —$(CH_2)_uYR_5$; —$(CH_2)_tC(Y)NR_5R_6$; —$(CH_2)_uNR_5C(Y)R_5$; —$(CH_2)_tC(Y)R_7$; —$(CH_2)_tCO_2R_5$; —$(CH_2)_uNR_5R_6$; —$(CH_2)_uCN$; —$C(Y)R_5$; —$C(Y)NR_5R_6$; —$CO_2R_5$; straight chained or branched $C_1$–$C_7$ alkyl; $C_1$–$C_7$ alkyl substituted with one or more F or Cl; $C_3$–$C_7$ cycloalkyl-$C_1$–$C_7$ alkyl; straight chained or branched $C_2$–$C_7$ alkenyl, or alkynyl; or $C_3$–$C_7$ cycloalkyl or cycloalkenyl; phenyl or $C_1$–$C_6$ phenylalkyl; wherein the phenyl or $C_1$–$C_6$ phenylalkyl may be substituted with one or more of F, Cl, —CN, —$NO_2$, —$NR_5R_6$, —$SO_2R_5$, —$(CH_2)_n$ $C(Y)R_7$, —$(CH_2)_nYR_5$, —$(CH_2)_nC(Y)NR_5R_6$, —$(CH_2)_nNR_5C(Y)R_5$, —$(CH_2)_nCO_2R_5$, —$(CH_2)_n$ $SO_2NR_5R_6$, a straight chained or branched $C_1$–$C_7$ alkyl, monofluoroalkyl, polyfluoroalkyl, aminoalkyl, a $C_2$–$C_7$ alkenyl or $C_2$–$C_7$ alkynyl, or a $C_3$–$C_7$ cycloalkyl or cycloalkenyl;

or $R_{12}$ and $R_{13}$ together with the amide linkage to which they are attached are pyrrolidinonyl or piperidonyl;

wherein $R_{14}$ is H; straight chained or branched $C_1$–$C_7$ alkyl; F; or —$(CH_2)_nOR_5$;

wherein $R_{15}$ is H, straight chained or branched $C_1$–$C_7$ alkyl, or F;

wherein $R_{16}$ is $NR_3R_4$, unsubstituted straight chained or branched $C_2$–$C_7$ alkyl, substituted straight chained or branched $C_1$–$C_7$ alkyl, wherein the $C_1$–$C_7$ alkyl may be substituted with one or more of F, Cl, —CN, —$NR_5R_6$, —$SO_2R_5$, —$(CH_2)_nC(Y)R_7$, —$(CH_2)_nYR_5$, —$(CH_2)_nC(Y)NR_5R_6$, —$(CH_2)_nNR_5C(Y)R_5$, —$(CH_2)_nCO_2R_5$, —$(CH_2)_n$ $OCF_3$, monofluoroalkyl, polyfluoroalkyl, or aminoalkyl, straight chained or branched $C_2$–$C_7$ alkenyl or $C_2$–$C_7$ alkynyl, or $C_3$–$C_7$ cycloalkyl or cycloalkenyl, phenyl, heteroaryl, or $C_1$–$C_7$ phenylalkyl, wherein the phenyl, heteroaryl, or $C_1$–$C_7$ phenylalkyl may be substituted with one or more of F, Cl, Br, I, —CN, —$NO_2$, —$NR_5R_6$, —$(CH_2)_nNR_5C(Y)R_5$, —$SO_2R_5$, —$(CH_2)_nC(Y)R_7$, —$(CH_2)_nYR_5$, —$(CH_2)_nC(Y)NR_5R_6$, —$(CH_2)_nCO_2R_5$, —$(CH_2)_nSO_2NR_5R_6$, ethylenedioxy, methylenedioxy, straight chained or branched $C_1$–$C_7$ alkyl, monofluoroalkyl, polyfluoroalkyl, or aminoalkyl, straight chained or branched $C_2$–$C_7$ alkenyl or alkynyl, or $C_3$–$C_7$ cycloalkyl or cycloalkenyl; quinolinyl, 1-naphthyl, 2-naphthyl, or 2,1,3-benzothiadiazolyl; with the provisos that when $R_1$ is F, Cl, Br, or I, then $R_{16}$ is 1-naphthyl; and when $R_1$ and $R_2$ are morpholinyl, then $R_{16}$ is not $NR_3R_4$;

wherein each m is independently an integer from 0 to 3 inclusive;

wherein each s is independently an integer from 1 to 6 inclusive;

wherein each p is independently an integer from 0 to 2 inclusive;

wherein each q is independently an integer from 1 to 2 inclusive;

wherein each r is independently an integer from 1 to 2 inclusive;

wherein X is N or C;

or a pharmaceutically acceptable salt thereof.

The invention provides a compound having the structure:

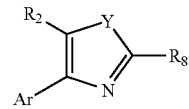

wherein Y is O, S or NH;

wherein Ar is a heteroaryl ring that may be optionally substituted with one or more $R_1$ groups;

wherein each $R_1$ independently is H, F, Cl, Br, —CN, —OH, —$NO_2$, —$NR_5R_6$, —$SO_2R_5$, —$(CH_2)_nOR_5$, —$SO_2C_6H_5$, —$SO_2NR_5R_6$, —$C_6H_5$, —$(CH_2)_nCONR_5R_6$, —$(CH_2)_n$ $NR_5COR_5$, ethylenedioxy, methylenedioxy, perfluoroalkyl, polyfluoroalkyl, aminoalkyl, or straight chained or branched $C_1$–$C_7$ alkyl; or phenyl, heteroaryl, or $C_1$–$C_7$ phenylalkyl, wherein the phenyl, heteroaryl, or $C_1$–$C_7$ phenylalkyl may be substituted with one or more of F, Cl, Br, —$CF_3$, —CN, —$NO_2$, —$NR_5R_6$, —$SO_2R_5$, —$(CH_2)_nOR_5$, or straight chained or branched $C_1$–$C_4$ alkyl;

wherein $R_2$ is H, straight chained or branched $C_1$–$C_4$ alkyl, —$(CH_2)_tOR_5$, phenyl optionally substituted with one or more of F, Cl, Br, —$CF_3$, —CN, —$NO_2$, —$NR_5R_6$, —$SO_2R_5$, —$(CH_2)_nOR_5$, or straight chained or branched $C_1$–$C_4$ alkyl;

wherein $R_5$ is independently H; or straight chained or branched $C_1$–$C_7$ alkyl;

wherein $R_6$ is independently H; or straight chained or branched $C_1$–$C_7$ alkyl;

wherein each n independently is an integer from 0 to 6 inclusive;

wherein $R_8$ is

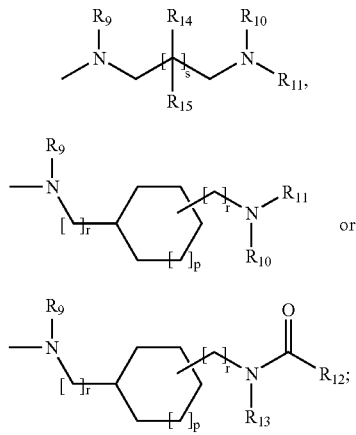

i)

ii)

iii)

provided that when $R_8$ is (iii), and Ar is thiazol-2-yl, $R_1$ cannot be H;

wherein $R_9$ is independently H; or straight chained or branched $C_1$–$C_4$ alkyl;

wherein $R_{10}$ is independently H; or straight chained or branched $C_1$–$C_4$ alkyl;

wherein $R_{11}$ is

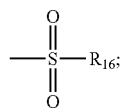

wherein $R_{12}$ is H, straight chained or branched $C_1$–$C_7$ alkyl; or $(CH_2)_nOR_{17}$;

wherein $R_{13}$ is independently —$(CH_2)_uOR_5$; —$(CH_2)_t$CONR$_5$R$_6$; —$(CH_2)_uNR_5COR_5$; —$(CH_2)_tCOR_7$; —$(CH_2)_t$CO$_2$R$_5$; —$(CH_2)_uNR_5R_6$; —$(CH_2)_uCN$; straight chained or branched $C_1$–$C_7$ alkyl; $C_1$–$C_7$ alkyl in which the $C_2$–$C_7$ atoms may be optionally substituted with one or more F or Cl; $C_3$–$C_7$ cycloalkyl-$C_1$–$C_7$ alkyl; straight chained or branched $C_2$–$C_7$ alkenyl; or $C_3$–$C_5$ cycloalkyl;

or $R_{12}$ and $R_{13}$ together with the amide linkage to which they are attached are pyrrolidinonyl, piperidonyl, or oxazolidinonyl;

wherein $R_7$ is independently straight chained or branched $C_1$–$C_7$ alkyl;

wherein $R_{14}$ is H; straight chained or branched $C_1$–$C_4$ alkyl; F; or —$(CH_2)_rOR_5$;

wherein $R_{15}$ is H, straight chained or branched $C_1$–$C_4$ alkyl, or F;

with the proviso that when $R_{14}$ is —OH, $R_{15}$ cannot be F;

wherein $R_{16}$ is —$NR_3R_4$, perfluoroalkyl, unsubstituted straight chained or branched $C_2$–$C_7$ alkyl, substituted straight chained or branched $C_2$–$C_7$ alkyl, wherein the $C_2$–$C_7$ alkyl may be substituted with one or more of F, Cl, —CN, —$NR_5R_6$, —$SO_2R_5$, —$(CH_2)_nCOR_7$, —$(CH_2)_nOR_5$, —$(CH_2)_nCONR_5R_6$, —$(CH_2)_nNR_5COR_5$, —$(CH_2)_nCO_2R_5$, —$(CH_2)_nOCF_3$, perfluoroalkyl, polyfluoroalkyl, or aminoalkyl, straight chained or branched $C_2$–$C_7$ alkenyl or alkynyl, or $C_3$–$C_7$ cycloalkyl; $C_3$–$C_7$ cycloalkyl; phenyl, thienyl, isoxazolyl, quinolinyl, or $C_1$–$C_7$ phenylalkyl, wherein the phenyl, thienyl, isoxazolyl, quinolinyl, or $C_1$–$C_7$ phenylalkyl may be substituted with one or more of F, Cl, Br, I, —CN, —$NO_2$, —$NR_5R_6$, —$(CH_2)_nNR_5COR_5$, —$SO_2R_5$, —$(CH_2)_nCOR_7$, —$(CH_2)_nOR_5$, —$(CH_2)_nCONR_5R_6$, —$(CH_2)_nCO_2R_5$, —$(CH_2)_nSO_2NR_5R_6$, ethylenedioxy, methylenedioxy, straight chained or branched $C_1$–$C_3$ alkyl, perfluoroalkyl, or aminoalkyl, straight chained or branched $C_2$–$C_7$ alkenyl or alkynyl, or $C_3$–$C_7$ cycloalkyl or cycloalkenyl; quinolinyl, 1-naphthyl, 2-naphthyl, or 2,1,3-benzothiadiazolyl; wherein the quinolinyl, 1-naphthyl, 2-naphthyl or 2,1,3-benzothiadiazolyl may be substituted with one or more of F, Cl, Br, —CN, —$NO_2$, —$NR_5R_6$, —$(CH_2)_nOR_5$, —$(CH_2)_nCONR_5R_6$, straight chained or branched $C_1$–$C_4$ alkyl, perfluoroalkyl, or aminoalkyl;

provided that when $R_{16}$ is quinolinyl and $R_8$ is (ii), Ar cannot be pyrrolyl;

provided that when $R_{16}$ is $N(CH_3)_2$ and $R_8$ is (i), Ar cannot be thiazol-2-yl;

wherein $R_3$ is independently H; —$(CH_2)_uOR_5$; —$(CH_2)_t$CONR$_5$R$_6$; —$(CH_2)_uNR_5COR_5$; —$(CH_2)_tCOR_7$; —$(CH_2)_t$CO$_2$R$_5$; —$(CH_2)_uNR_5R_6$; —$(CH_2)_uCN$; straight chained or branched $C_1$–$C_7$ alkyl; straight chained or branched $C_2$–$C_7$ alkenyl or alkynyl; or $C_3$–$C_7$ cycloalkyl or cycloalkenyl; phenyl, or $C_1$–$C_6$ phenylalkyl; wherein the phenyl, or $C_1$–$C_6$ phenylalkyl may be substituted with one or more of F, Cl, Br, —CN, —$NO_2$, —$NR_5R_6$, —$SO_2R_5$, —$(CH_2)_nCOR_7$, —$(CH_2)_nOR_5$, —$(CH_2)_nCONR_5R_6$, —$(CH_2)_nNR_5COR_5$, —$(CH_2)_nCO_2R_5$, —$(CH_2)_nSO_2NR_5R_6$, straight chained or branched $C_1$–$C_7$ alkyl, perfluoroalkyl, polyfluoroalkyl, or aminoalkyl, straight chained or branched $C_2$–$C_7$ alkenyl or alkynyl, or $C_3$–$C_7$ cycloalkyl or cycloalkenyl;

wherein $R_4$ is independently H; —$(CH_2)_uOR_5$; —$(CH_2)_t$CONR$_5$R$_6$; —$(CH_2)_uNR_5COR_5$; —$(CH_2)_tCOR_7$; —$(CH_2)_t$CO$_2$R$_5$; —$(CH_2)_uNR_5R_6$; —$(CH_2)_uCN$; straight chained or branched $C_1$–$C_7$ alkyl; straight chained or branched $C_2$–$C_7$ alkenyl or alkynyl; or $C_3$–$C_7$ cycloalkyl or cycloalkenyl; phenyl or $C_1$–$C_6$ phenylalkyl; wherein the phenyl or $C_1$–$C_6$ phenylalkyl may be substituted with one or more of F, Cl, Br, —CN, —$NO_2$, —$NR_5R_6$, —$SO_2R_5$, —$(CH_2)_nCOR_7$, —$(CH_2)_nOR_5$, —$(CH_2)_nCONR_5R_6$, —$(CH_2)_nNR_5COR_5$, —$(CH_2)_nCO_2R_5$, —$(CH_2)_nSO_2NR_5R_6$, straight chained or branched $C_1$–$C_7$ alkyl, perfluoroalkyl, polyfluoroalkyl, or aminoalkyl, straight chained or branched $C_2$–$C_7$ alkenyl or alkynyl, or $C_3$–$C_7$ cycloalkyl or cycloalkenyl;

or $R_3$ and $R_4$ taken together with the nitrogen atom to which they are attached are 1-azetidinyl, 1-pyrrolidinyl, 1-piperidinyl, or 1H-azepanyl, wherein the 1-azetidinyl, 1-pyrrolidinyl, 1-piperidinyl, or 1H-azepanyl is substituted with one or more of F, —CN, —$(CH_2)_nNR_5R_6$, —$SO_2R_5$, —$(CH_2)_nCOR_7$, —$(CH_2)_nOR_5$, —$(CH_2)_nCONR_5R_6$, —$(CH_2)_nNR_5COR_5$, —$(CH_2)_nCO_2R_5$, straight chained or branched $C_1$–$C_7$ alkyl, perfluoroalkyl, polyfluoroalkyl, or aminoalkyl, straight chained or branched $C_2$–$C_7$ alkenyl or alkynyl, or $C_3$–$C_7$ cycloalkyl or cycloalkenyl, or phenyl or thienyl, isoxazolyl, or quinolinyl; wherein if —$(CH_2)_nNR_5R_6$, —$(CH_2)_nOR_5$, or —$(CH_2)_nNR_5COR_5$ are in the 2-position, then n is not 0; wherein the phenyl, thienyl, isoxazolyl, or quinolinyl may be substituted with one or more of F, Cl, Br, I, —CN, —NO$_2$, —NR$_5$R$_6$, —SO$_2$R$_5$, —(CH$_2$)$_n$COR$_7$, —(CH$_2$)$_n$OR$_5$, —(CH$_2$)$_n$CONR$_5$R$_6$, —(CH$_2$)$_n$NR$_5$COR$_5$, —(CH$_2$)$_n$CO$_2$R$_5$, —(CH$_2$)$_n$SO$_2$NR$_5$R$_6$, straight chained or branched C$_1$–C$_7$ alkyl, perfluoroalkyl, polyfluoroalkyl, or aminoalkyl, straight chained or branched C$_2$–C$_7$ alkenyl or alkynyl, or C$_3$–C$_7$ cycloalkyl or cycloalkenyl;

or R$_3$ and R$_4$ taken together with the nitrogen atom to which they are attached are morpholinyl, thiomorpholinyl, [1,4]oxazepanyl, [1,4]thiazepanyl, piperazinyl, or [1,4]diazepanyl, wherein the morpholinyl, thiomorpholinyl, [1,4]oxazepanyl, [1,4]thiazepanyl, piperazinyl, or [1,4]diazepanyl is optionally substituted with straight chained or branched C$_1$–C$_5$ alkyl or —(CH$_2$)$_t$OR$_5$; and wherein the nitrogen atom of the piperazinyl or [1,4]diazepanyl ring may be optionally substituted with —(CH$_2$)$_u$OR$_5$; —COR$_5$; straight chained or branched C$_1$–C$_5$ alkyl; or phenyl; wherein the phenyl may be substituted with one or more of F, Cl, Br, —CN, —NO$_2$, —NR$_5$R$_6$—(CH$_2$)$_n$OR$_5$, straight chained or branched C$_1$–C$_3$ alkyl, perfluoroalkyl, polyfluoroalkyl, or aminoalkyl;

wherein R$_{17}$ is straight chained or branched C$_1$–C$_4$ alkyl, perfluoroalkyl, or polyfluoroalkyl;

wherein each p independently is an integer from 0 to 2 inclusive;

wherein each r independently is an integer from 0 to 3 inclusive;

wherein each s independently is an integer from 3 to 6 inclusive;

wherein t is an integer from 1 to 4 inclusive;

wherein each u independently is an integer from 2 to 4 inclusive;

or a pharmaceutically acceptable salt thereof.

The invention provides a compound having the structure:

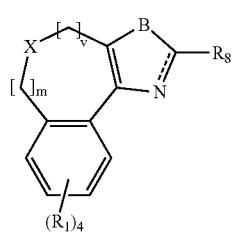

wherein each R$_1$ is independently H, F, Cl, Br, —CN, —OH, —NO$_2$, —NR$_5$R$_6$, —SO$_2$R$_5$, —(CH$_2$)$_n$OR, —(CH$_2$)$_n$CONR$_5$R$_6$, —(CH$_2$)$_n$NR$_5$COR$_5$, perfluoroalkyl, polyfluoroalkyl, aminoalkyl, or straight chained or branched C$_1$–C$_7$ alkyl;

wherein R$_5$ is independently H; or straight chained or branched C$_1$–C$_7$ alkyl;

wherein R$_6$ is independently H; or straight chained or branched C$_1$–C$_7$ alkyl;

wherein B is O, NH or S;

wherein X is S, SO or SO$_2$;

wherein each n independently is an integer from 0 to 6 inclusive;

wherein R$_8$ is

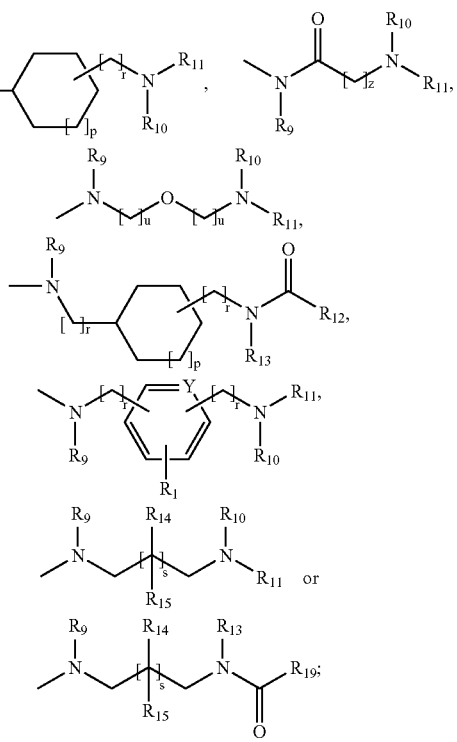

wherein Y is C or N;

wherein R$_7$ is independently straight chained or branched C$_1$–C$_7$ alkyl;

wherein R$_9$ is independently H; or straight chained or branched C$_1$–C$_4$ alkyl;

wherein R$_{10}$ is independently H; or straight chained or branched C$_1$–C$_4$ alkyl;

wherein R$_{11}$ is

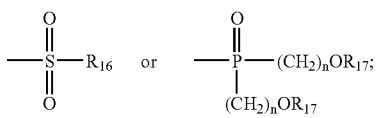

wherein R$_{12}$ is H, straight chained or branched C$_1$–C$_7$ alkyl, (CH$_2$)$_u$OR$_{17}$, or O(CH$_2$)$_u$OR$_{17}$; provided that when X is O, R$_{12}$ cannot be methyl;

wherein R$_{13}$ is independently H; —(CH$_2$)$_u$OR$_5$; —(CH$_2$)$_t$CONR$_5$R$_6$; —(CH$_2$)$_u$NR$_5$COR$_5$; —(CH$_2$)$_t$COR$_7$; —(CH$_2$)$_t$CO$_2$R$_5$; —(CH$_2$)$_u$NR$_5$R$_6$; —(CH$_2$)$_u$CN; straight chained or branched C$_1$–C$_7$ alkyl; C$_1$–C$_7$ alkyl in which the C$_2$–C$_7$ atoms may be optionally substituted with one or more F or Cl; C$_3$–C$_7$ cycloalkyl-C$_1$–C$_7$ alkyl; straight chained or branched C$_2$–C$_7$ alkenyl or alkynyl; or C$_3$–C$_7$ cycloalkyl; phenyl or C$_1$–C$_6$ phenylalkyl; wherein the phenyl or C$_1$–C$_6$ phenylalkyl may be substituted with one or more of F, Cl, —CN, —NO$_2$, —NR$_5$R$_6$, —SO$_2$R$_5$, —(CH$_2$)$_n$COR$_7$, —(CH$_2$)$_n$OR$_5$, —(CH$_2$)$_n$CONR$_5$R$_6$, —(CH$_2$)$_n$NR$_5$COR$_5$, —(CH$_2$)$_n$CO$_2$R$_5$, —(CH$_2$)$_n$SO$_2$NR$_5$R$_6$, straight chained or branched C$_1$–C$_7$ alkyl, perfluoroalkyl, polyfluoroalkyl, or aminoalkyl;

or R$_{12}$ and R$_{13}$ together with the amide linkage to which they are attached are pyrrolidinonyl, piperidonyl, or oxazolidinonyl;

wherein R$_{14}$ is H; straight chained or branched C$_1$–C$_4$ alkyl; F; or —(CH$_2$)$_r$OR$_5$;

wherein R$_{15}$ is H, straight chained or branched C$_1$–C$_4$ alkyl, or F;

with the proviso that when R$_{14}$ is —OH, R$_{15}$ cannot be F;

wherein R$_{16}$ is perfluoroalkyl, unsubstituted straight chained or branched C$_1$–C$_7$ alkyl, substituted straight chained or branched C$_2$–C$_7$ alkyl, wherein the C$_2$–C$_7$ alkyl may be substituted with one or more of F, Cl, —CN, —SO$_2$R$_5$, —(CH$_2$)$_n$COR$_7$, —(CH$_2$)$_n$OR$_5$, —(CH$_2$)$_n$CONR$_5$R$_6$, —(CH$_2$)$_n$NR$_5$COR$_5$, —(CH$_2$)$_n$CO$_2$R$_5$, —(CH$_2$)$_n$OCF$_3$, perfluoroalkyl, polyfluoroalkyl, or aminoalkyl, straight chained or branched C$_2$–C$_7$ alkenyl or alkynyl, or C$_3$–C$_7$ cycloalkyl or cycloalkenyl; C$_3$–C$_7$ cycloalkyl or cycloalkenyl; phenyl, heteroaryl, or C$_1$–C$_7$ phenylalkyl, wherein the phenyl, heteroaryl, or C$_1$–C$_7$ phenylalkyl may be substituted with one or more of F, Cl, Br, —CN, —NO$_2$, —NR$_5$R$_6$, —(CH$_2$)NR$_5$COR$_5$, —SO$_2$R$_5$, —(CH$_2$)$_n$COR$_7$, —(CH$_2$)$_n$OR$_5$, —(CH$_2$)$_n$CONR$_5$R$_6$, —(CH$_2$)$_n$CO$_2$R$_5$, —(CH$_2$)$_n$SO$_2$NR$_5$R$_6$, ethylenedioxy, methylenedioxy, straight chained or branched C$_1$–C$_7$ alkyl, perfluoroalkyl, polyfluoroalkyl, or aminoalkyl, straight chained or branched C$_2$–C$_7$ alkenyl or alkynyl, or C$_3$–C$_7$ cycloalkyl or cycloalkenyl; quinolinyl, 1-naphthyl, 2-naphthyl, or 2,1,3-benzothiadiazolyl; wherein the quinolinyl, 1-naphthyl, 2-naphthyl or 2,1,3-benzothiadiazolyl may be substituted with one or more of F, Cl, Br, —CN, —NO$_2$, —NR$_5$R$_6$, —(CH$_2$)$_n$NR$_5$COR$_5$, —SO$_2$R$_5$, —(CH$_2$)$_n$COR$_7$, —(CH$_2$)$_n$OR$_5$, —(CH$_2$)$_n$CONR$_5$R$_6$, —(CH$_2$)$_n$CO$_2$R$_5$, —(CH$_2$)$_n$SO$_2$NR$_5$R$_6$, ethylenedioxy, methylenedioxy, straight chained or branched C$_1$–C$_7$ alkyl, perfluoroalkyl, polyfluoroalkyl, or aminoalkyl;

with the proviso that when R$_8$ is NR$_9$ (R$_{14}$R$_{15}$)$_s$NR$_{10}$R$_{11}$, R$_{16}$ cannot be quinolinyl;

wherein R$_{17}$ is H, straight chained or branched C$_1$–C$_4$ alkyl, perfluoroalkyl, or polyfluoroalkyl;

wherein R$_{19}$ is —(CH$_2$)$_u$OR$_5$, —NR$_5$R$_6$, phenyl, or heteroaryl, wherein the phenyl or heteroaryl may be substituted with one or more of F, Cl, Br, —CN, —NO$_2$, —NR$_5$R$_6$, —(CH$_2$)$_n$NR$_5$COR$_5$, —SO$_2$R$_5$, —(CH$_2$)$_n$COR$_7$, —(CH$_2$)$_n$OR$_5$, —(CH$_2$)$_n$CONR$_5$R$_6$, —(CH$_2$)$_n$CO$_2$R$_5$, —(CH$_2$)$_n$SO$_2$NR$_5$R$_6$, ethylenedioxy, methylenedioxy, straight chained or branched C$_1$–C$_7$ alkyl, perfluoroalkyl, polyfluoroalkyl, or aminoalkyl, straight chained or branched C$_2$–C$_7$ alkenyl or alkynyl, or C$_3$–C$_7$ cycloalkyl or cycloalkenyl;

wherein m is 0 or 1;

wherein each p independently is an integer from 0 to 2 inclusive;

wherein each r independently is an integer from 0 to 3 inclusive;

wherein each s independently is an integer from 1 to 6 inclusive;

wherein t is an integer from 1 to 4 inclusive;

wherein each u independently is an integer from 2 to 4 inclusive;

wherein v is 1 or 2;

with the proviso that when v is 2, m is 0;

wherein z is an integer from 2 to 7;

or a pharmaceutically acceptable salt thereof.

The invention also provides a pharmaceutical composition comprising a therapeutically effective amount of the compound of the invention and a pharmaceutically acceptable carrier. This invention further provides a pharmaceutical composition made by combining a therapeutically effective amount of the compound of this invention and a pharmaceutically acceptable carrier. This invention further provides a process for making a pharmaceutical composition comprising combining a therapeutically effective amount of the compound of the invention and a pharmaceutically acceptable carrier.

DETAILED DESCRIPTION OF THE INVENTION

Figure 1A:
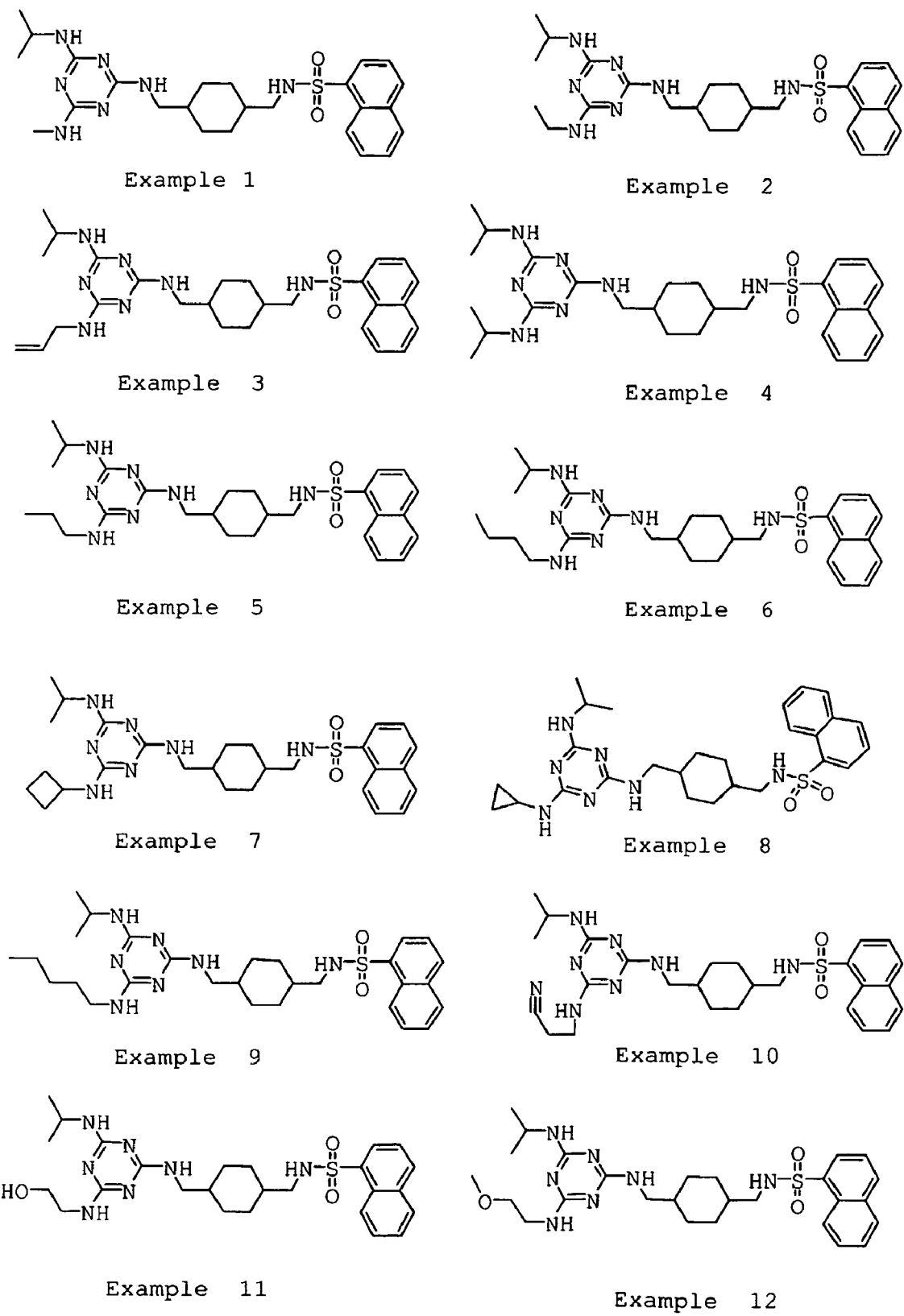
FIGS. 1A–1F
Structures of compounds described herein within the Experimental Details section in Examples 1–58.
Figure 1B:
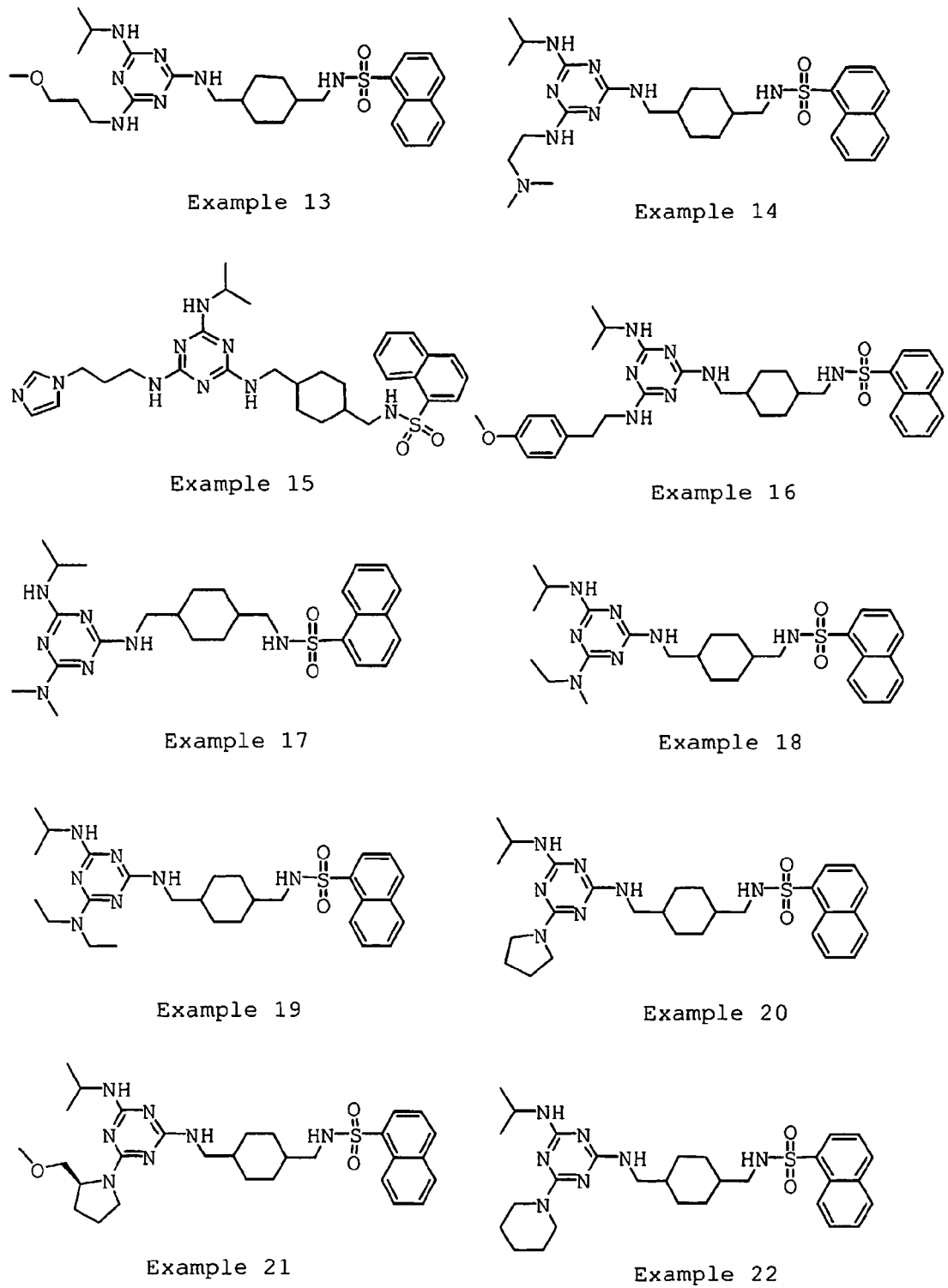
Figure 1C:
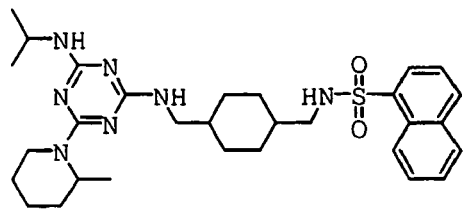
Figure 1C:
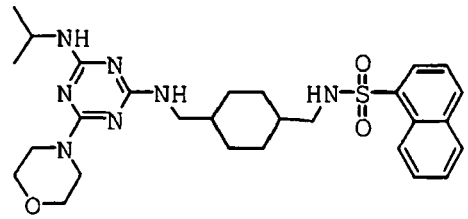
Figure 1C:
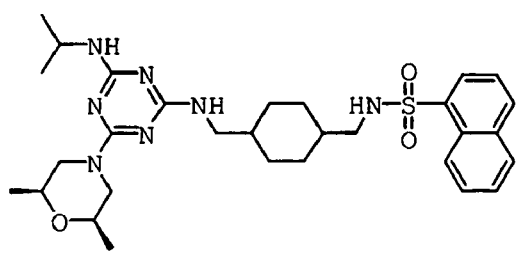
Figure 1C:
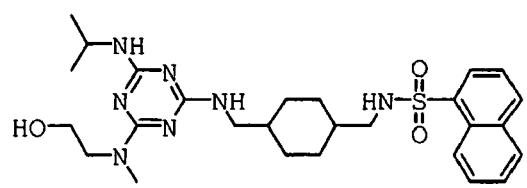
Figure 1C:
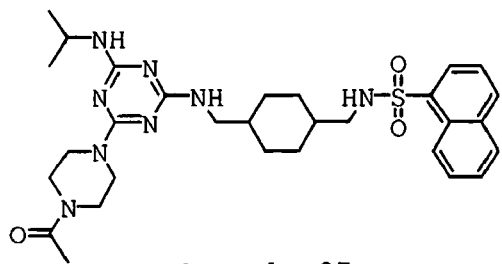
Figure 1C:
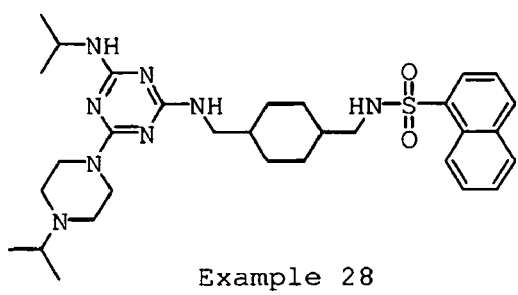
Figure 1C:
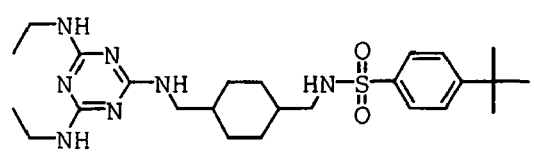
Figure 1C:
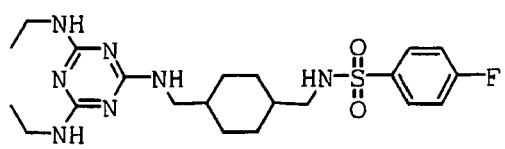
Figure 1D:
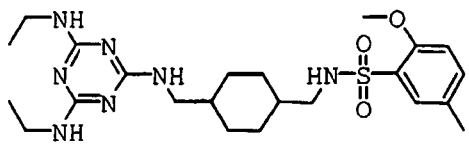
Figure 1D:
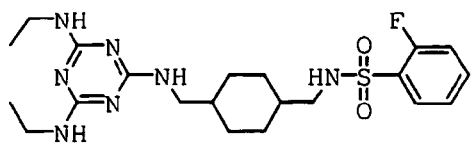
Figure 1D:
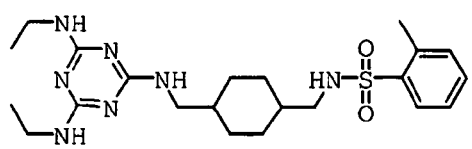
Figure 1D:
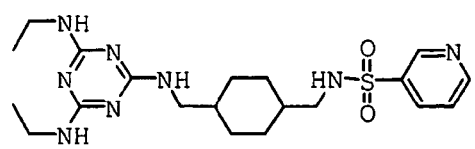
Figure 1D:
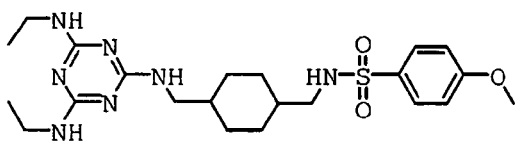
Figure 1D:
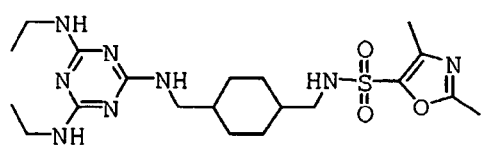
Figure 1D:
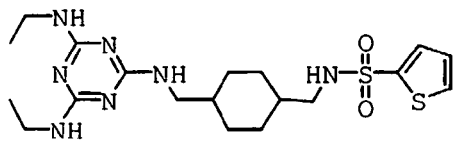
Figure 1D:
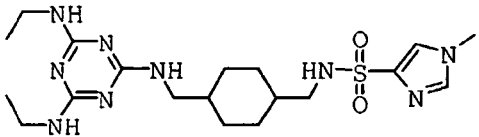
Figure 1D:
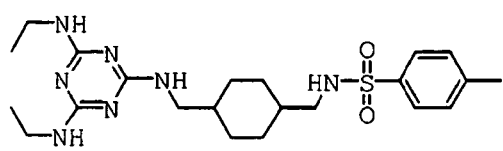
Figure 1D:
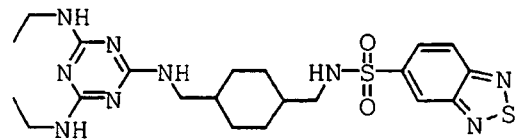
Figure 1D:
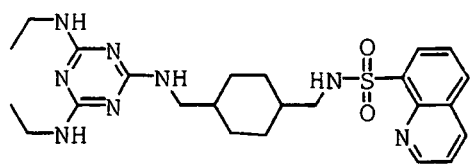
Figure 1D:
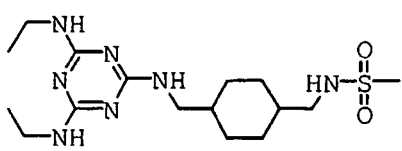
Figure 1E:
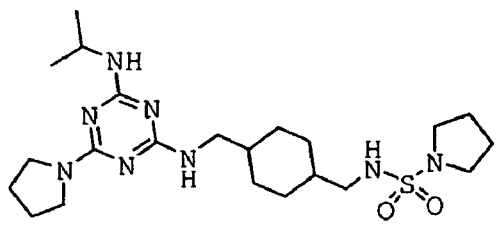
Figure 1E:
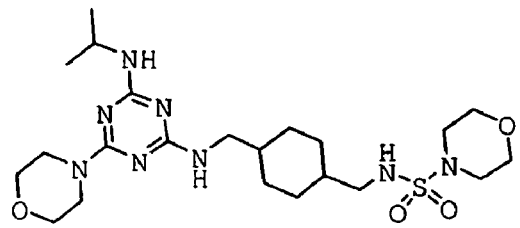
Figure 1E:
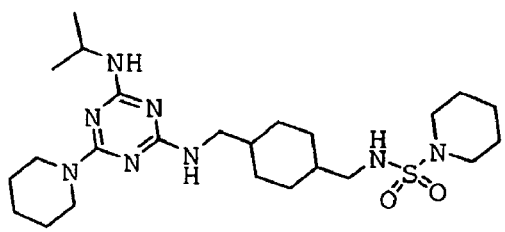
Figure 1E:
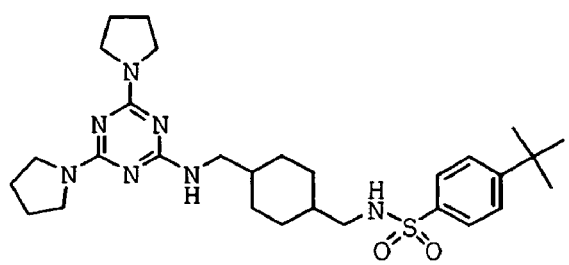
Figure 1E:
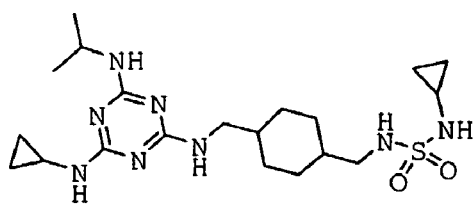
Figure 1E:
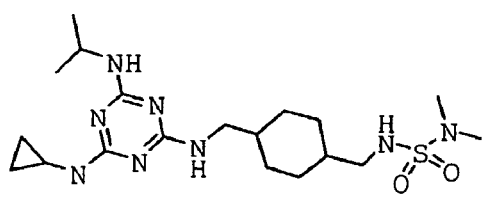
Figure 1E:
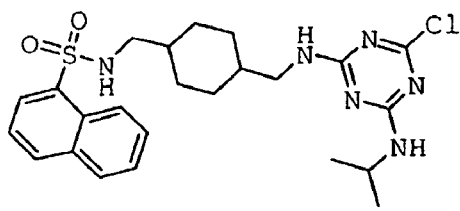
Figure 1E:
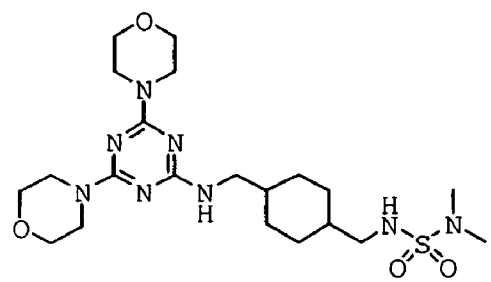
Figure 1E:
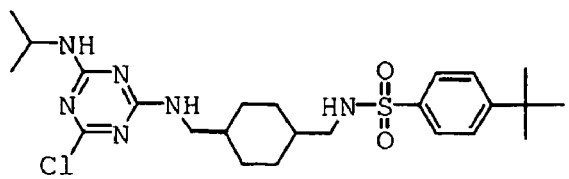
Figure 1E:
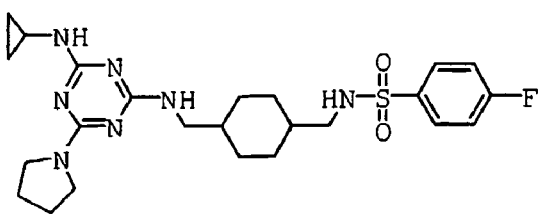
Figure 1F:
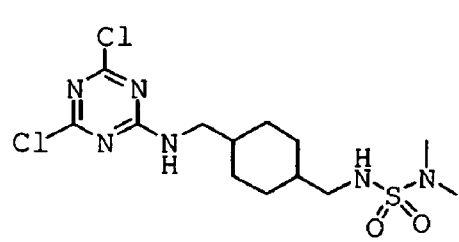
Figure 1F:
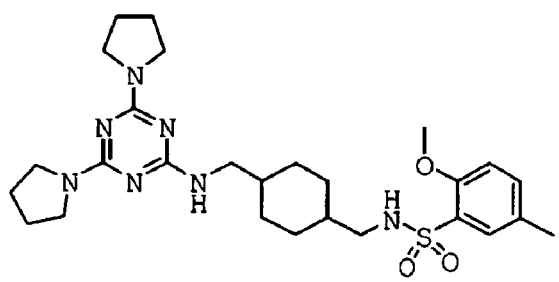
Figure 1F:
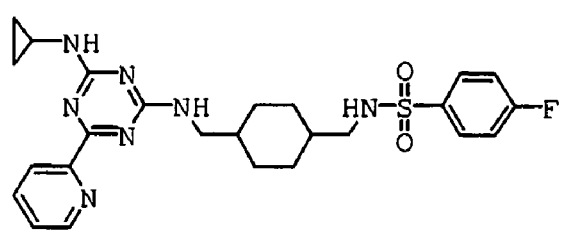
Figure 1F:
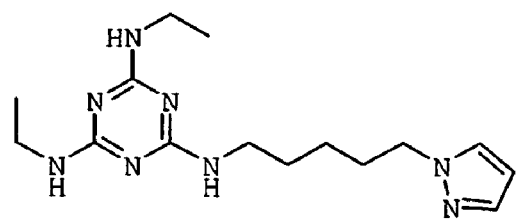
Figure 1F:
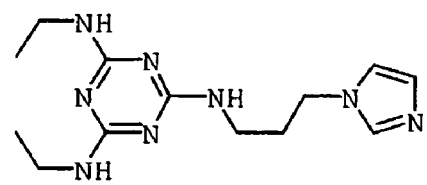
Figure 1F:
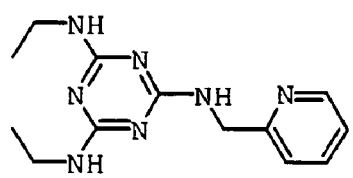

This invention provides a compound having the structure

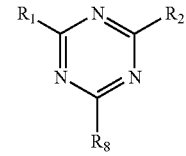

wherein R$_1$ is F; Cl; Br; I; NR$_3$R$_4$; or phenyl or heteroaryl; wherein the phenyl or heteroaryl may be substituted with one or more of F, Cl, Br, I, —CN, —NO$_2$, —NR$_5$R$_6$, —SO$_2$R$_5$, —(CH$_2$)$_n$C(Y)R$_7$, —(CH$_2$)$_n$YR$_5$, —(CH$_2$)$_n$C(Y)NR$_5$R$_6$, —(CH$_2$)$_n$NR$_5$C(Y)R$_5$, —(CH$_2$)$_n$CO$_2$R$_5$, —(CH$_2$)$_n$SO$_2$NR$_5$R$_6$, a straight chained or branched C$_1$–C$_7$ alkyl, monofluoroalkyl, polyfluoroalkyl, aminoalkyl, C$_2$–C$_7$ alkenyl or C$_2$–C$_7$ alkynyl, or a C$_3$–C$_7$ cycloalkyl or cycloalkenyl;

wherein R$_2$ is NR$_3$R$_4$;

wherein R$_3$ is independently H; —(CH$_2$)$_u$YR$_5$; —(CH$_2$)$_t$C(Y)NR$_5$R$_6$; —(CH$_2$)$_u$NR$_5$C(Y)R$_5$; —(CH$_2$)$_t$C(Y)R$_7$; —(CH$_2$)$_t$CO$_2$R$_5$; —(CH$_2$)$_u$NR$_5$R$_6$; —(CH$_2$)$_u$CN; —C(Y)R$_5$; —C(Y)NR$_5$R$_6$; —CO$_2$R$_5$; straight chained or branched C$_1$–C$_7$ alkyl, C$_2$–C$_7$ alkenyl, or C$_2$–C$_7$ alkynyl; C$_3$–C$_7$ cycloalkyl or cycloalkenyl; phenyl; C$_1$–C$_6$ phenylalkyl; or C$_1$–C$_6$ heteroarylalkyl; wherein the phenyl, C$_1$–C$_6$ phenylalkyl, or C$_1$–C$_6$ heteroarylalkyl may be substituted with one or more of F, Cl, Br, I, —CN, —NO$_2$, —NR$_5$R$_6$, —SO$_2$R$_5$, —(CH$_2$)$_n$C(Y)R$_7$, —(CH$_2$)$_n$YR$_5$, —(CH$_2$)$_n$C(Y)NR$_5$R$_6$, —(CH$_2$)$_n$NR$_5$C(Y)R$_5$, —(CH$_2$)$_n$CO$_2$R$_5$, —(CH$_2$)$_n$SO$_2$NR$_5$R$_6$, a straight chained or branched C$_1$–C$_7$ alkyl, monofluoroalkyl, polyfluoroalkyl, aminoalkyl, C$_2$–C$_7$ alkenyl or C$_2$–C$_7$ alkynyl, or a C$_3$–C$_7$ cycloalkyl or cycloalkenyl;

wherein R$_4$ is independently H; —(CH$_2$)$_u$YR$_5$; —(CH$_2$)$_t$C(Y)NR$_5$R$_6$; —(CH$_2$)$_u$NR$_5$C(Y)R$_5$; —(CH$_2$)$_t$C(Y)R$_7$; —(CH$_2$)$_t$CO$_2$R$_5$; —(CH$_2$)$_u$NR$_5$R$_6$; —(CH$_2$)$_u$CN; straight chained or branched $C_1$–$C_7$ alkyl; straight chained or branched $C_2$–$C_7$ alkenyl or $C_2$–$C_7$ alkynyl; $C_3$–$C_7$ cycloalkyl or cycloalkenyl; phenyl; or $C_1$–$C_6$ phenylalkyl; wherein the phenyl or $C_1$–$C_6$ phenylalkyl may be substituted with one or more of F, Cl, Br, I, —CN, —$NO_2$, —$NR_5R_6$, —$SO_2R_5$, —$(CH_2)_nC(Y)R_7$, —$(CH_2)_nYR_5$, —$(CH_2)_nC(Y)NR_5R_6$, —$(CH_2)_nNR_5C(Y)R_5$, —$(CH_2)_nCO_2R_5$, —$(CH_2)_nSO_2NR_5R_6$, a straight chained or branched $C_1$–$C_7$ alkyl, monofluoroalkyl, polyfluoroalkyl, aminoalkyl, $C_2$–$C_7$ alkenyl or $C_2$–$C_7$ alkynyl, or a $C_3$–$C_7$ cycloalkyl or cycloalkenyl;

or $R_3$ and $R_4$ taken together with the nitrogen atom to which they are attached are 1-azetidinyl, 1-pyrrolidinyl, 1-piperidinyl, or 1H-azepanyl, wherein the 1-azetidinyl, 1-pyrrolidinyl, 1-piperidinyl, or 1H-azepanyl is substituted with one or more of F, —CN, —$(CH_2)_nNR_5R_6$, —$SO_2R_5$, —$(CH_2)_nC(Y)R_7$, —$(CH_2)_nYR_5$, —$(CH_2)_nC(Y)N R_5R_6$, —$(CH_2)_nNR_5C(Y)R_5$, —$(CH_2)_nCO_2R_5$, a straight chained or branched $C_1$–$C_7$ alkyl, monofluoroalkyl, polyfluoroalkyl, aminoalkyl, a $C_2$–$C_7$ alkenyl or $C_2$–$C_7$ alkynyl, a $C_3$–$C_7$ cycloalkyl or cycloalkenyl, or phenyl or heteroaryl; wherein if —$(CH_2)_nNR_5R_6$, —$(CH_2)_nYR_5$, or —$(CH_2)_nNR_5C(Y)R_5$ are in the 2-position, then n is not 0; wherein the phenyl or heteroaryl may be substituted with one or more of F, Cl, Br, I, —CN, —$NO_2$, —$NR_5R_6$, —$SO_2R_5$, —$(CH_2)_nC(Y)R_7$, —$(CH_2)_nYR_5$, —$(CH_2)_nC(Y)N R_5R_6$, —$(CH_2)_nNR_5C(Y)R_5$, —$(CH_2)_nCO_2R_5$, —$(CH_2)_nSO_2NR_5R_6$, a straight chained or branched $C_1$–$C_7$ alkyl, monofluoroalkyl, polyfluoroalkyl, aminoalkyl, a $C_2$–$C_7$ alkenyl or $C_2$–$C_7$ alkynyl, or a $C_3$–$C_7$ cycloalkyl or cycloalkenyl;

or $R_3$ and $R_4$ taken together with the nitrogen atom to which they are attached are morpholinyl, thiomorpholinyl, [1,4]oxazepanyl, [1,4]thiazepanyl, piperazinyl, or [1,4]diazepanyl, wherein the morpholinyl, thiomorpholinyl, [1,4]oxazepanyl, [1,4]thiazepanyl, piperazinyl, or [1,4]diazepanyl is substituted with one or more straight chained or branched $C_1$–$C_7$ alkyl or $C_1$–$C_7$ phenylalkyl; and wherein the nitrogen atom of the piperazinyl or [1,4]diazepanyl ring is substituted with —$(CH_2)_uYR_5$; —$(CH_2)_tC(Y)NR_5R_6$; —$(CH_2)_uNR_5C(Y)R_5$; —$(CH_2)_tC(Y)R_7$; —$(CH_2)_tCO_2R_5$; —$(CH_2)_uNR_5R_6$; —$(CH_2)_uCN$; —$C(Y)R_5$; —$C(Y)NR_5R_6$; —$CO_2R_5$; straight chained or branched $C_1$–$C_7$ alkyl, $C_2$–$C_7$ alkenyl, or $C_2$–$C_7$ alkynyl; or $C_3$–$C_7$ cycloalkyl or cycloalkenyl; phenyl; $C_1$–$C_6$ phenylalkyl; or $C_1$–$C_6$ heteroarylalkyl; wherein the phenyl, $C_1$–$C_6$ phenylalkyl, or $C_1$–$C_6$ heteroarylalkyl may be substituted with one or more of F, Cl, Br, I, —CN, —$NO_2$, —$NR_5R_6$, —$SO_2R_5$, —$(CH_2)_nC(Y)R_7$, —$(CH_2)_nYR_5$, —$(CH_2)_nC(Y)NR_5R_6$, —$(CH_2)_nNR_5C(Y)R_5$, —$(CH_2)_nCO_2R_5$, —$(CH_2)_nSO_2NR_5R_6$, a straight chained or branched $C_1$–$C_7$ alkyl, monofluoroalkyl, polyfluoroalkyl, aminoalkyl, a $C_2$–$C_7$ alkenyl or $C_2$–$C_7$ alkynyl, or a $C_3$–$C_7$ cycloalkyl or cycloalkenyl;

wherein each of $R_5$, $R_6$ and $R_7$ is independently H; or straight chained or branched $C_1$–$C_7$ alkyl;

wherein each n is independently an integer from 0 to 6 inclusive;

wherein each t is independently an integer from 1 to 4 inclusive;

wherein each u is independently an integer from 2 to 4 inclusive;

wherein Y is O or S;

wherein $R_8$ is

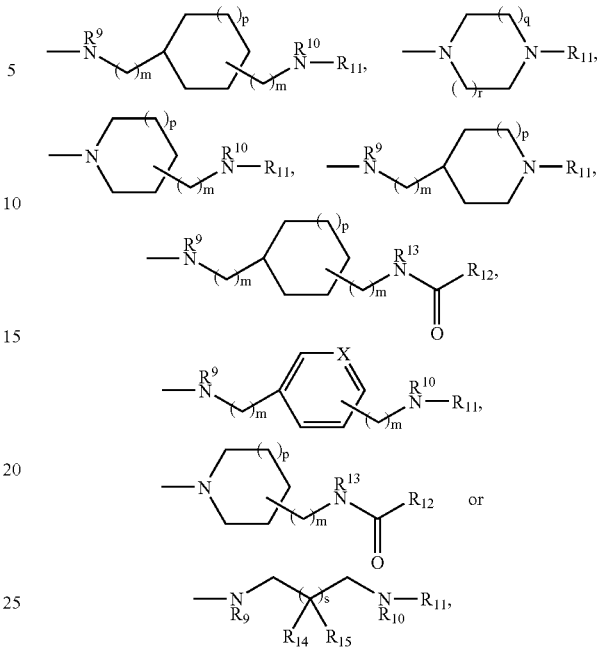

provided that if $R_8$ contains a piperidinyl group and m is O, then the compound is not an -aminal-containing compound;

wherein each of $R_9$ and $R_{10}$ is independently H; straight chained or branched $C_1$–$C_4$ alkyl;

wherein $R_{11}$ is H or

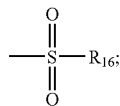

wherein $R_{12}$ is H;

wherein $R_{13}$ is independently H; —$(CH_2)_uYR_5$; —$(CH_2)_tC(Y)NR_5R_6$; —$(CH_2)_uNR_5C(Y)R_5$; —$(CH_2)_tC(Y)R_7$; —$(CH_2)_tCO_2R_5$; —$(CH_2)_uNR_5R_6$; —$(CH_2)_uCN$; —$C(Y)R_5$; —$C(Y)NR_5R_6$; —$CO_2R_5$; straight chained or branched $C_1$–$C_7$ alkyl; $C_1$–$C_7$ alkyl substituted with one or more F or Cl; $C_3$–$C_7$ cycloalkyl-$C_1$–$C_7$ alkyl; straight chained or branched $C_2$–$C_7$ alkenyl, or alkynyl; or $C_3$–$C_7$ cycloalkyl or cycloalkenyl; phenyl or $C_1$–$C_6$ phenylalkyl; wherein the phenyl or $C_1$–$C_6$ phenylalkyl may be substituted with one or more of F, Cl, —CN, —$NO_2$, —$NR_5R_6$, —$SO_2R_5$, —$(CH_2)_n C(Y)R_7$, —$(CH_2)_nYR_5$, —$(CH_2)_nC(Y)NR_5R_6$, —$(CH_2)_nNR_5C(Y)R_5$, —$(CH_2)_nCO_2R_5$, —$(CH_2)_nSO_2NR_5R_6$, a straight chained or branched $C_1$–$C_7$ alkyl, monofluoroalkyl, polyfluoroalkyl, aminoalkyl, a $C_2$–$C_7$ alkenyl or $C_2$–$C_7$ alkynyl, or a $C_3$–$C_7$ cycloalkyl or cycloalkenyl;

or $R_{12}$ and $R_{13}$ together with the amide linkage to which they are attached are pyrrolidinonyl or piperidonyl;

wherein $R_{14}$ is H; straight chained or branched $C_1$–$C_7$ alkyl; F; or —$(CH_2)_nOR_5$;

wherein $R_{15}$ is H, straight chained or branched $C_1$–$C_7$ alkyl, or F;

wherein $R_{16}$ is $NR_3R_4$, unsubstituted straight chained or branched $C_2$–$C_7$ alkyl, substituted straight chained or branched $C_1$–$C_7$ alkyl, wherein the $C_1$–$C_7$ alkyl may be substituted with one or more of F, Cl, —CN, —$NR_5R_6$, —$SO_2R_5$, —$(CH_2)_nC(Y)R_7$, —$(CH_2)_nYR_5$, —$(CH_2)_nC(Y)NR_5R_6$, —$(CH_2)_nNR_5C(Y)R_5$, —$(CH_2)_nCO_2R_5$, —$(CH_2)_nOCF_3$, monofluoroalkyl, polyfluoroalkyl, or aminoalkyl, straight chained or branched $C_2$–$C_7$ alkenyl or $C_2$–$C_7$ alkynyl, or $C_3$–$C_7$ cycloalkyl or cycloalkenyl, phenyl, heteroaryl, or $C_1$–$C_7$ phenylalkyl, wherein the phenyl, heteroaryl, or $C_1$–$C_7$ phenylalkyl may be substituted with one or more of F, Cl, Br, I, —CN, —$NO_2$, —$NR_5R_6$, —$(CH_2)_nNR_5C(Y)R_5$, —$SO_2R_5$, —$(CH_2)_nC(Y)R_7$, —$(CH_2)_nYR_5$, —$(CH_2)_nC(Y)NR_5R_6$, —$(CH_2)_nCO_2R_5$, —$(CH_2)_nSO_2NR_5R_6$, ethylenedioxy, methylenedioxy, straight chained or branched $C_1$–$C_7$ alkyl, monofluoroalkyl, polyfluoroalkyl, or aminoalkyl, straight chained or branched $C_2$–$C_7$ alkenyl or alkynyl, or $C_3$–$C_7$ cycloalkyl or cycloalkenyl; quinolinyl, 1-naphthyl, 2-naphthyl, or 2,1,3-benzothiadiazolyl; with the provisos that when $R_1$ is F, Cl, Br, or I, then $R_{16}$ is 1-naphthyl; and when $R_1$ and $R_2$ are morpholinyl, then $R_{16}$ is not $NR_3R_4$;

wherein each m is independently an integer from 0 to 3 inclusive;

wherein each s is independently an integer from 1 to 6 inclusive;

wherein each p is independently an integer from 0 to 2 inclusive;

wherein each q is independently an integer from 1 to 2 inclusive;

wherein each r is independently an integer from 1 to 2 inclusive;

wherein X is N or C;

or a pharmaceutically acceptable salt thereof.

An α-aminal-containing compound is a compound in which a nitrogen is directly attached to the -carbon of the piperidinyl group.

In one embodiment, the compound of this invention comprises the (+) enantiomer. In another embodiment, the compound comprises the (−) enantiomer.

In one embodiment, $R_8$ is

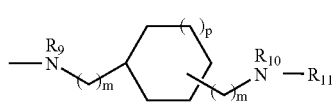

In another embodiment, $R_1$ is F, Cl, Br, I, or $NR_3R_4$.

In another embodiment, $R_1$ and $R_2$ are both $NR_3R_4$ where $R_3$ and $R_4$ are independently H; straight chained or branched $C_1$–$C_7$ alkyl; straight chained, or branched $C_2$–$C_7$ alkenyl or alkynyl; or $R_3$ and $R_4$ taken together with the nitrogen atom to which they are attached are morpholinyl, piperazinyl, or 1-pyrrolidinyl, wherein the morpholinyl, piperazinyl, or 1-pyrrolidinyl is substituted with one or more straight chained or branched $C_1$–$C_7$ alkyl or $C_1$–$C_7$ phenylalkyl; and wherein the nitrogen atom of the piperazinyl ring is substituted with H; —$(CH_2)_uYR_5$; —$(CH_2)_rC(Y)NR_5R_6$; —$(CH_2)_u NR_5C(Y)R_5$; —$(CH_2)_rC(Y)R_7$; —$(CH_2)_rCO_2R_5$; —$(CH_2)_uNR_5R_6$; —$(CH_2)_uCN$; —$C(Y)R_5$; —$C(Y)NR_5R_6$; —$CO_2R_5$; straight chained or branched $C_1$–$C_7$ alkyl; straight chained or branched $C_2$–$C_7$ alkenyl or alkynyl; $C_3$–$C_7$ cycloalkyl or cycloalkenyl; phenyl; $C_1$–$C_6$ phenylalkyl; or $C_1$–$C_6$ heteroarylalkyl.

In another embodiment, $R_{16}$ is phenyl, 1-naphthyl, quinolinyl, or 2,1,3-benzothiadiazolyl; wherein the phenyl may be substituted with one or more of F, Cl, Br, I, —CN, —$NO_2$, —$NR_5R_6$, —$(CH_2)_nNR_5C(Y)R_5$, —$SO_2R_5$, —$(CH_2)_nC(Y)R_7$, —$(CH_2)_nYR_5$, —$(CH_2)_nC(Y)NR_5R_6$, —$(CH_2)_nCO_2R_5$, —$(CH_2)_nSO_2NR_5R_6$, ethylenedioxy, methylenedioxy, straight chained or branched $C_1$–$C_7$ alkyl, monofluoroalkyl, polyfluoroalkyl, or aminoalkyl, straight chained or branched $C_2$–$C_7$ alkenyl or alkynyl, or $C_3$–$C_7$ cycloalkyl or cycloalkenyl.

In another embodiment, $R_9$ is H, $R_{10}$ is H, p is 1, and m is 1.

In a presently preferred embodiment, the compound is selected from the group consisting of:

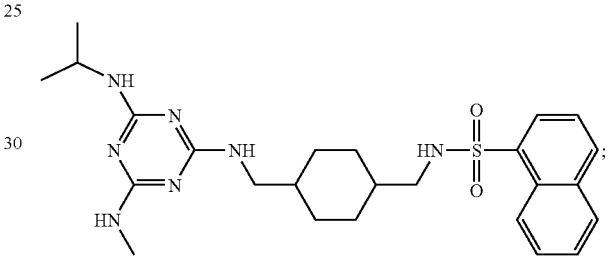

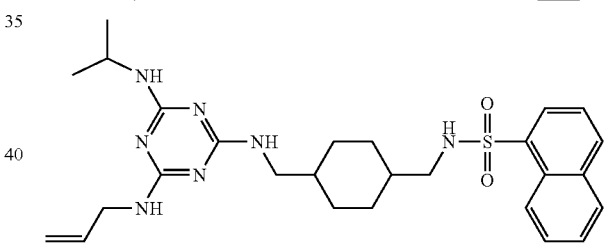

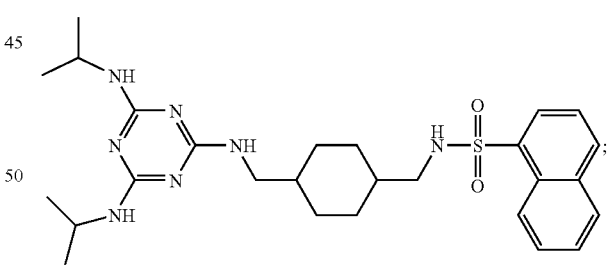

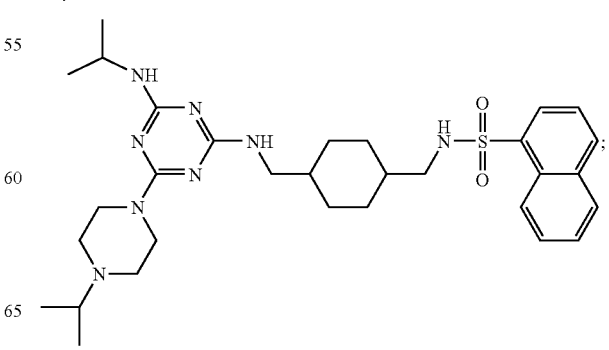

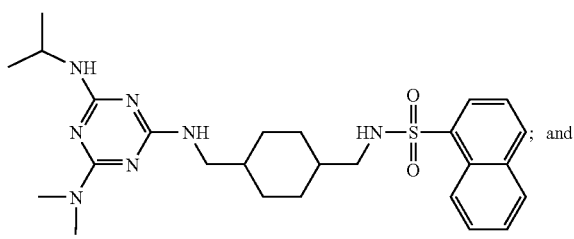
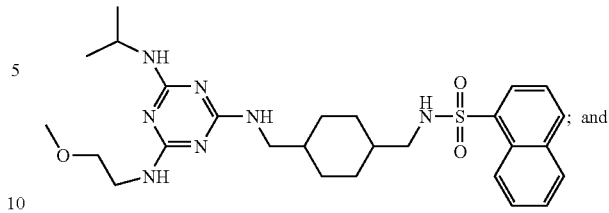
; and
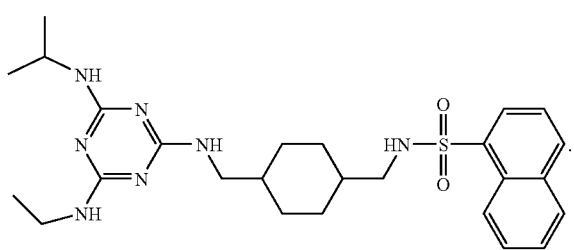
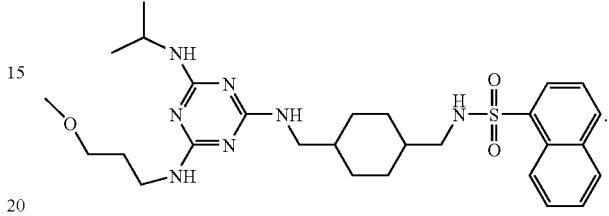
In a further presently preferred embodiment, the compound is selected from the group consisting of:
In another presently preferred embodiment, the compound is selected from the group consisting of:
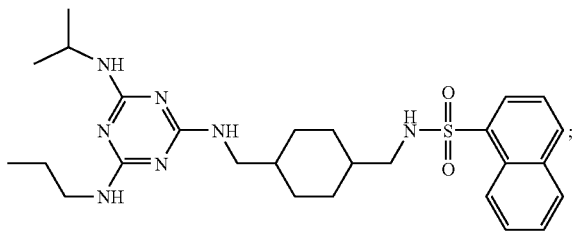
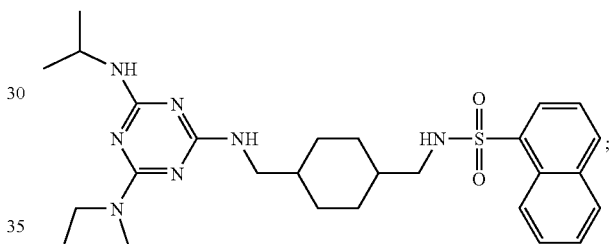
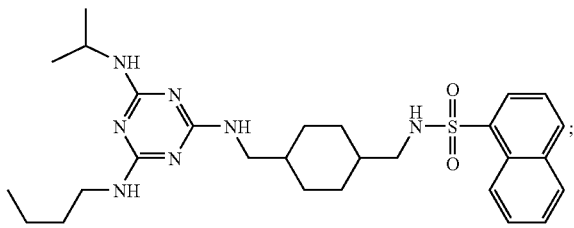
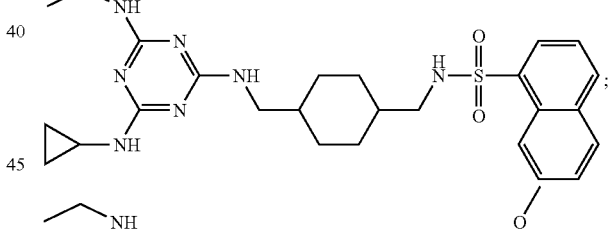
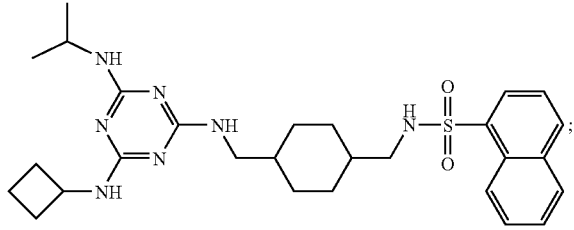
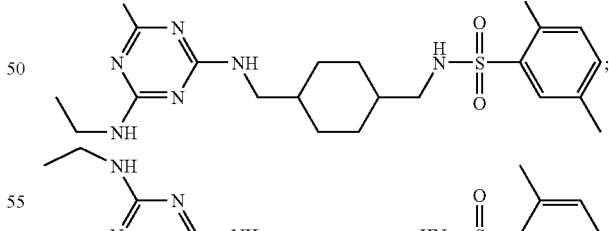
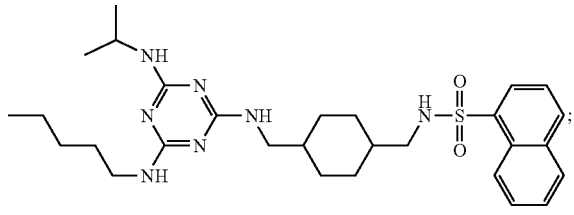
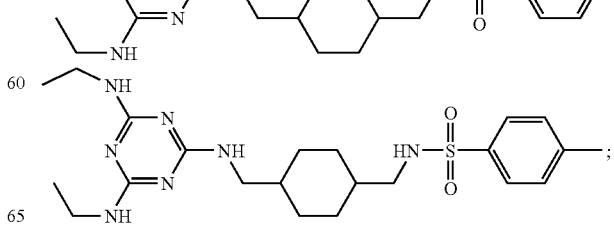

-continued

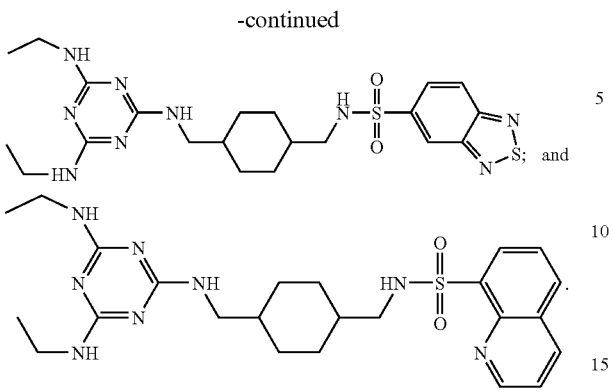

and

In the present invention as relates to triazine compounds, the term "heteroaryl" is used to mean and include five and six membered aromatic rings that may contain one or more heteroatoms such as oxygen, sulfur, nitrogen. Heteroaryl groups include, but are not limited to, pyrazolyl (preferably 1-pyrazolyl), pyrrolyl, furanyl, pyridyl (preferably 2-pyridyl or 3-pyridyl), imidazolyl (preferably 1-imidazolyl), oxazolyl, pyrimidinyl, isoxazolyl, and thienyl.

The invention provides a compound having the structure:

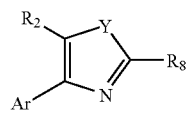

wherein Y is O, S or NH;

wherein Ar is a heteroaryl ring that may be optionally substituted with one or more $R_1$ groups;

wherein each $R_1$ independently is H, F, Cl, Br, —CN, —OH, —$NO_2$, —$NR_5R_6$, —$SO_2R_5$, —$(CH_2)_nOR_5$, —$SO_2C_6H_5$, —$SO_2NR_5R_6$, —$C_6H_5$, —$(CH_2)_nCONR_5R_6$, —$(CH_2)_n$ $NR_5COR_5$, ethylenedioxy, methylenedioxy, perfluoroalkyl, polyfluoroalkyl, aminoalkyl, or straight chained or branched $C_1$–$C_7$ alkyl; or phenyl, heteroaryl, or $C_1$–$C_7$ phenylalkyl, wherein the phenyl, heteroaryl, or $C_1$–$C_7$ phenylalkyl may be substituted with one or more of F, Cl, Br, —$CF_3$, —CN, —$NO_2$, —$NR_5R_6$, —$SO_2R_5$, —$(CH_2)_nOR_5$, or straight chained or branched $C_1$–$C_4$ alkyl;

wherein $R_2$ is H, straight chained or branched $C_1$–$C_4$ alkyl, —$(CH_2)_rOR_5$, phenyl optionally substituted with one or more of F, Cl, Br, —$CF_3$, —CN, —$NO_2$, —$NR_5R_6$, —$SO_2R_5$, —$(CH_2)_nOR_5$, or straight chained or branched $C_1$–$C_4$ alkyl;

wherein $R_5$ is independently H; or straight chained or branched $C_1$–$C_7$ alkyl;

wherein $R_6$ is independently H; or straight chained or branched $C_1$–$C_7$ alkyl;

wherein each n independently is an integer from 0 to 6 inclusive;

wherein $R_8$ is

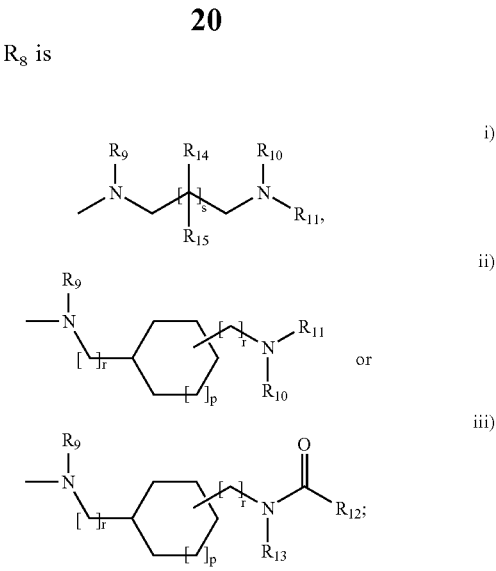

provided that when $R_8$ is (iii), and Ar is thiazol-2-yl, $R_1$ cannot be H;

wherein $R_9$ is independently H; or straight chained or branched $C_1$–$C_4$ alkyl;

wherein $R_{10}$ is independently H; or straight chained or branched $C_1$–$C_4$ alkyl;

wherein $R_{11}$ is

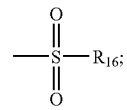

wherein $R_{12}$ is H, straight chained or branched $C_1$–$C_7$ alkyl; or $(CH_2)_nOR_{17}$;

wherein $R_{13}$ is independently —$(CH_2)_uOR_5$; —$(CH_2)_t$ $CONR_5R_6$; —$(CH_2)_uNR_5COR_5$; —$(CH_2)_tCOR_7$; —$(CH_2)_t$ $CO_2R_5$; —$(CH_2)_uNR_5R_6$; —$(CH_2)_uCN$; straight chained or branched $C_1$–$C_7$ alkyl; $C_1$–$C_7$ alkyl in which the $C_2$–$C_7$ atoms may be optionally substituted with one or more F or Cl; $C_3$–$C_7$ cycloalkyl-$C_1$–$C_7$ alkyl; straight chained or branched $C_2$–$C_7$ alkenyl; or $C_3$–$C_5$ cycloalkyl;

or $R_{12}$ and $R_{13}$ together with the amide linkage to which they are attached are pyrrolidinonyl, piperidonyl, or oxazolidinonyl;

wherein $R_7$ is independently straight chained or branched $C_1$–$C_7$ alkyl;

wherein $R_{14}$ is H; straight chained or branched $C_1$–$C_4$ alkyl; F; or —$(CH_2)_rOR_5$;

wherein $R_{15}$ is H, straight chained or branched $C_1$–$C_4$ alkyl, or F;

with the proviso that when $R_{14}$ is —OH, $R_{15}$ cannot be F;

wherein $R_{16}$ is —$NR_3R_4$, perfluoroalkyl, unsubstituted straight chained or branched $C_2$–$C_7$ alkyl, substituted straight chained or branched $C_2$–$C_7$ alkyl, wherein the $C_2$–$C_7$ alkyl may be substituted with one or more of F, Cl, —CN, —$NR_5R_6$, —$SO_2R_5$, —$(CH_2)_nCOR_7$, —$(CH_2)_nOR_5$, —$(CH_2)_nCONR_5R_6$, —$(CH_2)_nNR_5COR_5$, —$(CH_2)_nCO_2R_5$, —(CH$_2$)$_n$OCF$_3$, perfluoroalkyl, polyfluoroalkyl, or aminoalkyl, straight chained or branched C$_2$–C$_7$ alkenyl or alkynyl, or C$_3$–C$_7$ cycloalkyl; C$_3$–C$_7$ cycloalkyl; phenyl, thienyl, isoxazolyl, quinolinyl, or C$_1$–C$_7$ phenylalkyl, wherein the phenyl, thienyl, isoxazolyl, quinolinyl, or C$_1$–C$_7$ phenylalkyl may be substituted with one or more of F, Cl, Br, I, —CN, —NO$_2$, —NR$_5$R$_6$, —(CH$_2$)$_n$NR$_5$COR$_5$, —SO$_2$R$_5$, —(CH$_2$)$_n$COR$_7$, —(CH$_2$)$_n$OR$_5$, —(CH$_2$)$_n$CONR$_5$R$_6$, —(CH$_2$)$_n$CO$_2$R$_5$, —(CH$_2$)$_n$SO$_2$NR$_5$R$_6$, ethylenedioxy, methylenedioxy, straight chained or branched C$_1$–C$_3$ alkyl, perfluoroalkyl, or aminoalkyl, straight chained or branched C$_2$–C$_7$ alkenyl or alkynyl, or C$_3$–C$_7$ cycloalkyl or cycloalkenyl; quinolinyl, 1-naphthyl, 2-naphthyl, or 2,1,3-benzothiadiazolyl; wherein the quinolinyl, 1-naphthyl, 2-naphthyl or 2,1,3-benzothiadiazolyl may be substituted with one or more of F, Cl, Br, —CN, —NO$_2$, —NR$_5$R$_6$, —(CH$_2$)$_n$OR$_5$, —(CH$_2$)$_n$CONR$_5$R$_6$, straight chained or branched C$_1$–C$_4$ alkyl, perfluoroalkyl, or aminoalkyl;

provided that when R$_{16}$ is quinolinyl and R$_8$ is (ii), Ar cannot be pyrrolyl;

provided that when R$_{16}$ is N(CH$_3$)$_2$ and R$_8$ is (i), Ar cannot be thiazol-2-yl;

wherein R$_3$ is independently H; —(CH$_2$)$_u$OR$_5$; —(CH$_2$)$_t$CONR$_5$R$_6$; —(CH$_2$)$_u$NR$_5$COR$_5$; —(CH$_2$)$_t$COR$_7$; —(CH$_2$)$_t$CO$_2$R$_5$; —(CH$_2$)$_u$NR$_5$R$_6$; —(CH$_2$)$_u$CN; straight chained or branched C$_1$–C$_7$ alkyl; straight chained or branched C$_2$–C$_7$ alkenyl or alkynyl; or C$_3$–C$_7$ cycloalkyl or cycloalkenyl; phenyl, or C$_1$–C$_6$ phenylalkyl; wherein the phenyl, or C$_1$–C$_6$ phenylalkyl may be substituted with one or more of F, Cl, Br, —CN, —NO$_2$, —NR$_5$R$_6$, —SO$_2$R$_5$, —(CH$_2$)$_n$COR$_7$, —(CH$_2$)$_n$OR$_5$, —(CH$_2$)$_n$CONR$_5$R$_6$, —(CH$_2$)$_n$NR$_5$COR$_5$, —(CH$_2$)$_n$CO$_2$R$_5$, —(CH$_2$)$_n$SO$_2$NR$_5$R$_6$, straight chained or branched C$_1$–C$_7$ alkyl, perfluoroalkyl, polyfluoroalkyl, or aminoalkyl, straight chained or branched C$_2$–C$_7$ alkenyl or alkynyl, or C$_3$–C$_7$ cycloalkyl or cycloalkenyl;

wherein R$_4$ is independently H; —(CH$_2$)$_u$OR$_5$; —(CH$_2$)$_t$CONR$_5$R$_6$; —(CH$_2$)$_u$NR$_5$COR$_5$; —(CH$_2$)$_t$COR$_7$; —(CH$_2$)$_t$CO$_2$R$_5$; —(CH$_2$)$_u$NR$_5$R$_6$; —(CH$_2$)$_u$CN; straight chained or branched C$_1$–C$_7$ alkyl; straight chained or branched C$_2$–C$_7$ alkenyl or alkynyl; or C$_3$–C$_7$ cycloalkyl or cycloalkenyl; phenyl or C$_1$–C$_6$ phenylalkyl; wherein the phenyl or C$_1$–C$_6$ phenylalkyl may be substituted with one or more of F, Cl, Br, —CN, —NO$_2$, —NR$_5$R$_6$, —SO$_2$R$_5$, —(CH$_2$)$_n$COR$_7$, —(CH$_2$)$_n$OR$_5$, —(CH$_2$)$_n$CONR$_5$R$_6$, —(CH$_2$)$_n$NR$_5$COR$_5$, —(CH$_2$)$_n$CO$_2$R$_5$, —(CH$_2$)$_n$SO$_2$NR$_5$R$_6$, straight chained or branched C$_1$–C$_7$ alkyl, perfluoroalkyl, polyfluoroalkyl, or aminoalkyl, straight chained or branched C$_2$–C$_7$ alkenyl or alkynyl, or C$_3$–C$_7$ cycloalkyl or cycloalkenyl;

or R$_3$ and R$_4$ taken together with the nitrogen atom to which they are attached are 1-azetidinyl, 1-pyrrolidinyl, 1-piperidinyl, or 1H-azepanyl, wherein the 1-azetidinyl, 1-pyrrolidinyl, 1-piperidinyl, or 1H-azepanyl is substituted with one or more of F, —CN, —(CH$_2$)$_n$NR$_5$R$_6$, —SO$_2$R$_5$, —(CH$_2$)$_n$COR$_7$, —(CH$_2$)$_n$OR$_5$, —(CH$_2$)$_n$CONR$_5$R$_6$, —(CH$_2$)$_n$NR$_5$COR$_5$, —(CH$_2$)$_n$CO$_2$R$_5$, straight chained or branched C$_1$–C$_7$ alkyl, perfluoroalkyl, polyfluoroalkyl, or aminoalkyl, straight chained or branched C$_2$–C$_7$ alkenyl or alkynyl, or C$_3$–C$_7$ cycloalkyl or cycloalkenyl, or phenyl or thienyl, or isoxazolyl, or quinolinyl; wherein if —(CH$_2$)$_n$NR$_5$R$_6$, —(CH$_2$)$_n$OR$_5$, or —(CH$_2$)$_n$NR$_5$COR$_5$ are in the 2-position, then n is not 0; wherein the phenyl, thienyl, isoxazolyl, or quinolinyl may be substituted with one or more of F, Cl, Br, I, —CN, —NO$_2$, —NR$_5$R$_6$, —SO$_2$R$_5$, —(CH$_2$)$_n$COR$_7$, —(CH$_2$)$_n$OR$_5$, —(CH$_2$)$_n$CONR$_5$R$_6$, —(CH$_2$)$_n$NR$_5$COR$_5$, —(CH$_2$)$_n$CO$_2$R$_5$, —(CH$_2$)$_n$SO$_2$NR$_5$R$_6$, straight chained or branched C$_1$–C$_7$ alkyl, perfluoroalkyl, polyfluoroalkyl, or aminoalkyl, straight chained or branched C$_2$–C$_7$ alkenyl or alkynyl, or C$_3$–C$_7$ cycloalkyl or cycloalkenyl;

or R$_3$ and R$_4$ taken together with the nitrogen atom to which they are attached are morpholinyl, thiomorpholinyl, [1,4]oxazepanyl, [1,4]thiazepanyl, piperazinyl, or [1,4]diazepanyl, wherein the morpholinyl, thiomorpholinyl, [1,4]oxazepanyl, [1,4]thiazepanyl, piperazinyl, or [1,4]diazepanyl is optionally substituted with straight chained or branched C$_1$–C$_5$ alkyl or —(CH$_2$)$_t$OR$_5$; and wherein the nitrogen atom of the piperazinyl or [1,4]diazepanyl ring may be optionally substituted with —(CH$_2$)$_u$OR$_5$; —COR$_5$; straight chained or branched C$_1$–C$_5$ alkyl; or phenyl; wherein the phenyl may be substituted with one or more of F, Cl, Br, —CN, —NO$_2$, —NR$_5$R$_6$—(CH$_2$)$_n$OR$_5$, straight chained or branched C$_1$–C$_3$ alkyl, perfluoroalkyl, polyfluoroalkyl, or aminoalkyl;

wherein R$_{17}$ is straight chained or branched C$_1$–C$_4$ alkyl, perfluoroalkyl, or polyfluoroalkyl;

wherein each p independently is an integer from 0 to 2 inclusive;

wherein each r independently is an integer from 0 to 3 inclusive;

wherein each s independently is an integer from 3 to 6 inclusive;

wherein t is an integer from 1 to 4 inclusive;

wherein each u independently is an integer from 2 to 4 inclusive;

or a pharmaceutically acceptable salt thereof.

In one embodiment, the compound comprises the (+) enantiomer. In another embodiment, the compound comprises the (−) enantiomer.

In one embodiment, the compound has the structure:

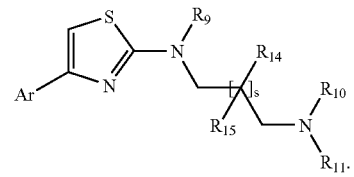

In another embodiment, the compound has the structure:

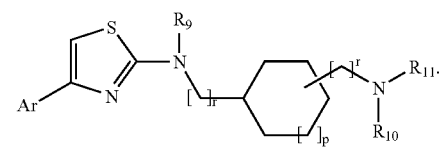

In still another embodiment, the compound has the structure:

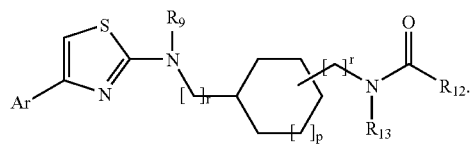

In a further embodiment, the compound has the structure:

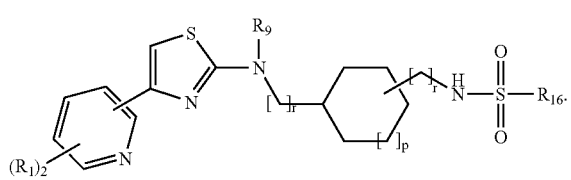

In still further embodiments, the compound has the structure selected from the group consisting of:

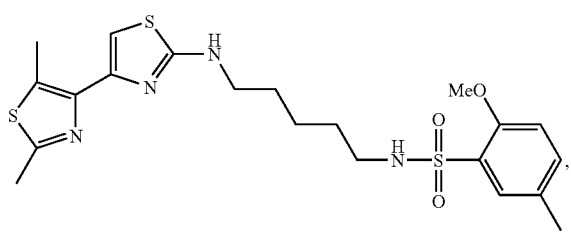

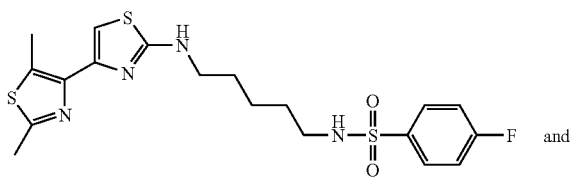
and

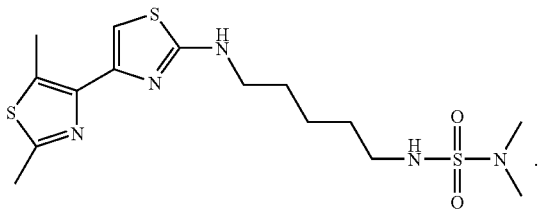

In another embodiment, the compound has the structure:

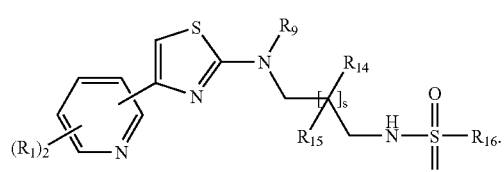

In further embodiments, the compound has the structure selected from the group consisting of:

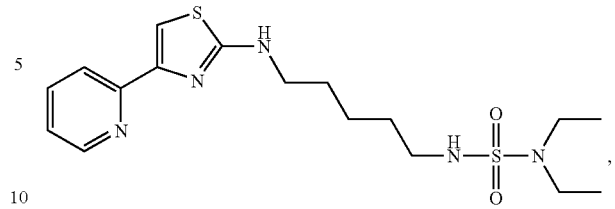

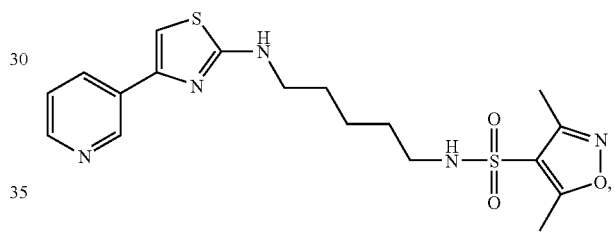

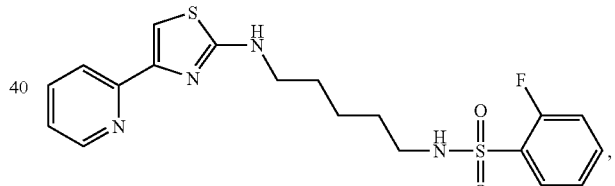

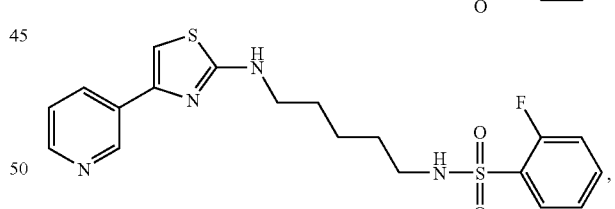

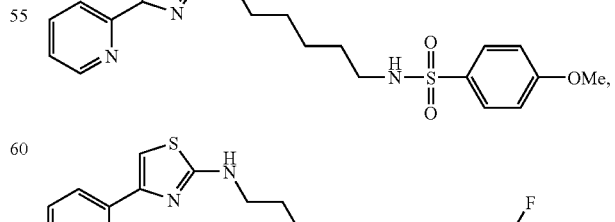

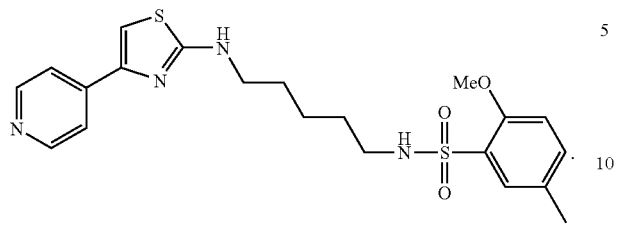

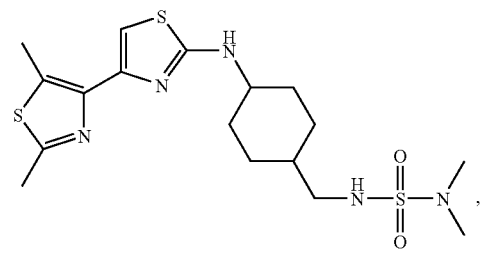

In still other embodiments, the compound has the structure selected from the group consisting of:

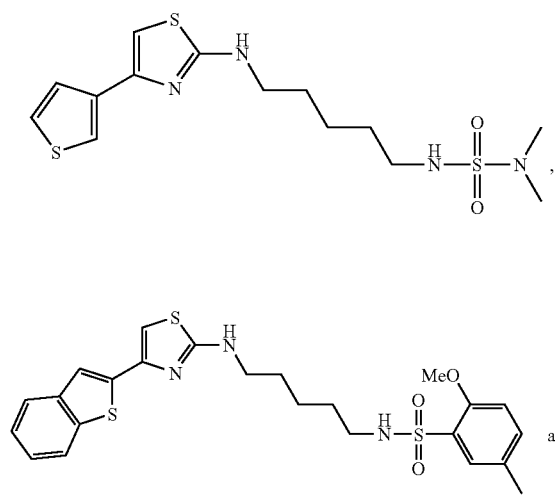

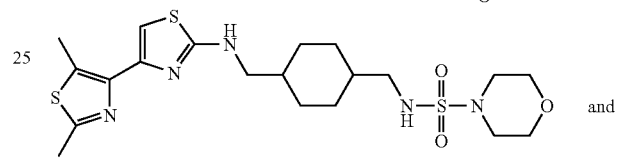

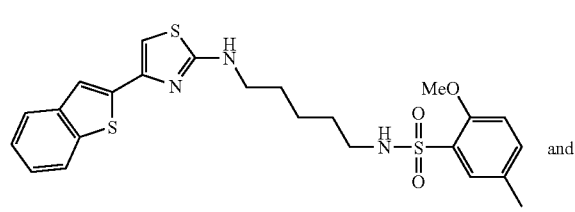

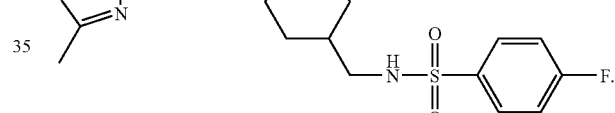

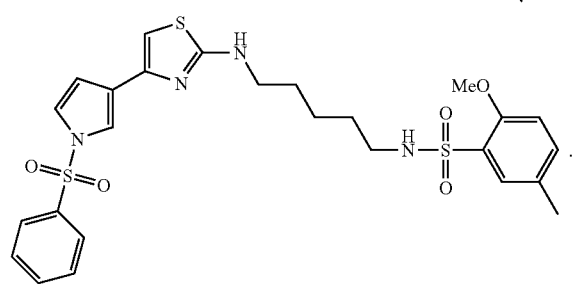

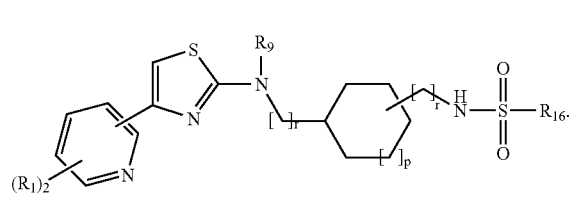

In another embodiment; the compound has the structure:

In a further embodiment, the compound has the structure:

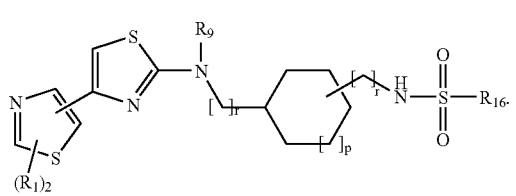

In still other embodiments, the compound has the structure selected from the group consisting of:

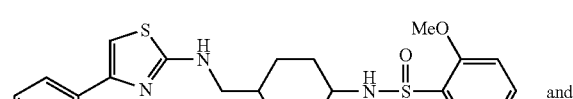

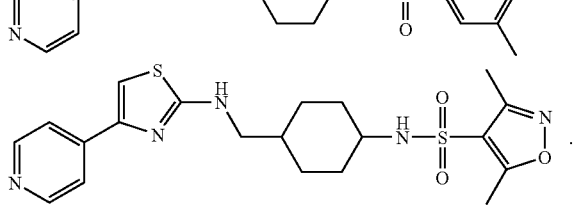

In still further embodiments, the compound has the structure selected from the group consisting of:

In a further embodiment, the compound has the structure:

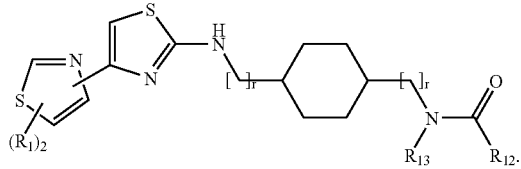

In still a further embodiment, the compound has the structure:

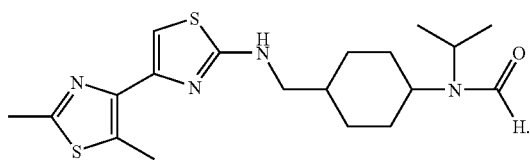

In the present invention as relates to bicyclic compounds, the term "heteroaryl" is used to include five and six membered unsaturated rings that may contain one sulfur or nitrogen atom or one or more oxygen, sulfur, or nitrogen atoms. Examples of heteroaryl groups include, but are not limited to, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl. In addition the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, benzthiazolyl, purinyl, imidazo[2,1-b]thiazolyl, quinolinyl, isoquinolinyl, quinolizinyl, and 2,1,3-benzothiazolyl.

The invention provides a compound having the structure:

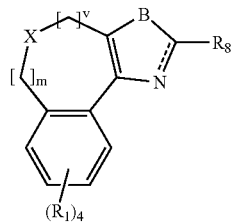

wherein each $R_1$ is independently H, F, Cl, Br, —CN, —OH, —NO$_2$, —NR$_5$R$_6$, —SO$_2$R$_5$, —(CH$_2$)$_n$OR$_5$, —(CH$_2$)$_n$CONR$_5$R$_6$, —(CH$_2$)$_n$NR$_5$COR$_5$, perfluoroalkyl, polyfluoroalkyl, aminoalkyl, or straight chained or branched $C_1$–$C_7$ alkyl;

wherein $R_5$ is independently H; or straight chained or branched $C_1$–$C_7$ alkyl;

wherein $R_6$ is independently H; or straight chained or branched $C_1$–$C_7$ alkyl;

wherein B is O, NH or S;

wherein X is S, SO or SO$_2$;

wherein each n independently is an integer from 0 to 6 inclusive;

wherein $R_8$ is

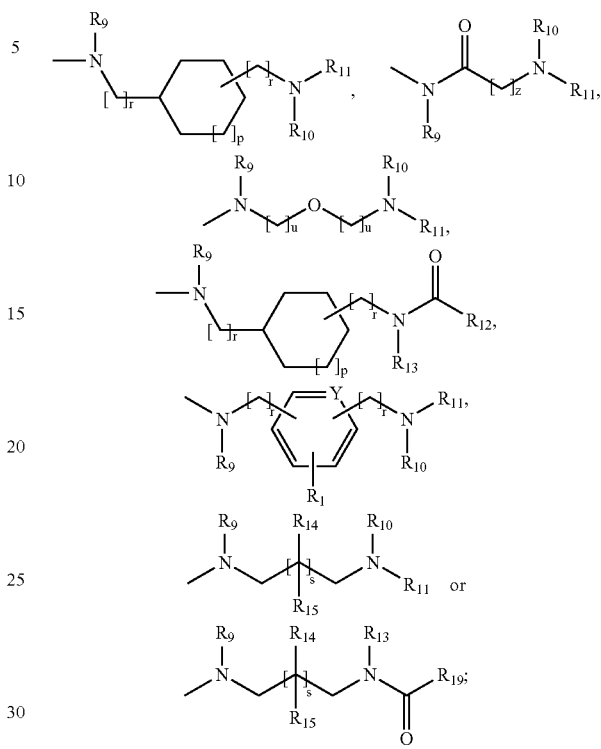

wherein Y is C or N;

wherein $R_7$ is independently straight chained or branched $C_1$–$C_7$ alkyl;

wherein $R_9$ is independently H; or straight chained or branched $C_1$–$C_4$ alkyl;

wherein $R_{10}$ is independently H; or straight chained or branched $C_1$–$C_4$ alkyl;

wherein $R_{11}$ is

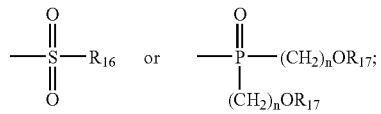

wherein $R_{12}$ is H, straight chained or branched $C_1$–$C_7$ alkyl, (CH$_2$)$_u$OR$_{17}$, or O(CH$_2$)$_u$OR$_{17}$; provided that when X is O, $R_{12}$ cannot be methyl;

wherein $R_{13}$ is independently H; —(CH$_2$)$_u$OR$_5$; —(CH$_2$)$_t$CONR$_5$R$_6$; —(CH$_2$)$_u$NR$_5$COR$_5$; —(CH$_2$)$_t$COR$_7$; —(CH$_2$)$_t$CO$_2$R$_5$; —(CH$_2$)$_u$NR$_5$R$_6$; —(CH$_2$)$_u$CN; straight chained or branched $C_1$–$C_7$ alkyl; $C_1$–$C_7$ alkyl in which the $C_2$–$C_7$ atoms may be optionally substituted with one or more F or Cl; $C_3$–$C_7$ cycloalkyl-$C_1$–$C_7$ alkyl; straight chained or branched $C_2$–$C_7$ alkenyl or alkynyl; or $C_3$–$C_7$ cycloalkyl; phenyl or $C_1$–$C_6$ phenylalkyl; wherein the phenyl or $C_1$–$C_6$ phenylalkyl may be substituted with one or more of F, Cl, —CN, —NO$_2$, —NR$_5$R$_6$, —SO$_2$R$_5$, —(CH$_2$)$_n$COR$_7$, —(CH$_2$)$_n$OR$_5$, —(CH$_2$)$_n$CONR$_5$R$_6$, —(CH$_2$)$_n$NR$_5$COR$_5$, —$(CH_2)_nCO_2R_5$, —$(CH_2)_nSO_2NR_5R_6$, straight chained or branched $C_1$–$C_7$ alkyl, perfluoroalkyl, polyfluoroalkyl, or aminoalkyl;

or $R_{12}$ and $R_{13}$ together with the amide linkage to which they are attached are pyrrolidinonyl, piperidonyl, or oxazolidinonyl;

wherein $R_{14}$ is H; straight chained or branched $C_1$–$C_4$ alkyl; F; or —$(CH_2)_rOR_5$;

wherein $R_{15}$ is H, straight chained or branched $C_1$–$C_4$ alkyl, or F;

with the proviso that when $R_{14}$ is —OH, $R_{15}$ cannot be F;

wherein $R_{16}$ is perfluoroalkyl, unsubstituted straight chained or branched $C_1$–$C_7$ alkyl, substituted straight chained or branched $C_2$–$C_7$ alkyl, wherein the $C_2$–$C_7$ alkyl may be substituted with one or more of F, Cl, —CN, —$SO_2R_5$, —$(CH_2)_nCOR_7$, —$(CH_2)_nOR_5$, —$(CH_2)_nCONR_5R_6$, —$(CH_2)_nNR_5COR_5$, —$(CH_2)_nCO_2R_5$, —$(CH_2)_nOCF_3$, perfluoroalkyl, polyfluoroalkyl, or aminoalkyl, straight chained or branched $C_2$–$C_7$ alkenyl or alkynyl, or $C_3$–$C_7$ cycloalkyl or cycloalkenyl; $C_3$–$C_7$ cycloalkyl or cycloalkenyl; phenyl, heteroaryl, or $C_1$–$C_7$ phenylalkyl, wherein the phenyl, heteroaryl, or $C_1$–$C_7$ phenylalkyl may be substituted with one or more of F, Cl, Br, —CN, —$NO_2$, —$NR_5R_6$, —$(CH_2)_n NR_5COR_5$, —$SO_2R_5$, —$(CH_2)COR_7$, —$(CH_2)_nOR_5$, —$(CH_2)_nCONR_5R_6$, —$(CH_2)_nCO_2R_5$, —$(CH_2)_n SO_2NR_5R_6$, ethylenedioxy, methylenedioxy, straight chained or branched $C_1$–$C_7$ alkyl, perfluoroalkyl, polyfluoroalkyl, or aminoalkyl, straight chained or branched $C_2$–$C_7$ alkenyl or alkynyl, or $C_3$–$C_7$ cycloalkyl or cycloalkenyl; quinolinyl, 1-naphthyl, 2-naphthyl, or 2,1,3-benzothiadiazolyl; wherein the quinolinyl, 1-naphthyl, 2-naphthyl or 2,1,3-benzothiadiazolyl may be substituted with one or more of F, Cl, Br, —CN, —$NO_2$, —$NR_5R_6$, —$(CH_2)_nNR_5COR_5$, —$SO_2R_5$, —$(CH_2)_nCOR_7$, —$(CH_2)_nOR_5$, —$(CH_2)_n CONR_5R_6$, —$(CH_2)_nCO_2R_5$, —$(CH_2)_nSO_2NR_5R_6$, ethylenedioxy, methylenedioxy, straight chained or branched $C_1$–$C_7$ alkyl, perfluoroalkyl, polyfluoroalkyl, or aminoalkyl;

with the proviso that when $R_8$ is $NR_9(R_{14}R_{15})_sNR_{10}R_{11}$, $R_{16}$ cannot be quinolinyl;

wherein $R_{17}$ is H, straight chained or branched $C_1$–$C_4$ alkyl, perfluoroalkyl, or polyfluoroalkyl;

wherein $R_{19}$ is —$(CH_2)_uOR_5$, —$NR_5R_6$, phenyl, or heteroaryl, wherein the phenyl or heteroaryl may be substituted with one or more of F, Cl, Br, —CN, —$NO_2$, —$NR_5R_6$, —$(CH_2)_nNR_5COR_5$, —$SO_2R_5$, —$(CH_2)_nCOR_7$, —$(CH_2)_n OR_5$, —$(CH_2)_nCONR_5R_6$, —$(CH_2)_nCO_2R_5$, —$(CH_2)_n SO_2NR_5R_6$, ethylenedioxy, methylenedioxy, straight chained or branched $C_1$–$C_7$ alkyl, perfluoroalkyl, polyfluoroalkyl, or aminoalkyl, straight chained or branched $C_2$–$C_7$ alkenyl or alkynyl, or $C_3$–$C_7$ cycloalkyl or cycloalkenyl;

wherein m is 0 or 1;

wherein each p independently is an integer from 0 to 2 inclusive;

wherein each r independently is an integer from 0 to 3 inclusive;

wherein each s independently is an integer from 1 to 6 inclusive;

wherein t is an integer from 1 to 4 inclusive;

wherein each u independently is an integer from 2 to 4 inclusive;

wherein v is 1 or 2;

with the proviso that when v is 2, m is 0;

wherein z is an integer from 2 to 7;

or a pharmaceutically acceptable salt thereof.

In one embodiment, the compound comprises the (+) enantiomer. In another embodiment, the compound comprises the (−) enantiomer.

In one embodiment, the compound has the structure:

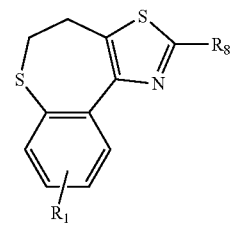

In another embodiment, the compound has the structure:

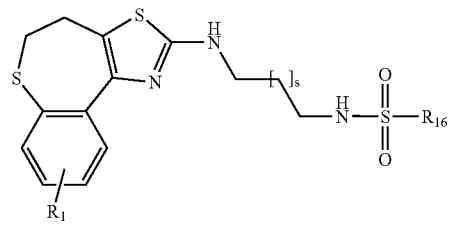

In still another embodiment, the compound has the structure:

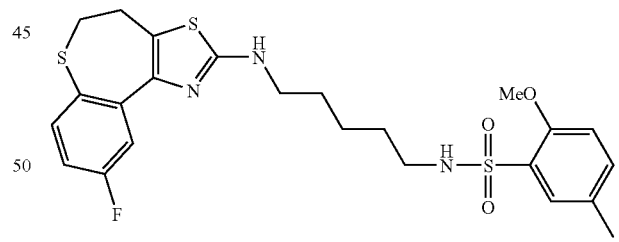

In a further embodiment, the compound has the structure:

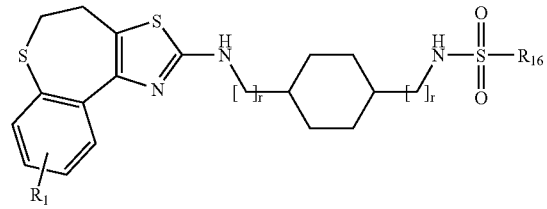

In still further embodiments, the compound has the structure selected from the group consisting of:

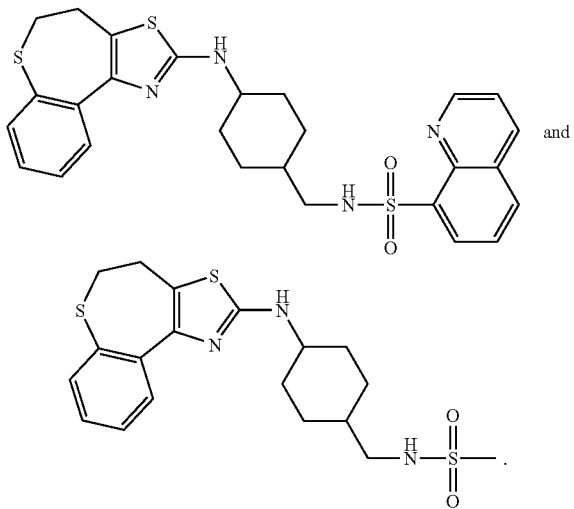

In another embodiment, the compound has the structure:

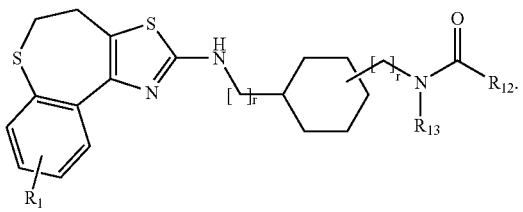

In still another embodiment, the compound has the structure:

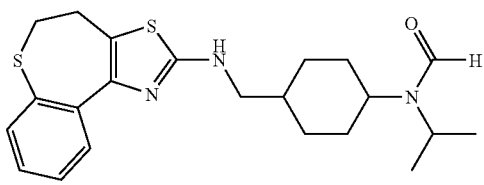

In the present invention as relates to tricyclic compounds, the term "heteroaryl" is used to include five and six membered unsaturated rings that may contain one or more heteroatoms such as oxygen, sulfur, and nitrogen. Examples of heteroaryl groups include, but are not limited to, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl. In addition the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, benzthiazolyl, purinyl, imidazo[2,1-b]thiazolyl, quinolinyl, isoquinolinyl, quinolizinyl, and 2,1,3-benzothiazolyl. Furthermore, any of the heteroaryl groups recited above may be substituted with thienyl, isoxazolyl, or pyridyl.

Included within the scope of this invention are pharmaceutically acceptable salts and complexes of all of the compounds described herein. The salts include but are not limited to the acids and bases listed herein. The salts include, but are not limited to the following inorganic acids: hydrochloric acid, hydrobromic acid, hydroiodic acid, sulfuric acid and boric acid. The salts include, but are not limited to the following organic acids: acetic acid, malonic acid, succinic acid, fumaric acid, tartaric acid, maleic acid, citric acid, methanesulfonic acid, benzoic acid, glycolic acid, lactic acid and mandelic acid. The salts include, but are not limited to the inorganic base, ammonia. The salts include, but are not limited to the following organic bases: methylamine, ethylamine, propylamine, dimethylamine, diethylamine, trimethylamine, triethylamine, ethylenediamine, hydroxyethylamine, morpholine, piperazine and guanidine. This invention further provides for the hydrates and polymorphs of all of the compounds described herein.

The present invention includes within its scope prodrugs of the compounds of the invention. In general, such prodrugs will be functional derivatives of the compounds of the invention which are readily convertible in vivo into the required compound. Thus, in the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in Design of Prodrugs, ed. H. Bundgaard, Elsevier, 1985.

The present invention further includes metabolites of the compounds of the present invention. Metabolites include active species produced upon introduction of compounds of this invention into the biological milieu.

This invention further provides a pharmaceutical composition comprising a therapeutically effective amount of a compound of the invention and a pharmaceutically acceptable carrier. In one embodiment, the amount of the compound is an amount from about 0.01 mg to about 800 mg. In another embodiment, the amount of the compound is an amount from about 0.01 mg to about 500 mg. In another embodiment, the amount of the compound is an amount from about 0.01 mg to about 250 mg. In another embodiment, the amount of the compound is an amount from about 0.1 mg to about 60 mg. In another embodiment, the amount of the compound is an amount from about 1 mg to about 20 mg. In a further embodiment, the carrier is a liquid and the composition is a solution. In another embodiment, the carrier is a solid and the composition is a tablet. In a further embodiment, the carrier is a gel and the composition is a suppository.

This invention provides a pharmaceutical composition made by combining a therapeutically effective amount of a compound of this invention and a pharmaceutically acceptable carrier.

This invention provides a process for making a pharmaceutical composition comprising combining a therapeutically effective amount of a compound of this invention and a pharmaceutically acceptable carrier.

This invention provides a use of a compound of this invention for the preparation of a pharmaceutical composition for treating an abnormality, wherein the abnormality is alleviated by decreasing the activity of a human Y5 receptor. In different embodiments, the abnormality is an eating disorder, obesity, bulimia nervosa, a sexual disorder, a reproductive disorder, depression, an epileptic seizure, hypertension, cerebral hemorrhage, congestive heart failure, or a sleep disturbance.

In the subject invention a "therapeutically effective amount" is any amount of a compound which, when administered to a subject suffering from a disease against which the compounds are effective, causes reduction, remission, or regression of the disease.

In the practice of this invention the "pharmaceutically acceptable carrier" is any physiological carrier known to those of ordinary skill in the art useful in formulating pharmaceutical compositions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The compound can be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

One skilled in the art will readily appreciate that appropriate biological assays will be used to determine the therapeutic potential of the claimed compounds for treating the above noted disorders.

This invention further provides compositions which need not be pharmaceutical as that term is understood in the art. Such compositions comprise a compound in accordance with the subject invention in an amount effective to agonize and/or antagonize a Y5 receptor and a suitable carrier.

Still further, the invention provides a method of agonizing and/or antagonizing a Y5 receptor which comprises contacting the receptor, e.g. in vitro or in vivo, with an amount of a compound of this invention effective to agonize and/or antagonize the receptor.

This invention will be better understood from the Experimental Details which follow. However, one skilled in the art will readily appreciate that the specific methods and results discussed are merely illustrative of the invention as described more fully in the claims which follow thereafter.

Experimental Details and Results

I. Synthetic Methods for Examples

A. Triazine Compounds

General Procedures Relating to Examples:

For the stepwise addition of amines to cyanuric chloride (2,4,6-trichloro-1,3,5-triazine), see, for example, Campbell, J. R. and Hatton, R. E., 1961; and Nestler, H. and Furst, H., 1963.

For more recent references concerning the formation of amino-1,3,5-triazines, see, for example, Kreutzberger, A, et al., 1991; U.S. Pat. Nos. 4,383,113; and US 3,947,374.

For the formation of cyanoguanidines from amines and sodium dicyanamide ($NaN(CN)_2$) and/or formation of the biguinides, see, for example, Shaw, J. T. and Gross, F. J., 1959; Curd, F. H. S., et al., 1948; Curd, F. H. S. and Rose, F. L., 1946; May, E. L., 1947; and Neelakantan, L., 1957.

The cyclization of biguinides to 2,4-diamino-1,3,5-triazines can be accomplished using a number of carboxylic acid derivatives such as acid chlorides, esters, anhydrides, carboxylates, etc. See, for example, Furukawa, M., et al., 1961; Koshelev, V. N., et al., 1995; Tsitsa, P., et al., 1993; Shaw, J. T., et al., 1959; Vanderhoek, R., et al., 1973; Nagasaka, H., et al., 1967; U.S. Pat. No. 3,891,705; US 5,348,956; and US 5,258,513.

All reactions were performed under an inert atmosphere (Argon) and the reagents, neat or in appropriate solvents, were transferred to the reaction vessel via syringe and cannula techniques. The parallel synthesis reaction arrays were performed in vials (without an inert atmosphere) using J-KEM heating shakers (Saint Louis, Mo.). Unless stated otherwise all solvents were AR grade and used as supplied. Anhydrous solvents were purchased from Aldrich Chemical Company and used as received. The examples described in the patent (1–58) were named using ACD/Name program (version 2.51, Advanced Chemistry Development Inc., Toronto, Ontario, M5H2L3, Canada).

Flash chromatography (silica gel, mesh size 230-400) and preparative thin layer chromatography (Analtech, 2000 micron) were used for chromatographic separations. Thin layer chromatography was used for analytical analysis of the mixtures. $^1$H NMR spectra were recorded on a GE (QE Plus, 300 MHz) instrument and the spectra were either calibrated by the lock signal of the deuterated solvent or tetramethylsilane (TMS) as the internal standard. Signals in the $^1$H NMR spectra are described as: s, singlet; d, doublet; t, triplet; q, quartet; p, pentet; sextet; septet; m, multiplet; b, broad. Elemental analyses were performed by Robertson Microlit Laboratories, Inc., Madison, N.J.

General Procedure for the Synthesis of the Amino Side Chains ($H_2N$—$(CH_2)_n$-pyrazole and imidazole):

The synthesis of 5-(1H-1-pyrazolyl)-1-pentanamine is typical: Sodium hydride (1.2 mol-equivalents) was added to a mixture of pyrazole or imidazole (one mol-equivalent) and 1-N-bromoalkylphthalimide (one mol-equivalent) in DMF (1 M with respect to the reagents). Once the bubbling subsided, the mixture was heated at reflux temperature for two days. The reaction mixture was cooled, triturated with water, the precipitate was collected, washed with water and dried under reduced pressure to give the phthalimide protected product.

A mixture of the phthalimide such as 2-[5-(1H-1-pyrazolyl)pentyl]-1,3-isoindolinedione and hydrazine (one equivalent) in methanol were heated to reflux temperature for 12 hours and cooled. 1 N HCl (1–5 equivalents) was added and the mixture was filtered and washed with methanol and water and then concentrated to give 5-(1H-1-pyrazolyl)-1-pentanamine as a viscous oil. (Scheme 1G)

General Procedure for the Synthesis of the Amino Side Chains Such as:

N1-[4-(aminomethyl)cyclohexyl]methyl-1-naphthalenesulfonamide

N1-[4-(aminomethyl)cyclohexyl]methyl-4-fluoro-1-benzenesulfonamide

N1-[4-(aminomethyl)cyclohexyl]methyl-4-(tert-butyl)-1-benzenesulfonamide

N'-[4-(aminomethyl)cyclohexyl]methyl-N,N-dimethylsulfamide

Dimethylsulfamoyl chloride (one mol-equivalent, $ClSO_2N(CH_3)_2$) was added to a stirred solution of 1,4-bis-aminomethylcyclohexane (3 mol-equivalents) and diisopropylethylamine (1 mol-equivalent) in dichloromethane at 0° C. The reaction mixture was stirred at room temperature for 24 hours, concentrated under reduced pressure and chromatographed (silica) to give the desired product as viscous oils. (Scheme 1A).

N1-[4-(aminomethyl)cyclohexyl]methyl-4-fluoro-1-benzenesulfonamide: Synthesized According to Scheme 1A, $^1$H NMR (CDCl$_3$) 7.86 (m, 2H), 7.19 (apparent t, J=8.1 Hz), 4.65 (broad, 1H), 2.86 and 2.78 (two d, 2H, ratio of 2:1 respectively, J=7.2 and 6.9 Hz respectively), 2.55 and 2.50 (two d, 2H, ratio of 2:1 respectively, J=6.3 Hz each), 1.82–0.90 (m, 10H).

General Procedure for the synthesis of 2,4-dichloro-6-amino-1,3,5-Triazines:

One mole equivalent of the amine was added dropwise to a solution of one mole-equivalent of 1,3,5-trichlorotriazine and 2 mole-equivalents of diisopropylethylamine in dichloromethane or THF at −78° C. under argon. The resulting solution was stirred for 1 hour at −78° C., quenched with ether, precipitated salts removed by filtration, solvent removed under reduced pressure and the crude product was chromatographed (silica) to give the desired product.

2,4-Dichloro-6-isopropylamino-1,3,5-triazine: Isopropylamine (neat, 4.13 g, 69.8 mmmol) was added dropwise to a stirred solution of diisopropylethylamine (9.02 g, 69.8 mmmol) and 2,4,6-trichlorotriazine (12.9 g, 69.8 mmmol) in 100 ml of dry THF at −78° C. under argon. The resulting mixture was stirred at −78° C. for 0.5 hour, 200 ml of ether was added, filtered and the solids were washed with ether. The combined filtrates were concentrated and chromatographed (5% ethyl acetate-hexane, silica) to give 8.06 g of the desired product: Synthesized According to Scheme 2 and 3; $^1$H NMR (CDCl$_3$) 5.80 (broad, 1H, 4.21 (septet, 1H, J=6.6 Hz), 1.25 (d, 6H, J=6.6 Hz).

2,4-Dichloro-6-cyclopropylamino-1,3,5-triazine: Synthesized According to Scheme 2 and 3; $^1$H NMR (CDCl$_3$) 5.93 (broad, 1H), 2.88 (m, 1H), 0.94 (m, 2H), 0.63 (m, 1H).

General Procedure for the Synthesis of 2-Chloro-4,6-di-amino-1,3,5-triazines:

One mole-equivalent of an amine, one mol-equivalent of 2,4-dichloro-6-amino-1,3,5-triazines and 2 mole-equivalents of diisopropylethylamine were stirred at room temperature for 3 days. The solvent was removed under reduced pressure and the crude product was chromatographed on silica to give the desired product:

N1-{[4-({[4-Chloro-6-(isopropylamino)-1,3,5-triazin-2-yl]amino}methyl)cyclohexyl]methyl}-1-naphthalene-sulfonamide: A suspension of 2,4-dichloro-6-isopropyltriazine (1.04 g, 5.02 mmol), diisopropylethylamine (1.50 g, 10.0 mmol) and cyclohexylmethylamine (1.66 g, 5.00 mmol) in 15 ml of dry THF were stirred at room temperature for 3 days under argon. The initial suspension turned clear. The solvent was removed under reduced pressure, the solids were partitioned between ethyl acetate-hexane (50 ml, 1:9) and water (50 ml), separated and solvent removed to give 2.75 g of a white solid in 60% yield: Synthesized According to Scheme 2; 503 and 505 (MH$^+$, ESI); $^1$H NMR (CDCl$_3$) 8.62 (d, 1H, J=8.7 Hz), 8.25 (d, 1H, J=8.7 Hz), 8.07 (d, 1H, J=8.0 Hz), 7.95 (dd, J=8.0, 0.9 Hz), 7.72–7.50 (m, 3H), 5.20–3.95 (m, 4H), 4.04 (septet, 1H, J=6.6 Hz), 3.21 and 3.06 (two t, 2H, J=6.6 Hz), 2.72 (t, 2H, J=6.6 Hz), 1.80–0.65 (m, 7H), 1.19 (d, 6H, J=6.6 Hz).

General Procedure for the Synthesis of 2,4,6-Triamino-1,3,5-triazines from 2,4-diamino-6-chlorotriazines:

Parallel synthesis was used to prepare the triaminotriazines. The crude products were chromatographed (Preparative TLC) to give the final products.

A solution of 0.0200 mmol of N1-{[4-({[4-Chloro-6-(isopropylamino)-1,3,5-triazin-2-yl]amino}methyl)cyclohexyl]methyl}-1-naphthalenesulfonamide, 10 mg of a primary or secondary amine and 30 l of diisopropylethylamine in 200 l l of DMF or dioxane were heated to 100–140° C. for at least 8 hours. The resulting mixture was cooled, applied to a preparative thin layer chromatography plate (2000 microns, Analtech) and eluted with an appropriate solvent to give the desired product. In cases where DMF was used as the solvent, a side product corresponding to a dimethylamino substitution (Example 17) of the chloro group of N1-{[4-({[4-chloro-6-(isopropylamino)-1,3,5-triazin-2-yl]amino}methyl)cyclohexyl]methyl}-1-naphthalenesulfonamide in about 20% yield was also obtained especially when primary amines were used to displace the chloro group. This product was separated from the desired product using Preparative Thin Layer Chromatography. (Scheme 2)

General Procedure for the Synthesis of 2,4,6-Triamino-1,3,5-triazines from 2,4-diamino-6-chlorotriazines:

A mixture of 2,4-diethylamino-6-chloro-1,3,5-triazine (1 mol-equivalents), diisopropylethylamine (one mol-equivalent) and 1,4-bis-aminomethylcyclohexane (3 equivalents) in dioxane were heated at reflux temperature for 3 days, cooled, concentrated and chromatographed on silica to give N1-[4-(aminomethyl)cyclohexyl]methyl-N3,N5-diethyl-1,3,5-benzenetriamine in 65% yield: Anal. Calc. for $C_{15}H_{29}N_7$: C, 58.60; H, 9.51; N, 31.89. Found: C, 58.84; N, 9.61; N, 31.64; $^1$H NMR (CDCl$_3$) 4.78 (broad, 3H), 3.45–3.10 (m, 6H), 2.60 and 2.51 (two d, 2H, J=6.3 Hz), 1.90–0.70 (m, 11H), 1.17 (t, 6H, J=7.3 Hz). (Scheme 3)

General Procedure for the Synthesis of 2,4,6-Triamino-1,3,5-triazines Containing Sulfonyl Ureas from 2,4-diamino-6-chlorotriazines or 2,4,6-Triaminotriazines Containing Dimethylamino Sulfonyl Ureas:

A transamination reaction was used to synthesize the sulfonyl ureas from dimethylaminosulfonyl ureas. A solution of one mol-equivalent of dimethyl sulfonyl urea, two mol-equivalents of diisopropylethylamine and one mol-equivalent of an amine such as morpholine or cyclopropylamine were heated at 100° C. in dioxane for 16 hours. The reaction mixture was cooled, concentrated and chromatographed to give the desired product. (Schemes 4A, 4B, 4C, and 4D).

Compounds in Table 1 (DMF as Solvent Unless Otherwise noted):

EXAMPLE 1

Synthesized According to Scheme 2.

N1-{[4-({[4-(Isopropylamino)-6-(methylamino)-1,3,5-triazin-2-yl]amino}methyl)cyclohexyl]methyl}-1-naphthalenesulfonamide: 60% yield (90% yield in dioxane), Anal. Calc. For $C_{25}H_{35}N_7O_2S_1+0.2H_2O$: C, 59.90; H, 7.12; N, 19.56. Found: C, 59.91; H, 7.31; N, 19.23; 498 (MH$^+$, ESI); $^1$H NMR (CDCl$_3$) 8.63 (d, 1H, J=8.5 Hz), 8.24 (dd, 1H, J=7.2, 0.9 Hz), 8.07 (d, 1H, J=8.4 Hz), 7.95 (dd, 1H, J=7.2, 0.9 Hz), 7.68–7.52 (m, 3H), 4.73 (broad, 4H), 4.11 (m, 1H), 3.13 (m, 2H), 2.88 (broad, 3H), 2.72 (apparent t, 2H, J=6.6 Hz), 1.90–0.70 (m, 7H), 1.16 (d, 6H, J=6.3 Hz).

EXAMPLE 2

Synthesized According to Scheme 2.

N1-[4-([4-(ethylamino)-6-(isopropylamino)-1,3,5-triazin-2-yl]aminomethyl)cyclohexyl]methyl-1-naphthalenesulfonamide: 41% yield, 512 (MH$^+$, ESI); $^1$H NMR (CDCl$_3$) 8.64 (d, 1H, J=8.7 Hz), 8.25 (dd, 1H, J=8.7, 1.3 Hz), 8.08 (d, 1H, J=8.0 Hz), 7.96 (dd, 1H, J=8.0, 1.3 Hz), 7.70–7.50 (m, 3H), 4.76 (broad, 1H), 4.10 (broad, 1H), 3.37 (broad, 1H), 3.14 (broad, 1H), 2.73 (apparent t, 2H, J=6.6 Hz), 1.80–0.65 (m, 9H), 1.18 (d, 6H, J=6.6 Hz), 1.15 (t, 2H, J=7.2 Hz).

EXAMPLE 3

Synthesized According to Scheme 2.

N1-{[4-({[4-(Allylamino)-6-(isopropylamino)-1,3,5-triazin-2-yl]amino}methyl)cyclohexyl]methyl}-1-naphthalenesulfonamide: 20% yield (84% yield in dioxane); Anal. Calc. for $C_{27}H_{37}N_7O_2S_1+1.0H_2O$: C, 59.87; N, 7.26; N, 18.10. Found: C, 60.32; H, 7.08; N, 17.89; 524 (MH$^+$, ESI); $^1$H NMR (CDCl$_3$) 8.62 (d, 1H, J=8.6 Hz), 8.24 (dd, 1H, J=8.6, 1.3 Hz), 8.07 (d, 1H, J=8.1 Hz), 7.95 (dd, 1H, J=8.1, 0.6 Hz), 7.68–7.52 (m, 3H), 5.90 (ddt, 1H, J=17.1, 10.3, 1.5 Hz), 5.20 (apparent dq, 1H, J=17.1, 1.5 Hz), 5.10 (apparent dq, 1H, J=10.3, 1.5 Hz), 4.85 (broad, 1H), 4.62 (m, 1H), 4.08 (broad, 1H), 3.97 (m, 2H), 3.14 (m, 2H), 2.72 (t, 2H, J=6.6 Hz), 1.80–0.70 (m, 11H), 1.16 (d, 6H, J=6.6 Hz).

EXAMPLE 4

Synthesized According to Scheme 2.

N1-{[4-({[4,6-Di(isopropylamino)-1,3,5-triazin-2-yl]amino}methyl)cyclohexyl]methyl}-1-naphthalenesulfonamide: 29% yield; 526 (MH$^+$, ESI); $^1$H NMR (CDCl$_3$) 8.64 (d, 1H, J=8.4 Hz), 8.24 (d, 1H, J=7.5 Hz), 8.07 (d, 1H, J=8.4 Hz), 7.95 (dd, 1H, J=7.5 Hz), 7.68–7.52 (m, 3H), 5.10–4.40 (broad, 3H), 4.71 (apparent t, 1H, J=6.6 Hz), 4.15 (m, 2H), 3.18 (m, 2H), 2.72 (apparent t, 2H, J=6.6 Hz), 2.20–0.65 (m, 7H), 1.17 (d, 12H, J=6.6 Hz).

EXAMPLE 5

Synthesized According to Scheme 2.

N1-[4-([4-(isopropylamino)-6-(propylamino)-1,3,5-triazin-2-yl]aminomethyl)cyclohexyl]methyl-1-naphthalenesulfonamide: 55% yield; 526 (MH$^+$, ESI); $^1$H NMR (CDCl$_3$) 8.65 (d, 1H, J=8.7 Hz), 8.25 (d, 1H, J=8.0 Hz), 8.08 (d, 1H, J=8.0 Hz), 7.95 (d, 1H, J=8.0 Hz), 7.72–7.50 (m, 3H), 5.10 (broad, 1H), 4.88 (m, 1H), 4.09 (m, 1H), 3.40–3.00 (m, 4H), 2.72 (apparent t, 2H, J=6.6 Hz), 1.80–0.65 (m, 9H), 1.18 (d, 6H, J=6.6 Hz), 0.94 (t, 3H, J=7.2 Hz).

EXAMPLE 6

Synthesized According to Scheme 2.

N1-[4-([4-(butylamino)-6-(isopropylamino)-1,3,5-triazin-2-yl]aminomethyl)cyclohexyl]methyl-1-naphthalenesulfonamide: 56% yield; 540 (MH$^+$, ESI); $^1$H NMR (CDCl$_3$) 8.65 (d, 1H, J=8.7 Hz), 8.25 (d, 1H, J=8.0 Hz), 8.08 (d, 1H, J=8.0 Hz), 7.95 (d, 1H, J=8.0 Hz), 7.70–7.50 (m, 3H), 5.20–4.60 (broad, 3H), 4.10 (broad, 1H), 3.33 (broad, 2H), 3.14 (broad, 2H), 2.72 (apparent t, 2H, J=6.6 Hz), 1.70–0.60 (m, 11H), 2.72 (d, 6H, J=6.6 Hz), 0.92 (t, 3H, J=7.1 Hz).

EXAMPLE 7

Synthesized According to Scheme 2.

N1-[4-([4-(cyclobutylamino)-6-(isopropylamino)-1,3,5-triazin-2-yl]aminomethyl)cyclohexyl]methyl-1-naphthalenesulfonamide: 58% yield; 538 (MH$^+$, ESI); $^1$H NMR (CDCl$_3$) 8.65 (d, 1H, J=8.7 Hz), 8.25 (dd, 1H, J=8.7, 0.9 Hz), 8.08 (d, 1H, J=8.0 Hz), 7.95 (dd, 1H, J=8.0, 0.9 Hz), 7.72–7.52 (m, 3H), 5.50–4.50 (broad, 4H), 4.40 (m, 1H), 4.09 (M, 1H), 3.13 (m, 2H), 2.72 (apparent t, 2H, J=6.6 Hz), 2.34 (m, 2H), 2.00–0.65 (m, 13H), 1.17 (d, 6H, J=6.6 Hz).

EXAMPLE 8

Synthesized According to Scheme 2.

N1-[4-([4-(cyclopropylamino)-6-(isopropylamino)-1,3,5-triazin-2-yl]aminomethyl)cyclohexyl]methyl-1-naphthalenesulfonamide: 57% yield; 524 (MH$^+$, ESI); $^1$H NMR (CDCl$_3$) 8.67 (d, 1H, J=8.7 Hz), 8.26 (d, 1H, J=7.5 Hz), 8.09 (d, 1H, J=8.1 Hz), 7.70–7.52 (m, 3H), 5.20–4.60 (broad, 4H), 4.11 (broad, 1H), 3.14 (broad, 2H, 2.71 2.19 (broad, 2H), 1.80–0.40 (m, 11H), 1.16 (d, 6H, J=6.3 Hz).

EXAMPLE 9

Synthesized According to Scheme 2.

N1-[4-([4-(isopropylamino)-6-(pentylamino)-1,3,5-triazin-2-yl]aminomethyl)cyclohexyl]methyl-1-naphthalenesulfonamide: 49% yield; 554 (MH$^+$, ESI); $^1$H NMR (CDCl$_3$) 8.64 (d, 1H, J=8.7 Hz), 8.24 (dd, 1H, J=8.7, 1.3 Hz), 8.08 (d, 1H, J=8.0 Hz), 7.95 (d, J=8.0 Hz), 7.72–7.50 (m, 3H), 5.05 (broad, 1H), 4.78 (broad, 1H), 3.81 (broad, 2H), 3.14 (broad, 1H), 2.72 (apparent t, 2H, J=6.6 Hz), 1.80–0.65 (m, 13H), 1.18 (d, 6H, J=6.6 Hz), 0.89 (t, 3H, J=7.1 Hz).

EXAMPLE 10

Synthesized According to Scheme 2.

N1-[4-([4-[(2-cyanoethyl)amino]-6-(isopropylamino)-1,3,5-triazin-2-yl]aminomethyl)cyclohexyl]methyl-1-naphthalenesulfonamide: 43% yield; 537 (MH$^+$, ESI); $^1$H NMR (CDCl$_3$) 8.64 (d, 1H, J=8.7 Hz), 8.24 (dd, 1H, J=8.7, 1.3 Hz), 8.08 (d, 1H, J=8.0 Hz), 7.95 (d, J=8.0 Hz), 7.72–7.50 (m, 3H), 6.08 (broad, 1H), 5.30 (broad, 1H), 4.81 (apparent t, 1H, J=6.6 Hz), 4.08 (broad, 1H), 3.70–2.50 (m, 6H), 1.80–0.65 (m, 7H), 1.17 (d, 6H, J=6.6 Hz).

EXAMPLE 11

Synthesized According to Scheme 2.

N1-[4-([4-[(2-hydroxyethyl)amino]-6-(isopropylamino)-1,3,5-triazin-2-yl]aminomethyl)cyclohexyl]methyl-1-naphthalenesulfonamide: 36% yield; 528 (MH$^+$, ESI); $^1$H NMR (CDCl$_3$) 8.64 (d, 1H, J=8.7 Hz), 8.24 (d, 1H, J=8.7 Hz), 8.07 (d, 1H, J=8.0 Hz), 7.95 (d, J=8.0 Hz), 7.72–7.50 (m, 3H), 5.58 (broad, 1H), 5.26 (broad, 1H), 5.10 (broad, 1H), 4.91 (broad, 1H), 4.08 (broad, 1H), 3.70 (t, 2H, J=6.6 Hz), 3.37 (p, 2H, J=6.6 Hz), 3.203.50–2.65 (m, 4H), 1.80–0.65 (m, 7H), 1.18 (d, 6H, J=6.6 Hz).

EXAMPLE 12

Synthesized According to Scheme 2.

N1-(4-[(4-(isopropylamino)-6-[(2-methoxyethyl)amino]-1,3,5-triazin-2-ylamino)methyl]cyclohexylmethyl)-1-naphthalenesulfonamide: 63% yield; 542 (MH$^+$, ESI); $^1$H NMR (CDCl$_3$) 8.64 (d, 1H, J=8.7 Hz), 8.24 (dd, 1H, J=8.7, 1.3 Hz), 8.08 (d, 1H, J=8.0 Hz), 7.95 (d, J=8.0 Hz), 7.72–7.50 (m, 3H), 5.93 (broad, 1H), 5.23 (broad, 1H), 4.80 (apparent t, 1H, J=6.6 Hz), 4.10 (m, 1H), 3.60–3.05 (m, 6H), 3.75 (s, 3H), 2.72 (t, apparent 2H, J=6.6 Hz), 1.75–0.65 (m, 7H, 1.17 (d, 6H, J=6.6 Hz).

EXAMPLE 13

Synthesized According to Scheme 2.

N1-(4-[(4-(isopropylamino)-6-[(3-methoxypropyl)amino]-1,3,5-triazin-2-ylamino)methyl]cyclohexylmethyl)-1-naphthalenesulfonamide: 83% yield; 556 (MH$^+$, ESI); $^1$H NMR (CDCl$_3$) 8.64 (d, 1H, J=8.7 Hz), 8.24 (dm, 1H, J=8.7 Hz), 8.07 (d, 1H, J=8.0 Hz), 7.95 (d, J=8.0 Hz), 7.72–7.50 (m, 3H), 6.30–5.80 (broad, 2H), 5.20–4.50 (broad, 2H), 4.10 (broad, 1H), 3.60–3.05 (m, 6H), 2.72 (apparent t, 2H, J=6.6 Hz), 1.80–0.65 (m, 9H), 1.18 (d, 6H, J=6.6 Hz).

EXAMPLE 14

Synthesized According to Scheme 2.

N1-{[4-({[4-{[2-(dimethylamino)ethyl]amino}-6-(isopropylamino)-1,3,5-triazin-2-yl]amino}methyl) cyclohexyl]methyl}-1-naphthalenesulfonamide: 78% yield; 555 (MH$^+$, ESI); $^1$H NMR (CDCl$_3$) 8.63 (d, 1H, J=8.5 Hz), 8.24 (dd, 1H, J=7.2, 0.9 Hz), 8.07 (d, 1H, J=8.4 Hz), 7.95 (dd, 1H, J=7.2, 0.9 Hz), 7.68–7.52 (m, 3H), 5.70–4.60 (broad, 3H), 4.15 (septet, 1H, J=6.6 Hz), 3.70 (broad, 1H), 3.45 (m, 2H), 3.14 (m, 2H), 2.71 (apparent t, 2H, J=6.3 Hz), 2.53 (t, 2H, J=6.0 Hz), 2.30 (s, 6H), 1.80–0.65 (m, 7H), 1.17 (d, 6H, J=6.6 Hz).

EXAMPLE 15

Synthesized According to Scheme 2.

N1-[4-([4-[[3-(1H-1-imidazolyl)propyl]amino-6-(isopropylamino)-1,3,5-triazin-2-yl]aminomethyl)cyclohexyl]methyl-1-naphthalenesulfonamide: 93% yield; 592 (MH$^+$, ESI); $^1$H NMR (CDCl$_3$) 8.69 (d, 1H, J=8.7 Hz), 8.26 (d, 1H, J=7.5 Hz), 8.09 (d, 1H, J=8.1 Hz), 7.70–7.52 (m, 4H), 7.05 (m, 1H), 6.94 (m, 1H), 6.15 (broad, 1H), 5.70–5.00 (broad, 3H), 4.02 (t, 2H, J=6.9 Hz), the triplet at 4.02 partially covers a multiplet at 4.09 (1H), 3.40–3.00 (m, 4H), 2.71 (t, 2H, J=6.3 Hz), 2.00–0.65 (m, 13H), 1.16 (d, 6H, J=6.7 Hz).

EXAMPLE 16

Synthesized According to Scheme 2.

N1-({4-[({4-(isopropylamino)-6-[(4-methoxyphenethyl)amino]-1,3,5-triazin-2-yl}amino)methyl]cyclohexyl}methyl)-1-naphthalenesulfonamide: 50% yield, 618 (MH$^+$, ESI); $^1$H NMR (CDCl$_3$) 8.64 (d, 1H, J=8.7 Hz), 8.24 (dd, 1H, J=7.5, 0.9 Hz), 8.09 (d, 1H, J=8.1 Hz), 7.95 (d, J=8.0 Hz), 7.70–7.52 (m, 3H), 5.10–4.60 (m, 4H), 4.15 (m, 1H), 3.79 (s, 3H), 3.54 (m, 2H), 3.14 (m, 2H), 2.80 (m, 2H), 2.71 (t, 2H, J=6.6 Hz), 1.80–0.65 (m, 7H), 1.17 (d, 6H).

EXAMPLE 17

Synthesized According to Scheme 2.

N1-{[4-({[4-(dimethylamino)-6-(isopropylamino)-1,3,5-triazin-2-yl]amino}methyl)cyclohexyl]methyl}-1-naphthalenesulfonamide: 512 (MH$^+$, ESI); $^1$H NMR (CDCl$_3$) 8.63 (d, 1H, J=8.7 Hz), 8.25 (dd, 1H, J=8.7, 1.3 Hz), 8.08 (d, 1H, J=8.0 Hz), 7.95 (dd, 1H, J=8.0, 1.3 Hz), 7.72–7.50 (m, 3H), 5.90 (broad, 1H), 4.65 (apparent t, 1H, J=6.6 Hz), 4.12 (septet, 1H, J=6.6 Hz), 3.15 (m, 2H), 3.09 (broad s, 6H), 2.72 (apparent t, 2H, J=6.6 Hz), 1.80–0.65 (m, 7H), 1.18 (d, 6H, J=6.6 Hz).

EXAMPLE 18

Synthesized According to Scheme 2.

N1-[4-([4-[ethyl(methyl)amino]-6-(isopropylamino)-1,3,5-triazin-2-yl]aminomethyl)cyclohexyl]methyl-1-naphthalenesulfonamide: 58% yield; 556 (MH$^+$, ESI); $^1$H NMR (CDCl$_3$) 8.64 (d, 1H, J=8.7 Hz), 8.24 (dd, 1H, J=7.5, 0.9 Hz), 8.09 (d, 1H, J=8.1 Hz), 7.95 (d, J=8.0 Hz), 7.70–7.52 (m, 3H), 4.68 (t, 1H, J=6.3 Hz), 4.12 (septet, 1H, J=6.6 Hz), 3.57 (q, 2H, J=7.1 Hz), 3.13 (t, 2H, J=6.6 Hz), 3.03 (broad s, 3H), 2.72 (t, 2H, J=6.6 Hz), 1.80–0.65 (m, 7H), 1.18 (d, 6H, J=6.6 Hz), 1.12 (t, 3H, J=7.1 Hz).

EXAMPLE 19

Synthesized According to Scheme 2.

N1-[4-([4-(diethylamino)-6-(isopropylamino)-1,3,5-triazin-2-yl]aminomethyl)cyclohexyl]methyl-1-naphthalenesulfonamide: 95% yield; 540 (MH$^+$, ESI); $^1$H NMR (CDCl$_3$) 8.64 (d, 1H, J=8.7 Hz), 8.26 (d, 1H, J=8.7 Hz), 8.07 (d, 1H, J=8.0 Hz), 7.96 (d, J=8.0 Hz), 7.72–7.50 (m, 3H), 5.50–4.50 (broad, 2H), 4.10 (septet, 1H, J=6.6 Hz), 3.52 (q, 4H, J=7.1 Hz), 3.13 (apparent t, 2H, J=6.6 Hz), 2.71 (apparent t, 2H, J=6.6 Hz), 1.80–0.65 (m, 7H), 1.17 (d, 6H, J=6.6 Hz), 1.14 (t, 6H, J=7.1 Hz).

EXAMPLE 20

Synthesized According to Scheme 2.

N1-[4-([4-(isopropylamino)-6-tetrahydro-1H-1-pyrrolyl-1,3,5-triazin-2-yl]aminomethyl)cyclohexyl]methyl-1-naphthalenesulfonamide: 12% yield; 538 (MH$^+$, ESI); $^1$H NMR (CDCl$_3$) 8.64 (d, 1H, J=8.7 Hz), 8.25 (dd, 1H, J=8.7, 1.3 Hz), 8.07 (d, 1H, J=8.0 Hz), 7.95 (d, J=8.0 Hz), 7.72–7.50 (m, 3H), 5.15 (broad, 1H), 4.90 (broad, 1H), 4.70 (broad, 1H), 4.12 (septet, 1H, J=6.6 Hz), 3.50 (m, 4H), 3.15 (apparent t, 2H, J=6.6 Hz), 2.72 (apparent t, 2H, J=6.6 Hz), 1.70–0.60 (m, 11H), 1.18 (d, 6H, J=6.6 Hz).

EXAMPLE 21

Synthesized According to Scheme 2.

N1-(4-[(4-(isopropylamino)-6-[(2S)-2-(methoxymethyl)tetrahydro-1H-1-pyrrolyl]-1,3,5-triazin-2-ylamino)methyl]cyclohexylmethyl)-1-naphthalenesulfonamide: 87% yield; 554 (MH$^+$, ESI); $^1$H NMR (CDCl$_3$) 8.64 (d, 1H, J=8.7 Hz), 8.24 (dd, 1H, J=7.5, 0.9 Hz), 8.09 (d, 1H, J=8.1 Hz), 7.95 (d, J=8.0 Hz), 7.70–7.52 (m, 3H), 5.50–4.40 (m, 4H), 4.15 (m, 1H), 3.92 (m, 2H), 3.70–3.20 m, 6H), 3.75 (s, 3H), 2.72 (t, 2H, J=6.6 Hz), 2.20–0.60 (m, 11H), 1.17 (d, 6H).

EXAMPLE 22

Synthesized According to Scheme 2.

N1-{[4-({[4-(isopropylamino)-6-piperidino-1,3,5-triazin-2-yl]amino}methyl)cyclohexyl]methyl}-1-naphthalenesulfonamide: Anal. Calc. For C$_{29}$H$_{41}$N$_7$O$_2$S$_1$+0.3EtOAc: C, 62.74; H, 7.57; N, 16.96. Found: C, 62.70; H, 7.57; N, 16.94; 552 (MH$^+$, ESI); $^1$H NMR (CDCl$_3$) 8.64 (d, 1 H, J=8.7 Hz), 8.24 (dd, 1H, J=7.5, 0.9 Hz), 8.09 (d, 1H, J=8.1 Hz), 7.95 (d, J=8.0 Hz), 7.70–7.52 (m, 3H), 4.67 (b, 2H), 4.55 (b, 1H), 4.11 (septet, 1H, J=6.3 Hz), 3.67 (m, 4H), 3.48 (apparent t, 2 H, J=5.7 Hz), 3.30 (apparent t, 2H, J=5.7 Hz), 3.14 (m, 2H), 2.71 (t, 2H, J=6.3 Hz), 2.00–0.60 (m, 13H), 1.16 (d, 6H, J=6.3 Hz).

EXAMPLE 23

Synthesized According to Scheme 2.

N1-[4-([4-(isopropylamino)-6-(2-methylpiperidino)-1,3,5-triazin-2-yl]aminomethyl)cyclohexyl]methyl-1-naphthalenesulfonamide: 92% yield; 566 (MH$^+$, ESI); $^1$H NMR (CDCl$_3$) 8.64 (d, 1H, J=8.7 Hz), 8.24 (dd, 1H, J=7.5, 0.9 Hz), 8.09 (d, 1H, J=8.1 Hz), 7.95 (d, J=8.0 Hz), 7.70–7.52 (m, 3H), 5.10–4.60 (broad, 4H), 4.15 (septet, 1H, J=6.6 Hz), 3.40–2.70 (m, 6H), 2.80 and 2.64 (two s, 3H), 2.74 (apparent t, 2H, J=6.3 Hz), 1.75–0.60 (m, 13H), 1.13 (d, 6H, J=6.6 Hz).

EXAMPLE 24

Synthesized According to Scheme 2.

N1-[4-([4-(isopropylamino)-6-morpholino-1,3,5-triazin-2-yl]aminomethyl)cyclohexyl]methyl-1-naphthalenesulfonamide: 93% yield; 554 (MH$^+$, ESI); $^1$H NMR (CDCl$_3$) 8.64 (d, 1 H, J=8.7 Hz), 8.24 (dd, 1H, J=7.5, 0.9 Hz), 8.09 (d, 1H, J=8.1 Hz), 7.95 (d, J=8.0 Hz), 7.70–7.52 (m, 3H), 5.2–4.6 (broad, 4H), 4.15 (septet, 1H, J=6.6 Hz), 4.00–3.00 (m, 8H), 2.72 (t, 2H, J=6.6 Hz), 1.80–0.60 (m, 7H), 1.18 (d, 6H, J=6.6 Hz).

EXAMPLE 25

Synthesized According to Scheme 2.

N1-{[4-({[4-[(2R,6S)-2,6-dimethyl-1,4-oxazinan-4-yl]-6-(isopropylamino)-1,3,5-triazin-2-yl]amino}methyl)cyclohexyl]methyl}-1-naphthalenesulfonamide: 94% yield, 582 (MH$^+$, ESI); $^1$H NMR (CDCl$_3$) 8.63 (d, 1H, J=8.5 Hz), 8.24 (dd, 1H, J=7.2, 0.9 Hz), 8.07 (d, 1H, J=8.4 Hz), 7.95 (dd, 1H, J=7.2, 0.9 Hz), 7.68–7.52 (m, 3H), 4.76–4.30 (m, 4H), 4.09 (septet, 1H, J=6.6 Hz), 3.54 (m, 4H), 3.14 (apparent t, 2H, J=6.6 Hz), 2.74 (t, 2H, J=6.6 Hz), 2.60–0.65 (m, 7H), 1.18 (d, 6H, J=6.6 Hz), 1.16 (dm, 6H, J=6.6 Hz).

EXAMPLE 26

Synthesized According to Scheme 2.

N1-[4-({4-[(2-hydroxyethyl)(methyl)amino]-6-(isopropylamino)-1,3,5-triazin-2-yl]aminomethyl)cyclohexyl]methyl-1-naphthalenesulfonamide: 93% yield; 542 (MH$^+$, ESI); $^1$H NMR (CDCl$_3$) 8.64 (d, 1 H, J=8.7 Hz), 8.24 (dd, 1H, J=7.5, 0.9 Hz), 8.09 (d, 1H, J=8.1 Hz), 7.95 (d, J=8.0 Hz), 7.70–7.52 (m, 3H), 5.10–4.60 (broad, 4H, 4.15 m, 1H), 3.75–2.80 (m, 6H), 3.05 (s, 3H), 2.72 (t, 2H, J=6.6 Hz), 1.80–0.65 (m, 7H), 1.18 (d, 6H, J=6.6 Hz).

EXAMPLE 27

Synthesized According to Scheme 2.

N1-{[4-({[4-(4-acetylpiperazino)-6-(isopropylamino)-1,3,5-triazin-2-yl]amino}methyl)cyclohexyl]methyl}-1-naphthalenesulfonamide: 77% yield; 595 (MH$^+$, ESI); $^1$H NMR (CDCl$_3$) 8.63 (d, 1H, J=8.5 Hz), 8.24 (d, 1H, J=7.2 Hz), 8.07 (d, 1H, J=8.4 Hz), 7.95 (d, 1H, J=7.2 Hz), 7.68–7.52 (m, 3H), 5.00–4.40 (broad, 3H), 4.70 (t, 1H, J=6.6 Hz), 4.15 (septet, 1H, J=6.6 Hz), 3.71 (m, 4H), 3.61 (m, 2H), 3.47 (m, 2H), 3.15 (m, 2H), 2.72 (t, 2H, J=6.3 Hz), 2.13 (s, 3H), 1.90–0.65 (m, 7H), 1.17 (d, 6H, J=6.6 Hz).

EXAMPLE 28

Synthesized According to Scheme 2.

N1-{[4-({[4-(isopropylamino)-6-(4-isopropylpiperazino)-1,3,5-triazin-2-yl]amino}methyl)cyclohexyl]methyl}-1-naphthalenesulfonamide: 60% yield; 595 (MH$^+$, ESI); $^1$H NMR (CDCl$_3$) 8.64 (d, 1H, J=8.5 Hz), 8.24 (dd, 1H, J=7.2, 0.9 Hz), 8.07 (d, 1H, J=8.4 Hz), 7.95 (dd, 1H, J=7.2, 0.9 Hz), 7.68–7.52 (m, 3H), 5.20–4.40 (broad, 2H), 4.71 (apparent t, 1H, J=6.6 Hz), 4.13 (septet, 1H, J=6.6 Hz), 3.76 (m, 4H), 3.16 (apparent t, 2H, J=6.6 Hz), 2.74 overlapping a multiplet (t, 3H, J=6.6 Hz), 2.53 (m, 4H), 1.64 (ABm, 4H), 1.50–0.60 (m, 3H), 1.16 (d, 6H, J=6.6 Hz), 1.06 (d, 6H, J=6.6 Hz).

Compounds in Table 2 (dichloromethane as solvent):

EXAMPLE 29

Synthesized According to Scheme 3.

N1-[4-([4,6-di(ethylamino)-1,3,5-triazin-2-yl]aminomethyl)cyclohexyl]methyl-4-(tert-butyl)-1-benzenesulfonamide: 40% yield; Anal. Calc. For $C_{25}H_{41}N_7SO_2+0.10$ $CH_2Cl_2$: C, 59.60; H, 8.20; N, 19.40. Found: C, 58.42; H, 7.98; N, 18.16; 504 (MH$^+$, ESI); $^1$H NMR (CDCl$_3$) 7.80 (d, 2H, J=8.6 Hz), 7.50 (d, 2H, J=8.6 Hz), 5.40 (broad, 1H), 5.20–4.75 (broad, 3H), 3.40–3.15 (m, 6H), 2.75 (t, 2H, J=4.5 Hz), 1.80–1.10 (m, 14H), 1.25 (s, 9H), 0.80–0.70 (broad, 2H).

EXAMPLE 30

Synthesized According to Scheme 3.

N1-[4-([4,6-di(ethylamino)-1,3,5-triazin-2-yl]aminomethyl)cyclohexyl]methyl-4-fluoro-1-benzenesulfonamide: 30% yield, Anal. Calc. For $C_{21}H_{30}N_7FSO_2 +0.10\ CH_2Cl_2$: C, 54.10; H, 6.90; N, 21.00. Found: C, 53.77; H, 6.75; N, 20.43; $^1$H NMR (CDCl$_3$) 7.85 (d, 2H, J=8.6 Hz), 7.15 (d, 2H, J=8.6 Hz), 5.00–4.50 (broad, 4H), 3.40–3.15 (m, 6H), 2.80–2.70 (m, 2H), 1.80–1.20 (m, 14H), 0.90–0.80 (broad, 2H).

EXAMPLE 31

Synthesized According to Scheme 3.

N1-[4-([4,6-di(ethylamino)-1,3,5-triazin-2-yl]aminomethyl)cyclohexyl]methyl-2-methoxy-5-methyl-1-benzenesulfonamide: 86% yield; 492 (MH$^+$, ESI); Anal. Calc. for $C_{23}H_{37}N_7O_3S_1+1.5CH_3OH$: C, 54.52; H, 8.03; N, 18.17. Found: C, 54.09; H, 7.84; N, 18.18; $^1$H NMR (CDCl$_3$) 7.81 (m, 1H), 7.33 (broad d, 1H, J=8.0 Hz), 6.93 (d, 1H, J=8.0 Hz), 5.20–4.60 (broad, 4H), 3.94 (s, 3H), 3.50–3.10 (m, 6H), 2.76 and 2.67 (two t, 2H, J=6.3 Hz), 2.50–2.30 (m, 4H), 1.90–0.70 (m, 11H), 1.17 (t, 6H, J=7.2 Hz).

EXAMPLE 32

Synthesized According to Scheme 3.

N1-[4-([4,6-di(ethylamino)-1,3,5-triazin-2-yl]aminomethyl)cyclohexyl]methyl-2-fluoro-1-benzenesulfonamide: 86% yield; 466 (MH$^+$, ESI); Anal. Calc. for $C_{21}H_{32}F_1N_7O_2S_1+1.5CH_3OH$: C, 52.61; H, 7.46; N, 19.09. Found: C, 52.14, H, 7.10; N, 19.17; $^1$H NMR (CDCl$_3$) 7.90 (m, 1H), 7.58 (m, 1H), 7.40–7.18 (m, 2H), 5.50–4.60 (broad, 4H), 3.50–3.10 (m, 6H), 2.91 and 2.82 (two t, 2H, J=6.2 Hz), 1.90–0.60 (m, 11H), 1.17 (t, 6H, J=7.2 Hz).

EXAMPLE 33

Synthesized According to Scheme 3.

N1-[4-([4,6-di(ethylamino)-1,3,5-triazin-2-yl]aminomethyl)cyclohexyl]methyl-2-methyl-1-benzenesulfonamide: 28% yield; 462 (MH$^+$, ESI); Anal. Calc. for $C_{22}H_{35}N_7O_2S_1+0.7CH_3OH$: C, 56.33; H, 7.87, N, 20.26. Found: C, 56.34; H, 7.82; N, 20.01; $^1$H NMR (CDCl$_3$) 7.40 (m, 4H), 5.10–4.60 (broad, 4H), 4.26 and 4.25 (two t, 2H, J=6.2 Hz), 2.10–0.70 (m, 11H), 1.18 (t, 6H, J=7.2 Hz).

EXAMPLE 34

Synthesized According to Scheme 3.

N3-[4-([4,6-di(ethylamino)-1,3,5-triazin-2-yl]aminomethyl)cyclohexyl]methyl-3-pyridinesulfonamide: 94% yield; 449 (MH$^+$, ESI); Anal. Calc. for $C_{20}H_{32}N_8O_2S_1+1.5CH_3OH$: C, 52.00; H, 7.71; N, 22.56. Found: C, 51.84; H, 7.65; N, 22.27; $^1$H NMR (CDCl$_3$) 9.08 (m, 1H), 8.81 (dm, 1H, J=5.3 Hz), 8.16 (dm, 1H, J=8.1 Hz), 7.46 (ddm, 1H, J=5.3, 8.1 Hz), 5.20–4.60 (broad, 4H), 3.50–3.10 (m, 6H), 2.92 and 2.83 (two d, 2H, J=6.3 Hz), 1.85–0.80 (m, 11H), 1.15 (t, 6H, J=7.3 Hz).

EXAMPLE 35

Synthesized According to Scheme 3.

N1-[4-([4,6-di(ethylamino)-1,3,5-triazin-2-yl]aminomethyl)cyclohexyl]methyl-4-methoxy-1-benzenesulfonamide: 86% yield; 478 (MH$^+$, ESI); Anal. Calc. for $C_{22}H_{35}N_7O_3S_1+0.5CH_3OH$: C, 54.30; H, 7.46; N, 20.15. Found: C, 54.30; H, 7.42; N, 19.66; $^1$H NMR (CDCl$_3$) 7.80 (dm, 2H, J=8.9 Hz), 6.98 (dm, 2H, J=8.9 Hz), 5.20–4.60 (broad, 4H), 3.86 (s, 3H), 1.90–0.70 (m, 11H), 1.16 (t, 6H, J=7.3 Hz).

EXAMPLE 36

Synthesized According to Scheme 3.

N5-[4-([4,6-di(ethylamino)-1,3,5-triazin-2-yl]aminomethyl)cyclohexyl]methyl-2,4-dimethyl-1,3-oxazole-5-sulfonamide: 86% yield; 467 (MH$^+$, ESI); Anal. Calc. for $C_{20}H_{34}N_8O_3S_1$: C, 51.48; H, 7.34; N, 24.01. Found: C, 51.26; H, 7.34; N, 23.81; $^1$H NMR (CDCl$_3$) 5.10–4.50 (broad, 4H), 3.50–2.70 (m, 6H), 2.64 (two s, 3H), 2.40 (two s, 3H), 2.10–0.80 m, 11H), 1.18 t, 6H, J=7.3 Hz).

EXAMPLE 37

Synthesized According to Scheme 3.

N2-[4-([4,6-di(ethylamino)-1,3,5-triazin-2-yl]aminomethyl)cyclohexyl]methyl-2-thiophenesulfonamide: 93% yield; 454 (MH$^+$, ESI); Anal. Calc. for $C_{19}H_{31}N_7O_2S_2+0.5H_2O$: C, 49.33; H, 6.97; N, 21.19. Found: C, 49.36; H, 6.91; N, 20.82; $^1$H NMR (CDCl$_3$) 7.62 (m, 2H), 7.10 (m, 1H), 5.30–4.50 (broad, 3H), 3.50–2.80 (m, 8H), 2.60–1.90 (b, 1H), 1.90–0.70 (m, 11H), 1.17 (t, 6H, J=7.3 Hz).

EXAMPLE 38

Synthesized According to Scheme 3.

N4-[4-([4,6-di(ethylamino)-1,3,5-triazin-2-yl]aminomethyl)cyclohexyl]methyl-1-methyl-1H-4-imidazolesulfonamide: 90% yield; 452 (MH$^+$, ESI); Anal. Calc. for $C_{19}H_{33}N_9O_2S_1+0.7CH_3OH$: C, 49.92; H, 7.61; N, 26.59. Found: C, 49.65; H, 7.18; N, 27.09; $^1$H NMR (CDCl$_3$) 7.50 (m, 1H), 7.46 (m, 1H), 5.50–4.80 (broad, 4H), 3.75 (s, 3H), 3.50–2.70 (m, 6H), 2.70–2.00 (broad, 1H), 1.90–0.70 (m, 11H), 1.16 (t, 6H, J=6.3 Hz).

EXAMPLE 39

Synthesized According to Scheme 3.

N1-[4-([4,6-di(ethylamino)-1,3,5-triazin-2-yl]aminomethyl)cyclohexyl]methyl-4-methyl-1-benzenesulfonamide: 95% yield; 462 (MH$^+$, ESI); Anal. Calc. for $C_{22}H_{35}N_7O_2S_1+0.5CH_3OH$: C, 56.58; H. 7.81; N, 20.53. Found: C, 56.79; H, 7.74; N, 20.36; $^1$H NMR (CDCl$_3$) 7.76 (dm, 2H, J=8.1 Hz), 7.32 (dm, 2H, J=8.1 Hz), 5.30–4.6 (broad, 4H), 3.50–3.00 (m, 6H), 2.42 (s, 3H), 1.90–0.70 (m, 11H), 1.14 (t, 6H, J=7.3 Hz).

EXAMPLE 40

Synthesized According to Scheme 3.

N5-[4-([4,6-di(ethylamino)-1,3,5-triazin-2-yl]aminomethyl)cyclohexyl]methyl-2,1,3-benzothiadiazole-5-sulfonamide: 84% yield; 506 (MH$^+$, ESI); $^1$H NMR (CDCl$_3$) 8.27 (m, 2H), 7.73 (m, 1H), 5.60 (broad, 1H), 5.40 (broad, 3H), 3.45–3.00 (m, 6H), 2.82 and 2.72 (two d, 2H, J=6.8 Hz), 1.80–0.70 (m, 11H), 1.15 (t, 6H, 7.3 Hz).

EXAMPLE 41

Synthesized According to Scheme 3.

N8-[4-([4,6-di(ethylamino)-1,3,5-triazin-2-yl]aminomethyl)cyclohexyl]methyl-8-quinolinesulfonamide: 48% yield; 499 (MH$^+$, ESI); Anal. Calc. for C$_{24}$H$_{34}$N$_8$O$_2$S$_1$+ 0.5CH$_3$OH: C, 57.18; H, 7.05; N, 21.77. Found: C, 57.22; H, 7.15; N, 21.67; $^1$H NMR (CDCl$_3$) 9.03 (m, 1H), 8.45 (dm, 1H, J=8.0 Hz), 8.30 (d, 1H, J=8.0 Hz), 8.06 (dm, 1H, J=8.0 Hz), 7.67 (mt, 1H, J=8.0 Hz), 7.57 (dd, 1H, 4.8, 8.0 Hz)6.34 (m, 1H), 4.88 (broad, 3H), 3.50–3.00 (m, 6H), 2.76 and 2.67 (two t, 2H, J=6.4 Hz), 2.30 (broad, 2H, 1.80–0.70 (m, 11H), 1.15 (t, 6H, J=7.3 Hz).

EXAMPLE 42

Synthesized According to Scheme 3.

N-[4-([4,6-di(ethylamino)-1,3,5-triazin-2-yl]aminomethyl)cyclohexyl]methylmethanesulfonamide: 55% yield; 386 (MH$^+$, ESI); Anal. Calc. for C$_{16}$H$_{31}$N$_7$O$_2$S$_1$+ 0.5CH$_3$OH: C, 49.35; H, 8.28; N, 24.42. Found: C, 49.10; H, 7.78; N, 24.81; $^1$H NMR (CDCl$_3$) 5.20–4.60 (broad, 5H), 3.50–3.00 (m, 8H), 2.95 and 2.93 (two s, 3H), 1.90–0.70 (m, 11H), 1.18 (t, 6H).

Compounds in Table 3 (dioxane as solvent):

EXAMPLE 43

Synthesized According to Scheme 4A.

N1-[4-([4-(isopropylamino)-6-tetrahydro-1H-1-pyrrolyl-1,3,5-triazin-2-yl]aminomethyl)cyclohexyl]methyl-1-pyrrolidinesulfonamide: 35% yield; Anal. Calc. For C$_{22}$H$_{40}$N$_8$SO$_2$ +0.10 CH$_2$Cl$_2$: C, 54.26; H, 8.28; N; 22.91. Found: C, 53.93; H, 8.25; N, 22.86; 481 (MH$^+$, ESI); $^1$H NMR (CDCl$_3$) 5.00–4.80 (m, 1H), 4.80–4.60 (m, 1H), 4.60–4.40 (m, 1H), 3.60–3.40 (m, 6H), 2.95–2.80 (m, 3H), 1.90–1.80 (m, 8H), 1.50–1.30 (m, 8H), 1.20–1.050 (m, 6H), 0.90–0.80 (m, 2H).

EXAMPLE 44

Synthesized According to Scheme 4B.

N4-[4-([4-(isopropylamino)-6-morpholino-1,3,5-triazin-2-yl]aminomethyl)cyclohexyl]methyl-4-morpholinesulfonamide: 30% yield; Anal. Calc. For C$_{22}$H$_{40}$N$_8$SO$_2$ +1.10 CH$_2$C$_2$: C, 48.30; H, 7.40; N, 19.60. Found: C, 48.16; H, 7.28; N, 20.01; 513 (MH$^+$, ESI); $^1$H NMR (CDCl$_3$) 5.05–4.60 (m, 3H), 3.80–3.60 (m, 12H), 3.35–3.10 (m, 6H), 3.05–2.80 (m, 3H), 1.80–1.30 (m, 8H), 1.20–1.05 (m, 6H), 1.00–0.80 (m, 2H).

EXAMPLE 45

Synthesized According to Scheme 4B.

N1-[4-([4-(isopropylamino)-6-piperidino-1,3,5-triazin-2-yl]aminomethyl)cyclohexyl]methyl-1-piperidinesulfonamide: 30% yield; Anal. Calc. For C$_{24}$H$_{44}$N$_8$SO$_2$ +0.3 CH$_2$C$_{12}$: C, 54.64; H, 8.41; N, 20.98. Found: C, 54.53; H, 8.24; N, 20.94; 509 (MH$^+$, ESI); $^1$H NMR (CDCl$_3$) 4.80–4.60 (m, 1H), 4.60–4.50 (m, 1H), 4.20–4.10 (m, 1H), 3.80–3.60 (m, 4H), 3.40–3.30 (m, 2H), 3.20–3.10 (m, 4H), 3.00–2.90 (m, 3H), 1.80–1.40 (m, 20H), 1.20–1.050 (m, 6H), 0.90–0.80 (m, 2H).

EXAMPLE 46

Synthesized According to Scheme 2.

N1-[(4-[(4,6-ditetrahydro-1H-1-pyrrolyl-1,3,5-triazin-2-yl)amino]methylcyclohexyl)methyl]-4-(tert-butyl)-1-benzenesulfonamide: 30% yield; Anal. Calc. For C$_{29}$H$_{45}$N$_7$SO$_2$+ 0.2 CH$_2$Cl$_2$: C, 61.20; H, 8.00; N, 17.10. Found: C, 61.60; H, 8.12; N, 16.41; 556 (MH$^+$, ESI); $^1$H NMR (CDCl$_3$) 7.75 (d, 2H, J=8.7 Hz), 7.50 (d, 2H, J=8.7 Hz), 4.85 (broad, 1H), 4.70–650 (broad, 1H), 3.60–3.50 (broad, 8H), 3.20 (t, 2H, J=7.5 Hz), 2.75 (t, 2H, J=7.5 Hz), 1.95–1.15 (m, 16H), 1.15 (s, 9H), 0.90–0.80 (m, 2H).

EXAMPLE 47

Synthesized According to Scheme 4C and 4D.

N-cyclopropyl-N'-[4-([4-(cyclopropylamino)-6-(isopropylamino)-1,3,5-triazin-2-yl]aminomethyl)cyclohexyl]methylsulfamide: 20% yield; Anal. Calc. For C$_{20}$H$_{36}$N$_8$SO$_2$+ 0.15 CH$_2$Cl$_2$: C, 52.00; H, 7.86; N; 24.08. Found: C, 51.87; H, 7.83; N, 23.74; 453 (MH$^+$, ESI); $^1$H NMR (CDCl$_3$) 5.40–5.00 (m, 3H), 4.95–4.60 (m, 2H), 3.30–3.20 (m, 2H), 2.90–2.60 (m, 3H), 2.50–2.40 (m, 2H), 1.80–1.30 (m, 8H), 1.25–1.10 (m, 6H), 0.90–0.80 (m, 2H), 0.70–0.60 (m, 4H), 0.50–0.40 (m, 4H).

EXAMPLE 48

Synthesized According to Scheme 2.

N'-[4-([4-(cyclopropylamino)-6-(isopropylamino)-1,3,5-triazin-2-yl]aminomethyl)cyclohexyl]methyl-N,N-dimethylsulfamide: 28% yield; Anal. Calc. For C$_{19}$H$_{36}$N$_8$SO$_2$+0.60 CH$_3$COOC$_2$H$_5$ +0.10 CH$_2$Cl$_2$: C, 50.90; H, 7.95; N, 22.30. Found: C, 50.42; H, 7.52; N, 22.87; 441 (MH$^+$, ESI); $^1$H NMR (CDCl$_3$) 4.90–4.80 (m, 1H), 4.70–4.60 (m, 1H), 4.50–4.40 (m, 1H), 4.20–4.10 (m, 1H), 3.40–3.20 (m, 3H), 3.10 (s, 6H), 3.00–2.80 (m, 3H), 1.90–1.30 (m, 8H), 1.15–1.05 (m, 6H), 0.95–0.85 (m, 2H), 0.70–0.50 (m, 4H).

EXAMPLE 49

Synthesized According to Scheme 2.

N1-{[4-({[4-chloro-6-(isopropylamino)-1,3,5-triazin-2-yl]amino}methyl)cyclohexyl]methyl}-1-naphthalenesulfonamide: 60% yield; 503.08 and 505.09 (MH$^+$, ESI): 60% yield; $^1$H NMR (CDCl$_3$) 8.62 (d, 1H, J=8.7 Hz), 8.25 (d, 1H, J=8.7 Hz), 8.07 (d, 1H, J=8.0 Hz), 7.95 (dd, J=8.0, 0.9 Hz), 7.72–7.50 (m, 3H), 5.203.95 (m, 4H), 4.04 (septet, 1H, J=6.6 Hz), 3.21 and 3.06 (two t, 2H, J=6.6 Hz), 2.72 (t, 2H, J=6.6 Hz), 1.80–0.65 (m, 7H), 1.19 (d, 6H, J=6.6 Hz).

EXAMPLE 50

Synthesized According to Scheme 3.

N'-[(4-[(4,6-dimorpholino-1,3,5-triazin-2-yl)amino]methylcyclohexyl)methyl]-N,N-dimethylsulfamide: 40% yield; Anal. Calc. For $C_{21}H_{38}N_8SO_2$ +0.70 $CH_2Cl_2$: C, 46, 80; H, 6.75; N, 19.90. Found: C, 46.68; H, 6.75; N, 19.98; $^1$H NMR (CDCl$_3$) 4.90–4.80 (m, 1H), 4.60–4.50 (m, 1H), 3.80–3.60 (m, 16H), 3.20 (t, 2H, J=4.5 Hz), 2.75 (t, 2H, J=4.5 Hz), 2.8 (s, 6H), 1.8–1.3 (m, 8H), 1.1–0.9 (m, 2H).

EXAMPLE 51

Synthesized According to Scheme 2.

N1-[4-([4-chloro-6-(isopropylamino)-1,3,5-triazin-2-yl]aminomethyl)cyclohexyl]methyl-4-(tert-butyl)-1-benzenesulfonamide: 30% yield; 509 (MH$^+$, ESI); 1H NMR (CDCl$_3$) 7.80 (d, 2H, J=8.80 Hz), 7.50 (d, 2H, J=8.80 Hz), 5.30–5.20 (m, 1H), 4.70–4.50 (m, 2H), 3.35–3.25 (m, 2H), 2.90–2.75 (m, 3H), 1.80–1.30 (m, 8H), 1.35 (s, 9H), 1.25–1.15 (m, 6H), 0.90–0.85 (m, 2H).

EXAMPLE 52

Synthesized According to Scheme 2.

N1-[4-([4-(cyclopropylamino)-6-tetrahydro-1H-1-pyrrolyl-1,3,5-triazin-2-yl]aminomethyl)cyclohexyl]methyl-4-fluoro-1-benzenesulfonamide: 504 (MH$^+$, ESI); $^1$H NMR (CDCl$_3$) 7.65 (d, 2H, J=8.7 Hz), 6.63 (d, 2H, J=8.7 Hz), 4.95–4.70 (m, 2H), 4.30 (m, 1H), 3.50 (m, 3H), 3.40–3.20 (m, 4H), 2.85 (t, 2H, J=5.5 Hz), 1.90 (m, 4H), 1.80–1.30 (m, 8H), 0.90 (m, 2H), 0.70 (m, 2H), 0.50 (m, 2H)

EXAMPLE 53

Synthesized According to Scheme 2.

N'-((4-(((4,6-dichloro-1,3,5-triazin-2-yl)amino)methyl)cyclohexyl)methyl)-N,N-dimethylsulfamide: 35% yield; 397 (MH$^+$, ESI); $^1$H NMR (CDCl$_3$) 6.40 (m, 1H), 4.65–4.55 (m, 1H), 3.40 (t, 2H, J=5.20 Hz), 3.0 (t, 2H, J=5.20 Hz), 2.80 (s, 6H), 1.85–1.30 (m, 8H), 0.950–0.85 (m, 2H).

EXAMPLE 54

Synthesized According to Scheme 2.

N1-[(4-[(4,6-ditetrahydro-1H-1-pyrrolyl-1,3,5-triazin-2-yl)amino]methylcyclohexyl)methyl]-2-methoxy-5-methyl-1-benzenesulfonamide: 35% yield; Anal. Calc. For $C_{27}H_{41}N_7SO_3$+0.35 $CH_2Cl_2$: C, 57.30; H, 7.35; N, 17.10. Found: C, 57.72; H, 7.43; N, 16.43; $^1$H NMR (CDCl$_3$) 7.7 (s, 1H), 7.40–7.30 (dd, 1H), 6.90 (d, 1H), 4.90–4.80 (m, 2H), 3.95 (s, 3H), 3.60–3.40 (broad s, 8H), 3.25 (t, 2H, J=5.5 Hz), 2.75 (t, 2H, J=5.5), 2.30 (s, 3H), 1.95–1.85 (broad, s, 8H), 1.80–1.20 (m, 8H), 0.95–0.8 (m, 2H).

EXAMPLE 55

Synthesized According to Scheme 5.

N1-[4-([4-(cyclopropylamino)-6-(2-pyridyl)-1,3,5-triazin-2-yl]aminomethyl)cyclohexyl]methyl-4-fluoro-1-benzenesulfonamide N1-[4-(aminomethyl)cyclohexyl]methyl-4-fluoro-1-benzenesulfonamide: A solution of 2.37 g of 4-fluorophenylsulfonyl chloride (12.2 mmol) in 30 ml of dichloromethane was added over 10 minutes to a stirred solution of 5.20 g of 1,4-bis-aminomethylcyclohexane (36.6 mmol) and 3.15 g of diisopropylethylamine (24.4 mmol) in 100 ml of dichloromethane at room temperature. The reaction mixture was stirred at room temperature for 16 hours, concentrated, and chromatographed on 200 g of silica packed with 5% MeOH (containing 2M NH$_3$)—CHCl$_3$, eluted with 5%, 7.5%, 10% (1 liter each) to give 3.63 g of the desired product.

A Mixture of 564 mg

N1-[4-(aminomethyl)cyclohexyl]methyl-4-fluoro-1-benzenesulfonamide (2.0 mmol) in MeOH was triturated with 1M HCl in ether. The precipitate was filtered and heated with 248 mg of cyclopropylcyanoguanidine (2.00 mmol) in 5 ml of 1-butanol for 16 hours. The solvent was removed in vacuo and the product was used in the next step.

Pickoninyl chloride (67.7 mg, 0.38 mmol) was added to a stirred mixture of 175 mg of biguanide (0.38 mmol) in acetone-5% aqueous NaOH (3 mL, 2:1) at 0° C. (ice bath). After five minutes, the ice bath was removed and the mixture was stirred for 1 hour at room temperature. The solvent was removed and chromatographed on silica to give the desired compound: 11% yield; 512 (MH$^+$, ESI); $^1$H NMR (CDCl$_3$) 8.75 (m, 1H), 7.90–7.70 (m, 7H), 7.20 (m, 1H), 7.10 (m, 1H), 5.60 (broad, 1H, 5.40 (broad, 2H), 4.50 (broad, 1H), 3.45 (m, 2H), 3.00–2.60 (m, 4H), 1.90–1.00 (m, 11H), 1.00–0.50 (m, 4H).

Compounds in Table 4 (dioxane as solvent):

EXAMPLE 56

Synthesized According to Scheme 2.

N2,N4-diethyl-N6-[5-(1H-1-pyrazolyl)pentyl]-1,3,5-triazine-2,4,6-triamine: $^1$H NMR (CDCl$_3$) 7.54 (d, 1H, J=1.8 Hz), 7.32 (d, 1H, J=2.1 Hz), 6.19 (dd, 1H, J=1.8, 2.1 Hz), 5.10 (b, 3H), 4.08 (t, 2H, J=6.9 Hz), 3.32 (m, 6H), 1.85 (p, 2H, J=6.9 Hz), 1.54 (p, 2H, J=6.9 Hz), 1.31 (p, 2H, J=6.9 Hz), 1.12 (t, 6H, J=7.2 Hz).

EXAMPLE 57

Synthesized According to Scheme 2.

N2,N4-diethyl-N6-[3-(1H-1-imidazolyl)propyl]-1,3,5-triazine-2,4,6-triamine: $^1$H NMR (CDCl$_3$) 7.45 (s, 1H), 6.99 (s, 1H), 6.86 (s, 1H), 5.42 (broad, 1H), 5.15 (broad, 2H), 3.92 (t, 2H, J=6.9 Hz), 3.55 (broad, 1H), 3.31 (m, 6H), 1.98 (p, 2H, J=6.9 Hz), 1.10 (t, 6H, J=7.2 Hz).

EXAMPLE 58

Synthesized According to Scheme 2.

N2,N4-diethyl-N6-(2-pyridylmethyl)-1,3,5-triazine-2,4,6-triamine: $^1$H NMR (CDCl$_3$) 8.44 (d, 1H, J=4.8 Hz), 7.55 (apparent dt, 1H, J=7.8, 1.3 Hz), 7.32 (d, 1H, J=7.8 Hz), 7.07 (dd, 1H, J=1.3, 4.8 Hz), 6.00 (broad, 1H), 4.63 (m, 2H), 3.32 (m, 4H), 1.08 (t, 6H, J=7.2 Hz).

I. Synthetic Methods for Examples

B. Bicyclic Compounds

General Procedures Relating to Examples:

For the formation of 2-aminothiazoles from 2-haloketones and thioureas, see, for example, Kearney, P. C., et al., 1998; Di Fabio, R. and Pentassuglia, G., 1998; De Kimpe, N., et al., 1996; Plazzi, P. V., et al., 1995; and Novikova, A. P., 1991.

For the formation of thiazoles from 2-haloketones and thioamides, see, for example, Critcher, D. J. and Pattenden, G., 1996; and Friedman, B. S., et al., 1937.

For the formation of 2-aminoimidazoles from 2-haloketones and guanidines, see, for example, Little, T. L. and Webber, 1994; and Chabaka, L. M., et al., 1994.

For the formation of imidazoles from 2-haloketones and amidines, see, for example, Demchenko, A. M., et al., 1997; and Nagao, Y., et al., 1996.

For the synthesis of 2-aminooxazoles from 2-haloketones and ureas, see, for example, Pathak, V. N., et al., 1993; Crangk, G. and Foulis, M. J., 1971; and Marchetti, E., et al., 1968.

For the formation of oxazoles from 2-haloketones and amides, see, for example, Hammar, W. J. and Rustad, M. A., 1981; and Zhao, Z., et al., 1991.

Benzotriazole-1-carboxaldehyde was purchased from Aldrich Chemical Company and is recommended for the formation of formamides from amines.

All reactions were performed under an inert atmosphere (Argon) and the reagents, neat or in appropriate solvents, were transferred to the reaction vessel via syringe and cannula techniques. Anhydrous solvents were purchased from Aldrich Chemical Company and used as received. The examples 1–44 described in this application were named using ACD/Name program (version 2.51, Advanced Chemistry Development Inc., Toronto, Ontario, M5H2L3, Canada).

$^1$H and $^{13}$C spectra were recorded at 300 and 75 MHz (QE Plus) with CDCl$_3$ as solvent (unless otherwise noted) and tetramethylsilane as internal standard. s=singlet; d=doublet; t=triplet; q=quartet; p=pentet; sextet; septet; b=broad; m=multiplet. Elemental analyses were performed by Robertson Microlit Laboratories, Inc. Low-resolution electrospray MS spectra were measured (ESMS, MS) and MH$^+$ is reported. Thin-layer chromatography (TLC) was carried out on glass plates precoated with silica gel 60 F$_{254}$ (0.25 mm, EM Separations Tech.). Preparative thin-layer chromatography was carried out on glass sheets precoated with silica gel GF (2 mm, Analtech). Flash column chromatography was performed on Merck silica gel 60 (230–400 mesh). Melting points were determined in open capillary tubes on a Med-Temp apparatus and are uncorrected.

General Procedure for the Synthesis of Bromoketones:

In general, to the solution of a ketone (1 equivalent) in acetic acid or an appropriate solvent, cooled in a water bath, was added bromine or a brominating agent such as tetrabutylammonium perbromide (1 equivalent) slowly. The reaction mixture was stirred at room temperature. The solvents were evaporated, the residue was dissolved in dichloromethane, and washed with saturated sodium bicarbonate and water. The organic phase was dried over sodium sulfate. Evaporation of the combined decolored organic phase afforded a light yellow oil. In some cases, the desired product precipitated upon concentration of the reaction mixture.

General Procedure for the Synthesis of Bromoketones (from acetylpyridines).

To the solution of an acetylpyridine (1 equivalent) and concentrated hydrogen bromide (2 equivalents, 48% in acetic acid) and methanol (AcOH/MeOH=3.5/1), was added bromine (1 equivalent) dropwise at room temperature with stirring. The reaction mixture was heated to 60° C. for 4 hours. The evaporation of the solvent afforded a yellow solid which was collected by filtration and washed with diethyl ether. The bromoketone was used for the next reaction without further purification.

2-Bromo-1-(2-pyridinyl)-1-ethanone hydrogen bromide was obtained as a yellow solid in 100% from 2-acetylpyridine and hydrogen bromide: $^1$H NMR (CD$_3$OD) δ 8.81 (d, 1H, J=5.4 Hz), 8.73 (t, 1H, J=8.1 Hz), 8.27 (d, 1H, J=8.1 Hz), 8.14 (t, 1H, J=6.6 Hz), 3.92 (d, 1H, J=11.4 Hz), 3.83 (d, 1H, J=11.4 Hz).

2-Bromo-1-(3-pyridinyl)-1-ethanone hydrogen bromide was obtained as a yellow solid in more than 95% from 3-acetylpyridine and hydrogen bromide: $^1$H NMR (CD$_3$OD) δ 8.96 (t, 1H, J=0.9 Hz), 8.89 (d, 1H, J=6.0 Hz), 8.88 (dt, 1H, J=1.5, 8.1 Hz), 8.16 (dd, 1H, J=6.0, 8.0 Hz), 3.82 (d, 1H, J=11.1 Hz), 3.72 (d, 1H, J=11.1 Hz).

2-Bromo-1-(4-pyridinyl)-1-ethanone hydrogen bromide was obtained as a yellow solid in more than 95% yield from 4-acetylpyridine and hydrogen bromide: $^1$H NMR (CD$_3$OD) δ 8.90 (d, 2H, J=6.9 Hz), 8.24 (d, 2H, J=6.9 Hz), 3.79 (d, 1H, J=11.1 Hz), 3.69 (d, 1H, J=11.1 Hz).

2-Bromo-1-(2,5-dimethyl-1,3-thiazol-4-yl)-1-ethanone hydrogen bromide was obtained from 4-acyl-2,5-dimethyl-1,3-thiazole and bromine in acetic acid: 70% yield; $^1$H NMR (DMSO-d$_6$) δ 5.48 (s, 1H), 3.37 (ABq, 2H), 2.91 (s, 3H), 2.54 (s, 3H).

2-Chloro-1-(thiphen-2-yl)-1-ethanone: Trimethylsilyl diazomethane (TMSCHN$_2$, 2M in hexanes, 100 ml, 0.200 mole) was added dropwise, over a period of 20 minutes, to an ice bath solution of thiophene-2-acetyl chloride (0.192 mole, 28.1 g) in 100 ml of dry 1,4-dioxane. The slush disappeared upon addition of TMSCHN$_2$. The reaction mixture was slowly warmed to room temperature and stirred for 24 hours. The reaction mixture was cooled in an ice bath and HCl gas was bubbled for 0.5 hour and stirred at room temperature for 2 days. The solvent was removed under reduced pressure, the residue partitioned between 100 ml of aqueous saturated NaHCO$_3$ solution and 250 ml of ethyl acetate and separated. The organic phase was washed with 100 ml of aqueous saturated NaHCO$_3$ solution, dried (Na$_2$SO$_4$) and the solvent was removed under reduced pressure. The crude product was chromatographed on 200 g of silica packed with 2.5% EtOAc-hexanes and the column was eluted with increasing amounts of ethyl acetate in hexanes (2.5%, 1 L, 5%, 1 L; 7.5%, 1 L, 10%, 1 L; 12.5%, 1 L; 15%, 1 L) to give 12.8 g of the desired product which was slightly contaminated: 42% yield; $^1$H NMR (CDCl$_3$) δ 7.80 (dd, 1H, J=0.9, 3.9 Hz), 7.74 (dd, 1H, J=0.9, 5.0 Hz average), 7.19 (dd, 1H, J=0.9, 5.0 Hz average), 4.61 (s, 2H). This product turned yellow and then brown over time and therefore was used in the formation of the 2-amino-1,3-thiazole derivatives as soon as possible.

2-Bromo-1-(1,3-thiazol-2-yl)-1-ethanone hydrogen bromide: tetra-n-Butylammonium perbromide (Bu$_4$NBr$_3$, 17.3 g, 35.8 mmol) was added, over a period of 30 seconds, to a stirred solution of 2-acyl-1,3-thiazole (4.55 g, 35.8 mmol) in 100 ml of dichloromethane at room temperature. The resulting orange to red solution was stirred at room temperature for 48 hours and approximately half of the solvent was removed under reduced pressure, filtered and the solids were washed with 50% EtOAc/hexanes to afford 8.60 g (84%) of the desired product: $^1$H NMR (DMSO-d$_6$) δ 8.92–8.60 (broad, 2H), 8.28 (d, 1H, J=3.2 Hz average), 8.17 (d, 1H, J=3.2 Hz average), 4.91 (s, 2H).

General Procedure for the Synthesis of Thioureas:

A protected diamine such as N-Boc-1,4-diaminobutane or N-Boc-1,5-diaminopentane (1 equivalent) was dissolved in tetrahydrofuran and stirred at room temperature. Benzoyl isothiocyanate (1 equivalent) was added dropwise to the reaction mixture. The resulting mixture was stirred at room temperature for 24 hours and the solvent was removed under reduced pressure to give a yellow oil. The yellow oil (1 equivalent) was then dissolved in methanol, and aqueous potassium carbonate (3 equivalents) solution added, and the mixture stirred for 48 hours. Water was added to the reaction mixture which was then extracted in 2×75 ml ethyl acetate. The combined extracts were washed with water, dried with anhydrous sodium sulfate, filtered and the solvent removed under reduced pressure to give the desired thiourea.

tert-Butyl 5-[(aminocarbothioyl)amino]pentylcarbamate was obtained as a light yellow wax from tert-butyl 5-{[(benzoylamino)carbothioyl]amino}-pentylcarbamate: $^1$H NMR (CD$_3$OD) δ 3.44 (m, 1H), 03.10 (m, 1H), 3.01 (t, 2H, J=6.7 Hz), 1.60–1.31 (m, 6H), 1.41 (s, 9H); 262 (ESMS, MH$^+$).

tert-Butyl 5-{[(benzoylamino)carbothioyl]amino}-pentylcarbamate was obtained a light yellow solid in 79% yield from N-BOC-1,5-diaminopentane and benzoyl isothiocyanate: m.p. 90–93° C.; $^1$H NMR δ NMR data.

trans-tert-Butyl-{4-[(aminocarbothioyl)amino]cyclohexyl}-methylcarbamate was obtained as a light yellow wax from trans-tert-butyl-(4-{[(benzoylamino)carbothioyl]amino}-cyclohexyl)-methylcarbamate: $^1$H NMR (CD$_3$OD) δ 3.92 (m, 1H), 2.86 (m, 2H), 2.00 (m, 2H), 1.76 (m, 2H), 1.41 (s, 9H), 1.37 (m, 1H), 1.06 (m, 4H); 288 (ESMS, MH$^+$).

trans-tert-Butyl-(4-{[(benzoylamino)carbothioyl]amino)-cyclohexyl)-methylcarbamate was obtained as a yellow solid in 97% yield from tert-butyl 4-aminocyclohexylmethylcarbamate and benzoyl isothiocyanate.

trans-tert-Butyl 4-aminocyclohexylmethylcarbamate was obtained in more than 95% yield by hydrogenation of benzyl 4-{[(tert-butoxycarbonyl)amino]methyl}cyclocarbamate.

Benzyl-4-[[[tert-butoxycarbonyl]amino]methyl]cyclohexylcarbamate: To a stirred suspension of 4-[[(tert-butoxycarbonyl)amino]methyl]cyclohexanecarboxylic acid (Maybridge Chemical Co., Ltd.) (45 g) and diphenylphosphoryl azide (44 ml) in toluene (600 ml) was added triethylamine (32 ml) over a period of 20 min whilst maintaining the internal temperature at −10–0 C. The mixture was slowly warmed and then stirred at 70 C for 4 h. After cooling to 40 C, benzyl alcohol (36 ml) was added and the reaction mixture heated at reflux for 20 h. The cold reaction mixture was washed with water and brine and dried over anhydrous magnesium sulfate. Removal of the solvent and recrystallization of the organic residue from ethyl acetate and diethyl ether gave the title compound, benzyl-4-[[[tert-butoxycarbonyl]amino]methyl]cyclohexylcarbamate as a white solid, m.p. 129–131 C.

trans-Benzyl-4-{[(aminocarbothioyl)amino]methyl}-cyclohexylcarbamate was obtained as a yellow solid in 71% yield from trans-benzyl 4-({[(Benzoylamino) carbothioyl]-amino}methyl)-cyclohexylcarbamate; 322 (ESMS, MH$^+$).

trans-Benzyl 4-({[(benzoylamino)carbothioyl] amino}methyl)-cyclohexylcarbamate was obtained as a yellow solid from benzyl 4-(aminomethyl)cyclohexylcarbamate and benzoyl isothiocyanate.

trans-Benzyl 4-(aminomethyl)cyclohexylcarbamate was obtained as a white solid in more than 95% yield by stirring benzyl 4-{[(tert-butoxycarbonyl)amino]methyl}-cyclocarbamate in 2N HCl (made from 1:1 of EtOAc and 4N HCl in dioxane).

General Procedure for the Synthesis of Bicyclic Thiazoles:

A mixture of a bromoketone (1 equivalent), thiourea (1 equivalent), and diisopropylethylamine (2 equivalents) in acetone or anhydrous ethanol was heated at reflux overnight. The solvent was evaporated, the brown residue dissolved in dichloromethane and washed with saturated aqueous sodium bicarbonate solution. The mixture was extracted with dichloromethane three times. The combined extracts were dried over anhydrous sodium sulfate and the solvent removed to afford a crude product which was purified by flash column chromatography (silica gel, hexanes:ethyl acetate).

tert-Butyl-5-{[4-(2-pyridinyl)-1,3-thiazol-2-yl]amino}-pentyl-carbamate was obtained as a brown syrup in 97% yield from 2-bromo-1-(2-pyridinyl)-1-ethanone hydrogen bromide and tert-butyl 5-[(aminocarbothioyl)amino]pentyl-carbamate: $^1$H NMR δ 9.57 (m, 1H), 7.91 (d, 1H, J=7.8 Hz), 7.70 (td, 1H, J=1.5, 7.8 Hz), 7.27 (s, 1H), 7.16 (dd, 1H, J=4.8, 7.2 Hz), 5.36 (b, 1H), 4.57 (b, 1H), 3.30 (q, 2H, J=6.1 Hz), 3.12 (m, 2H), 1.68 (m, 2H), 1.56–1.42 (m, 4H), 1.44 (s, 9H).

tert-Butyl-5-({[4-(3-pyridinyl)-1,3-thiazol-2-yl]amino}-pentylcarbamate was obtained as a light yellow solid in 55% yield from 2-bromo-1-(3-pyridinyl)-1-ethanone hydrogen bromide and tert-butyl 5-[(aminocarbothioyl)amino]-pentyl-carbamate: $^1$H NMR δ 9.03 (d, 1H, J=1.8 Hz), 8.51 (dd, 1H, J=0.9, 4.8 Hz), 8.07 (m, 1H), 7.29 (dd, 1H, J=4.8, 7.8 Hz), 6.78 (s, 1H), 5.32 (m, 1H), 4.55 (b, 1H), 3.32 (q, 2H, J=6.0 Hz), 3.15 (m, 2H), 1.74 (m, 2H), 1.48 (m, 4H), 1.45 (s, 9H); ESMS m/e=362.95 (MH$^+$).

tert-Butyl-5-{[4-(4-pyridinyl)-1,3-thiazol-2-yl]amino}-pentylcarbamate was obtained as a yellow solid in 51% yield from 2-bromo-1-(4-pyridinyl)-1-ethanone hydrogen bromide and tert-butyl 5-[(aminocarbothioyl)amino]pentylcarbamate: $^1$H NMR δ 8.59 (dd, 2H, J=1.5, 4.8 Hz), 7.65 (dd, J=1.5, 4.8 Hz), 6.93 (s, 1H), 5.30 (b, 1H), 4.56 (b, 1H), 6.32 (q, 2H, J=6.0 Hz), 3.14 (m, 2H), 1.75 (m, 2H), 1.48 (m, 2H), 1.44 (s, 9H); ESMS m/e=362.87 (MH$^+$).

trans-Benzyl-4-({[4-(2-pyridinyl)-1,3-thiazol-2-yl] amino}-methyl)cyclohexylcarbamate was obtained as a dark brown oil from 2-bromo-1-(2-pyridinyl)-1-ethanone hydrogen bromide and trans-benzyl 4-([(aminocarbothioyl) amino]methyl)-cyclohexylcarbamate: $^1$H NMR δ 8.57 (m, 1H), 7.89 (d, 1H, J=7.2 Hz), 7.71 (m, 1H), 7.45 (m, 1H), 7.35 (m, 5H), 7.17 (m, 1H), 5.33 (m, 1H), 5.08 (s, 2H), 4.61 (m, 1H), 3.48 (m, 1H), 3.16 (t, 2H, J=6.3 Hz), 2.07 (m, 2H), 1.88 (m, 2H), 1.63 (m, 1H), 1.13 (m, 4H); ESIMS m/e=423.2 (MH$^+$).

trans-Benzyl-4-({[4-(3-pyridinyl)-1,3-thiazol-2-yl] amino}-methyl)cyclohexylcarbamate was obtained as a dark brown oil from 2-bromo-1-(3-pyridinyl)-1-ethanone hydrogen bromide and trans-benzyl 4-{{[(aminocarbothioyl) amino]methyl}-cyclohexylcarbamate: $^1$H NMR δ 9.13 (d, 1H, J=2.1 Hz), 8.83 (dd, 1H, J=1.8, 4.8 Hz), 8.21 (m, 1H), 7.45 (m, 1H), 6.77 (s, 1H), 5.41 (m, 1H), 5.08 (s, 2H), 4.62 (m, 1H), 3.47 (m, 1H), 3.17 (t, 2H, J=6.5 Hz), 2.07 (m, 2H), 1.89 (m, 2H), 1.61 (m, 1H), 1.13 (m, 4H); ESIMS m/e=423.2 (MH$^+$).

trans-Benzyl-4-({[4-(4-pyridinyl)-1,3-thiazol-2-yl] amino}-methyl)cyclohexylcarbamate was obtained as a dark brown oil from 2-bromo-1-(4-pyridinyl)-1-ethanone hydrogen bromide and trans-benzyl 4-{[(aminocarbothioyl) amino]methyl}-cyclohexylcarbamate: $^1$H NMR δ 8.59 (d, 2H, J=4.5 Hz), 7.64 (d, 2H, J=4.5 Hz), 6.93 (s, 1H), 5.31 (m, 1H), 5.08 (s, 2H), 4.60 (m, 1H), 3.49 (m, 1H), 3.18 (t, 2H, J=6.6 HzO, 2.09 (m, 2H), 1.91 (m, 2H), 1.65 (m, 1H), 1.14 (m, 4H); ESIMS m/e=423.2 (MH$^+$).

tert-Butyl N-{[4-({4-[1-(Phenylsulfonyl)-1H-3-pyrrolyl]-1,3-thiazol-2-yl}amino)cyclohexyl]methyl}carbamate: 73% yield, 517 (ESMS, MH$^+$); $^1$H NMR (CDCl$_3$) δ 7.93 (d, 2H, J=7.6 Hz), 7.68–7.46 (m, 4H), 7.19 (m, 1H), 6.68 (b, 1H), 6.58 (m, 1H), 6.53 (s, 1H), 3.40 (m, 1H), 3.29 (m, 2H), 2.89 (t, 2H, J=6.5 Hz), 1.96 (ABm, 4H), 1.42 (s, 9H), 1.30–0.99 (m, 4H).

tert-Butyl N-[(4-[4-(1,3-thiazol-2-yl)-1,3-thiazol-2-yl] aminocyclohexyl)methyl]carbamate: 57% yield, 395 (ESMS, MH$^+$); $^1$H NMR (CDCl$_3$) δ 7.79 (d, 1H, J=3.4 Hz), 7.28 (d, 1H, J=3.1 Hz), 7.19 (s, 1H), 5.12 (d, 1H, J=8.0 Hz), 4.61 (b, 1H), 3.26 (m, 1H), 3.01 (t, 2H, J=6.5 Hz), 2.05 (ABm, 4H), 1.44 (s, 9H), 1.30–1.02 (m, 5H).

tert-Butyl N-[(4-[4-(1,3-Thiazol-2-yl)-1,3-thiazol-2-yl] aminocyclohexyl)methyl]carbamate: 31% yield, 394 (ESMS, MH$^+$); $^1$H NMR (CDCl$_3$) δ 7.74 (dd, 1H, J=1.3, 8.3 Hz), 7.51–7.39 (m, 2H), 5.91 (apparent d, 1H, J=7.1 Hz), 4.62 (b, 1H), 3.93 (m, 1H), 3.00 (apparent t, 2H, J=6.2 Hz), 1.98 (ABm, 4H), 1.77 (b, 1H), 1.44 (s, 9H), 1.43 (m, 1H), 1.28–1.09 (m, 4H).

trans-tert-Butyl N-[(4-[4-(5-phenyl-3-isoxazolyl)-1,3-thiazol-2-yl]aminocyclohexyl)methyl]carbamate: 75% yield, 455 (ESMS, MH$^+$); $^1$H NMR (CDCl$_3$) δ 7.89 (m, 2H), 7.44 (m, 3H), 7.09 (s, 1H), 6.83 (s, 1H), 5.62 (b, 1H), 4.61 (m, 1H), 3.31 (m, 1H), 3.03 (m, 2H), 2.08 (ABm, 4H), 1.47 (s, 9H), 1.42–1.05 (m, 5H).

trans-tert-Butyl N-[(4-[4-(2,5-dimethyl-1,3-thiazol-4-yl)-1,3-thiazol-2-yl]aminocyclohexyl)methyl]carbamate: 37% yield, 423 (ESMS, MH$^+$); $^1$H NMR (CDCl$_3$) δ 6.43 (s, 1H), 5.04 (d, 1H, J=8.2 Hz), 4.59 (m, 1H), 3.26 (m, 1H), 3.01 (d, 2H, J=6.0 Hz), 2.64 (s, 3H), 2.55 (s, 3H), 2.04 (ABm, 4H), 1.44 (s, 9H), 1.28–1.03 (m, 5H).

General Procedure for the Deprotection of the Boc-bicyclic Thiazoles Intermediates:

The Boc protected 2-amino-1,3-thiazole intermediate was treated with 2N hydrogen chloride in 1,4-dioxane and ethyl acetate (prepared from 4N HCl in dioxane) at room temperature for 2 hours or longer as needed. The solvent was removed in vacuo and the desired compound was collected by filtration.

trans-N2-[4-(Aminomethyl)cyclohexyl]-4-(1,3-thiazol-2-yl)-1,3-thiazol-2-amine hydrochloride: 100% yield, 295 (ESMS, MH$^+$); 1H NMR (CD$_3$OD) δ 8.02 (d, 1H, J=3.6 Hz), 7.84 (d, 1H, J=3.6 Hz), 7.59 (s, 1H), 3.60 (m, 1H), 2.83 (d, 2H, J=7.0 Hz), 2.19 (ABm, 4H), 1.69 (m, 1H), 1.45(m, 2H), 1.22 (m, 2H).

trans-N2-[4-(Aminomethyl)cyclohexyl]-4-(2,5-dimethyl-1,3-thiazol-4-yl)-1,3-thiazol-2-amine hydrochloride: 100% yield, 323 (ESMS, MH$^+$); $^1$H NMR (CD$_3$OD) δ 7.02 (s, 1H), 3.72 (m, 1H), 2.88 (s, 3H), 2.81 (d, 2H, J=7.5 Hz), 2.56 (s, 3H), 2.06 (ABm, 4H), 1.68 (m, 1H), 1.46–1.14 (m, 4H).

trans-N2-[4-(Aminomethyl)cyclohexyl]-4-(5-phenyl-3-isoxazolyl)-1,3-thiazol-2-amine hydrochloride: 100% yield, 355(ESMS, MH$^+$); $^1$H NMR (CD$_3$OD) δ 7.87 (m, 2H), 7.50–7.40 (m, 5H), 3.81 (m, 1H), 2.84 (d, 2H, J=7.5 Hz), 2.08 (ABm, 4H), 1.68 (m, 1H), 1.47–1.17 (m, 4H).

trans-N2-[4-(Aminomethyl)cyclohexyl]-4-[1-(phenylsulfonyl)-1H-3-pyrrolyl]-1,3-thiazol-2-amine hydrochloride: 100% yield, 417 (ESMS, MH$^+$); $^1$H NMR (CD$_3$OD) δ 8.00 (d, 2H, J=7.0 Hz), 7.88 (s, 1H), 7.71 (m, 1H), 7.60 (m, 2H), 7.36 (m, 1H), 6.90 (s, 1H), 6.67 (m, 1H), 3.65 (m, 1H), 2.83 (d, 2H, J=7.5 Hz), 2.06 (ABm, 4H), 1.69 (m, 1H), 1.54–1.13 (m, 4H).

$N^1$-[4-(2-Pyridinyl)-1,3-thiazol-2-yl]-1,5-pentanediamine trihydrogen chloride was obtained as a yellow solid in more than 95% yield from tert-butyl 5-{[4-(2-pyridinyl)-1,3-thiazol-2-yl]amino}pentylcarbamate: $^1$H NMR (CD$_3$OD) δ 8.65 (d, 1H, J=6.0 Hz), 8.48–8.37 (m, 2H), 7.85 (s, 1H), 7.80 (m, 1H), 3.51 (t, 2H, J=6.6 Hz), 2.94 (m, 2H), 1.74 (m, 4H), 1.53 (m, 2H); ESIMS m/e=(MH$^+$).

$N^1$-[4-(3-Pyridinyl)-1,3-thiazol-2-yl]-1,5-pentanediamine trihydrogen chloride was obtained as a yellow solid in more than 95% yield from tert-butyl 5-{[4-(3-pyridinyl)-1,3-thiazol-2-yl]amino}pentylcarbamate: $^1$H NMR (CD$_3$OD) δ 9.29 (d, 1H, J=1.8 Hz), 8.97 (m, 1H), 8.81 (d, 1H, J=5.7 Hz), 8.14 (dd, 1H, J=5.7, 8.1 Hz), 7.50 (s, 1H), 3.51 (t, 2H, J=6.9 Hz), 2.94 (m, 2H), 1.75 (m, 4H), 1.55 (m, 2H); ESIMS m/e=262.85 (MH$^+$).

$N^1$-[4-(4-Pyridinyl)-1,3-thiazol-2-yl]-1,5-pentanediamine trihydrogen chloride was obtained as a yellow solid in more than 95% yield from tert-butyl 5-([4-(4-pyridinyl)-1,3-thiazol-2-yl]amino}pentylcarbamate: $^1$H NMR (CD$_3$OD) δ 8.79 (d, 2H, J=6.6 Hz), 8.42 (d, 2H, J=6.6 Hz), 7.90 (s, 1H), 3.50 (t, 2H, J=6.8 Hz), 2.94 (m, 2H), 1.75 (m, 4H), 1.54 (m, 2H), ESIMS m/e=262.80 (MH$^+$).

N1-[4-(5-Phenyl-3-isoxazolyl)-1,3-thiazol-2-yl]-1,5-pentanediamine hydrochloride: 50% yield from the corresponding commercial bromoketone: $^1$H NMR (CDCl$_3$) δ 7.90–7.79 (m, 2H), 7.55–7.45 (m, 3H), 7.22 (s, 1H), 7.10 (s, 1H), 3.42 (t, 2H, J=5.6 Hz), 3.30–3.22 (m, 2H), 2.95 (t, 2H, J=5.6 Hz), 1.80–1.42 (m, 6H)

General Procedure for the Derivatization of Amines with Carboxylic Acid and Sulfonic Acid Derivatives An amine such as N1-[4-(5-phenyl-3-isoxazolyl)-1,3-thiazol-2-yl]-1,5-pentanediamine (0.305 mmol) was dissolved in 2 ml CH$_2$Cl$_2$ containing 2 equivalents of diisopropylethylamine. A sulfonyl chloride, sulfamoyl chloride, acid chloride or carbamoyl chloride (1–3 equivalents) was added dropwise. The reaction mixture was stirred at room temperature for 1–3 days, quenched with water, washed with 10% NaHCO$_3$ solution, dried over Na$_2$SO$_4$ and chromatographed using column chromatography or preparative TLC.

General Procedure for the Formation of Formamides:

tert-Butyl N-[4-(isopropylamino)cyclohexyl]methylcarbamate:

Isopropyl iodide (2 equivalents) was added dropwise to a suspension of tert-butyl N-[4-aminocyclohexyl]methyl-carbamate (1 equivalent) and diisopropylethyl amine (3 equivalents) in THF. The resulting mixture was stirred for 1 day. TLC analysis showed some starting amine. Additional isopropyl iodide (1 equivalent) and diisopropylethyl amine (3 equivalents) were added to the reaction mixture and heated at 40° C. for 1 day. The reaction mixture was concentrated and chromatrographed to give tert-butyl N-[4-(isopropylamino)cyclohexyl]methylcarbamate: 22% yield, 271 (ESMS, MH$^+$); $^1$H NMR (CDCl$_3$) δ 4.65 (broad, 1H), 2.91 (m, 3H), 2.42 (m, 1H), 1.80 (ABm, 4H), 1.38 (s, 9H), 0.98 (d, 6H, J=6.3 Hz), 1.32–0.85 (m, 5H).

Similarly, tert-butyl N-[4-(2-methoxyethylamino)-cyclohexyl]methylcarbamate was obtained (2-methoxyethyl bromide and n-Bu$_4$NI were used): 35% yield, 378 (ESMS, MH$^+$); 1H NMR (CDCl$_3$) δ 4.64 (broad, 1H), 3.44 (m, 2H), 3.31 & 3.30 (two s, 3H), 2.92 (m, 2H), 2.74 (m, 2H), 2.33 (m, 1H), 1.81 (ABm, 4H), 1.39 & 1.38 (two s, 9H), 1.34 (m, 1H), 0.98 (m, 4H).

tert-Butyl-N-[4-(isopropylformylamino)cyclohexyl]methyl-carbamate

A solution of a tert-butyl N-[4-(isopropylamino)-cyclohexyl]methylcarbamate (7.89 mmol, 1 equivalent) in 5 ml of THF was added dropwise to a solution of 1H-benzotriazole-1-carboxaldehyde (8.68 mmol, 1.2 equivalents) in 10 ml of THF at room temperature. The reaction mixture was stirred overnight and heated at reflux temperature for two hours. 1H-benzotriazole-1-carboxaldehyde (additional 1 equivalent) was added to the reaction mixture and stirred overnight. The solvent was removed and dichloromethane was added to the residue. The organic phase was washed with 2N NaOH solution, saturated with NaCl solution, dried over Na$_2$SO$_4$, the solvent removed, and the residue chromatographed to give tert-butyl N-[4-(isopropylformylamino)cyclohexyl]-methyl-carbamate: 100% yield, 299 (ESMS, MH⁺); $^1$H NMR (CD$_3$OD) δ 8.22 & 8.18 (two s, 1H), 4.63 (broad, 1H), 4.30 & 3.60 (two m, 1H), 3.76 (m, 1H), 2.99 (m, 2H), 1.44 (s, 9H), 1.27 (d, 3H, J=6.5 Hz), 1.21 (d, 3H, J=6.5 Hz), 1.91–0.82 (m, 9H).

Similarly, N-[4-(2-methoxyethylformylamino) cyclohexyl]-methylcarbamate was prepared: 58% yield; 315 (ESMS, MH⁺); $^1$H NMR (CDCl$_3$) δ 8.25 & 8.16 (two s, 1H), 4.80 (broad, 1H), 4.07 & 3.23 (two m, 1H), 3.50 (m, 2H), 3.40–3.33 (m, 2H), 3.31 (s, 3H), 2.99 (m, 2H), 1.46 (s, 9H), 1.86–0.95 (m, 9H).

N-[4-(Aminomethyl)cyclohexyl]-N-isopropylformamide: Dioxane containing HCl was added (10 ml of 4N HCl solution) to a solution of tert-butyl N-[4-(isopropylformylamino)-cyclohexyl]methylcarbamate dissolved in 10 ml Et$_2$O, stirred at room temperature for 2 hours and the solvent removed under reduced pressure to obtain N-[4-(aminomethyl)cyclohexyl]-N-isopropylformamide: 100% yield, 199 (ESMS, MH⁺); $^1$H NMR (CD$_3$OD) δ 8.16 (s, 1H), 4.16 & 3.57 (two m, 1H), 3.70 (m, 1H), 2.79 (m, 2H), 1.36 (m, 6H), 1.91–1.06 (m, 9H).

Similarly, N-[4-(aminomethyl)cyclohexyl]-N-(2-methoxyethyl-formamide was obtained: 100% yield; 215 (ESMS, MH⁺); $^1$H NMR (CD$_3$OD) δ 8.44 & 8.03 4.65 (two s, 1H), 3.79–3.36 (m, 7H), 3.71 (s, 3H), 2.12–1.13 (m, 9H).

N-Benzoyl-N'-[4-(isopropylformylamino)cyclohexyl]-methylthiourea:

A mixture of N-[4-(aminomethyl)cyclohexyl]-N-isopropyl-formamide salt (4.55 mmol, 1 equivalent), benzoyl isothiocyanate (5.46 mmol, 1.2 equivalent) and triethylamine (5.46 mmol, 1.2 equivalent) in THF (50 ml) were stirred at room temperature overnight. The removal of the solvent and chromatography (silica) afforded the desired product: 39% yield, 362 (ESMS, MH⁺); $^1$H NMR (CDCl$_3$) δ 10.87 (broad, 1H), 9.20 (broad, 1H), 8.20 & 8.18 (two s, 1H), 7.83 (d, 2H, J=7.7 Hz), 7.60 (m, 1H), 7.49 (m, 2H), 4.26 (m, 1H), 3.76 & 3.08 (two m, 1H), 3.57 (m, 2H), 1.25 (d, 3H, J=6.8 Hz), 1.19 (d, 3H, J=6.8 Hz), 1.97–1.03 (m, 9H).

Similarly, N-Benzoyl-N'-[4-(2-methoxyethylformylamino)-cyclohexyl]methylthiourea was obtained: 100% yield, 378 (ESMS, MH⁺); $^1$H NMR (CDCl$_3$) δ 10.85 (broad, 1H), 9.03 (broad, 1H), 8.18 & 8.08 (two s, 1H), 7.84 (d, 2H, J=7.9 Hz), 7.64 (m, 1H), 7.52 (d, 2H, J=7.8 Hz), 3.63–3.24 (m, 7H), 3.34 & 3.33 (two m, 3H), 2.03–1.13 (m, 9H).

N-[4-(Isopropylformylamino)cyclohexyl]methylthiourea:

An aqueous solution of K$_2$CO$_3$ (2 equivalents) in water was added to a solution of N-benzoyl-N'-[4-(isopropylformylamino)cyclohexyl]methylthiourea in MeOH and stirred at room temperature overnight. The solvent was removed in vacuo and the residue was dissolved in EtOH. The solution was filtered to remove a white precipitate and the filtrate was concentrated. The crude product was chromatographed to yield the desired product: 100% yield; 258 (ESMS, MH⁺); 1H NMR (CD$_3$OD) δ 8.15 & 8.13 (two s, 1H), 4.15 & 3.73 (two m, 1H), 3.34 & 2.97 (two m, 1H), 3.29 (m, 2H), 1.26 (d, 3H, J=6.7 Hz), 1.23 (d, 3H, J=6.7 Hz), 1.91–1.03 (m, 9H).

Similarly, N-[4-(2-methoxyethylformylamino)cyclohexyl]-methylthiourea was prepared: 77% yield, 274 (ESMS, MH⁺); $^1$H NMR (CD$_3$OD) δ 8.15 & 8.00 (two s, 1H), 7.55 & 7.43 (two m, 1H), 3.90 & 2.97 (two m, 1H), 3.46–3.28 (m, 10H), 1.90–0.99 (m, 9H).

General Procedure for the Formation of 2-aminothiazoles Containing a Formamide:

A thiourea such as N-[4-(isopropylformylamino)cyclohexyl]-methylthiourea (0.029 mmol, 1 equivalent), a bromoketone (0.044 mmol, 1.5 equivalent) and 2 equivalents of diisopropylethyl amine in 10 ml of EtOH were heated at reflux temperature for 2 days. The reaction mixture was concentrated in vacuo and the crude product chromatographed (silica) to obtain the desired product. This procedure was used to prepare examples 101–102.

A combination of procedures contained in Schemes 6–10 were used to prepare examples 59–100.

EXAMPLE 59

2-(5-Diethylaminosulfonylamino)pentylamino-4-(2-pyridyl)-thiazole hydrogen chloride was obtained as a brown oil in 2% from N$^1$-[4-(2-pyridinyl)-1,3-thiazol-2-yl]-1,5-pentanediamine trihydrogen chloride and diethyl sulfamoyl chloride: $^1$H NMR (free base) δ 8.56 (d, 1H, J=4.5 Hz), 7.89 (d, 1H, J=8.0 Hz), 7.67 (td, 1H, J=1.4, 7.8 Hz), 7.72 (s, 1H), 7.16 (m, 1H), 5.66 (m, 1H), 4.57 (t, 1H, J=6.0 Hz), 3.27 (m, 6H), 2.95 (q, 2H, J=6.6 Hz), 1.64 (m, 2H), 1.50 (m, 2H), 1.42 (m, 2H), 1.61 (t, 6H, J=7.1 Hz); ESIMS m/e=398 (MH⁺).

EXAMPLE 60

4-(2-Pyridyl)-2-(5-(2-thienyl)sulfonylaminopentyl)-amino-thiazole hydrogen chloride was obtained as a yellow solid in 67% from N$^1$-[4-(2-pyridinyl)-1,3-thiazol-2-yl]-1,5-pentanediamine trihydrogen chloride and 2-thiophene-sulfonyl chloride: m.p. 75–77° C.; $^1$H NMR (free base) δ 8.56 (d, 1H, J=4.6 Hz), 7.86 (dd, 1H, J=0.5, 7.8 Hz), 7.69 (td, 1H, J=1.3, 7.7 Hz), 7.61–7.56 (m, 2H), 7.24 (s, 1H), 7.16 (m, 1H), 7.07 (m, 1H), 5.56 (m, 1H), 5.24 (m, 1H), 3.26 (m, 2H), 3.02 (m, 2H), 1.60 (m, 2H), 1.48 (m, 2H), 1.39 (m, 2H); ESIMS m/e=409 (MH⁺).

EXAMPLE 61

2-(5-(2-Fluorophenyl)sulfonylamino)pentylamino-4-(2-pyridyl)-thiazole hydrogen chloride was obtained as a yellow solid in 81% from N$^1$-[4-(2-pyridinyl)-1,3-thiazol-2-yl]-1,5-pentanediamine trihydrogen chloride and 2-fluorobenzenesulfonyl chloride: m.p. 60–63° C.; $^1$H NMR (free base) δ 8.57 (dd, 1H, J=0.7, 4.8 Hz), 7.90 (m, 2H), 7.69 (td, 1H, J=1.7, 7.8 Hz), 7.57 (m, 1H), 7.20 (m, 3H), 5.46 (m, 1H), 5.13 (m, 1H), 3.24 (q, 2H, J=6.1 Hz), 2.98 (m, 2H), 1.59 (m, 2H), 1.50 (m, 2H), 1.38 (m, 2H); ESIMS m/e=421 (MH⁺)

EXAMPLE 62

2-(5-(4-Methoxyphenyl)sulfonylamino)pentylamino-4-(2-pyridyl)thiazole hydrogen chloride was obtained as a light brown solid in 46% from N$^1$-[4-(2-pyridinyl)-1,3-thiazol-2-yl]-1,5-pentanediamine trihydrogen chloride and 4-methoxy benzene sulfonyl chloride: m.p. 54–57° C.; $^1$H NMR (free base) δ 8.54 (m, 1H), 7.80 (m, 3H), 7.65 (td, 1H, J=1.7, 7.7 Hz), 7.22 (s, 1H), 7.14 (m, 1H), 6.92 (d, 2H, J=8.9 Hz), 5.81 (m, 1H), 5.49 (m, 1H), 3.82 (s, 3H), 3.18 (q, 2H, J=6.0 Hz), 2.86 (q, 2H, J=6.1 Hz), 1.52 (m, 2H), 1.40 (m, 2H), 1.30 (m, 2H); ESIMS m/e=433 (MH⁺).

EXAMPLE 63

2-(5-(3,5-Dimethylisoxazol-4-yl)sulfonylamino)pentylamino-4-(2-pyridyl)thiazole hydrogen chloride was obtained as a yellow solid in 87% from $N^1$-[4-(2-pyridinyl)-1,3-thiazol-2-yl]-1,5-pentanediamine trihydrogen chloride and 3,5-dimethylisoxazole-4-sulphonyl chloride: $^1$H NMR (free base) δ 8.55 (m, 1H), 7.84 (d, 1H, J=8.0 Hz), 7.69 (td, 1H, J=1.7, 7.6 Hz), 7.22 (s, 1H), 7.17 (m, 1H), 5.75 (b, 1H) 5.58 (b, 1H), 3.25 (t, 2H, J=6.4 Hz), 2.93 (t, 2H, J=6.7 Hz), 2.62 (s, 3H), 2.40 (s, 3H), 1.60 (m, 2H), 1.48 (m, 2H), 1.36 (m, 2H); ESIMS m/e=422 (MH$^+$).

EXAMPLE 64

2-(5-(3,4-Difluorophenyl)sulfonylamino)pentylamino-4-(2-pyridyl)thiazole hydrogen chloride was obtained as a yellow solid in 76% from $N^1$-[4-(2-pyridinyl)-1,3-thiazol-2-yl]-1,5-pentanediamine trihydrogen chloride and 3,4-difluorobenzenesulfonyl chloride: m.p. 65–68° C.; $^1$H NMR (free base) δ 8.55 (dt, 1H, J=0.8, 4.8 Hz), 7.84 (d, 1H, J=8.2 Hz), 7.75–7.63 (m, 3H), 7.33–7.15 (m, 3H), 5.59 (m, 1H), 5.36 (m, 1H), 3.25 (t, 2H, J=6.7 Hz), 2.94 (t, 2H, J=6.7 Hz), 1.60 (m, 2H), 1.48 (m, 2H), 1.37 (m, 2H); ESIMS m/e=439 (MH$^+$).

EXAMPLE 65

2-(5-(2-Methoxy-5-methylphenyl)sulfonylamino)pentylamino-4-(2-pyridyl)thiazole hydrogen chloride was obtained as a pale yellow solid in 69% from N1-[4-(2-pyridinyl)-1,3-thiazol-2-yl]-1,5-pentanediamine trihydrogen chloride and 6-methoxy-m-toluene-sulfonyl chloride: m.p. 155–156° C.; $^1$H NMR (free base) δ 8.57 (m, 1H), 7.88 (d, 1H, J=7.9 Hz), 7.69 (m, 2H), 7.30 (dd, 1H, J=1.6, 8.4 Hz), 7.15 (m, 1H), 6.90 (d, 1H, J=8.4 Hz), 5.40 (m, 1H), 5.04 (m, 1H) 3.91 (s, 3H), 3.24 (q, 2H, J=6.4 Hz), 2.86 (q, 2H, J=6.5 Hz), 2.32 (s, 3H), 1.59 (m, 2H), 1.47 (m, 2H), 1.37 (m, 2H); ESIMS m/e=447 (MH$^+$).

EXAMPLE 66

2-(5-(Benzylsulfonylamino)pentylamino-4-(2-pyridyl)thiazole hydrogen chloride was obtained as a yellow solid in 38% from $N^1$-[4-(2-pyridinyl)-1,3-thiazol-2-yl]-1,5-pentane-diamine trihydrogen chloride and α-toluene sulfonyl chloride: m.p. 62–64° C.; $^1$H NMR (free base) δ 8.56 (dt, 1H, J=0.7, 4.8 Hz), 8.55 (d, 1H, J=7.9 Hz), 7.70 (td, 1H, J=1.7, 7.7 Hz), 7.37 (m, 5H), 7.25 (s, 1H), 7.16 (m, 1H), 5.51 (m, 1H), 4.57 (m, 1H), 4.25 (s, 2H), 3.25 (q, 2H, J=6.2 Hz), 2.94 (q, 2H, J=6.4 Hz), 1.58 (m, 2H), 1.45 (m, 2H), 1.36 (m, 2H); ESIMS m/e=417 (MH$^+$).

EXAMPLE 67

2-(5-(Ethylsulfonylamino)pentyl)amino-4-(2-pyridyl)thiazole hydrogen chloride was obtained as a yellow solid from $N^1$-[4-(2-pyridinyl)-1,3-thiazol-2-yl]-1,5-pentanediamine trihydrogen chloride and ethanesulfonyl chloride: m.p. 49–51° C.; $^1$H NMR (CD$_3$OD) δ 8.64 (m, 1H), 8.45–8.35 (m, 2H), 7.84–7.77 (m, 2H), 3.49 (m, 2H), 3.01 (m, 4H), 1.72 (m, 2H), 1.61 (m, 2H), 1.52 (m, 2H), 1.27 (t, 3H, J=7.4 Hz); ESIMS m/e=355 (MH$^+$).

EXAMPLE 68

2-(5-(Trifluoromethylsulfonylamino)pentyl)amino-4-(2-pyridyl)thiazole hydrogen chloride was obtained as a yellow solid from $N^1$-[4-(2-pyridinyl)-1,3-thiazol-2-yl]-1,5-pentanediamine trihydrogen chloride and trifluoromethane sulfonyl chloride: m.p. 63–65° C.; $^1$H NMR (CD$_3$OD) δ 8.76 (m, 1H), 8.62 (m, 1H), 8.40 (m, 1H), 7.96 (m, 1H), 7.80 (m, 1H), 3.28 (m, 2H), 3.19 (m, 2H), 1.74–1.59 (m, 4H), 1.47 (m, 2H); ESIMS m/e=395 (MH$^+$).

EXAMPLE 69

2-(5-(Aminosulfonylamino)pentyl)amino-4-(2-pyridyl)thiazole hydrogen chloride was obtained as a yellow solid from $N^1$-[4-(2-pyridinyl)-1,3-thiazol-2-yl]-1,5-pentanediamine trihydrogen chloride and sulfamide: m.p. 68–70° C.; $^1$H NMR (CD$_3$OD) δ 8.46 (dd, 1H, J=0.6, 4.3 Hz), 7.93 (d, 1H, J=7.9 Hz), 7.81 (td, 1H, J=1.7, 7.7 Hz), 7.25 (m, 1H), 7.18 (s, 1H), 3.34 (t, 2H, J=7.0 Hz), 3.02 (t, 2H, J=7.0 Hz), 1.65 (m, 2H), 1.60 (m, 2H), 1.47 (m, 2H); ESIMS m/e=342 (MH$^+$).

EXAMPLE 70

2-(5-(2-Fluorophenyl)sulfonylamino)pentylamino-4-(3-pyridyl)thiazole hydrogen chloride was obtained as a yellow solid in 47% from $N^1$-[4-(3-pyridinyl)-1,3-thiazol-2-yl]-1,5-pentanediamine trihydrogen chloride and 2-fluorobenzenesulfonyl chloride: m.p. 84–85° C.; $^1$H NMR (free base) δ 9.02 (d, 1H, J=2.1 Hz), 8.51 (m, 1H), 8.05 (dt, 1H, J=1.5, 7.9 Hz), 7.90 (td, 1H, J=1.2, 7.3 Hz), 7.55 (m, 1H), 7.32–7.17 (m, 3H), 6.77 (s, 1H), 5.69 (m, 1H), 5.28 (m, 1H), 3.24 (q, 2H, J=6.4 Hz), 3.00 (q, 2H, J=6.5 Hz), 1.59 (m, 2H), 1.50 (m, 2H), 1.40 (m, 2H); ESIMS m/e=420.81 (MH$^+$).

EXAMPLE 71

2-(5-(3,5-Dimethylisoxazol-4-yl)sulfonylamino)pentylamino-4-(3-pyridyl)thiazole hydrogen chloride was obtained as a yellow solid in 41% from $N^1$-[4-(3-pyridinyl)-1,3-thiazol-2-yl]-1,5-pentanediamine trihydrogen chloride and 3,5-dimethylisoxazole-4-sulphonyl chloride: m.p. 114–115° C.; $^1$H NMR (free base) δ 9.00 (d, 1H), 8.52 (dd, 1H, J=0.9, 4.6 Hz), 8.01 (m, 1H), 7.30 (dd, 1H, J=4.9, 8.0 Hz), 6.75 (s, 1H), 6.51–6.44 (m, 2H), 3.18 (q, 2H, J=6.1 Hz), 2.93 (q, 2H, J=6.3 Hz), 2.60 (s, 3H), 2.37 (s, 3H), 1.57 (m, 2H), 1.47 (m, 2H), 1.37 (m, 2H); ESIMS m/e=421.82 (MH$^+$).

EXAMPLE 72

2-(5-(2-Methoxy-5-methyl)phenylsulfonylamino)pentylamino-4-(3-pyridyl)thiazole hydrogen chloride was obtained as a yellow solid in 34% from $N^1$-[4-(3-pyridinyl)-1,3-thiazol-2-yl]-1,5-pentanediamine trihydrogen chloride and 6-methoxy-m-toluene-sulfonyl chloride: m.p. 119–120° C.; $^1$H NMR (free base) δ 9.02 (m, 1H), 8.50 (dt, 1H, J=0.7, 4.6 Hz), 8.05 (dt, 1H, J=1.8, 7.9 Hz), 7.69 (d, 1H, J=2.1 Hz), 7.30 (m, 2H), 6.91 (d, 1H, J=8.4 Hz), 6.77 (s, 1H), 5.60 (m, 1H), 5.10 (t, 1H, J=6.4 Hz), 3.92 (s, 3H), 3.24 (q, 2H, J=6.4 Hz), 2.87 (q, 2H, J=6.5 Hz), 2.32 (s, 3H), 1.61 (m, 2H), 1.48 (m, 2H), 1.41 (m, 2H); ESIMS m/e=446.84 (MH$^+$).

EXAMPLE 73

2-(5-(2-Fluoro)phenylsulfonylamino)pentylamino-4-(4-pyridyl)thiazole hydrogen chloride was obtained as a yellow solid in 44% from $N^1$-[4-(4-pyridinyl)-1,3-thiazol-2-yl]-1,5-pentanediamine trihydrogen chloride and 2-fluorobenzenesulfonyl chloride: m.p. 97–98° C.; $^1$H NMR (free base) δ 8.57 (d, 2H, J=5.4 Hz), 7.89 (td, 1H, J=1.7, 7.7 Hz), 7.63 (d, 2H, J=5.4 Hz), 7.55 (m, 1H), 7.30–7.17 (m, 2H), 6.93 (s, 1H), 5.52 (m, 1H), 5.26 (m, 1H), 3.25 (q, 2H, J=6.4 Hz), 2.99 (q, 2H, J=6.5 Hz), 1.62 (m, 2H), 1.53 (m, 2H), 1.42 (m, 2H); ESIMS m/e=420.83 (MH+).

EXAMPLE 74

2-(5-(3,5-Dimethylisoxazol-4-yl)sulfonylamino)pentylamino-4-(4-pyridyl)thiazole hydrogen chloride was obtained as a yellow solid in 36% from $N^1$-[4-(4-pyridinyl)-1,3-thiazol-2-yl]-1,5-pentanediamine trihydrogen chloride and 3,5-dimethylisoxazole-4-sulphonyl chloride: m.p. 108–109° C.; $^1$H NMR (free base) δ 8.58 (dd, 2H, J=1.6, 4.7 Hz), 7.63 (dd, 2H, J=1.5, 4.6 Hz), 6.93 (s, 1H), 5.51 (m, 1H), 5.36 (m, 1H), 3.29 (q, 2H, J=6.4 Hz), 2.97 (q, 2H, J=6.4 Hz), 2.62 (s, 3H), 2.39 (s, 3H), 1.64 (m, 2H), 1.53 (m, 2H), 1.42 (m, 2H); ESIMS m/e=421.81 (MH+).

EXAMPLE 75

2-(5-(2-Methoxy-5-methyl)phenylsulfonylamino)pentylamino-4-(4-pyridyl)thiazole hydrogen chloride was obtained as a yellow solid in 29% from $N^1$-[4-(4-pyridinyl)-1,3-thiazol-2-yl]-1,5-pentanediamine trihydrogen chloride and 6-methoxy-m-toluene-sulfonyl chloride: m.p. 116–117° C.; $^1$H NMR (free base) δ 8.59 (d, 2H, J=6.0 Hz), 7.71 (d, 1H, J=1.8 Hz), 7.65 (d, 2H, J=6.3 Hz), 7.33 (m, 1H), 6.92 (m, 2H), 5.16 (m, 1H), 4.88 (m, 1H), 3.94 (s, 3H), 3.29 (q, 2H, J=6.0 Hz), 2.88 (q, 2H, J=6.6 Hz), 2.34 (s, 3H), 1.65–1.44 (m, 6H); ESIMS m/e=446 (MH+).

EXAMPLE 76

N1-{5-[(4-Benzo[b]thiophen-2-yl-1,3-thiazol-2-yl)amino]-pentyl}-2-methoxy-5-methyl-1-benzenesulfonamide: 45% yield; $^1$H NMR (CDCl$_3$) δ 8.22–7.82 (m, 1H), 7.76–7.65 (m, 3H), 7.43–7.27 (m, 4H), 6.86 (d, 1H, J=8.5 Hz), 6.45–6.20 (m, 1H), 5.30 (m, 1H), 3.80 (s, 3H), 3.35–3.9 (m, 2H), 2.75 (m, 2H), 2.31 (s, 3H), 1.49–1.29 (m, 6H).

EXAMPLE 77

N1-(5-{[4-(5-Chloro-3-methylbenzo[b]thiophen-2-yl)-1,3-thiazol-2-yl]amino}pentyl)-2-methoxy-5-methyl-1-benzenesulfonamide: 55% yield; Anal. Calc. for $C_{25}H_{28}C_{11}N_3S_3O_3$+0.3 $CH_2Cl_2$: C, 52.80; H, 5.00; N, 7.10. Found: C, 53.23; H, 4.68; N, 6.82; $^1$H NMR (CDCl$_3$) δ 7.75–7.65 (m, 3H), 7.30–7.25 (m, 2H), 6.91 (d, 1H, J=7.50 Hz), 6.65 (s, 1H), 5.28–5.20 (m, 1H), 4.95–4.85 (m, 1H), 3.95 (s, 3H), 3.35–3.25 (m, 2H), 2.95–2.85 (m, 2H), 2.55 (s, 3H), 2.35 (m, 3H), 2.65–1.25 (m, 6H).

EXAMPLE 78

N1-(4-{[4-(5-Phenyl-3-isoxazolyl)-1,3-thiazol-2-yl]amino}-pentyl)-2-methoxy-5-methyl-1-benzenesulfonamide: 40% yield: Anal. Calc. for $C_{25}H_{28}N_4S_2O_4$+0.30 $CH_3COOC_2H_5$: C, 58.40; H, 5.60; N, 10.30. Found: C, 58.50; H, 5.51; N, 10.10. $^1$H NMR (CDCl$_3$) δ 7.90–7.82 (m, 2H), 7.75–7.65 (m, 1H), 7.55–7.42 (m, 3H), 7.35–7.25 (m, 1H), 7.10 (s, 1H), 6.92–6.85 (m, 1H), 6.80 (s, 1H), 5.45–5.42 (m, 1H), 5.05–5.00 (m, 1H), 3.90 (s, 3H), 3.40–3.20 (m, 2H), 2.95–2.82 (m, 2H), 2.35 (s, 3H), 1.75–1.35 (m, 6H).

EXAMPLE 79

N1-(5-{[4-(3-Thienyl)-1,3-thiazol-2-yl]amino}pentyl)-2-methoxy-5-methyl-1-benzenesulfonamide: 45% yield; $^1$H NMR (CDCl$_3$) δ 7.82–7.75 (m, 2H), 7.70 (s, 1H), 7.55–7.30 (m, 3H), 6.95–6.85 (d, 1H, J=7.5 Hz), 6.35–6.25 (m, 1H), 5.12–5.05 (m, 1H), 3.90 (s, 3H), 3.45–3.35 (m, 2H), 2.92–2.82 (m, 2H), 2.35 (s, 3H), 1.60–1.35 (m, 6H).

EXAMPLE 80

N1-[5-({4-[1-(Phenylsulfonyl)-1H-3-pyrrolyl]-1,3-thiazol-2-yl}amino)pentyl]-2-methoxy-5-methyl-1-benzenesulfonamide: 43% yield; $^1$H NMR (CDCl$_3$) δ 7.80–7.95 (m, 1H), 7.60–7.91 (m, 2H), 7.35–7.45 (m, 5H), 7.15–7.05 (m, 2H), 6.95 (s, 1H), 6.75 (s, 1H), 4.60–4.15 (broad, 2H), 3.80 (s, 3H), 2.35–3.25 (m, 2H), 2.85–2.65 (m, 2H), 2.25 (s, 3H), 1.55–1.22 (m, 6H).

EXAMPLE 81 trans-N8-[(4-{[4-(3-Phenyl-5-isoxazolyl)-1,3-thiazol-2-yl]amino}cyclohexyl)methyl]-8-quinolinesulfonamide: 3.5% yield, 546 (ESMS, MH+); $^1$H NMR (CDCl$_3$) δ 9.04 (dd, 1H, J=1.7, 4.5 Hz), 8.45 (dd, 1H, J=0.6, 7.6 Hz), 8.31 (apparent td, 1H, J=1.8, 8.3 Hz), 8.09 (apparent td, 1H, J=1.8, 8.2 Hz), 7.84 (m, 1H), 7.68 (apparent dt, 1H, J=1.5, 7.7 Hz), 7.62–7.57 (m, 1H), 7.52–7.41 (m, 3H), 7.06 (s, 1H), 6.81 (s, 1H), 6.5–6.4 (m, 1H), 5.13 (d, 1H, J=8.2 Hz), 4.29 (b, 1H), 3.27 (m, 1H), 2.71 (apparent dt, 2H, J=3.1, 6.6 Hz), 2.21–0.94 (m, 9H).

EXAMPLE 82

N,N-Dimethyl-N'-(5-{[4-(3-Thienyl)-1,3-thiazol-2-yl]amino}pentyl)sulfamide: 45% yield; Anal. Calc. for $C_{14}H_{22}N_4S_3O_2$: C, 44.90; H, 5.70; N, 14.90. Found: C, 44.60; H, 5.77; N, 14.47. $^1$H NMR (CDCl$_3$) δ 7.59 (d, J=4.5 Hz), 7.37–7.26 (m, 2H), 6.55 (s, 1H), 5.60–5.58 (broad, 1H), 4.63–4.50 (m, 1H), 3.28–3.21 (m, 2H), 3.07–2.99 (m, 2H), 2.80 (s, 3H), 1.79–1.37 (m, 6H).

EXAMPLE 83 trans-2-(4-(2-Methoxy-5-methylphenyl)sulfonylamino)-cyclohexylmethylamino-4-(2-pyridyl)thiazole dihydrogen chloride was obtained as a yellow solid in 7% from N-[(4-aminocyclohexyl)methyl]-4-(2-pyridinyl)-1,3-thiazol-2-amine and 6-methoxy-m-toluene-sulfonyl chloride: m.p. 111–113° C.; $^1$H NMR (CD$_3$OD) δ 8.39 (m, 1H), 7.74 (m, 2H), 7.60 (s, 1H), 7.40 (m, 3H), 7.04 (dd, 1H, J=1.2, 8.2 Hz), 3.90 (s, 3H), 3.32 (m, 2H), 2.93 (m, 1H), 2.31 (s, 3H), 1.71 (m, 4H), 1.53 (m, 1H), 1.28 (m, 2H), 0.90 (m, 2H) ESIMS m/e=473.1 (MH+).

EXAMPLE 84 trans-2-(4-(2-Fluorophenyl)sulfonylamino)cyclohexylmethyl-amino-4-(2-pyridyl)thiazole dihydrogen chloride was obtained as a yellow solid in 5% from N-[(4-aminocyclohexyl)methyl]-4-(2-pyridinyl)-1,3-thiazol-2-amine and 2-fluorobenzene sulfonyl chloride: m.p. 113–115° C.; 1H NMR (CD$_3$OD) δ 8.40 (m, 1H), 7.88–7.71 (m, 3H), 7.60 (m, 1H), 7.43 (m, 2H), 7.30 (m, 2H), 3.33 (m, 2H), 3.09 (m, 1H), 1.78 (m, 4H), 1.53 (m, 1H), 1.42–1.24 (m, 2H), 0.90 (m, 2H); ESIMS m/e=473.2 (MH+)

EXAMPLE 85 trans-2-(4-(3,5-Dimethyl-4-isoxazolyl)sulfonylamino)-cyclohexylmethylamino-4-(2-pyridyl)thiazole dihydrogen chloride was obtained as a yellow solid in 7% from N-[(4-aminocyclohexyl)methyl]-4-(2-pyridinyl)-1,3-thiazol-2-amine and 3,5-dimethylisoxazole-4-sulfonyl chloride: m.p. 98–101° C.; $^1$H NMR (CD$_3$OD) δ 8.40 (m, 1H), 7.79 (m, 2H), 7.45 (m, 2H), 3.33 (m, 2H), 2.99 (m, 1H), 2.59 (s, 3H) 2.38 (s, 3H), 1.81 (m, 4H), 1.58 (m, 1H), 1.30 (m, 2H) 0.90 (m, 2H); ESIMS m/e=448.2 (MH$^+$)

EXAMPLE 86 trans-2-(4-(2-Fluorophenyl)sulfonylamino)cyclohexylmethyl-amino-4-(3-pyridyl)thiazole dihydrogen chloride was obtained as a grayish solid in 7% from N-[(4-aminocyclohexyl)methyl]-4-(3-pyridinyl)-1,3-thiazol-2-amine and 2-fluorobenzene sulfonyl chloride: m.p. 141–142° C.; $^1$H NMR (free base) δ 9.01 (s, 1H), 8.50 (d, 1H, J=4.6 Hz), 8.03 (d, 1H, J=7.9 Hz), 7.91 (td, 1H, J=1.2, 7.4 Hz), 7.56 (m, 1H), 7.31–7.7.17 (m, 3H), 6.75 (s, 1H), 5.62 (b, 1H), 4.90 (b, 1H), 3.17 (m, 1H), 3.11 (t, 2H, J=6.1 Hz), 1.92–1.79 (m, 4H), 1.56 (m, 1H), 1.20 (m, 2H), 1.01 (m, 2H); ESIMS m/e=447.1 (MH$^+$).

EXAMPLE 87 trans-2-(4-(2-Methoxy-5-methylphenyl)sulfonylamino)-cyclohexylmethylamino-4-(4-pyridyl)thiazole dihydrogen chloride was obtained as a brownish solid in 4% from N-[(4-aminocyclohexyl)methyl]-4-(4-pyridinyl)-1,3-thiazol-2-amine and 6-methoxy-m-toluene-sulfonyl chloride: $^1$H NMR (CD$_3$OD) δ 8.71 (dd, 2H, J=1.2, 6.9 Hz), 8.37 (dd, 2H, J=1.2, 7.0 Hz), 7.89 (s, 1H), 7.62 (s, 1H), 7.38 (m, 1H), 7.05 (d, 1H, J=8.6 Hz), 3.90 (s, 3H), 3.24 (m, 2H), 2.95 (m, 1H), 2.31 (s, 3H), 1.76 (m, 4H), 1.57 (m, 1H), 1.30 (m, 2H), 0.98 (m, 2H); ESIMS m/e=473.2 (MH$^+$).

EXAMPLE 88

N1-(5-[4-(1,3-thiazol-2-yl)-1,3-thiazol-2-yl]aminopentyl)-2-methoxy-5-methyl-1-benzenesulfonamide: Anal. Calc. for C$_{19}$H$_{24}$N$_4$S$_3$O$_3$+1.00 CH$_3$COOC$_2$H$_5$: C, 51.50; H, 5.90; H, 10.30. Found: C, 51.69; H, 5.60; N, 10.30. $^1$H NMR (CDCl$_3$) δ 7.75 (s, 1H), 7.66 (s, 1H), 7.44–7.25 (m, 3H), 6.88 (d, 1H, J=8.3 Hz), 5.67–5.64 (m, 1H), 5.20–5.15 (m, 1H), 3.89 (s, 3H), 3.73–3.17 (m, 2H), 2.87–2.81 (m, 2H), 2.30 (s, 3H), 1.80 1.25 (m, 6H).

EXAMPLE 89 trans-N1-[(4-[4-(2,5-Dimethyl-1,3-thiazol-4-yl)-1,3-thiazol-2-yl]aminocyclohexyl)methyl]-2-methoxy-5-methyl-1-benzenesulfonamide: 11% yield, 507 (ESMS, MH$^+$); $^1$H NMR (CDCl$_3$) δ 7.70 (d, 1H, J=2.1 Hz), 7.33 (dd, 1H, J=2.0, 8.8 Hz), 6.93 (d, 1H, J=8.5 Hz), 6.43 (s, 1H), 5.06 (m, 1H), 4.95 (m, 1H), 3.95 (s, 3H), 3.24 (m, 1H), 2.71 (t, 2H, J=6.7 Hz), 2.64 (s, 3H), 2.55 (s, 3H), 2.34 (s, 3H), 2.03 (ABm, 4H), 1.47 (m, 1H), 1.26–0.97 (m, 4H).

EXAMPLE 90 trans-N,N-dimethyl-N'-[(4-[4-(-1,3-thiazol-2-yl)-1,3-thiazol-2-yl]aminocyclohexyl)methyl]sulfamide: 12.3% yield, 402 (ESMS, MH$^+$); $^1$H NMR (CDCl$_3$) δ 7.80 (d, 1H, J=3.3 Hz), 7.29 (d, 1H, J=3.1 Hz), 7.19 (s, 1H), 5.16 (d, 1H, J=8.2 Hz), 4.14 (b, 1H), 3.30 (m, 1H), 2.95 (t, 2H, J=6.6 Hz), 2.81 (s, 6H), 2.09 (ABm, 4H), 1.51 (m, 1H), 1.30–0.85 (m, 4H).

EXAMPLE 91

N,N-Dimethyl-N'-(5-{[4-(2-thienyl)-1,3-thiazol-2-yl]amino}-pentyl)sulfamide: 45% Yield; $^1$H NMR (CDCl$_3$) δ 7.30 (d, 1H, J=4.5 Hz), 7.20 (d, 1H, J=4.5 Hz), 7.05–6.95 (m, 1H), 6.55 (s, 1H), 6.35–6.25 (m, 1H), 5.55–5.45 (m, 1H), 3.20–3.10 (m, 2H), 3.00–2.9 (m, 2H), 2.80 (s, 6H), 1.60–1.25 (m, 6H).

EXAMPLE 92

N1-(5-{[4-(2-Thienyl)-1,3-thiazol-2-yl]amino}pentyl)-2-methoxy-5-methyl-1-benzenesulfonamide: 40% Yield; $^1$H NMR (CDCl$_3$) δ 7.67 (s, 1H), 7.30–7.27 (m, 2H), 7.15 (d, 1H, J=4.3 Hz), 6.99–6.95 (m, 1H), 6.87 (d, 1H, J=8.3 Hz), 6.52 (s, 1H), 5.92 (broad, 1H), 5.36–5.31 (m, 1H), 3.88 (s, 3H), 3.15–3.11 (m, 2H), 2.85–2.78 (m, 2H), 2.30 (s, 3H), 1.54–1.30 (m, 6H).

EXAMPLE 93

N1-(5-[4-(2,5-Dimethyl-1,3-thiazol-4-yl)-1,3-thiazol-2-yl]aminopentyl)-2-methoxy-5-methyl-1-benzenesulfonamide: 40% Yield; Anal. Calc. For C$_{21}$H$_{28}$N$_4$S$_3$O$_3$+0.20 CH$_3$COOC$_2$H$_5$: C, 52.61; H, 6.00; N, 11.10. Found: C, 52.96; H, 5.93; N, 10.92; $^1$H NMR (CDCl$_3$) δ 7.70 (d, 1H, J=4.3 Hz), 7.33–7.30 (m, 1H), 9.91 (d, 1H, J=8.3 Hz), 6.43 (s, 1H), 5.28 (broad, 1H), 4.99–4.95 (m, 1H), 3.92 (s, 3H), 3.24–3.18 (m, 2H), 2.90–2.83 (m, 2H), 2.63 (s, 3H), 2.54 (s, 3H), 2.32 (s, 3H), 1.64–1.34 (m, 6H).

EXAMPLE 94

N1-(5-[4-(2,5-Dimethyl-1,3-thiazol-4-yl)-1,3-thiazol-2-yl]aminopentyl)-4-fluoro-1-benzenesulfonamide: 40% Yield; Anal. Calc. for C$_{19}$H$_{23}$F$_1$N$_4$S$_3$O$_2$+0.3CH$_3$COOC$_2$H$_5$: C, 50.50; H, 5.30; N, 11.60. Found: C, 50.71; H, 4.92; N, 11.25. $^1$H NMR (CDCl$_3$) δ 7.85 (q, 2H, J=4.3 Hz), 7.14 (t, 2H, J=7.5 Hz), 6.41 (s, 1H), 8.84–5.80 (m, 1H), 5.65 (t, 1H, J=4.3 Hz), 3.20–3.13 (m, 2H), 2.92–2.85 (m, 2H), 2.59 (s, 3H), 2.50 (s, 3H), 1.53–1.29 (m, 6H).

EXAMPLE 95

N1-(5-[4-(1,3-Thiazol-2-yl)-1,3-thiazol-2-yl]aminopentyl)-4-fluoro-1-benzenesulfonamide: 40% Yield; Anal. Calc. for C$_{17}$H$_{19}$F$_1$N$_4$S$_3$O$_2$: C, 51.52; H, 4.79; N, 11.01. Found: C, 51.41, H, 5.57; N, 10.60. $^1$H NMR (CDCl$_3$) δ 7.95–7.85 (m, 2H), 7.80–7.70 (m, 1H), 7.60–7.40 (m, 1H), 7.3 (d, 1H, J=4.3 Hz), 7.20–7.10 (m, 2H), 5.60–5.45 (m, 1H), 5.20–5.00 (m, 2H), 3.45–3.20 (m, 2H), 3.00–2.80 (m, 2H), 1.80–1.25 (m, 6H).

EXAMPLE 96

N'-(5-[4-(2,5-Dimethyl-1,3-thiazol-4-yl)-1,3-thiazol-2-yl]aminopentyl)-N,N-dimethylsulfamide: 35% Yield; Anal. Calc. for C$_{15}$H$_{25}$N$_4$S$_3$O$_2$: C, 44.85; H, 6.31; N, 16.90. Found: C, 44.74; H, 6.38; N, 16.61. $^1$H NMR (CDCl$_3$) δ 7.88 6.40 (s, 1H), 6.00–5.95 (m, 1H), 5.35–5.20 (m, 1H), 3.25–3.15 (m, 2H), 3.05–2.95 (m, 2H), 2.80 (s, 6H), 2.60 (s, 3H), 2.50 (s, 3H), 1.60–1.25 (m, 6H).

EXAMPLE 97 trans-N1-[(4-[4-(2,5-dimethyl-1,3-thiazol-4-yl])-1,3-thiazol-2-yl]aminocyclohexyl)methyl]-4-fluoro-1-benzene-sulfonamide: 99% yield, 481 (ESMS, MH+); $^1$H NMR (CDCl$_3$) δ 7.88 (m, 2H), 7.20(t, 2H, J=8.2 Hz), 6.42 (s, 1H), 5.23 (b, 1H), 5.11–4.81 (b, 1H), 3.21 (m, 1H), 2.80 (t, 2H, J=6.0 Hz), 2.62 (s, 3H), 2.53 (s, 3H), 2.00 (ABm, 4H), 1.42 (m, 1H), 1.24–0.96 (m, 4H).

EXAMPLE 98 trans-N'-[(4-[4-(2,5-dimethyl-1,3-thiazol-4-yl)-1,3-thiazol-2-yl]aminocyclohexyl)methyl]-N,N-dimethylsulfamide: 45% yield, 430 (ESMS, MH+); $^1$H NMR (CDCl$_3$) δ 6.44(s, 1H), 5.13(d, 1H, J=7.9 Hz), 4.26 (t, 1H, J=6.9 Hz), 3.27 (m, 1H), 2.93 (t, 2H, J=6.6 Hz), 2.81 (s, 6H), 2.64 (s, 3H), 2.55 (s, 3H), 2.07 (ABm, 4H), 1.51 (m, 1H), 1.30–1.03 (m, 4H).

EXAMPLE 99 trans-N'-[4-([5-(2,5-Dimethyl-1,3-thiazol-4-yl)-1,3-thiazol-2-yl]aminomethyl)cyclohexyl]methyl-N,N-dimethylsulfamide: 45% Yield; $^1$H NMR (CDCl$_3$) δ 6.40 (s, 1H), 5.82–5.70 (m, 1H), 4.82–4.75 (m, 1H), 3.20–3.05 (m, 2H), 3.00–2.82 (m, 2H), 2.80 (s, 6H), 2.60 (s, 3H), 2.50 (s, 3H) 1.85–1.35 (m, 8H), 1.05–0.82 (m, 2H).

EXAMPLE 100 trans-N4-[4-([4-(2,5-Dimethyl-1,3-thiazol-4-yl)-1,3-thiazol-2-yl]aminomethyl)cyclohexyl]methyl-4-morpholinesulfonamide: 40% Yield; Anal. Calc. for $C_{20}H_{31}N_4S_3O_3$: C, 49.40; H, 6.40; N, 14.40. Found: C, 49.19; H, 6.47; N, 13.92. $^1$H NMR (CDCl$_3$) δ 6.40 (s, 1H), 6.00–5.85 (m, 1H), 5.30–5.15 (m, 1H), 3.80–3.60 (m, 4H), 3.20–2.82 (m, 8H), 2.6 (s, 3H), 2.50 (s, 3H), 1.80–1.18 (m, 8H), 1.05–0.82 (m, 2H).

EXAMPLE 101 trans-N-[4-([4-(2,5-Dimethyl-1,3-thiazol-4-yl)-1,3-thiazol-2-yl]aminomethyl)cyclohexyl]-N-(2-methoxyethyl)formamide: 33% yield, 409 (ESMS, MH+); $^1$H NMR (CDCl$_3$) δ 8.18 & 8.08 (two s, 1H), 6.44 (s, 1H), 5.32 (b, 1H), 3.48 (two s, 3H), 3.46–3.39 (m, 4H), 3.34 & 3.33 (two d, 2H, J=2.6 Hz), 3.15 (m, 1H), 2.64 (s, 3H), 2.550 & 2.548 (two s, 3H), 2.00–0.83 (m, 9H).

EXAMPLE 102 trans-N-[4-([4-(2,5-Dimethyl-1,3-thiazol-4-yl)-1,3-thiazol-2-yl]aminomethyl)cyclohexyl]-N-isopropylformamide: 59% yield, 393 (ESMS, MH+); $^1$H NMR (CDCl$_3$) δ 8.20 & 8.18 (two s, 1H), 6.44 (s, 1H), 5.43 (b, 1H), 4.29 & 3.60 (two m, 1H), 3.74 (m, 1H), 3.13 (m, 2H), 2.64 (s, 3H), 2.54 (s, 3H), 1.27 (dd, 3H, J=1.2, 7.0 Hz), 1.21 (dd, 3H, J=1.2, 7.0 Hz), 1.98–1.06 (m, 9H).

I. Synthetic Methods for Examples

C. Tricyclic Compounds

General Procedures Relating to Examples:

For the formation of 2-aminothiazoles from 2-haloketones and thioureas, see, for example, Kearney, P. C., et al., 1998; Di Fabio, R. and Pentassuglia, G., 1998; De Kimpe, N., et al., 1996; Plazzi, P. V., et al., 1995; and Novikova, A. P., 1991.

For the formation of thiazoles from 2-haloketones and thioamides, see, for example, Critcher, D. J. and Pattenden, G., 1996; and Friedman, B. S., et al., 1937.

For the formation of 2-aminoimidazoles from 2-haloketones and guanidines, see, for example, Little, T. L. and Webber, 1994; and Chabaka, L. M., et al., 1994.

For the formation of imidazoles from 2-haloketones and amidines, see, for example, Demchenko, A. M., et al., 1997; and Nagao, Y., et al., 1996.

For the synthesis of 2-aminooxazoles from 2-haloketones and ureas, see, for example, Pathak, V. N., et al., 1993; Crangk, G. and Foulis, M. J., 1971; and Marchetti, E., et al., 1968.

For the formation of oxazoles from 2-haloketones and amides, see, for example, Hammar, W. J. and Rustad, M. A., 1981; and Zhao, Z., et al., 1991.

All reactions were performed under an inert atmosphere (Argon) and the reagents, neat or in appropriate solvents, were transferred to the reaction vessel via syringe and cannula techniques. The parallel synthesis reaction arrays were performed in vials (without an inert atmosphere) using J-KEM heating shakers (Saint Louis, Mo.). Unless stated otherwise all solvents were AR grade and used as supplied. Anhydrous solvents were purchased from Aldrich Chemical Company and used as received. Examples 1–64 described in this patent application were named using ACD/Name program (version 2.51, Advanced Chemistry Development Inc., Toronto, Ontario, M5H2L3, Canada).

[1]H and $^{13}$C spectra were recorded at 300 and 75 MHz (QE Plus) with CDCl$_3$ as solvent (unless otherwise noted) and tetramethylsilane as internal standard. s=singlet; d=doublet; t=triplet; q=quartet; p=pentet; sextet; septet; b=broad; m=multiplet. Elemental analyses were performed by Robertson Microlit Laboratories, Inc. Low-resolution electrospray MS spectra were measured (ESMS, MS) and MH+ is reported. Thin-layer chromatography (TLC) was carried out on glass plates precoated with silica gel 60 $F_{254}$ (0.25 mm, EM Separations Tech.). Preparative thin-layer chromatography was carried out on glass sheets precoated with silica gel GF (2 mm, Analtech). Flash column chromatography was performed on Merck silica gel 60 (230–400 mesh). Melting points were determined in open capillary tubes on a Med-Temp apparatus and are uncorrected.

General Procedure for the Synthesis of Benzothiepin-5-ones:

2,3,4,5-Tetrahydro-1-benzothiepin-5-one:

Step 1.

4-(phenylsulfanyl)butanoic acid:

Sodium methoxide (1.2 equivalent) was added to 60 ml of ethanol, in one portion, and the suspension was stirred at room temperature. Thiophenol (1 equivalent) was added to the above suspension and stirred at room temperature for 30 minutes. Butyrolactone (1.1 equivalent) was added to the reaction mixture and the resulting mixture was stirred at reflux temperature for 6 hours, cooled to room temperature and concentrated in vacuo. The resulting solid was washed with 200 ml hexane/ether 2:1, v/v. The solid was suspended into ice cold 2N HCl solution and stirred for 15 minutes. The resulting solid was filtered, washed with 100 ml hexane/ether and dried under reduced pressure at room temperature to give 4-(phenylsulfanyl)butanoic acid as tan solid: 52% yield; $^1$H NMR (CDCl$_3$) δ 7.32–7.12 (m, 5H), 2.94 (t, 2H, J=7.2 Hz), 2.41 (t, 2H, J=7.2 Hz), 1.85 (p, 2H, J=7.2 Hz); Anal. Calc. For $C_{10}H_{12}S_1O_2$: C, 61.22; H, 6.12. Found: C, 61.16; H, 6.28.

A similar procedure was used for the synthesis of 4-(4-fluorophenylsulfanyl)butanoic acid: 60% yield; $^1$H NMR (CDCl$_3$) δ 7.34 (m, 2H, 7.00 (m, 2H), 2.94 (t, 2H, J=7.2 Hz), 2.51 (t, 2H, J=7.2 Hz), 1.93 (p, 2H, J=7.2 Hz); Anal. Calc. For $C_{10}H_{11}F_1S_1O_2$: C, 56.07; H, 5.14. Found: C, 55.80; H, 5.19.

Step 2.

Benzothiepin-5-ones:

Polyphosphoric acid (6 equivalents) was heated to 80° C. under argon. 4-(Phenylsulfanyl)butanoic acid from the step above, (1 equivalent) was added in portions and the mixture was kept at 100° C. for 2 hours. The reaction mixture was cooled, dropped into ice cold water and extracted with 2×100 ml ethyl acetate. The combined ethyl acetate extracts were washed with 100 ml water, 100 ml saturated sodium bicarbonate, and 100 ml water. The ethyl acetate extract was dried (anhydrous sodium sulfate), filtered and the solvent removed in vacuo to give a tan solid. The solid was dried under vacuum to give 2,3,4,5-tetrahydro-1-benzothiepin-5-one: 52% yield; $^1$H NMR (CDCl$_3$) δ 7.824 (dd, 1H, J=0.9, 7.5 Hz), 7.45 (dd, 1H, J=0.6, 6.9 Hz), 7.34–7.21 (m, 2H), 3.05 (t, 2H, J=6.6 Hz), 2.97 (t, 2H, J=6.6 Hz), 2.29 (p, 2H, J=6.6 Hz).

The above described procedure was also used to give 7-fluoro-2,3,4,5-tetrahydro-1-benzothiepin-5-one: 60% yield; $^1$H NMR (CDCl$_3$) δ 7.51 (dd, 1H, J=3.0, 9.3 Hz), 7.41 (dd, 1H, J=8.7, 5.1 Hz), 7.04 (apparent dt, 1H, J=3.0, 4.8 Hz), 3.06 (t, 2H, J=6.6 HZ), 2.96 (t, 2H, J=6.6 Hz), 2.64 (t, 2H, J=6.9 Hz); Anal. Calc. For $C_{10}H_{10}S_1O_1$: C, 67.41; H, 5.61. Found: C, 67.48; H, 5.68.

General Procedure for the Synthesis of Bromoketones:

To the solution of the ketone (1 equivalent) in acetic acid, cooled in a water bath, was added bromine (1 equivalent) slowly. The reaction mixture was stirred at room temperature for 3 hours. Solvents were evaporated, the residue was dissolved in dichloromethane and the resultant solution washed with saturated sodium bicarbonate and water and dried over sodium sulfate. Evaporation of the combined decolorized organic phase afforded the desired product as a light yellow oil in more than 80% yield in most cases.

7-Fluoro-2,3,4,5-tetrahydro-1-benzothiepin-5-one was brominated according to the procedure described below to give 4-bromo-7-fluoro-2,3,4,5-tetrahydro-1-benzothiepin-5-one. A similar procedure was also used to brominate 2,3,4,5-tetrahydro-1-benzothiepin-5-one.

4-Bromo-7-fluoro-2,3,4,5-tetrahydro-1-benzothiepin-5-one:

7-Fluoro-2,3,4,5-tetrahydro-1-benzothiepin-5-one (1 equivalent) was dissolved in glacial acetic acid and stirred at room temperature. Bromine (2.5 equivalents) was added to the above mixture dropwise and stirring continued at room temperature for 4 hours. Water was added to the reaction mixture and the mixture was then extracted with 2×25 ml ethyl acetate. The combined ethyl acetate extracts were washed with water, saturated sodium bicarbonate, and water. The combined ethyl acetate extracts were dried over anhydrous sodium sulfate, filtered, and concentrated in vacuo to afford a solid which was re-crystallized from ethyl acetate/hexane 1:1 v/v to afford 4-bromo-7-fluoro-2,3,4,5-tetrahydro-1-benzothiepin-5-one: $^1$H NMR (CDCl$_3$) δ 7.55 (dd, 1H, J=2.7, 9.0 Hz), 7.44 (dd, 1H, J=8.7, 5.1 Hz), 7.11 (Apparent dt, 1H, J=2.7, 4.8 Hz), 5.34 (dd, 1H, J=5.7, 10.2 Hz), 3.20–2.50 (m, 4H).

4-bromo-2,3,4,5-tetrahydro-1-benzothiepin-5-one: $^1$H NMR (CDCl$_3$) δ 7.83 (d, 1H, J=7.8 Hz), 5.35 (dd, 1H, J=5.7, 10.5 Hz), 3.30–2.50 (m, 4H).

General Procedure for the Synthesis of Boc Protected Thioureas:

A protected diamine such as N-Boc-1,4-diaminobutane or N-Boc-1,5-diaminopentane (1 equivalent) was dissolved in tetrahydrofuran and stirred at room temperature. Benzoyl thioisocyanate (1 equivalent) was added dropwise to the aforementioned solution. The resulting mixture was stirred at room temperature for 24 hours. The solvent was removed under reduced pressure to give a yellow oil. The yellow oil (1 equivalent) from the above step was dissolved in methanol, an aqueous potassium carbonate (3 equivalents) solution was added, and the mixture stirred for 48 hours. Water was added to the reaction mixture, which was then extracted with 2×75 ml ethyl acetate. The combined ethyl acetate extracts were washed with water, dried with anhydrous sodium sulfate, filtered and the solvent removed under reduced pressure to give the desired thiourea.

tert-Butyl 5-[(aminocarbothioyl)amino]pentylcarbamate was obtained as a light yellow wax from tert-butyl 5-{[(benzoylamino)carbothioyl]amino}-pentylcarbamate. $^1$H NMR (CD$_3$OD) δ 3.44 (m, 1H), 3.10 (m, 1H), 3.01 (t, 2H, J=6.7 Hz), 1.60–1.31 (m, 6H), 1.41 (s, 9H); 262 (ESMS, MH$^+$).

tert-Butyl 5-{[(benzoylamino)carbothioyl]amino}-pentylcarbamate was obtained as a light yellow solid in 79% yield from N-BOC-1,5-diaminopentate and benzoyl isothiocyanate; m.p. 90–93° C.

tert-Butyl 4-[(aminocarbothioyl)amino]butylcarbamate was obtained as a light yellow wax from tert-butyl 4-{[(benzoylamino)carbothioyl]amino}-butylcarbamate. $^1$H NMR (CD$_3$OD) δ 3.48 (m, 1H), 3.10 (m, 1H), 3.05 (t, 2H, J=6.5 Hz), 1.60 (m, 4H), 1.42 (s, 9H); 248 (ESMS, MH$^+$).

Tert-Butyl 4-{[(benzoylamino)carbothioyl]amino}butylcarbamate was obtained as a light brown oil in 93% yield from N-BOC-1,4-diaminobutane and benzoyl isothiocyanate.

trans-tert-Butyl {4-[(aminocarbothioyl)amino]cyclohexyl}methylcarbamate was obtained as a light yellow wax from trans-tert-butyl (4-{[(benzoylamino)carbothioyl]amino}cyclohexyl)-methylcarbamate. $^1$H NMR (CD$_3$OD) δ 3.92 (m, 1H), 2.86 (m, 2H), 2.00 (m, 2H), 1.76 (m, 2H), 1.41 (s, 9H), 1.37 (m, 1H), 1.06 (m, 4H); 288 (ESMS, MH$^+$).

trans-tert-Butyl (4-{[(benzoylamino)carbothioyl]amino}cyclohexyl)-methylcarbamate was obtained as a yellow solid in 97% yield from tert-butyl 4-aminocyclohexylmethylcarbamate and benzoyl isothiocyanate.

trans-tert-Butyl 4-Aminocyclohexylmethylcarbamate was obtained in more than 95% yield from hydrogenation of benzyl 4-{[(tert-butoxycarbonyl)amino]methyl}cyclocarbamate.

Benzyl-4-[[[tert-butoxycarbonyl]amino]methyl]cyclohexylcarbamate: To a stirred suspension of 4-[[(tert-butoxycarbonyl)amino]methyl]cyclohexanecarboxylic acid (Maybridge Chemical Co., Ltd.) (45 g) and diphenylphosphoryl azide (44 ml) in toluene (600 ml) was added triethylamine (32 ml) over a period of 20 min whilst maintaining the internal temperature at −10–0 C. The mixture was slowly warmed and then stirred at 70 C for 4 h. After cooling to 40 C, benzyl alcohol (36 ml) was added and the reaction mixture heated at reflux for 20 h. The cold reaction mixture was washed with water and brine and dried over anhydrous magnesium sulfate. Removal of the solvent and recrystallization of the organic residue from ethyl acetate and diethyl ether gave the title compound, benzyl-4-[[[tert-butoxycarbonyl]amino]methyl]cyclohexylcarbamate as a white solid, m.p. 129–131 C.

trans-tert-Butyl {4-[(aminocarbothioyl)amino]cyclohexyl}carbamate was obtained as a yellow solid from trans-tert-butyl 4-{[(benzoylamino)carbothioyl]amino}cyclohexyl)-carbamate: $^1$H NMR (CD$_3$OD) δ 3.94 (m, 1H), 3.30 (m, 1H), 2.00 (m, 2H), 1.90 (m, 2H), 1.41 (s, 9H) 1.26 (m, 4H); 274 (ESMS, MH$^+$).

trans-tert-Butyl 4-{[(Benzoylamino)carbothioyl]amino}cyclohexyl)-carbamate was obtained as a white solid in 66% yield from tert-butyl 4-aminocyclohexylcarbamate and benzoyl isothiocyanate.

trans-tert-Butyl 4-aminocyclohexylcarbamate was obtained as a light yellow wax in more than 95% yield by hydrogenation of benzyl 4-[(tert-butoxycarbonyl)amino]cyclohexylcarbamate.

trans-Benzyl 4-{[(aminocarbothioyl)amino]methyl}cyclohexylcarbamate was obtained as a yellow solid in 71% yield from trans-benzyl 4-({[(Benzoylamino)carbothioyl]amino}methyl)-cyclohexylcarbamate; 322 (ESMS, MH$^+$).

trans-Benzyl 4-({[(Benzoylamino)carbothioyl]amino}methyl)-cyclohexylcarbamate was obtained as a yellow solid from benzyl 4-(aminomethyl)cyclohexylcarbamate and benzoyl isothiocyanate.

trans-benzyl 4-(aminomethyl)cyclohexylcarbamate was obtained as a white solid in more than 95% yield by stirring benzyl-4-{[(tert-butoxycarbonyl)amino]-methyl}cyclocarbamate in 2N HCl (made from 1:1 of EtOAc and 4N HCl in dioxane).

General Procedure for the Synthesis of the (4,5-dihydrobenzo[2,3]thiepino[4,5-d][1,3]thiazol-2-ylamino Template:

A mixture of a bromoketone such as 7-fluoro-2,3,4,5-tetrahydro-1-benzothiepin-5-one (1 equivalent), a thiourea (1 equivalent), and diisopropylethylamine (2 equivalents) in anhydrous ethanol was stirred and heated at reflux temperature overnight. The solvent was evaporated, the brown residue dissolved in dichloromethane and the resultant solution washed with saturated aqueous sodium bicarbonate. The aqueous phase was extracted with dichloromethane three times. The combined extracts were dried over anhydrous sodium sulfate. The crude product was purified by flash column chromatography (Silica Gel, hexanes:ethyl acetate). An example of the aforementioned general procedure follows.

4-Bromo-2,3,4,5-tetrahydro-1-benzothiepin-5-one (1.2 equivalent, 29.76 mmol) and tert-butyl 5-[(aminocarbothioyl)amino]pentylcarbamate (1 equivalent, 24.8 mmol) were mixed with 2 equivalents diisopropylethyl amine in 200 ml of EtOH. The reaction mixture was heated at reflux temperature overnight. The dark brown reaction mixture was concentrated and chromatographed (silica) to obtain tert-butyl-N-{5-[(9-fluoro-4,5-dihydrobenzo[2,3]-thiepino[4,5-d][1,3]thiazol-2-yl)amino]pentyl}-carbamate as a light tan solid.

General Procedure for the Deprotection of BOC-Protected Amines:

tert-butyl N-{[4-(4,5-dihydrobenzo[2,3]thiepino[4,5-d][1,3]thiazol-2-ylamino)cyclohexyl]methyl}carbamate or tert-butyl N-[6-(4,5-dihydrobenzo[2,3]-thiepino[4,5-d][1,3]thiazol-2-ylamino)hexyl]carbamate were separately dissolved in Et$_2$O. The same volume of 4N HCl in dioxane was added to make a 2N solution. The reaction mixture was stirred at room temperature overnight, and the solvent removed under reduced pressure to obtain the desired product as its HCl salt.

N1-(4,5-dihydrobenzo[2,3]thiepino[4,5-d][1,3]thiazol-2-yl)-1,4-butanediamine: 45% yield; $^1$H NMR (CDCl$_3$) δ 8.05 (dd, 1H, J=0.56, 8.4 Hz), 7.33 (dd, 1H, J=0.6, 8.4 Hz), 7.26 (t, 1H, J=6.5 Hz), 7.17 (t, 1H, J=6.5 Hz), 5.91 (broad, 1H), 3.20 (m, 6H), 2.69 (t, 2H, J=6.5 Hz), 1.61–1.27 (m, 6H).

N1-(4,5-Dihydrobenzo[2,3]thiepino[4,5-d][1,3]thiazol-2-yl)-1,5-pentanediamine: 50% yield; $^1$H NMR (CDCl$_3$) δ8.03 (dd, 1H, J=0.6, 8.4 Hz), 7.49 (dd, 1H, J=0.6, 8.4 Hz), 7.28 (t, 1H, J=6.5 Hz), 7.16 (t, 1H, J=6.5 Hz), 5.92 (broad, 1H), 3.13 (m, 6H), 2.63 (t, 2H, J=6.5 Hz), 1.57–1.37 (m, 8H).

tert-Butyl N-(5-[(9-Fluoro-4,5-dihydrobenzo-[2,3]thiepino[4,5-d][1,3]thiazol-2-yl)amino]pentyl}carbamate: 60% yield; Anal. Calc. for C$_{21}$H$_{28}$N$_3$FS$_2$O$_2$+0.15 CH$_2$Cl$_2$: C, 56.41; H, 6.33; N, 9.3. Found: C, 56.45; H, 6.17; N, 8.9; $^1$H NMR (CDCl$_3$) δ 7.72 (dd, 1H, J=1.15, 7.5 Hz), 7.47–7.04 (m, 1H), 6.89–6.83 (m, 1H), 6.190–6.142 (m, 1H), 4.747–4.690 (m, 1H), 3.370–2.803 (m, 8H), 1.64–1.048 (m, 6H), 1.407 (s, 9H).

N2-[4-(Aminomethyl)cyclohexyl]-4,5-dihydrobenzo[2,3]thiepino[4,5-d][1,3]thiazol-2-amine: 73% yield, 346 (ESMS, MH$^+$); $^1$H NMR (CDCl$_3$) δ 8.05 (dd, 1H, J=1.2, 7.9 Hz), 7.50 (dd, 1H, J=1.2, 7.7 Hz), 7.32 (apparent dt, 1H, J=1.8, 7.2 Hz), 7.15 (apparent dt, 1H, J=1.7, 7.2 Hz), 4.93 (b, 1H), 3.23 (m, 1H), 2.99 (t, 2H, J=6.3 Hz), 2.56 (d, 2H, J=6.6 Hz), 2.04 (ABM, 4H), 1.70–0.80 (m, 12H).

tert-Butyl N-[6-(4,5-dihydrobenzo[2,3]thiepino[4,5-d][1,3]thiazol-2-ylamino)hexyl]carbamate: 51% yield; 434 (ESMS, MH$^+$); $^1$H NMR (CD$_3$OD) δ 7.92 (d, 1H, J=7.5 Hz), 7.48 (d, 1H, J=7.6 Hz), 7.30 (apparent dt, 1H, J=1.2, 7.7 Hz), 7.15 (apparent dt, 1H, J=1.5, 7.5 Hz), 3.30(t, 2H, J=1.6 Hz), 3.16 (t, 2H, J=6.3 Hz), 3.05 (t, 2H, J=5.9 Hz), 3.01 (t, 2H, J=6.5 Hz), 1.63 (m, 2H), 1.42 (s, 9H), 1.51–1.28 (m, 6H).

N1-(4,5-Dihydrobenzo[2,3]thiepino[4,5-d][1,3]thiazol-2-yl)-1,6-hexanediamine: 75% yield, 334 (ESMS, MH$^+$); $^1$H NMR (CDCl$_3$) δ 8.05 (dd, 1H, J=1.0, 8.1 Hz), 7.51 (dd, 1H, J=1.1, 7.8 Hz), 7.32 (apparent dt, 1H, J=1.4, 7.4 Hz), 7.15, (apparent dt, 1H, J=1.6, 7.6 Hz), 5.15 (broad, 1H), 3.23(m, 4H), 3.19 (s, 2H), 2.68 (t, 2H, J=5.7 Hz), 1.70–1.21 (m, 8H).

tert-Butyl N-{[4-(4,5-Dihydrobenzo[2,3]thiepino[4,5-d][1,3]thiazol-2-ylamino)cyclohexyl]methyl}carbamate: 44% yield, 446 (ESMS, MH$^+$); $^1$H NMR (CD$_3$OD) δ 7.90 (dd, 1H, J=1.2, 7.8 Hz), 7.49 (dd, 1H, J=0.8, 7.8 Hz), 7.32 (apparent dt, 1H, J=1.4, 7.7 Hz), 7.16 (apparent dt, 1H, J=1.3, 7.6 Hz), 3.41 (m, 1H), 3.30 (m, 2H), 3.19 (t, 2H, J=6.5 Hz), 3.06, (t, 2H, J=5.8 Hz), 2.90 (d, 2H, J=7.0 Hz), 1.99 (ABm, 4H), 1.43 (s, 9H), 1.32–1.05 (m, 3H).

General Procedure for the Derivatization of Amines with Carboxylic Acid and Sulfonic Acid Derivatives:

An amine such as N1-(4,5-dihydrobenzo-[2,3]thiepino[4,5-d][1,3]thiazol-2-yl)-1,6-hexanediamine or N2-[4-(Aminomethyl)cyclohexyl]-4,5-dihydrobenzo[2,3]thiepino[4,5-d][1,3]thiazol-2-amine (0.305 mmol) was dissolved in 2 ml CH$_2$Cl$_2$ containing 2 equivalents of diisopropylethylamine. A sulfonyl or acid chloride (1–3 equivalents) was added dropwise. The reaction mixture was stirred at room temperature for 1–3 days, quenched with water, washed with 10% NaHCO$_3$, dried over Na$_2$SO$_4$ and chromatographed using column chromatography or preparative TLC.

General Procedure for the Derivatization of Tricyclic Amino Template such as N1-(4,5-Dihydrobenzo[2,3]thiepino[4,5-d][1,3]thiazol-2-yl)-1,6-hexanediamine Using Parallel Synthesis:

Tricyclic amine templates such as N1-(4,5-dihydrobenzo[2,3]thiepino[4,5-d][1,3]thiazol-2-yl)-1,6-hexanediamine (1 equivalent) or N2-[4-(aminomethyl)cyclohexyl]-4,5-dihydrobenzo[2,3]thiepino[4,5-d][1,3]thiazol-2-amine (1 equivalent), contained in a Robbins Scientific FlexChem 96-well assay, were treated with dichloromethane and poly (4-vinylpyridine). The required sulfonyl chloride, acid chloride, isocyanate or carbamyl chloride (1 equivalent) was added to each well. The reaction plates were rotated in a Robbins Scientific FlexChem rotating oven at room temperature for 24 hours, the contents filtered into a second reaction plate, and dichloromethane and polymer-supported tris(2-aminoethyl)amine were added. The second FlexChem plate was rotated at room temperature for an additional 24 hours. The contents were then filtered through a silica gel pad contained in a third Robbins plate and the filtrate collected in a 96-deep well plate. The wells were eluted with hexanes followed by EtOAc and a mixture of EtOAc: MeOH=8:2. The solvent was removed and the crude products screened for affinity at hY5 (single point, 100 nM). Compounds exhibiting more than 50% inhibition were chromatographed for full pharmacological evaluation.

General Procedure for the Formation of Formamides:

tert-Butyl-N-[4-(Isopropylamino)cyclohexyl]methyl-carbamate

Isopropyl iodide (2 equivalents) was added dropwise to a suspension of tert-butyl N-[4-aminocyclohexyl]methylcarbamate (1 equivalent, [229 (ESMS, MH$^+$): $^1$H NMR (CD$_3$OD) δ 3.33 (m, 1H), 3.29 (m, 2H), 2.85 (d, 2H, J=6.4 Hz), 2.57 (m, 1H), 1.80 (ABm, 4H), 1.41 (s, 9H), 1.35 (m, 1H), 1.20–0.88 (m, 4H)]) and diisopropylethyl amine (3 equivalents) in THF. The resulting mixture was stirred for 1 day. TLC analysis showed some starting amine. Isopropyl iodide (1 equivalent) and diisopropylethyl amine (3 equivalents) were added to the reaction mixture which was then heated at 40° C. for 1 day. The reaction mixture was concentrated and chromatographed to give tert-butylN-[4-(isopropylamino)cyclohexyl]methyl carbamate: 22% yield, 271 (ESMS, MH$^+$); $^1$H NMR (CDCl$_3$) δ 4.65 (broad, 1H), 2.91 (m, 3H), 2.42 (m, 1H), 1.80 (ABm, 4H), 1.38 (s, 9H), 0.98 (d, 6H, J=6.3 Hz), 1.32–0.85 (m, 5H).

tert-Butyl-N-[4-(2-methoxyethylamino)-cyclohexyl]methylcarbamate was similarly obtained (2-methoxyethyl bromide and n-Bu$_4$NI were used): 35% yield, 378 (ESMS, MH$^+$); $^1$H NMR (CDCl$_3$) δ 4.64 (broad, 1H), 3.44 (m, 2H), 3.31 & 3.30 (two s, 3H), 2.92 (m, 2H), 2.74 (m, 2H), 2.33 (m, 1H), 1.81 (ABm, 4H), 1.39 & 1.38 (two s, 9H), 1.34 (m, 1H), 0.98 (m, 4H).

tert-Butyl-N-[4-(isopropylformylamino)cyclohexyl]-methylcarbamate:

A solution of a tert-butyl N-[4-(isopropylamino)-cyclohexyl]methylcarbamate (7.89 mmol, 1 equivalent) in THF (5 ml) was added dropwise to a solution of 1H-benzotriazole-1-carboxaldehyde (8.68 mmol, 1.2 equivalent) in THF (10 ml) at room temperature, stirred overnight and heated at reflux temperature for two hours. 1H-Benzotriazole-1-carboxaldehyde (1 equivalent) was added and stirred overnight. The solvent was removed and dichloromethane was added to the residue. The organic extract was washed with 2N NaOH solution, washed with saturated NaCl solution, and dried over Na$_2$SO$_4$. The solvent was then removed and the product chromatographed to give tert-butyl N-[4-(isopropylformylamino)cyclohexyl]methylcarbamate: 100% yield, 299 (ESMS, MH$^+$); $^1$H NMR (CD$_3$OD) δ 8.22 & 8.18 (two s, 1H), 4.63 (broad, 1H), 4.30 & 3.60 (two m, 1H), 3.76 (m, 1H), 2.99 (m, 2H), 1.44 (s, 9H), 1.27 (d, 3H, J=6.5 Hz), 1.21 (d, 3H, J=6.5 Hz), 1.91–0.82 (m, 9H).

N-[4-(2-Methoxyethylformylamino)-cyclohexyl]methylcarbamate was similarly prepared: 58% yield; 315 (ESMS, MH$^+$); $^1$H NMR (CDCl$_3$) δ 8.25 & 8.16 (two s, 1H), 4.80 (broad, 1H), 4.07 & 3.23 (two m, 1H), 3.50 (m, 2H), 3.40–3.33 (m, 2H), 3.31 (s, 3H), 2.99 (m, 2H), 1.46 (s, 9H), 1.86–0.95 (m, 9H).

N-[4-(Aminomethyl)cyclohexyl]-N-isopropylformamide:

Dioxane containing HCl was added (10 ml of 4N HCl solution) to the solution of tert-Butyl N-[4-(isopropylformylamino)cyclohexyl]methylcarbamate dissolved in 10 ml Et$_2$O, stirred at room temperature for 2 hours, and the solvent removed to obtain N-[4-(aminomethyl)cyclohexyl]-N-isopropylformamide: 100% yield, 199 (ESMS, MH$^+$); $^1$H NMR (CD$_3$OD) δ 8.16 (s, 1H), 4.16 & 3.57 (two m, 1H), 3.70 (m, 1H), 2.79 (m, 2H), 1.36 (m, 6H), 1.91–1.06 (m, 9H).

N-[4-(Aminomethyl)cyclohexyl]-N-(2-methoxyethylformamide was similarly obtained: 100% yield; 215 (ESMS, MH$^+$); $^1$H NMR (CD$_3$OD) δ 8.44 & 8.03 4.65 (two s, 1H), 3.79–3.36 (m, 7H), 3.71 (s, 3H), 2.12–1.13 (m, 9H).

N-Benzoyl-N'-[4-(isopropylformylamino)cyclohexyl]-methylthiourea

N-[4-(Aminomethyl)cyclohexyl]-N-isopropylformamide hydrochloride salt (4.55 mmol, 1 equivalent, obtained from previous step) was stirred at room temperature with benzoyl isothiocyanate (5.46 mmol, 1.2 equivalents) and triethylamine (5.46 mmol, 1.2 equivalents) in THF (50 ml) overnight. Removal of the solvent followed by chromatography afforded a light tan solid: 39% yield, 362 (ESMS, MH$^+$); $^1$H NMR (CDCl$_3$) δ 10.87 (broad, 1H), 9.20 (broad, 1H), 8.20 & 8.18 (two s, 1H), 7.83 (d, 2H, J=7.7 Hz), 7.60 (m, 1H), 7.49 (m, 2H), 4.26 (m, 1H), 3.76 & 3.08 (two m, 1H), 3.57 (m, 2H), 1.25 (d, 3H, J=6.8 Hz), 1.19 (d, 3H, J=6.8 Hz), 1.97–1.03(m, 9H).

N-Benzoyl-N'-[4-(2-methoxyethylformyl-amino) cyclohexyl]methylthiourea was similarly obtained: 100% yield, 378 (ESMS, MH$^+$); $^1$H NMR (CDCl$_3$) δ 10.85 (broad, 1H), 9.03 (broad, 1H), 8.18 & 8.08 (two s, 1H), 7.84 (d, 2H, J=7.9 Hz), 7.64 (m, 1H), 7.52 (d, 2H, J=7.8 Hz), 3.63–3.24 (m, 7H), 3.34 & 3.33 (two m, 3H), 2.03–1.13 (m, 9H).

N-[4-(Isopropylformylamino)cyclohexyl]methylthiourea: K$_2$CO$_3$ (2 equivalent) was dissolved in 20 ml of water and added to a solution of N-benzoyl-N'-[4-(isopropylformylamino)cyclohexyl]methylthiourea (obtained from the previous step) in MeOH, and the mixture stirred at room temperature overnight. The solvent was removed in vacuo and the residue was dissolved in EtOH. The solution was filtered to remove a white precipitate and the filtrate was concentrated to afford a crude product which was chromatographed to yield the desired material: 100% yield; 258 (ESMS, MH$^+$); $^1$H NMR (CD$_3$OD) δ 8.15 & 8.13 (two s, 1H), 4.15 & 3.73 (two m, 1H), 3.34 & 2.97 (two m, 1H), 3.29 (m, 2H), 1.26 (d, 3H, J=6.7 Hz), 1.23(d, 3H, J=6.7 Hz), 1.91–1.03 (m, 9H).

N-[4-(2-Methoxyethylformylamino)-cyclohexyl]methylthiourea was similarly prepared: 77% yield, 274 (ESMS, MH$^+$); $^1$H NMR (CD$_3$OD) δ 8.15 & 8.00 (two s, 1H), 7.55 & 7.43 (two m, 1H), 3.90 & 2.97 (two m, 1H), 3.46–3.28 (m, 10H), 1.90–0.99 (m, 9H).

N-4-[(4,5-Dihydrobenzo[2,3]thiepino[4,5-d][1,3]-thiazol-2-ylamino)methyl]cyclohexyl-N-isopropyl-formamide N-[4-(Isopropylformylamino)cyclohexyl]methylthiourea (obtained from the previous step) (0.029 mmol, 1 equivalent) and 4-bromo-2,3,4,5-tetrahydro-1-benzothiepin-5-one (0.044 mmol, 1.5 equivalent) were mixed with 2 equivalents diisopropylethyl amine in 10 ml of EtOH. The resulting mixture was heated at reflux temperature for 2 days. The resulting mixture was concentrated and the crude product was chromatographed (silica) to obtain the desired product. This procedure was used to prepare examples 163–166.

The following examples were prepared according to the reaction sequence of Schemes 11, 12 and 13 which describe the syntheses of sulfonamides, amides and ureas:

EXAMPLE 103

N-[6-(4,5-Dihydrobenzo[2,3]thiepino[4,5-d][1,3]thiazol-2-ylamino)hexyl]methanesulfonamide: 74% yield, 413 (ESMS, MH$^+$); $^1$H NMR (CDCl$_3$) δ 8.02 (d, 1H, J=7.9 Hz), 7.52 (d, 1H, J=7.8 Hz), 7.33 (apparent t, 1H, J=7.1 Hz), 7.16 (apparent t, 1H, J=6.6 Hz), 5.24 (broad, 1H), 4.38 (broad, 1H), 3.20 (s, 2H), 4.15–3.09 (m, 4H), 2.95, (s, 2H), 1.63 (m, 6H), 1.41 (m, 4H).

EXAMPLE 104

N-{[4-(4,5-Dihydrobenzo[2,3]thiepino[4,5-d][1,3]thiazol-2-ylamino)cyclohexyl]methyl}-methanesulfonamide: 81% yield, 424 (ESMS, MH$^+$); $^1$H NMR (CDCl$_3$) δ 8.03 (dd, 1H, J=0.7, 7.6 Hz), 7.52 (dd, 1H, J=0.8, 7.6 Hz), 7.33 (apparent dt, 1H, J=0.5, 7.6 Hz), 7.16 (apparent dt, 1H, J=1.3, 7.6 Hz), 4.32 (m, 1H), 3.27 (m, 1H), 3.19 (s, 2H), 3.01 (t, 2H, J=6.5 Hz), 2.96 (s, 3H), 2.08 (ABm, 4H), 1.75–1.46 (m, 4H), 1.32–1.05 (m, 3H).

EXAMPLE 105

N1-[6-(4,5-Dihydrobenzo[2,3]thiepino[4,5-d][1,3]thiazol-2-ylamino)hexyl]-1-ethanesulfonamide: 68% yield, 427 (ESMS, MH$^+$); $^1$H NMR (CDCl$_3$) δ 8.05 (dd, 1H, J=1.0, 8.4 Hz), 7.53 (dd, 1H, J=0.9, 7.6 Hz), 7.33 (apparent dt, 1H, J=1.3, 7.6 Hz), 7.16 (apparent dt, 1H, J=1.3, 7.6 Hz), 5.06 (m, 1H), 4.05 (m, 1H), 3.26 (m, 2H), 3.20 (s, 2H), 3.11 (m, 2H), 3.03 (q, 2H, J=7.5 Hz), 1.37 (t, 3H, J=7.5 Hz), 1.73–1.32 (m, 10H).

EXAMPLE 106

N1-[6-(4,5-Dihydrobenzo[2,3]thiepino[4,5-d][1,3]thiazol-2-ylamino)hexyl]-1-ethanesulfonamide: 87% yield; 480 (ESMS, MH$^+$); $^1$H NMR (CDCl$_3$) δ 8.01 (dd, 1H, J=1.6, 7.6 Hz), 7.61–7.57 (m, 2H), 7.52 (dd, 1H, J=0.8, 7.4 Hz), 7.33 (apparent dt, 1H, J=1.5, 7.2 Hz), 7.15 (apparent dt, 1H, J=1.3, 7.2 Hz), 7.09 (dd, 1H, J=3.8, 4.8 Hz), 5.30 (broad, 1H), 4.78 (broad, 1H), 3.23 (broad m, 6H), 3.02 (broad m, 2H), 1.80–1.20 (m, 8H); Anal. Calcd. For C$_{21}$H$_{25}$N$_3$O$_2$S$_4$+ 0.15CHCl$_3$: C, 51.05; H, 5.43; N, 8.50. Found: C, 51.05; H, 5.09; N, 8.44.

EXAMPLE 107

N1-{[4-(4,5-Dihydrobenzo[2,3]thiepino[4,5-d][1,3]thiazol-2-ylamino)cyclohexyl]methyl}-1-ethanesulfonamide: 68% yield, 438 (ESMS, MH$^+$); $^1$H NMR (CDCl$_3$) δ 8.05 (dd, 1H, J=1.3, 8.0 Hz), 7.52 (dd, 1H, J=1.0, 7.9 Hz), 7.33 (apparent dt, 1H, J=1.3, 7.6 Hz), 7.16 (apparent dt, 1H, J=1.3, 7.6 Hz), 4.89 (m, 1H), 4.20 (m, 1H), 3.29 (m, 1H), 3.19 (s, 2H), 3.05 (q, 2H, J=7.5 Hz), 2.99 (t, 2H, J=6.4 Hz), 2.09 (ABm, 4H), 1.53 (m, 2H), 1.38 (t, 3H, J=7.5 Hz), 1.17 (m, 5H).

EXAMPLE 108

N2-{[4-(4,5-Dihydrobenzo[2,3]thiepino[4,5-d][1,3]thiazol-2-ylamino)cyclohexyl]methyl}-2-thiophenesulfonamide: 58% yield; 492 (ESMS, MH$^+$); $^1$H NMR (CDCl$_3$) δ 8.00 (dd, 1H, J=0.9, 7.5 Hz), 7.62–7.59 (m, 2H), 7.52 (dd, 1H, J=7.9, 0.9 Hz), 7.32–7.09 (m, 3H), 5.01 (broad, 1H), 4.76 (broad, 1H), 3.23 (broad m, 5H), 2.88 (t, 2H, J=6.6 Hz), 2.00 (ABm, 4H), 1.70–0.80 (m, 6H); Anal. Calcd. For C$_{22}$H$_{25}$N$_3$O$_2$S$_4$+0.5H$_2$O: C, 52.77; H, 5.23; N, 8.39. Found: C, 53.02; H, 5.02; N, 8.26.

EXAMPLE 109

N1-[5-(4,5-Dihydrobenzo[2,3]thiepino[4,5-d][1,3]thiazol-2-ylamino)pentyl]-1-ethanesulfonamide: 55% yield; Anal. Calc. for C$_{18}$H$_{26}$N$_4$S$_3$O$_2$ +0.7 CH$_2$Cl$_2$: C, 47.68; H, 5.65; N, 8.92. Found: C, 47.89; H, 5.40; N, 8.83; $^1$H NMR (CDCl$_3$) δ 7.98 (dd, 1H, J=0.6, 7.5 Hz), 7.5 (dd, 1H, J=0.6, 7.5 Hz), 7.30 (t, 1H, J=6.5 Hz), 7.14 (t, 1H, J=6.5 Hz), 6.30 (broad, 1H), 5.50 (broad, 1H), 3.16 (s, 4H), 3.03–2.90 (m, 6H), 1.42–1.20 (m, 9H).

EXAMPLE 110

N2-[5-(4,5-Dihydrobenzo[2,3]thiepino[4,5-d][1,3]thiazol-2-ylamino)pentyl]-2-thiophenesulfonamide: 50% yield; Anal. Calc. For C$_{20}$H$_{23}$N$_3$S$_3$O$_2$ +0.20 CH$_2$C$_{12}$: C, 50.27; H, 4.89; N, 8.71. Found: C, 50.33; H, 4.84; N, 8.47; $^1$H NMR (CDCl$_3$) δ 7.86 (dd, 1H, J=0.6, 7.5 Hz), 7.60–7.50 (m, 2H), 7.47 (dd, 1H, J=0.6, 7.5 Hz), 7.26–7.04 (m, 3H) 6.22–6.14 (broad, 2H), 3.16 (m, 4H), 3.01 (t, 2H, J=6.5 Hz), 2.83 (t, 2H, J=6.5 Hz), 1.45–1.11 (m, 6H).

EXAMPLE 111

N4-[5-(4,5-Dihydrobenzo[2,3]thiepino[4,5-d][1,3]thiazol-2-ylamino)pentyl]-1-methyl-1H-4-imidazolesulfonamide: 45% yield; Anal. Calc. for C$_{20}$H$_{25}$N$_5$S$_3$O$_2$ +0.25 CH$_2$C$_{12}$: C, 50.16; H, 5.30; N, 14.44. Found: C, 50.04; N, 5.24; H, 14.50; $^1$H NMR (CDCl$_3$) δ 7.10 (dd, 1H, J=0.6, 7.5 Hz), 7.72 (s, 1H), 7.66 (s, 1H), 7.44 (dd, 1H, J=0.6, 7.5 HZ), 7.31 (m, 1H), 7.147 (t, 1H, J=6.5 Hz), 3.311 (apparent s, 4H), 3.153–3.140 (m, 2H), 3.09 (s, 3H), 2.75 (t, 2H, J=4.5 Hz), 1.48–1.25 (m, 6H).

EXAMPLE 112

N4-[6-(4,5-Dihydrobenzo[2,3]thiepino[4,5-d][1,3]thiazol-2-ylamino)hexyl]-2,1,3-benzothiadiazole-4-sulfonamide: 69% yield; 532 (ESMS, MH$^+$); $^1$H NMR (CDCl$_3$) δ 8.26 (m, 2H), 8.03 (dd, 1H, J=1.5, 7.5 Hz), 7.73 (dd, 1H, J=6.9, 8.7 Hz), 7.52 (dd, 1H, J=1.5, 7.2 Hz), 7.31 (apparent dt, 1H, J=1.5, 7.2 Hz), 7.15 (apparent dt, 1H, J=1.5, 7.2 Hz), 5.37 (broad, 1H), 5.03 (broad, 1H), 3.33 (m, 6H), 2.92 (apparent q, 2H, J=6.0 Hz), 1.70–1.20 (m, 8H); Anal. Calcd. For C$_{23}$H$_{25}$N$_5$O$_2$S$_4$+0.5H$_2$O: C, 51.09; H, 4.85; N, 12.95. Found: C, 51.09; H, 4.62; H, 12.68.

EXAMPLE 113

N1-[6-(4,5-Dihydrobenzo[2,3]thiepino[4,5-d][1,3]thiazol-2-ylamino)hexyl]-2-methoxy-5-methyl-1-benzenesulfonamide: 74% yield; 518 (ESMS, MH$^+$); $^1$H NMR (CDCl$_3$) δ 8.04 (dd, 1H, J=1.6, 8.2 Hz), 7.71 (d, 1H, J=1.8 Hz), 7.52 (dd, 1H, J=1.1, 7.8 Hz), 7.35–7.23 (m, 2H), 7.16 (apparent dt, 1H, J=7.2, 1.2 Hz), 6.91 (d, 1H, J=8.4 Hz), 5.08 (broad t, 1H, J=4.7 Hz), 4.88 (t, 1H, J=6.3 Hz), 3.93 (s, 3H), 3.23 (m, 6H), 2.86 (apparent q, 2H, J=6.6 Hz), 2.33 (s, 3H), 1.70–1.20 (m, 8H); Anal. Calcd. For C$_{25}$H$_{31}$N$_3$O$_3$N$_3$+0.5H$_2$O: C, 57.01; H, 6.12; N, 7.98. Found: C, 56.56; H, 5.85; N, 7.56.

EXAMPLE 114

N1-[6-(4,5-Dihydrobenzo[2,3]thiepino[4,5-d][1,3]thiazol-2-ylamino)hexyl]-1-naphthalenesulfonamide: 83% yield; 524 (ESMS, MH$^+$); $^1$H NMR (CDCl$_3$) δ 8.65 (d, 1H, J=9.2 Hz), 8.26 (dd, 1H, J=1.0, 7.0 Hz), 8.07 (d, 1H, J=8.2 Hz), 8.02 (dd, 1H, J=1.2, 7.7 Hz), 7.97–7.50 (d, 4H), 7.28 (apparent dt, 1H, J=1.3, 7.2 Hz), 7.14 (apparent dt, 1H, J=1.5, 7.2 Hz), 5.13 (broad, 1H), 4.78 (broad, 1H), 3.12 (apparent q, 6H, J=6.0 Hz), 2.89 (apparent q, 2H, J=6.6 Hz), 1.70–1.20 (m, 8H); Anal. Calcd. For $C_{27}H_{29}N_3O_2S_3$+0.4CH$_2$Cl$_2$: C, 61.50; H, 5.62; N, 7.97. Found: C, 61.42; H, 5.43; N, 7.64.

EXAMPLE 115

N1-[6-(4,5-Dihydrobenzo[2,3]thiepino[4,5-d][1,3]thiazol-2-ylamino)hexyl]-5-(dimethylamino)-1-naphthalenesulfonamide: 81% yield; 567 (ESMS, MH$^+$); $^1$H NMR (CDCl$_3$) δ 8.64 (d, 1H, J=8.9 Hz), 8.29 (d, 1H, J=8.4 Hz), 8.25 (dd, 1H, J=1.2, 7.4 Hz), 8.02 (dd, 1H, J=1.6, 7.6 Hz), 7.59–7.12 (m, 6H), 3.12 (m, 6H), 2.86 (m, partially covered by singlet, 2H), 2.89 (s, 6H), 1.70–1.20 (m, 8H); Anal. Calcd. For $C_{29}H_{34}N_4O_2S_3$: C, 61.45; H, 6.05; N, 9.88. Found: C, 61.38; H, 6.00; N, 9.50.

EXAMPLE 116

N1-[6-(4,5-Dihydrobenzo[2,3]thiepino[4,5-d][1,3]thiazol-2-ylamino)hexyl]-2-nitro-1-benzenesulfonamide: 84% yield; 519 (ESMS, MH$^+$); $^1$H NMR (CDCl$_3$) δ 8.15–8.12 (m, 1H), 8.04 (dd, 1H, J=1.6, 8.0 Hz), 7.87–7.84 (m, 1H), 7.74–7.71 (m, 2H), 7.33 (apparent dt, 1H, J=1.3, 7.2 Hz), 7.16 (apparent dt, 1H, J=1.2, 7.2 Hz), 5.30 (broad, 1H), 5.05 (broad, 1H), 3.23 (broad m, 6H), 3.12 (apparent q, 2H, J=6.6 Hz), 1.70–1.20 (m, 8H); Anal. Calcd. For $C_{23}H_{26}N_4O_4S_3$+0.5H$_2$O: C, 52.35; H, 5.16; N, 10.62. Found: C, 52.18; H, 4.85; N, 10.14.

EXAMPLE 117

N5-[6-(4,5-Dihydrobenzo[2,3]thiepino[4,5-d][1,3]thiazol-2-ylamino)hexyl]-6-chloroimidazo[2,1-b][1,3]thiazole-5-sulfonamide: 68% yield; 554 (ESMS, MH$^+$); $^1$H NMR (CDCl$_3$) δ 8.01 (dd, 1H, J=1.1, 7.6 Hz), 7.93 (d, 1H, J=4.6 Hz), 7.52 (dd, 1H, J=1.3, 7.6 Hz), 7.31 (apparent dt, 1H, J=1.2, 7.2 Hz), 7.15 (apparent dt, 1H, J=1.2, 7.2 Hz), 7.03 (d, 1H, J=4.6 Hz), 5.22 (broad, 2H), 3.23 (broad m, 6H), 3.02 (t, 2H, J=6.6 Hz), 1.70–1.20 (m, 8H); Anal. Calcd. For $C_{24}H_{24}Cl_1N_5O_2S_4$+0.5H$_2$O: C, 46.92; H, 4.47; N, 12.44. Found: C, 47.10; H, 4.25; N, 12.18.

EXAMPLE 118

N4-{[4-(4,5-Dihydrobenzo[2,3]thiepino[4,5-d][1,3]thiazol-2-ylamino)cyclohexyl]methyl}-2,1,3-benzothiadiazole-4-sulfonamide: 59% yield; 544 (ESMS, MH$^+$); $^1$H NMR (CDCl$_3$) δ 8.29–8.24 (m, 2H), 8.03 (dd, 1H, J=1.5, 7.9 Hz), 7.75 (dd, 1H, J=7.0, 8.8 Hz), 7.51 (dd, 1H, J=1.1, 7.8 Hz), 7.32 (apparent dt, 1H, J=1.2, 7.2 Hz), 7.15 (apparent dt, 1H, J=1.2, 7.2 Hz), 5.45 (t, 1H, J=6.9 Hz), 4.87 (broad d, 1H, J=8.1 Hz), 3.23 (broad m, 6H), 2.76 (t, 2H, J=5.7 Hz), 2.01 (ABm, 4H), 1.70–0.80 (m, 5H); Anal. Calcd. For $C_{24}H_{25}N_5O_2S_2$+0.5H$_2$O: C, 52.15; H, 4.74; N, 12.67. Found: C, 52.52; H, 4.59; N, 12.36.

EXAMPLE 119

N1-{[4-(4,5-Dihydrobenzo[2,3]thiepino[4,5-d][1,3]thiazol-2-ylamino)cyclohexyl]methyl}-2-methoxy-5-methyl-1-benzenesulfonamide: 58% yield; 530 (ESMS, MH$^+$); $^1$H NMR (CDCl$_3$) δ 8.03 (dd, 1H, J=1.6, 7.6 Hz), 7.71 (d, 1H, J=1.6 Hz), 7.51 (dd, 1H, J=1.2, 7.8 Hz), 7.35–7.25 (m, 2H), 7.16 (apparent dt, 1H, J=1.2, 7.2 Hz), 6.93 (d, 1, J=8.5 Hz), 5.95 (t, 1H, J=7.2 Hz), 4.86 (d, 1H, J=8.4 Hz), 3.95 (s, 3H), 3.23 (broad m, 5H), 2.71 (t, 2H, J=6.9 Hz), 2.35 (s, 3H), 2.02 (ABm, 4H), 1.70–0.80 (m, 5H); Anal. Calcd. For $C_{26}H_{31}N_3O_3S_3$+0.35CHCl$_3$: C, 55.38; H, 5.53; N, 7.35. Found: C, 55.15; H, 5.41; N, 7.13.

EXAMPLE 120

N2-{[4-(4,5-Dihydrobenzo[2,3]thiepino[4,5-d][1,3]thiazol-2-ylamino)cyclohexyl]methyl}-5-(2-pyridyl)-2-thiophenesulfonamide: 56% yield; 569 (ESMS, MH$^+$); $^1$H NMR (CDCl$_3$) δ 8.60 (dd, 1H, J=5.5 Hz), 8.00 (dd, 1H, J=1.6, 6.6 Hz), 7.80–7.25 (m, 7H), 7.15 (apparent dt, 1H, J=1.2, 7.2 Hz), 5.00 (broad m, 1H), 4.81 (broad m, 1H), 3.23 (broad m, 5H), 2.93 (m, 2H), 2.00 (ABm, 4H), 1.70–0.80 (m, 5H); Anal. Calcd. For $C_{27}H_{28}N_4O_2S_4$: C, 57.01; H, 4.96; N, 9.85. Found: C, 56.60; H, 4.78; N, 9.49.

EXAMPLE 121

N1-{[4-(4,5-Dihydrobenzo[2,3]thiepino[4,5-d][1,3]thiazol-2-ylamino)cyclohexyl]methyl}-1-naphthalenesulfonamide: 58% yield; 536 (ESMS, MH$^+$); $^1$H NMR (CDCl$_3$) δ 8.65 (d, 1H, J=8.9 Hz), 7.25 (dd, 1H, J=7.3, 0.9 Hz), 8.10 (d, 1H, J=8.2 Hz), 7.98 (apparent dt, 2H, J=0.9, 6.5 Hz), 7.69–7.25 (m, 5H), 7.15 (apparent dt, 1H, J=1.2, 7.2 Hz), 5.00–4.80 (broad, 2H), 3.23 (broad m, 5H), 2.74 (t, 2H, J=6.9 Hz), 2.20–0.80 (m, 9H); Anal. Calcd. For $C_{28}H_{29}N_3O_2S_3$+0.5H$_2$O: C, 61.74; H, 5.55; N, 7.71. Found: C, 61.59; H, 5.19; N, 7.47.

EXAMPLE 122

N1-{[4-(4,5-Dihydrobenzo[2,3]thiepino[4,5-d][1,3]thiazol-2-ylamino)cyclohexyl]methyl}-5-(dimethylamino)-1-naphthalenesulfonamide: 66% yield; 579 (ESMS, MH$^+$); $^1$H NMR (CDCl$_3$) δ 8.56 (d, 1H, J=8.1 Hz), 8.28 (d, 1H, J=8.9 Hz), 8.24 (dd, 1H, J=7.5, 0.9 Hz), 8.01 (dd, 1H, J=8.0, 0.9 Hz), 7.60–7.49 (m, 3H), 7.32–7.10 (m, 3H), 4.87 (d, 1H, J=6.6 Hz), 4.75 (t, 1H, J=5.4 Hz), 3.23 (broad m, 5H), 2.89 (s, 6H), 2.73 (t, 2H, J=6.6 Hz), 1.87 (ABm, 4H), 1.20–0.80 (m, 5H); Anal. Calcd. For $C_{30}H_{34}N_4O_2S_3$+0.5H$_2$O: C, 61.30; H, 6.00; N, 9.53. Found: C, 61.16; H, 5.76; N, 9.18.

EXAMPLE 123

N1-[5-(4,5-Dihydrobenzo[2,3]thiepino[4,5-d][1,3]thiazol-2-ylamino)pentyl]-5-(dimethylamino)-1 naphthalenesulfonamide: 45% yield; Anal. Calc. for $C_{28}H_{32}N_4S_3O_2$ +0.3 CH$_3$COOC$_2$H$_5$: C, 60.55; H, 5.99; N, 9.67. Found: C, 60.60; H, 5.86; N, 9.33; $^1$H NMR (CDCl$_3$) δ 8.54 (dd, 1H, J=0.6, 7.5 Hz), 8.34 (dd, 1H, J=0.6, 7.5 Hz), 8.22 (dd, 1H, J=0.6, 7.5 Hz), 7.98 (dd, 1H, J=0.6, 7.5 Hz), 7.57–7.49 (m, 3H), 7.26–7.06 (m, 3H), 7.92 (broad, 1H), 5.66 (broad, 1H), 3.13 (apparent s, 4H), 2.94–2.82 (m, 2H), 2.87 (s, 6H), 2.83–2.76 (m, 2H), 1.31–1.04 (m, 6H).

EXAMPLE 124

N1-{[4-(4,5-Dihydrobenzo[2,3]thiepino[4,5-d][1,3]thiazol-2-ylamino)cyclohexyl]methyl}-2-nitro-1-benzenesulfonamide: 54% yield; 531 (ESMS, MH$^+$); $^1$H NMR (CDCl$_3$) δ 8.15–8.12 (m, 1H), 8.04 (dd, 1H, J=0.9, 7.1 Hz), 7.89–7.76 (m, 2H), 7.76 (dd, 1H, J=0.9, 7.2 Hz), 7.32 (apparent dt, 1H, J=1.2, 7.2 Hz), 7.15 (apparent dt, 1H, J=1.2, 7.2 Hz), 5.36 (broad m, 1H), 4.86 (broad m, 1H), 3.25 (broad m, 5H), 2.96 (t, 2H, J=6.6 Hz), 2.03 (ABm, 4H), 1.70–0.80 (m, 5H); Anal. Calcd. For C$_{24}$H$_{26}$N$_4$O$_4$S$_3$+0.5H$_2$O: C, 53.41; H, 5.04; N, 10.38. Found: C, 53.63; H, 4.72; N, 10.91.

EXAMPLE 125

N4-{[4-(4,5-Dihydrobenzo[2,3]thiepino[4,5-d][1,3]thiazol-2-ylamino)cyclohexyl]methyl}-1-methyl-1h-4-imidazolesulfonamide: 28% yield; 490 (ESMS, MH$^+$).

EXAMPLE 126

N2-{[4-(4,5-Dihydrobenzo[2,3]thiepino[4,5-d][1,3]thiazol-2-ylamino)cyclohexyl]methyl}-5-(3-isoxazolyl)-2-thiophenesulfonamide: 94% yield; 559 (ESMS, MH$^+$); $^1$H NMR (CDCl$_3$) δ 8.32 (d, 1H, J=1.8 Hz), 7.98 (dd, 1H, J=8.1, 1.5 Hz), 7.59 (d, 1H, J=3.9 Hz), 7.50 (dd, 1H, J=1.6, 7.8 Hz), 7.46 (d, 1H, J=3.9 Hz), 7.31 (apparent dt, 1H, J=1.2, 7.2 Hz), 7.15 (apparent dt, 1H, J=1.2, 7.2 Hz), 6.53 (d, 1H, J=1.8 Hz), 5.01 (broad, 2H), 3.23 (broad m, 5H), 2.92 (broad m, 2H), 2.02 (ABm, 4H), 1.70–0.80 (m, 5H); Anal. Calcd. For C$_{25}$H$_{26}$N$_4$O$_3$S$_4$: C, 53.74; H, 4.69; N, 10.03. Found: C, 53.51; H, 4.56; N, 9.56.

EXAMPLE 127

N1-[5-(4,5-Dihydrobenzo[2,3]thiepino[4,5-d][1,3]thiazol-2-ylamino)pentyl]-1-naphthalenesulfonamide: 45% yield; Anal. Calc. for C$_{26}$H$_{27}$N$_3$S$_3$O$_2$ +0.2 CH$_3$COOC$_2$H$_5$: C, 61.04; H, 5.47; N; 9.97. Found: C, 61.35; H, 5.64; N, 7.67; $^1$H NMR (CDCl$_3$) δ 8.67 (dd, 1H, J=0.6, 7.5 Hz), 8.26 (dd, 1H, J=0.6, 7.5 Hz), 8.05 (dd, 1H, J=0.6, 7.5 Hz), 8.00–7.93 (m, 2H), 7.69–7.48 (m, 4H) 7.19–7.09 (m, 2H), 5.54–5.52 (m, 1H), 5.34–5.29 (m, 1H), 3.18 (apparent s, 4H), 3.02–2.96 (m, 2H), 2.81–2.82 (m, 2H), 1.39–1.08 (m, 6H).

EXAMPLE 128

N1-[5-(4,5-Dihydrobenzo[2,3]thiepino[4,5-d][1,3]thiazol-2-ylamino)pentyl]-2-fluoro-1-benzenesulfonamide: 45% yield; Anal. Calc. for C$_{22}$H$_{24}$FN$_3$S$_3$O$_2$ +0.3 CH$_3$COOC$_2$H$_5$: C, 55.28; H, 5.28; N, 8.3. Found: C, 55.43; H, 5.25; N, 8.0. $^1$H NMR (CDCl$_3$) δ 7.97 (dd, 1H, J=0.6, 7.5 Hz), 7.84 (t, 1H, J=6.5 Hz), 7.58–7.48 (m, 2H), 7.27–7.09 (m, 4H), 6.09–6.08 (m, 1H), 5.69–5.60 (m, 1H), 3.16 (apparent s, 4H), 3.02 (t, 2H, J=6.5 Hz), 2.85 (t, 2H, J=6.5 Hz), 1.45–1.10 (m, 6H).

EXAMPLE 129

N2-[6-(4,5-Dihydrobenzo[2,3]thiepino[4,5-d][1,3]thiazol-2-ylamino)hexyl]-5-(3-isoxazolyl)-2-thiophenesulfonamide: 59% yield; 547 (ESMS, MH$^+$); $^1$H NMR (CDCl$_3$) δ 8.31 (d, 1H, J=1.9 Hz), 7.98 (dd, 1H, J=1.6, 8.3 Hz), 7.57 (d, 1H, J=4.2 Hz), 7.51 (dd, 1H, J=1.3, 7.8 Hz), 7.44 (d, 1H, J=3.4 Hz), 7.28 (apparent dt, 1H, J=1.2, 7.2 Hz), 7.15 (apparent dt, 1H, J=1.2, 7.2 Hz), 6.51 (d, 1H, J=1.9 Hz), 5.33 (broad, 1H), 5.13 (broad, 1H), 3.23 (broad m, 6H), 3.03 (t, 2H, J=6.6 Hz), 1.80–1.20 (m, 8H); Anal. Calcd. For C$_{24}$H$_{26}$N$_4$O$_3$S$_4$+1.0H$_2$O: C, 51.04; H, 5.00; N, 9.92. Found: C, 50.80; H, 4.69; N, 9.45.

EXAMPLE 130

N1-[5-(4,5-Dihydrobenzo[2,3]thiepino[4,5-d][1,3]thiazol-2-ylamino)pentyl]-2-nitro-1-benzenesulfonamide: 40% yield; $^1$H NMR (CDCl$_3$) δ 8.35–8.25 (m, 1H), 8.05 (d, 1H, J=7.5 Hz), 7.90–7.80 (m, 1H), 7.75–7.70 (m, 1H), 7.55 (d, 1H, J=7.5 Hz), 7.45–7.15 (m, 3H), 5.35–5.25 (m, 1H), 5.10–4.95 (broad, 1H), 3.25–3.10 (m, 6H), 2.40–2.30 (m, 2H), 1.80–1.25 (m, 6H).

EXAMPLE 131

N1-[5-(4,5-Dihydrobenzo[2,3]thiepino[4,5-d][1,3]thiazol-2-ylamino)pentyl]-2,6-dichloro-1-benzenesulfonamide: 40% yield; $^1$H NMR (CDCl$_3$), δ 8.10–8.05 (m, 1H), 8.00 (d, 1H, J=7.5 Hz), 7.50 (d, 1H J=7.5 Hz), 7.48–7.42 (m, 1H), 7.35–7.25 (m, 3H), 5.05 (broad, 1H), 4.1 (broad, 1H), 3.28–3.18 (m, 6H), 3.00–2.90 (m, 2H), 1.75–1.25 (m, 6H).

EXAMPLE 132

N1-[5-(4,5-Dihydrobenzo[2,3]thiepino[4,5-d][1,3]thiazol-2-ylamino)pentyl]-2-bromo-6-methoxy-1-benzenesulfonamide: 35% yield; $^1$H NMR (CDCl$_3$), δ 8.05–7.95 (m, 1H), 7.90–7.85 (m, 1H), 7.65–7.60 (m, 1H), 7.55–7.45 (m, 1H), 7.35–7.18 (m, 2H), 6.90–6.85 (m, 1H), 5.25–5.20 (m, 1H), 4.9 (broad, 1H), 3.95–3.90 (s, 3H), 3.30–3.18 (m, 6H), 2.95–2.85 (m, 2H), 1.75–1.18 (m, 6H).

EXAMPLE 133

N-[5-(4,5-dihydrobenzo[2,3]thiepino[4,5-d][1,3]thiazol-2-ylamino)pentyl]phenyl-methanesulfonamide: 40% yield; $^1$H NMR (CDCl$_3$), δ 8.05–7.95 (m, 2H), 7.65–7.50 (m, 2H), 7.4 (s, 5H), 5.30 (broad, 1H), 4.25 (broad, 1H), 3.30–3.15 (m, 6H), 3.05–2.95 (m, 2H), 2.35–2.25 (m, 2H), 1.80–1.25 (m, 6H).

EXAMPLE 134

N1-[5-(4,5-Dihydrobenzo[2,3]thiepino[4,5-d][1,3]thiazol-2-ylamino)pentyl]-2-fluoro-6-methyl-1-benzenesulfonamide: 30% yield; $^1$H NMR (CDCl$_3$) δ 8.00 (d, 1H, J=7.5 Hz), 7.72–7.65 (m, 2H), 7.52 (d, 1H, J=7.5 Hz), 7.35–7.15 (m, 3H), 5.30 (broad, 1H), 4.65–4.55 (m, 1H), 3.25–3.18 (m, 6H), 3.00–2.90 (m, 2H), 2.60 (s, 3H), 1.82–1.25 (m, 6H).

EXAMPLE 135

N1-[4-(4,5-dihydrobenzo[2,3]thiepino[4,5-d][1,3]thiazol-2-ylamino)butyl]-2-fluoro-6-methyl-1-benzenesulfonamide: 35% yield; $^1$H NMR (CDCl$_3$) δ 8.00 (d, 1H, J=7.5 Hz), 7.72–7.65 (m, 2H), 7.52 (d, 1H, J=7.5 Hz), 7.35–7.15 (m, 3H), 5.30 (broad, 1H), 4.85–4.74 (m, 1H), 3.25–3.18 (m, 6H), 3.05–2.95 (m, 2H), 2.6 (s, 3H), 1.82–1.25 (m, 4H).

EXAMPLE 136

N1-[5-(4,5-Dihydrobenzo[2,3]thiepino[4,5-d][1,3]thiazol-2-ylamino)pentyl]-1-propanesulfonamide: 30% yield;

¹H NMR (CDCl₃) δ 8.0 (d, 1H, J=7.5 Hz), 7.5 (d, 1H, J=7.5 Hz), 7.35–7.15 (m, 2H), 3.30–3.22 (m, 6H), 3.15–3.00 (m, 2H), 2.40–2.30 (m, 2H), 1.85–1.20 (m, 6H), 1.10–1.05 (m, 2H), 0.90–0.80 (m, 3H).

EXAMPLE 137

N1-[5-(4,5-Dihydrobenzo[2,3]thiepino[4,5-d][1,3]thiazol-2-ylamino)pentyl]-2,4-difluoro-1-benzenesulfonamide: 35% yield; ¹H NMR (CDCl₃) δ 8.00 (d, 1H, J=7.5 Hz), 7.95–7.85 (m, 1H), 7.50 (d, 1H, J=7.5 Hz), 7.35–7.15 (m, 2H), 6.95–7.05 (m, 2H), 4.82–4.75 (m, 1H), 4.80–4.75 (broad, 1H), 3.28–3.20 (m, 6H), 3.18–3.00 (m, 2H), 1.80–1.20 (m, 6H),

EXAMPLE 138

N1-[4-(4,5-Dihydrobenzo[2,3]thiepino[4,5-d][1,3]thiazol-2-ylamino)butyl]-2,4-difluoro-1-benzenesulfonamide: 35% yield; ¹H NMR (CDCl₃) δ 8.00 (d, 1H, J=7.5 Hz), 7.95–7.85 (m, 1H), 7.50 (d, 1H, J=7.5 Hz), 7.35–7.15 (m, 2H), 6.95–7.05 (m, 1H), 5.15–5.08 (m, 1H), 4.90–4.80 (broad, 1H), 3.30–3.20 (m, 6H), 3.20–3.00 (m, 2H), 1.80–1.20 (m, 4H).

EXAMPLE 139

N'-[5-(4,5-Dihydrobenzo[2,3]thiepino[4,5-d][1,3]thiazol-2-ylamino)pentyl]-N,N-dimethylurea: 30% yield; ¹H NMR (CDCl₃), δ 8.05 (d, 1H, J=7.5 Hz), 7.5 (d, 1H, J=7.5 Hz), 7.42–7.15 (m, 2H), 5.48–5.35 (m, 1H), 4.5–4.4 (broad, 1H), 3.35–3.20 (m, 6H), 2.90 (s, 6H), 1.85–1.18 (m, 6H).

EXAMPLE 140

N1-[4-(4,5-Dihydrobenzo[2,3]thiepino[4,5-d][1,3]thiazol-2-ylamino)butyl]-1-naphthamide: 40% yield; ¹H NMR (CDCl₃), δ 8.32–8.25 (m, 1H), 8.05 (d, 1H, J=7.5 Hz), 7.92–7.85 (m, 2H), 7.60–7.40 (m, 4H), 7.32–7.25 (m, 2H), 7.18–7.10 (m, 1H), 6.20–6.10 (m, 1H), 5.40–5.30 (m, 1H), 3.65–3.55 (m, 2H), 3.40–3.30 (m, 2H), 3.20–3.15 (m, 4H), 1.80–1.18 (m, 4H).

EXAMPLE 141

N2-[5-(4,5-Dihydrobenzo[2,3]thiepino[4,5-d][1,3]thiazol-2-ylamino)pentyl]-2-thiophenecarboxamide: 35% yield; ¹H NMR (CDCl₃) δ 8.05 (d, 1H, J=7.5 Hz), 7.55–7.45 (m, 3H), 7.35–7.28 (m, 1H), 7.20–7.12 (m, 1H), 7.10–7.05 (m, 1H), 6.08–6.02 (m, 1H), 5.30–5.20 (m, 1H), 3.50–3.40 (m, 2H), 3.31–3.22 (m, 1H), 3.20–3.15 (m, 4H), 1.80–1.12 (m, 6H).

EXAMPLE 142

N2-[5-(4,5-Dihydrobenzo[2,3]thiepino[4,5-d][1,3]thiazol-2-ylamino)pentyl]-2-naphthamide: 30% yield; ¹HNMR (CDCl₃), δ 8.15 (s, 1H), 8.10 (d, 1H, J=7.5 Hz), 7.95–7.80 (m, 4H), 7.60–7.55 (m, 3H), 7.25–7.22 (m, 1H), 7.18–7.08 (m, 1H), 6.20–6.15 (m, 1H), 5.15–5.10 (m, 1H), 3.55–3.45 (m, 2H), 3.35–3.22 (m, 2H), 3.20–3.15 (m, 4H), 2.20–1.25 (m, 6H).

EXAMPLE 143

N1-[6-(4,5-Dihydrobenzo[2,3]thiepino[4,5-d][1,3]thiazol-2-ylamino)hexyl]-1-propanesulfonamide: 10% yield, 440 (ESMS, MH⁺); ¹H NMR (CDCl₃) δ 8.05 (dd, 1H, J=1.6, 8.0 Hz), 7.51 (dd, 1H, J=1.4, 7.9 Hz), 7.33 (apparent dt, 1H, J=1.6, 7.5 Hz), 7.16 (apparent dt, 1H, J=1.4, 8.0 Hz), 5.03 (m, 1H), 4.15 (m, 1H), 3.27 (m, 2H), 3.20 (m, 2H), 3.11 (q, 2H, J=7.1 Hz), 2.98 (t, 2H, J=8.0 Hz), 1.84 (q, 2H, J=7.7), 1.69–1.40 (m, 10H), 1.26 (t, 3H, J=7.1 Hz).

EXAMPLE 144

N1-[6-(4,5-dihydrobenzo[2,3]thiepino[4,5-d][1,3]thiazol-2-ylamino)hexyl]-3-(trifluoromethyl)-1-benzenesulfonamide: 18% yield, 542 (ESMS, MH⁺); ¹H NMR (CDCl₃) δ 8.13 (s, 1H), 8.05 (d, 1H, J=8.0 Hz), 8.00 (dd, 1H, J=1.7, 8.0 Hz), 7.84 (dd, 1H, J=0.8, 7.1 Hz), 7.67 (apparent dt, 1H, J=0.5, 8.0 Hz), 7.52 (dd, 1H, J=1.2, 7.5 Hz), 7.30 (apparent dt, 1H, J=1.0, 7.6 Hz), 7.15 (apparent dt, 1H, J=1.2, 7.5 Hz), 5.23 (m, 1H), 4.75 (m, 1H), 3.21 (m, 2H), 3.20 (s, 2H), 2.96 (m, 2H), 1.75–1.28 (m, 10H).

EXAMPLE 145

N1-[6-(4,5-Dihydrobenzo[2,3]thiepino[4,5-d][1,3]thiazol-2-ylamino)hexyl]-2,4-difluoro-1-benzenesulfonamide: 14% yield, 510 (ESMS, MH⁺); 1H NMR (CDCl₃) δ 8.03 (dd, 1H, J=1.6, 7.7 Hz), 7.92 (apparent q, 1H, J=7.7 Hz), 7.52 (dd, 1H, J=1.2, 6.6 Hz), 7.30 (apparent dt, 1H, J=1.6, 7.6 Hz), 7.16 (apparent dt, 1H, J=1.5, 7.6 Hz), 6.99 (m, 2H), 5.07 (m, 1H), 4.72 (m, 1H), 3.23 (m, 2H), 3.20 (s, 1H), 2.98 (m, 2H), 1.62–1.28 (m, 10H).

EXAMPLE 146

N1-[6-(4,5-Dihydrobenzo[2,3]thiepino[4,5-d][1,3]thiazol-2-ylamino)hexyl]-2,6-dichloro-1-benzenesulfonamide: 6% yield, 542 (ESMS, MH⁺); 1H NMR (CDCl₃) δ 8.09 (m, 1H), 8.03 (dm, 1H, J=8.5 Hz), 7.52 (dm, 1H, J=7.7 Hz), 7.47 (m, 2H), 7.36–7.3 (m, 1H), 7.15 (tm, 1H, J=7.2 Hz), 4.98 (b, 1H), 3.30–3.20 (m, 3H), 2.95 (apparent q, 2H, J=7.4 Hz), 1.70–1.20 (m, 12H).

EXAMPLE 147

N1-[6-(4,5-Dihydrobenzo[2,3]thiepino[4,5-d][1,3]thiazol-2-ylamino)hexyl]-2-bromo-6-methoxy-1-benzenesulfonamide: 20% yield, 582 (ESMS, MH⁺); ¹H NMR (CDCl₃) δ 8.06–8.03 (m, 2H), 7.62 (dd, 1H, J=2.6, 8.9 Hz), 7.54–7.47 (m, 1H), 7.23 (apparent dt, 1H, J=1.2, 7.2 Hz), 7.15 (apparent dt, 1H, J=1.2, 7.2 Hz), 6.91 (d, 1H, J=9.2 Hz), 4.95 (b, 1H), 4.83 (t, 1H, J=6.6 Hz), 3.95 (s, 3H), 3.23 (m, 2H), 2.90 (apparent q, 2H, J=6.8 Hz), 1.70–1.20 (m, 9H).

EXAMPLE 148

N-[6-(4,5-Dihydrobenzo[2,3]thiepino[4,5-d][1,3]thiazol-2-ylamino)hexyl]phenylmethane-sulfonamide: 8% yield, 488 (ESMS, MH⁺); ¹H NMR (CDCl₃) δ 8.05 (dd, 1H, J=1.1, 7.8 Hz), 7.48 (dd, 1H, J=1.1, 7.2 Hz), 7.39 (m, 5H), 7.23 (apparent dt, 1H, J=1.2, 7.2 Hz), 7.15 (apparent dt, 1H, J=1.2, 7.2 Hz), 4.98 (b, 1H), 4.55 (s, 2H), 4.03 (b, 1H), 3.25 (m, 2H), 2.97 (m, 2H), 1.70–1.20 (m, 8H).

EXAMPLE 149

N1-[6-(4,5-Dihydrobenzo[2,3]thiepino[4,5-d][1,3]thiazol-2-ylamino)hexyl]-2-fluoro-6-methyl-1-benzenesulfonamide: 24% yield, 506 (ESMS, MH⁺); ¹H NMR (CDCl₃) δ 8.03 (dd, 1H, J=1.5, 8.0 Hz), 7.69 (dd, 1H, J=2.8, 8.7 Hz), 7.52 (dd, 1H, J=1.3, 7.6 Hz), 7.31 (m, 2H), 7.16 (m, 2H), 5.11 (m, 1H), 4.62 (m, 1H), 3.21 (m, 2H), 3.20 (s, 2H), 2.95 (m, 2H), 2.60 (s, 3H), 1.59–1.25 (m, 10H).

EXAMPLE 150

N1-{[4-(4,5-Dihydrobenzo[2,3]thiepino[4,5-d][1,3]thiazol-2-ylamino)cyclohexyl]methyl}-3-(trifluoromethyl)-1-benzenesulfonamide: 12% yield, 554 (ESMS, MH$^+$); $^1$H NMR (CDCl$_3$) δ 8.13 (s, 1H), 8.06 (dd, 1H, J=1.0, 7.2 Hz), 8.00 (dd, 1H, J=0.7, 7.3 Hz), 7.86 (dd, 1H, J=1.0, 8.0 Hz), 7.69 (t, 1H, J=7.8 Hz), 7.51 (dd, 1H, J=1.0, 7.6 Hz), 7.30 (t, 1H, J=8.0 Hz), 7.15 (apparent dt, 1H, J=1.0, 7.2 Hz), 4.99 (m, 1H), 4.62 (m, 1H), 3.24 (m, 2H), 3.19 (s, 2H), 2.86 (t, 2H, J=6.4 Hz), 2.00 (ABm, 4H), 1.63–1.03 (m, 6H).

EXAMPLE 151

N1-{[4-(4,5-Dihydrobenzo[2,3]thiepino[4,5-d][1,3]thiazol-2-ylamino)cyclohexyl]methyl}-2,4-difluoro-1-benzenesulfonamide: 16% yield, 522 (ESMS, MH$^+$); $^1$H NMR (CDCl$_3$) δ 8.03 (dd, 1H, J=1.0, 8.0 Hz), 7.9(m, 1H), 7.51 (dd, 1H, J=1.0, 7.7 Hz), 7.32 (apparent dt, 1H, J=1.2, 7.6 Hz), 7.16 (apparent dt, 1H, J=1.3, 7.6 Hz), 7.00 (m, 1H), 4.88 (m, 1H), 4.75 (m, 1H), 3.25 (m, 1H), 3.19 (s, 2H), 2.85 (t, 2H, J=6.5 Hz), 2.05 (ABm, 4H), 1.60–1.45 (m, 4H), 1.26–1.04 (m, 3H).

EXAMPLE 152

N1-{[4-(4,5-Dihydrobenzo[2,3]thiepino[4,5-d][1,3]thiazol-2-ylamino)cyclohexyl]methyl}-2,6-dichloro-1-benzenesulfonamide: 18% yield, 554 (ESMS, MH$^+$); $^1$H NMR (CDCl$_3$) δ 8.09 (d, 1H, J=1.0, Hz), 8.0 (m, 1H), 7.53–7.48 (m, 3H), 7.32 (apparent dt, 1H, J=0.9, 7.5 Hz), 7.15 (apparent dt, 1H, J=1.5, 7.5 Hz), 5.09 (m, 1H), 4.90 (m, 1H), 3.23 (m, 1H), 3.19 (s, 2H), 2.79 (t, 1H, J=6.4 Hz), 2.04 (ABm, 4H), 1.61 (m, 2H), 1.45 (m, 2H), 1.27–1.03 (m, 3H).

EXAMPLE 153

N-{[4-(4,5-Dihydrobenzo[2,3]thiepino[4,5-d][1,3]thiazol-2-ylamino)cyclohexyl]methyl}phenyl-methanesulfonamide: 4% yield, 500 (ESMS, MH$^+$); $^1$H NMR (CDCl$_3$) δ 8.03 (dm, 1H, J=8.1 Hz), 7.51 (dm, 1H, J=8.1 Hz), 7.40 (s, 5H), 7.32 (tm, 1H, J=7.1 Hz), 7.16 (tm, 1H, J=7.1 Hz), 4.93 (b, 1H), 4.26 (s, 2H), 4.09 (b, 1H), 3.24 (b, 2H), 3.19 (s, 2H), 2.85 (t, 2H, J=6.7 Hz), 2.02 (ABm, 4H), 1.70–1.01 (m, 6H).

EXAMPLE 154

N1-{[4-(4,5-Dihydrobenzo[2,3]thiepino[4,5-d][1,3]thiazol-2-ylamino)cyclohexyl]methyl}-2-cyano-1-benzenesulfonamide: 16% yield, 511 (ESMS, MH$^+$); $^1$H NMR (CDCl$_3$) δ 8.04 (dm, 1H, J=7.8 Hz), 7.93–7.78 (m, 4H), 7.51 (dm, 1H, J=7.3 Hz), 7.35–7.15 (m, 2H), 4.95 (b, 1H), 4.10 (b, 1H), 3.66 (m, 2H), 3.33 (m, 2H), 2.40–1.20 (m, 12H).

EXAMPLE 155

N1-{[4-(4,5-Dihydrobenzo[2,3]thiepino[4,5-d][1,3]thiazol-2-ylamino)cyclohexyl]methyl}-4-fluoro-1-benzenesulfonamide: 4% yield, 504 (ESMS, MH$^+$); $^1$H NMR (CDCl$_3$) δ 8.02 (dm, 1H, J=8.7 Hz), 7.90–7.85 (m, 2H), 7.51 (dm, 1H, J=7.9 Hz), 7.36–7.16 (m, 4H), 4.86 (b, 1H), 4.42 (b, 1H), 3.30–3.20 (m, 2H), 2.83 (t, 2H, J=6.7 Hz), 2.02 (ABm, 4H), 1.70–0.80 (m, 12H).

EXAMPLE 156

N1-{[4-(4,5-Dihydrobenzo[2,3]thiepino[4,5-d][1,3]thiazol-2-ylamino)cyclohexyl]methyl}-4-methyl-1-benzenesulfonamide: 10% yield, 500 (ESMS, MH$^+$); $^1$H NMR (CDCl$_3$) δ 8.02 (dd, 1H, J=1.5, 8.0 Hz), 7.41 (d, 1H, J=7.6 Hz), 7.51 (d, 1H, J=7.0 Hz), 7.33–7.28 (m, 3H), 7.15 (apparent dt, 1H, J=1.2, 7.7 Hz), 4.92 (m, 1H), 4.39 (m, 1H), 3.24 (m, 1H), 3.19 (s, 2H), 2.80 (t, 2H, J=6.7 Hz), 2.44 (s, 3H), 2.02 (ABm, 4H), 1.60–1.01 (m, 7H).

EXAMPLE 157

N8-{[4-(4,5-Dihydrobenzo[2,3]thiepino[4,5-d][1,3]thiazol-2-ylamino)cyclohexyl]methyl}-8-quinolinesulfonamide: 53% yield, 537 (ESMS, MH$^+$); $^1$H NMR (CDCl$_3$) δ 9.04 (dd, 1H, J=1.6,4.2), 8.45 (dd, 1H, J=1.6, 7.4 Hz), 8.31 (dd, 1H, J=1.8, 8.3 Hz), 8.08 (dd, 1H, J=1.3, 8.2 Hz), 8.02 (dd, 1H, J=1.4, 7.9 Hz), 7.68 (t, 1H, J=7.7 Hz), 7.59 (dd, 1H, J=4.1, 8.2 Hz), 7.51 (dd, 1H, J=1.3, 7.7 Hz), 7.31 (apparent dt, 1H, J=1.5, 7.6 Hz), 7.15 (apparent dt, 1H, J=1.5, 7.3 Hz), 6.41 (t, 1H, J=6.1 Hz), 4.89 (broad, 1H), 4.15 (broad, 1H), 3.23 (broad, 1H), 3.18 (s, 2H), 2.71 (t, 2H, J=6.6 Hz), 2.35 (t, 2H, J=7.5 Hz), 1.99 (ABm, 4H), 1.74–0.86 (m, 5H).

EXAMPLE 158

N1-{[4-(4,5-Dihydrobenzo[2,3]thiepino[4,5-d][1,3]thiazol-2-ylamino)cyclohexyl]methyl}-2-fluoro-6-methyl-1-benzenesulfonamide: 10% yield, 518 (ESMS, MH$^+$); $^1$H NMR (CDCl$_3$) δ 8.04 (d, 1H, J=7.2 Hz), 7.54 (d, 1H, J=5.2 Hz), 7.37–7.26 (m, 4H), 7.16 (tm, 1H, J=7.0 Hz), 4.94 (broad, 1H), 4.59 (broad, 1H), 3.26 (m, 1H), 3.19 (s, 2H), 3.01 (m, 2H), 2.05 (ABM, 4H), 1.45 (s, 3H), 1.63–0.88 (m, 7H).

EXAMPLE 159

N-{5-[(9-Fluoro-4,5-dihydrobenzo[2,3]thiepino[4,5-d][1,3]thiazol-2-yl)amino]pentyl}methanesulfonamide: 45% yield; Anal. Calc. for C$_{17}$H$_{22}$N$_3$S$_3$O$_2$F: C, 49.2; H, 5.34; N, 10.10. Found: C, 49.35; H, 5.33; N, 9.84; $^1$H NMR (CDCl$_3$) δ 7.77 (dd, 1H, J=1.1, 7.5 Hz), 7.47 (dd, 1H, J=1.5, 7.5 Hz), 6.87 (m, 1H), 5.46–5.41 (m, 1H), 4.77–4.71 (m, 1H), 3.30–3.00 (m, 8H), 2.96 (s, 3H), 1.76–1.20 (m, 6H).

EXAMPLE 160

N1-{5-[(9-Fluoro-4,5-dihydrobenzo[2,3]thiepino[4,5-d][1,3]thiazol-2-yl)amino]pentyl}-2-methoxy-5-methyl-1-benzenesulfonamide: 55% yield; Anal. Calc. for C$_{24}$H$_{28}$N$_3$FS$_3$O$_3$: C, 55.26; H, 5.41; N, 8.05. Found: C, 55.18; H, 5.58; N, 7.82; $^1$H NMR (CDCl$_3$), δ 7.75 (dd, 1H, J=1.1, 7.5 Hz), 7.70 (s, 1H), 7.45 (m, 1H), 7.29 (dd, 1H, J=1.1, 7.5 Hz), 6.94–6.86 (m, 2H), 5.14–5.13 (m, 1H), 4.94–4.98 (m, 1H), 3.93 (s, 3H), 3.26–3.12 (m, 6H), 2.91–2.83 (m, 2H), 2.33 (s, 3H), 1.70–1.13 (m, 6H).

EXAMPLE 161

N1-{5-[(9-Fluoro-4,5-dihydrobenzo[2,3]thiepino[4,5-d][1,3]thiazol-2-yl)amino]pentyl}-2-fluoro-1-benzenesulfonamide: 45% yield; Anal. Calc. for C$_{22}$H$_{23}$N$_3$F$_2$S$_3$O$_2$: C, 53.31; H, 4.68; N, 8.48. Found: C, 53.40; H, 4.87, N, 8.15; $^1$H NMR (CDCl$_3$) δ 7.92 (t, 1H, J=6.5 Hz), 7.74 (dd, 1H, J=1.1, 7.5 Hz), 7.60–7.53 (m, 1H), 7.47–7.46 (m, 1H), 7.30–7.18 (m, 2H), 6.89–6.83 (m, 1H), 5.43–5.40 (m, 1H), 5.16–5.12 (m, 1H), 3.24–3.12 (m, 6H), 2.99–2.92 (m, 2H), 1.59–1.29 (m, 6H).

EXAMPLE 162

N2-{5-[(9-Fluoro-4,5-dihydrobenzo[2,3]thiepino[4,5-d][1,3]thiazol-2-yl)amino]pentyl}-2-thiophenesulfonamide: 45% yield; Anal. Calc. for $C_{20}H_{22}N_3FS_4O_2$: C, 49.67; H, 4.58; N, 8.6. Found: C, 49.25; H, 4.67; N, 8.2; M⁺ At 484. $^1$H NMR (CDCl$_3$), δ 7.74 (dd, 1H, J=1.1, 7.5 Hz), 7.59–7.54 (m, 2H), 7.49–7.44 (m, 1H), 7.09–7.01 (m, 1H), 6.88–6.83 (m, 1H), 5.47–5.44 (m, 1H), 5.06–5.02 (m, 1H), 3.26–3.12 (m, 6H), 3.02–2.96 (m, 2H), 1.60–1.15 (m, 6H).

The following examples were prepared according to Scheme 11b which describes the synthesis of formamides:

EXAMPLE 163 trans-N-4-[(4,5-dihydrobenzo[2,3]thiepino[4,5-d][1,3]thiazol-2-ylamino)methyl]cyclohexyl-N-(2-methoxyethyl)formamide: 40% yield, 432 (ESMS, MH⁺); $^1$H NMR (CDCl$_3$) δ 8.17 & 8.08 (two s, 1H), 8.01 (dm, 1H, J=8.0 Hz), 7.53 (dm, 1H, J=7.7 Hz), 7.34 (tm, 1H, J=7.5 Hz), 7.17 (dt, 1H, J=1.0, 8.0 Hz), 5.53 (b, 1H), 3.53–3.38 (m, 3H), 3.48 (s, 3H), 3.19 (s, 2H), 3.24–3.07 (m, 4H), 1.98–1.01 (m, 11H).

EXAMPLE 164 trans-N-(4-[(9-Fluoro-4,5-dihydrobenzo[2,3]thiepino-[4,5-d][1,3]thiazol-2-yl)amino]methylcyclohexyl)-N-(2-methoxyethyl)formamide: 24% yield, 450 (ESMS, MH⁺); $^1$H NMR (CDCl$_3$) δ 8.18 & 8.08 (two s, 1H), 7.77 (m, 1H), 7.47 (m, 1H), 6.80 (m, 1H), 5.21(m, 1H), 3.48 (s, 3H), 3.43 (m, 3H), 3.33 (s, 2H), 3.15 (m, 4H), 1.99–1.05 (m, 11H).

EXAMPLE 165 trans-N-4-[(4,5-Dihydrobenzo[2,3]thiepino[4,5-d][1,3]thiazol-2-ylamino)methyl]cyclohexyl-N-isopropylformamide: 43% yield; 416 (ESMS, MH⁺); $^1$H NMR (CDCl$_3$) δ 8.22 & 8.18 (two s, 1H), 8.03 (dd, 1H, J=1.4, 7.8 Hz), 7.52 (dd, 1H, J=1.5, 8.4 Hz), 7.33 (apparent t, 1H, J=7.0 Hz), 7.16 (apparent dt, 1H, J=1.5, 8.4 Hz), 5.62–5.31 (b, 1H), 3.19 (s, 2H), 3.16 (m, 2H), 3.08 (m, 3H), 1.94–1.54 (m, 7H), 1.23 & 1.20 (two s, 6H), 1.14–1.01 (m, 3H)

EXAMPLE 166

N-(4-[(9-Fluoro-4,5-dihydrobenzo[2,3]thiepino[4,5-d][1,3]thiazol-2-yl)amino]methylcyclohexyl)-N-isopropylformamide: 62% yield, 434 (ESMS,MH⁺); $^1$H NMR (CDCl$_3$) δ 8.21 & 8.18 (two s, 1H), 7.76 (dd, 1H, J=2.9, 10.7 Hz), 7.47 (m, 1H), 6.87 (m, 1H), 5.52 (m, 1H), 4.29 & 3.60 (two m, 1H), 3.88 (m, 1H), 3.22–3.06 (m, 6H), 1.27 (d, 3H, J=6.9 Hz), 1.21 (d, 3H, J=6.9 Hz), 1.92–0.90 (m, 9H).

II. Synthetic Methods for General Structures

A. Triazine Compounds

The examples described in Section IA are merely illustrative of the methods used to synthesize triazine derivatives. Further derivatives may be obtained utilizing methods shown in Schemes 1–5. The substituents in Schemes 1–5 are described in the Detailed Description as relates to triazine compounds.

It may be necessary to incorporate protection and deprotection strategies for substituents such as amino, amido, carboxylic acid, and hydroxyl groups in the synthetic methods described above to form triazine derivatives. Methods for protection and deprotection of such groups are well-known in the art, and may be found, for example in Green, T. W. and Wuts, P. G. M. (1991) *Protection Groups in Organic Synthesis*, 2$^{nd}$ Edition John Wiley & Sons, New York.

B. Bicyclic Compounds

The examples described in Section IB are merely illustrative of the methods used to synthesize bicyclic derivatives. Further derivatives may be obtained utilizing methods shown in Schemes 6–10. The substituents in Schemes 6–10 are described in the Detailed Description as relates to bicyclic compounds.

It may be necessary to incorporate protection and deprotection strategies for substituents such as amino, amido, carboxylic acid, and hydroxyl groups in the synthetic methods described above to form bicyclic derivatives. Methods for protection and deprotection of such groups are well-known in the art, and may be found, for example in Green, T. W. and Wuts, P. G. M. (1991) *Protection Groups in Organic Synthesis*, 2$^{nd}$ Edition John Wiley & Sons, New York.

C. Tricyclic Compounds

The examples described in Section IC are merely illustrative of the methods used to synthesize tricyclic compounds. Further compounds may be obtained utilizing methods shown in Schemes 11–15. The substituents in Schemes 11–15 are described in the Detailed Description as relates to tricyclic compounds.

It may be necessary to incorporate protection and deprotection strategies for substituents such as amino, amido, carboxylic acid, and hydroxyl groups in the synthetic methods described above to form tricyclic derivatives. Methods for protection and deprotection of such groups are well-known in the art, and may be found, for example in Green, T. W. and Wuts, P. G. M. (1991) *Protection Groups in Organic Synthesis*, 2$^{nd}$ Edition John Wiley & Sons, New York.

III. Oral Compositions

As a specific embodiment of an oral composition of a compound of this invention, 100 mg of one of the compounds described herein is formulated with sufficient finely divided lactose to provide a total amount of 580 to 590 mg to fill a size O hard gel capsule.

IV. Pharmacological Evaluation of Compounds at Cloned Neuropeptide Y-type Receptors The pharmacological properties of the compounds of the present invention were evaluated at one or more of the cloned human neuropeptide Y-type receptors Y1, Y2, Y4, and Y5, using protocols described below.

Cell Culture

COS-7 cells were grown on 150 mm plates in D-MEM with supplements (Dulbecco's Modified Eagle Medium with 10% bovine calf serum, 4 mM glutamine, 100 units/ml penicillin/100 μg/ml streptomycin) at 37° C., 5% $CO_2$. Stock plates of COS-7 cells were trypsinized and split 1:6 every 3–4 days. Human embryonic kidney 293 cells were grown on 150 mm plates in D-MEM with supplements (minimal essential medium) with Hanks' salts and supplements (Dulbecco's Modified Eagle Medium with 10% bovine calf serum, 4 mM glutamine, 100 units/ml penicillin/100 μg/ml streptomycin) at 37° C., 5% $CO_2$. Stock plates of 293 cells were trypsinized and split 1:6 every 3–4 days. Mouse fibroblast LM(tk-) cells were grown on 150 mm plates in D-MEM with supplements (Dulbecco's Modified Eagle Medium with 10% bovine calf serum, 4 mM glutamine, 100 units/mL penicillin/100 μg/mL streptomycin) at 37° C., 5% $CO_2$. Stock plates of LM(tk-) cells were trypsinized and split 1:10 every 3–4 days.

LM(tk-) cells stably transfected with the human Y5 receptor were routinely converted from an adherent monolayer to a viable suspension. Adherent cells were harvested with trypsin at the point of confluence, resuspended in a minimal volume of complete DMEM for a cell count, and further diluted to a concentration of $10^6$ cells/ml in suspension media (10% bovine calf serum, 10% 10× Medium 199 (Gibco), 9 mM $NaHCO_3$, 25 mM glucose, 2 mM L-glutamine, 100 units/ml penicillin/100 μg/ml streptomycin, and 0.05% methyl cellulose). The cell suspension was maintained in a shaking incubator at 37° C., 5% $CO_2$ for 24 hours. Membranes harvested from cells grown in this manner may be stored as large, uniform batches in liquid nitrogen. Alternatively, cells may be returned to adherent cell culture in complete DMEM by distribution into 96-well microtiter plates coated with poly-D-lysine (0.01 mg/ml) followed by incubation at 37° C., 5% $CO_2$ for 24 hours. Cells prepared in this manner yielded a robust and reliable NPY-dependent response in cAMP radio-immunoassays as further described hereinbelow.

Mouse embryonic fibroblast NIH-3T3 cells were grown on 150 mm plates in Dulbecco's Modified Eagle Medium (DMEM) with supplements (10% bovine calf serum, 4 mM glutamine, 100 units/ml penicillin/100 μg/ml streptomycin) at 37° C., 5% $CO_2$. Stock plates of NIH-3T3 cells were trypsinized and split 1:15 every 3–4 days.

Sf9 and Sf21 cells were grown in monolayers on 150 mm tissue culture dishes in TMN-FH media supplemented with 10% fetal calf serum, at 27° C., no $CO_2$. High Five insect cells were grown on 150 mm tissue culture dishes in Ex-Cell 400™ medium supplemented with L-Glutamine, also at 27° C., no $CO_2$.

Transient Transfection

All receptor subtypes studied (human and rat Y1, human and rat Y2, human and rat Y4, human and rat Y5) were transiently transfected into COS-7 cells by the DEAE-dextran method, using 1 μg of DNA/$10^6$ cells (Cullen, 1987). The human Y1 receptor was prepared using known methods (Larhammar, et al., 1992).

Stable Transfection

Human Y1, human Y2, and rat Y5 receptors were co-transfected with a G-418 resistant gene into the human embryonic kidney 293 cell line by a calcium phosphate transfection method (Cullen, 1987). Stably transfected cells were selected with G-418. Human Y4 and human Y5 receptors were similarly transfected into mouse fibroblast LM(tk-) cells and NIH-3T3 cells.

Binding of the compounds of the present invention to human Y1, Y2, Y4, and Y5 receptors was evaluated using stably transfected 293 or LM(tk-) cells as described above. Stably transfected cell lines which may be used for binding assays include, for example, for the human Y1 receptor, 293-hY1-5 (deposited Jun. 4, 1996, under ATCC Accession No. CRL-12121), for the human Y2 receptor, 293-hY2-10 (deposited Jan. 27, 1994, under ATCC Accession No. CRL-11537), for the human Y4 receptor, L-hY4-3 (deposited Jan. 11, 1995, under ATCC Accession No. CRL-11779), and for human Y5 receptor, L-hY5-7 (deposited Nov. 15, 1995, under ATCC Accession No. CRL-11995). These cell lines were deposited with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure.

Membrane Harvest

Membranes were harvested from COS-7 cells 48 hours after transient transfection. Adherent cells were washed twice in ice-cold phosphate buffered saline (138 mM NaCl, 8.1 mM $Na_2HPO_4$, 2.5 mM KCl, 1.2 mM $KH_2PO_4$, 0.9 mM $CaCl_2$, 0.5 mM $MgCl_2$, pH 7.4) and lysed by sonication in ice-cold sonication buffer (20 mM Tris-HCl, 5 mM EDTA, pH 7.7). Large particles and debris were cleared by low speed centrifugation (200×g, 5 min, 4° C.). Membranes were collected from the supernatant fraction by centrifugation (32,000×g, 18 min, 4° C.), washed with ice-cold hypotonic buffer, and collected again by centrifugation (32,000×g, 18 min, 4° C.). The final membrane pellet was resuspended by sonication into a small volume of ice-cold binding buffer (~1 ml for every 5 plates: 10 mM NaCl, 20 mM HEPES, 0.22 mM $KH_2PO_4$, 1.26 mM $CaCl_2$, 0.81 mM $MgSO_4$, pH 7.4). Protein concentration was measured by the Bradford method (Bradford, 1976) using Bio-Rad Reagent, with bovine serum albumin as a standard. Membranes were held on ice for up to one hour and used fresh, or flash-frozen and stored in liquid nitrogen.

Membranes were prepared similarly from 293, LM(tk-), and NIH-3T3 cells. To prepare membranes from baculovirus infected cells, $2\times10^7$ Sf21 cells were grown in 150 mm tissue culture dishes and infected with a high-titer stock of hY5BB3. Cells were incubated for 2–4 days at 27° C., no $CO_2$ before harvesting and membrane preparation as described above.

Membranes were prepared similarly from dissected rat hypothalamus. Frozen hypothalami were homogenized for 20 seconds in ice-cold sonication buffer with the narrow probe of a Virtishear homogenizer at 1000 rpm (Virtis, Gardiner, N.Y.). Large particles and debris were cleared by centrifugation (200×g, 5 min, 4° C.) and the supernatant fraction was reserved on ice. Membranes were further extracted from the pellet by repeating the homogenization and centrifugation procedure two more times. The supernatant fractions were pooled and subjected to high speed centrifugation (100,000×g, 20 min. 4° C.). The final membrane pellet was resuspended by gentle homogenization into a small volume of ice-cold binding buffer (1 mL/gram wet weight tissue) and held on ice for up to one hour, or flash-frozen and stored in liquid nitrogen.

Radioligand Binding to Membrane Suspensions

Membrane suspensions were diluted in binding buffer supplemented with 0.1% bovine serum albumin to yield an optimal membrane protein concentration so that $^{125}$I-PYY (or alternative radioligand such as $^{125}$I-NPY, $^{125}$I-$NYY_{3-36}$, or $^{125}$I-[$Leu^{31}Pro^{34}$]PYY) bound by membranes in the assay was less than 10% of $^{125}$I-PYY (or alternative radioligand) delivered to the sample (100,000 dpm/sample=0.08 nM for competition binding assays). $^{125}$I-PYY (or alternative radioligand) and peptide competitors were also diluted to desired concentrations in supplemented binding buffer. Individual samples were then prepared in 96-well polypropylene microtiter plates by mixing $^{125}$I-PYY (25 μL) (or alternative radioligand), competing peptides or supplemented binding buffer (25 μL), and finally, membrane suspensions (200 μL). Samples were incubated in a 30° C. water bath with constant shaking for 120 min. Incubations were terminated by filtration over Whatman GF/C filters (pre-coated with 1% polyethyleneimine and air-dried before use), followed by washing with 5 mL of ice-cold binding buffer. Filter-trapped membranes were impregnated with MeltiLex solid scintillant (Wallac, Turku, Finland) and counted for $^{125}$I in a Wallac Beta-Plate Reader. Alternatively, incubations were carried out in GF/C filter plates (pre-coated with 1% polyethyleneimine and air-dried before use), followed by vacuum filtration and three washes of 300 μL of ice-cold binding buffer. 50 μL of UltimaGold (Packard) scintillant were added and counted for $^{125}$I, in a Wallac MicroBeta Trilux. Non-specific binding was defined by 300 nM human NPY for all receptors except the Y4 subtypes; 100 nM human PP was used for the human Y4 and 100 nM rat PP for the rat Y4. Specific binding in time course and competition studies was typically 80%; most non-specific binding was associated with the filter. Binding data were analyzed using nonlinear regression and statistical techniques available in the GraphPAD Prism package (San Diego, Calif.).

Functional Assay: Radioimmunoassay of cAMP

Stably transfected cells were seeded into 96-well microtiter plates and cultured until confluent. To reduce the potential for receptor desensitization, the serum component of the media was reduced to 1.5% for 4 to 16 hours before the assay. Cells were washed in Hank's buffered saline, or HBS (150 mM NaCl, 20 mM HEPES, 1 mM $CaCl_2$, 5 mM KCl, 1 mM $MgCl_2$, and 10 mM glucose) supplemented with 0.1% bovine serum albumin plus 5 mM theophylline and pre-equilibrated in the same solution for 20 min at 37° C. in 5% $CO_2$. Cells were then incubated 5 min with 10 μM forskolin and various concentrations of receptor-selective ligands. The assay was terminated by the removal of HBS and acidification of the cells with 100 mM HCl. Intracellular cAMP was extracted and quantified with a modified version of a magnetic bead-based radioimmunoassay (Advanced Magnetics, Cambridge, Mass.). The final antigen/antibody complex was separated from free $^{125}$I-cAMP by vacuum filtration through a PVDF filter in a microtiter plate (Millipore, Bedford, Mass.). Filters were punched and counted for $^{125}$I, in a Packard gamma counter. Binding data were analyzed using nonlinear regression and statistical techniques available in the GraphPAD Prism package (San Diego, Calif.).

Functional Assay: Intracellular Calcium Mobilization

The intracellular free calcium concentration was measured by microspectroflourometry using the fluorescent indicator dye Fura-2/AM. Stably transfected cells were seeded onto a 35 mm culture dish containing a glass coverslip insert. Cells were washed with HBS and loaded with 100 μl of Fura-2/AM (10 μM) for 20 to 40 min. After washing with HBS to remove the Fura-2/AM solution, cells were equilibrated in HBS for 10 to 20 min. Cells were then visualized under the 40× objective of a Leitz Fluovert FS microscope and fluorescence emission was determined at 510 nM with excitation wave lengths alternating between 340 nM and 380 nM. Raw fluorescence data were converted to calcium concentrations using standard calcium concentration curves and software analysis techniques.

Materials

Cell culture media and supplements were from Specialty Media (Lavallette, N.J.). Cell culture plates (150 mm and 96-well microtiter) were from Corning (Corning, N.Y.). Sf9, Sf21, and High Five insect cells, as well as the baculovirus transfer plasmid, pBlueBacIII™, were purchased from Invitrogen (San Diego, Calif.). TMN-FH insect medium complemented with 10% fetal calf serum, and the baculovirus DNA, BaculoGold™, was obtained from Pharmingen (San Diego, Calif.). Ex-Cell 400™ medium with L-Glutamine was purchased from JRH Scientific. Polypropylene 96-well microtiter plates were from Co-star (Cambridge, Mass.). All radioligands were from New England Nuclear (Boston, Mass.). Commercially available NPY and related peptide analogs were either from Bachem California (Torrance, Calif.) or Peninsula (Belmont, Calif.); [D-Trp$^{32}$]NPY and PP C-terminal fragments were synthesized by custom order from Chiron Mimotopes Peptide Systems (San Diego, Calif.). Bio-Rad Reagent was from Bio-Rad (Hercules, Calif.). Bovine serum albumin (ultra-fat free, A-7511) was from Sigma (St. Louis. Mo.). All other materials were reagent grade.

Radioligand Binding Assay Results

The compounds described above were assayed using cloned human NPY receptors. The preferred compounds were found to be selective NPY (Y5) antagonists. Example 49 has been assayed using the cloned human NPY receptors and a $K_i$ (nM)>100000 was determined for NPY (Y1), NPY (Y2), and NPY (Y4). The binding affinities of several compounds for NPY (Y5) are illustrated in Tables 1–6.

TABLE 1

| Example # | R | $K_i$ (nM) hNPY-5 |
|---|---|---|
| 1 | $CH_3NH-$ | 13 |
| 2 | $CH_3CH_2NH-$ | 7 |
| 3 | $CH_2=CH_2CH_2NH-$ | 12 |
| 4 | $(CH_3)_2CHNH-$ | 23 |
| 5 | $CH_3CH_2CH_2NH-$ | 18 |
| 6 | $CH_3CH_2CH_2CH_2NH-$ | 22 |
| 7 | cyclobutyl-NH— | 22 |
| 8 | cyclopropyl-NH— | 9 |
| 9 | $CH_3CH_2CH_2CH_2CH_2NH-$ | 6 |
| 10 | $NCCH_2CH_2NH-$ | 81 |
| 11 | $HOCH_2CH_2NH-$ | 35 |
| 12 | $CH_3OCH_2CH_2NH-$ | 18 |
| 13 | $CH_3OCH_2CH_2CH_2NH-$ | 22 |
| 14 | $(CH_3)_2NCH_2CH_2NH-$ | 194 |
| 15 | imidazolyl-$(CH_2)_3$-NH— | 83 |

TABLE 1-continued

[Structure: triazine with HN-isopropyl, R, and NH-CH2-cyclohexyl-CH2-NH-SO2-naphthalene]

| Example # | R | K_i (nM) hNPY-5 |
|---|---|---|
| 16 | [4-methoxyphenethyl-N(H)(CH3)-] | 313 |
| 17 | (CH$_3$)$_2$N— | 27 |
| 18 | CH$_3$CH$_2$(CH$_3$)N— | 32 |
| 19 | (CH$_3$CH$_2$)$_2$N— | 53 |
| 20 | pyrrolidin-1-yl | 19 |
| 21 | (S)-2-(methoxymethyl)pyrrolidin-1-yl | 71 |
| 22 | piperidin-1-yl | 38 |
| 23 | 2-methylpiperidin-1-yl | 68 |
| 24 | morpholin-4-yl | 40 |
| 25 | 2,6-dimethylmorpholin-4-yl | 135 |
| 26 | HOCH$_2$CH$_2$(CH$_3$)N— | 86 |
| 27 | 4-acetylpiperazin-1-yl | 31 |
| 28 | 4-isopropyl-piperazin-1-yl (methyl) | 22 |

TABLE 2

[Structure: triazine with HN-ethyl, NH-ethyl, and NH-CH2-cyclohexyl-CH2-NH-SO2-R]

| Example # | R | K_i (nM) hNPY-5 |
|---|---|---|
| 29 | 4-t-butylphenyl | 50 |
| 30 | 4-fluorophenyl | 40 |
| 31 | 2-methoxy-5-methylphenyl | 25 |
| 32 | 2-fluorophenyl | 35 |
| 33 | 2-methylphenyl | 22 |
| 34 | 3-methylpyridinyl | 427 |
| 35 | 4-methoxyphenyl | 82 |
| 36 | 2,4,5-trimethyloxazolyl | 71 |
| 37 | thiophen-2-yl | 55 |
| 38 | 1,4-dimethylimidazol-yl | 313 |
| 39 | 4-methylphenyl | 28 |
| 40 | 5-methylbenzothiadiazolyl | 5 |
| 41 | 8-methylquinolinyl | 13 |
| 42 | Methyl | 3067 |

TABLE 3

[Structure: triazine with R1, R2 substituents, NH-CH2-cyclohexyl-CH2-NH-SO2-R3]

| Example # | R₁ | R₂ | R₃ | Kᵢ (nM) hNPY-5 |
|---|---|---|---|---|
| 43 | isopropyl-NH- | pyrrolidin-1-yl | pyrrolidin-1-yl | 43 |
| 44 | isopropyl-NH- | morpholin-4-yl | morpholin-4-yl | 295 |
| 45 | isopropyl-NH- | piperidin-1-yl | piperidin-1-yl | 59 |
| 46 | pyrrolidin-1-yl | pyrrolidin-1-yl | 4-t-butylphenyl | 68 |
| 47 | isopropyl-NH- | cyclopropyl-NH- | cyclopropyl-NH- | 359 |
| 48 | isopropyl-NH- | cyclopropyl-NH- | dimethylamino | 192 |
| 49 | isopropyl-NH- | chloro | 1-naphthyl | 138 |
| 50 | morpholin-4-yl | morpholin-4-yl | dimethylamino | 3508 |
| 51 | isopropyl-NH- | chloro | 4-t-butylphenyl | 3544 |
| 52 | cyclopropyl-NH- | pyrrolidin-1-yl | 4-fluorophenyl | 101 |
| 53 | chloro | chloro | dimethylamino | 20654 |
| 54 | pyrrolidin-1-yl | pyrrolidin-1-yl | 2-methoxy-5-methylphenyl | — |
| 55 | cyclopropyl-NH- | 2-pyridyl | 4-fluorophenyl | 209 |

TABLE 4
| Example # | R₁ | R₂ | R₃ | $K_i$ (nM) hNPY-5 |
|---|---|---|---|---|
| 56 | 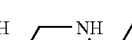 |  |  | 94406 |
| 57 | 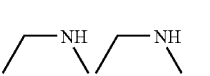 |  |  | >100000 |
| 58 |  |  | 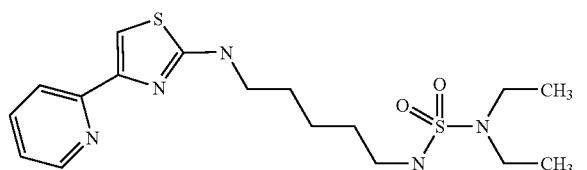 | >100000 |
TABLE 5
| EXAMPLE No. | STRUCTURE | $K_i$, nM hNPY-5 | $K_i$, nM hNPY-1,2,4 |
|---|---|---|---|
| 59 | 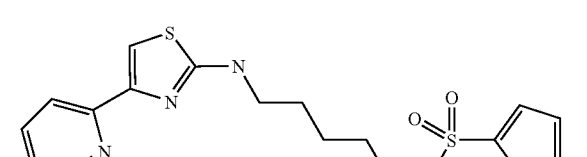 | 3.7 | >10000 |
| 60 | 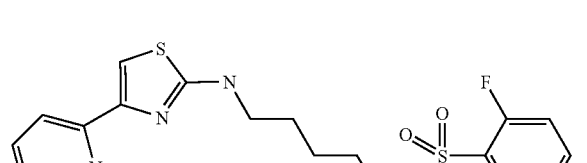 | 31 | |
| 61 | 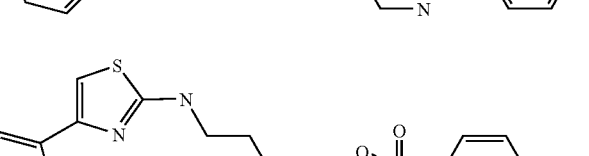 | 9.7 | >10000 |
| 62 | 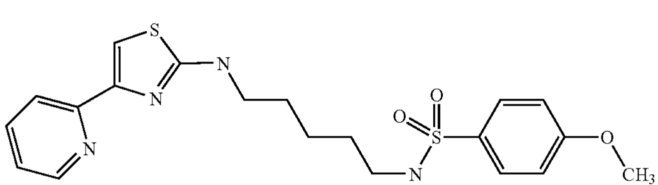 | 33 | |

TABLE 5-continued

| EXAMPLE No. | STRUCTURE | $K_i$, nM hNPY-5 | $K_i$, nM hNPY-1,2,4 |
|---|---|---|---|
| 63 | 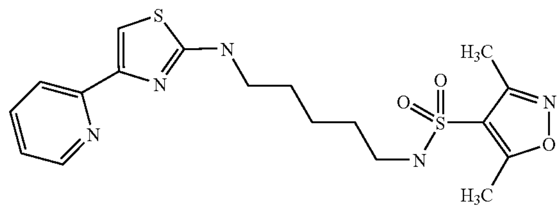 | 18.7 | >10000 |
| 64 | 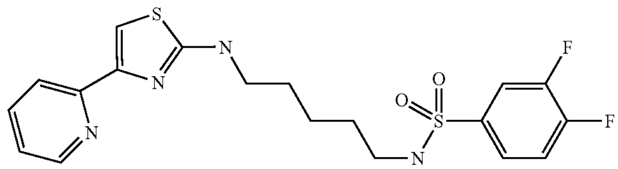 | 42 | |
| 65 | 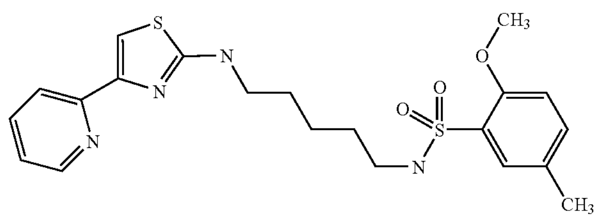 | 2.7 | >10000 |
| 66 | 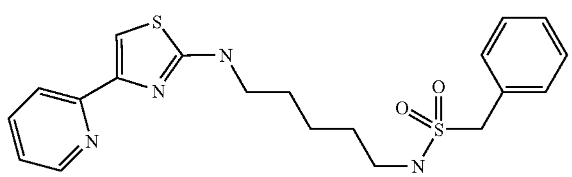 | 45 | |
| 67 | 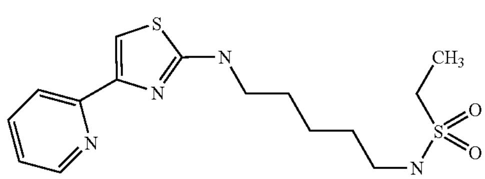 | 150 | |
| 68 | 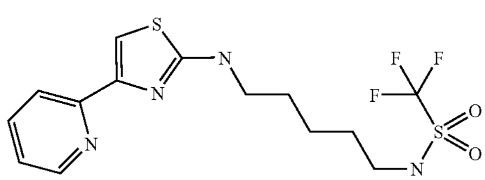 | 109 | |
| 69 | 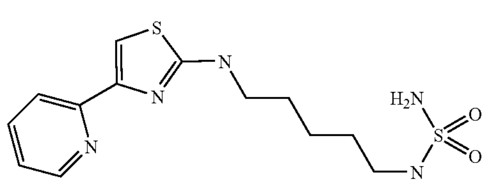 | 804 | |
| 70 | 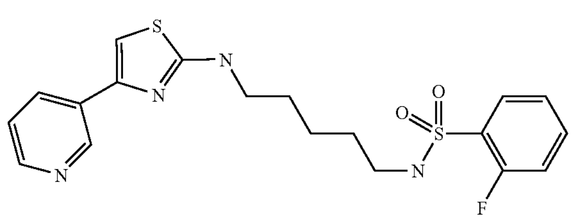 | 21 | >10000 |

TABLE 5-continued

| EXAMPLE No. | STRUCTURE | $K_i$, nM hNPY-5 | $K_i$, nM hNPY-1,2,4 |
|---|---|---|---|
| 71 | 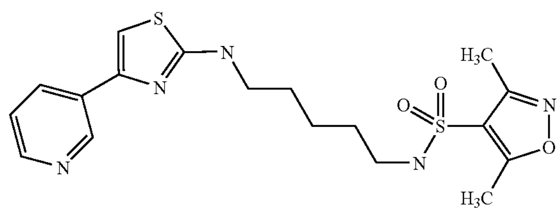 | 37 | >10000 |
| 72 | 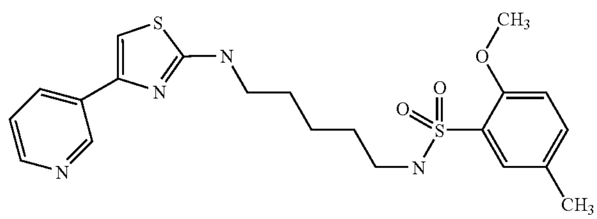 | 50 | >10000 |
| 73 | 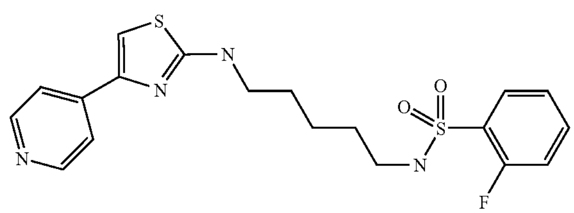 | 204 | >10000 |
| 74 | 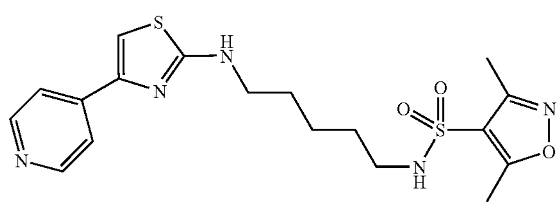 | 745 | >10000 |
| 75 | 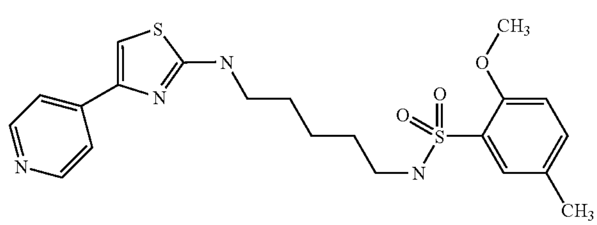 | 5 | >10000 |
| 76 | 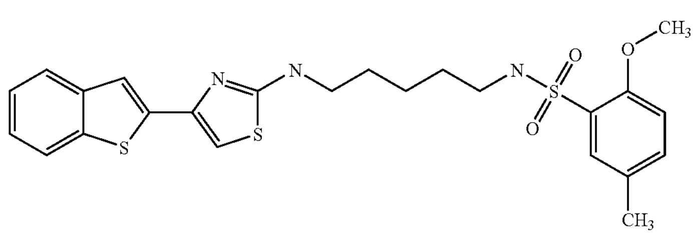 | 11 | >10000 |

TABLE 5-continued

| EXAMPLE No. | STRUCTURE | $K_i$, nM hNPY-5 | $K_i$, nM hNPY-1,2,4 |
|---|---|---|---|
| 77 | 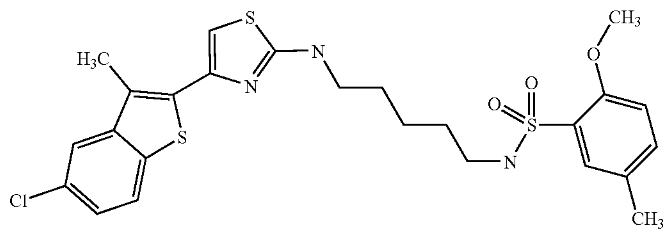 | 297 | >10000 |
| 78 | 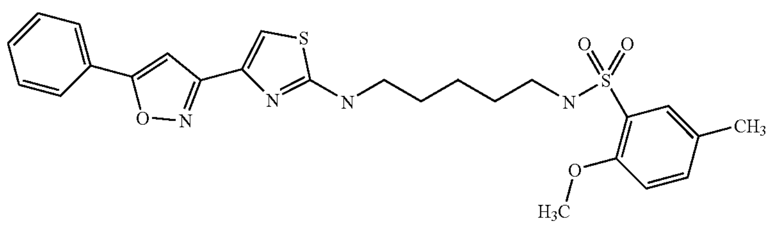 | 891 | >10000 |
| 79 | 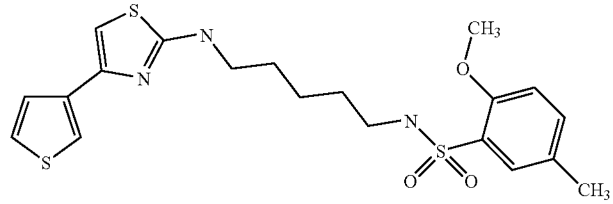 | 545 | >10000 |
| 80 | 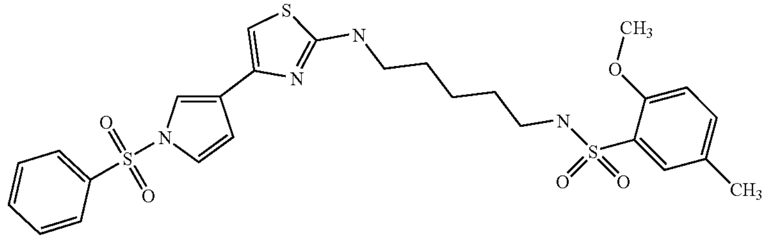 | 40 | >10000 |
| 81 | 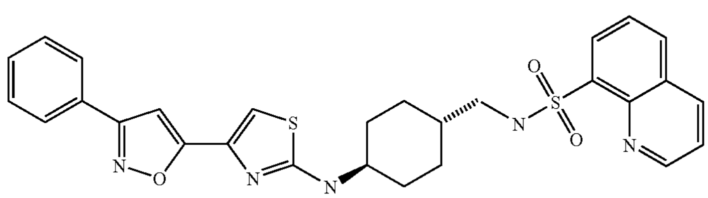 | 155 | >10000 |
| 82 | 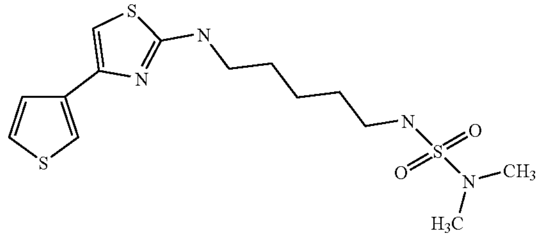 | 8.3 | >10000 |

TABLE 5-continued
| EXAMPLE No. | STRUCTURE | $K_i$, nM hNPY-5 | $K_i$, nM hNPY-1,2,4 |
|---|---|---|---|
| 83 | 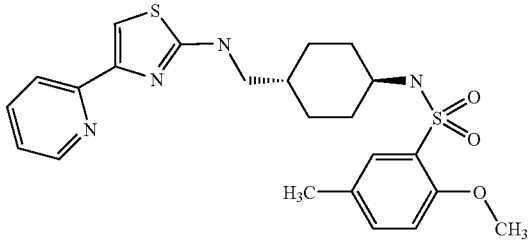 | 4 | |
| 84 | 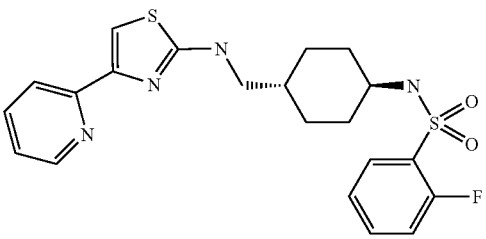 | 8.4 | |
| 85 | 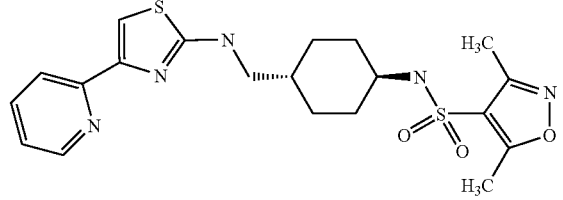 | 3.8 | |
| 86 | 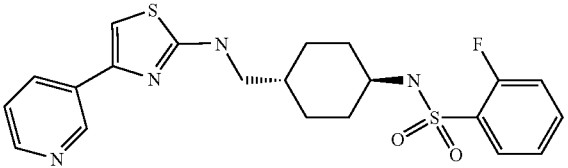 | 12.3 | |
| 87 | 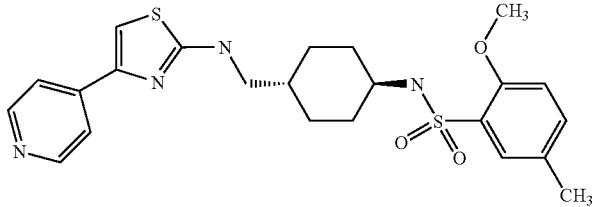 | 17 | |
| 88 | 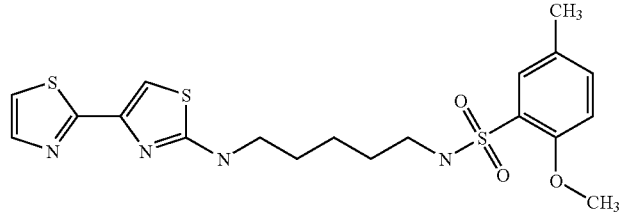 | 13.7 | |

TABLE 5-continued

| EXAMPLE No. | STRUCTURE | $K_i$, nM hNPY-5 | $K_i$, nM hNPY-1,2,4 |
|---|---|---|---|
| 89 | 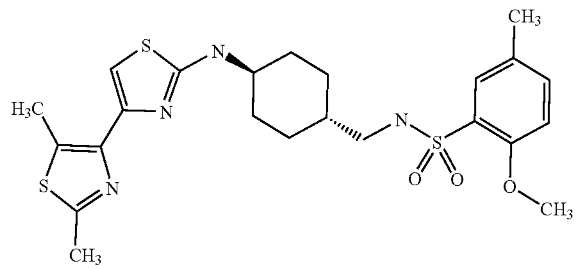 | 3.2 | |
| 90 | 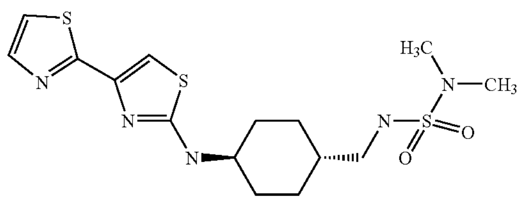 | 17.5 | |
| 91 | 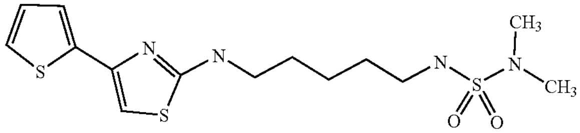 | 12.4 | |
| 92 | 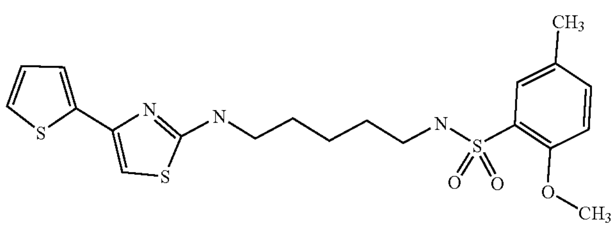 | 7.9 | |
| 93 | 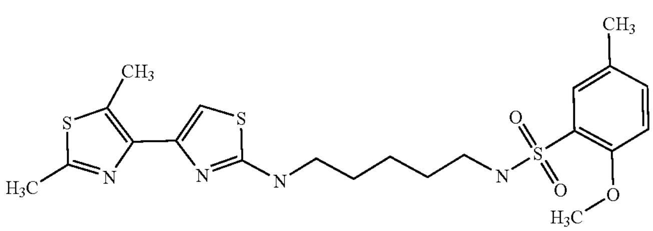 | 3.6 | |
| 94 | 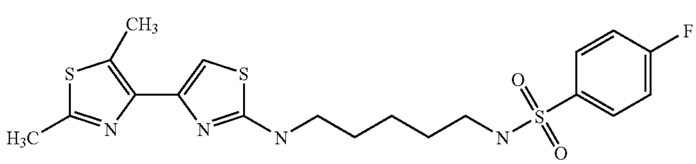 | 19.5 | |
| 95 | 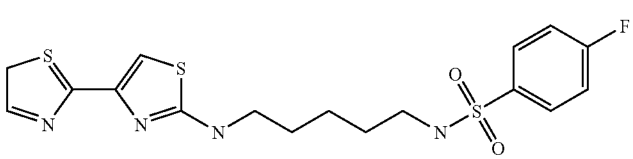 | 179 | |

TABLE 5-continued

| EXAMPLE No. | STRUCTURE | $K_i$, nM hNPY-5 | $K_i$, nM hNPY-1,2,4 |
|---|---|---|---|
| 96 | 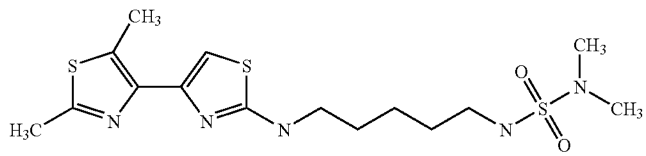 | 8.1 | |
| 97 | 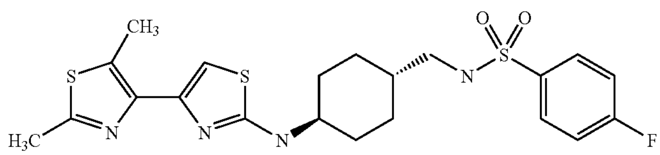 | 6.6 | |
| 98 | 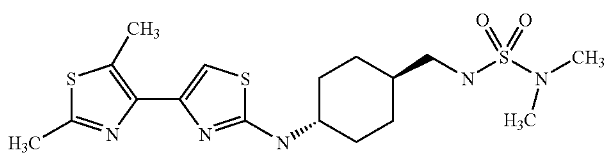 | 1.5 | |
| 99 | 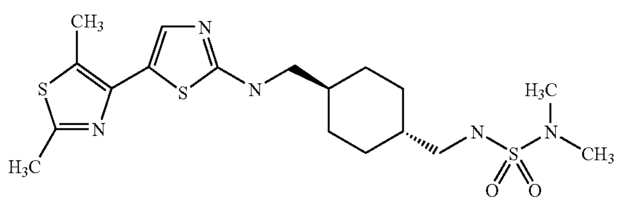 | 3.1 | |
| 100 | 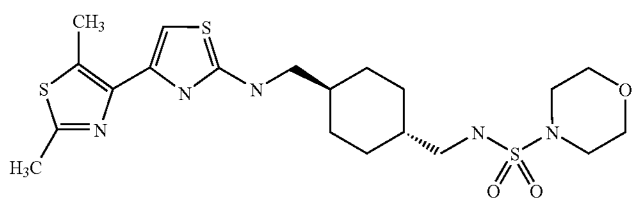 | 3.3 | |
| 101 | 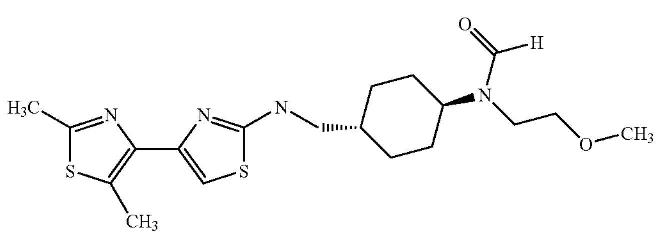 | 407 | |
| 102 | 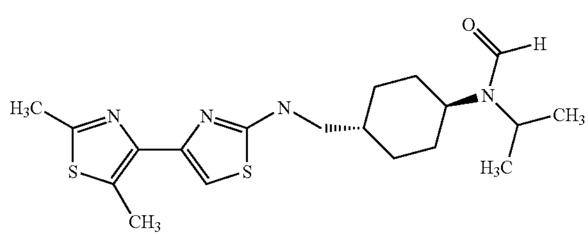 | 72 | |

TABLE 6

| EXAMPLE No. | STRUCTURE | K$_i$, nM hNPY-5 | K$_i$, nM hNPY-1,2,4 |
|---|---|---|---|
| 103 | 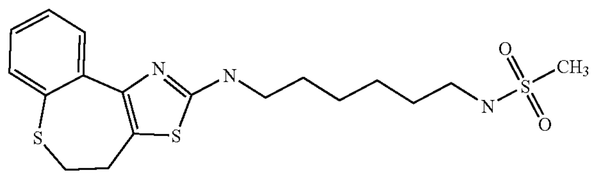 | 7.4 | |
| 104 | 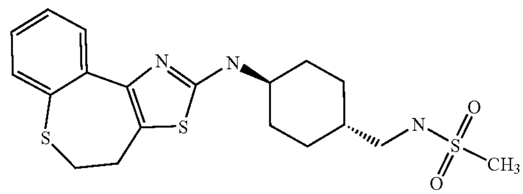 | 6.8 | |
| 105 | 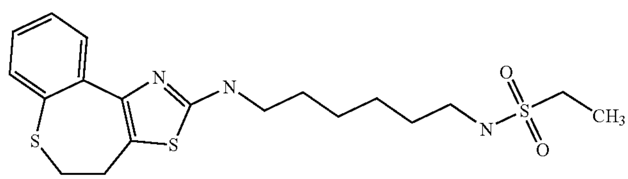 | 5.4 | |
| 106 | 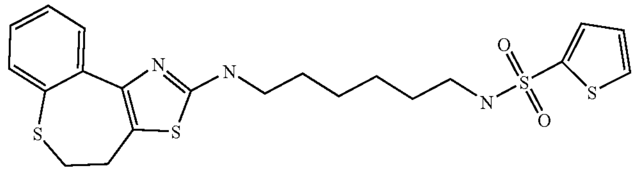 | 2.9 | >10000 |
| 107 | 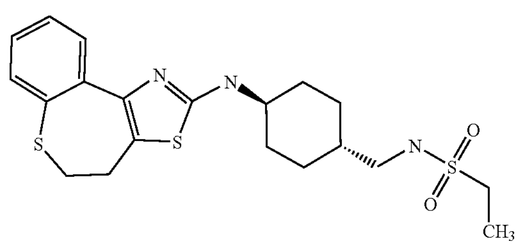 | 5.1 | >10000 |
| 108 | 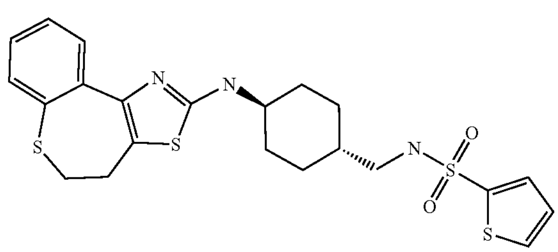 | 5.1 | |
| 109 | 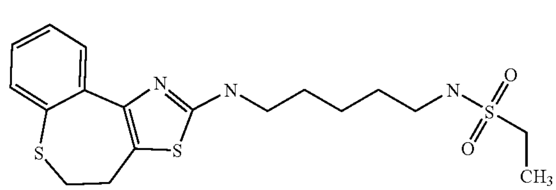 | 3.7 | >10000 |

TABLE 6-continued

| EXAMPLE No. | STRUCTURE | $K_i$, nM hNPY-5 | $K_i$, nM hNPY-1,2,4 |
|---|---|---|---|
| 110 | 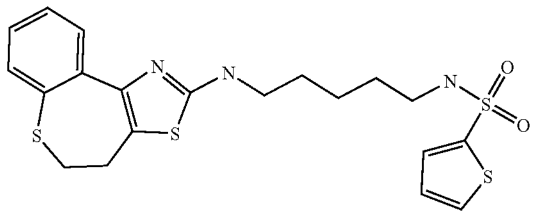 | 2.6 | >10000 |
| 111 | 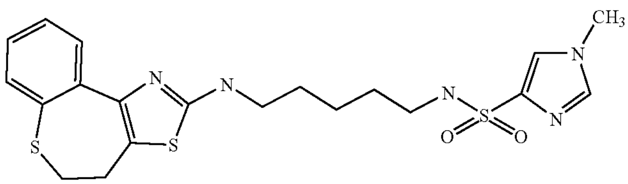 | 17.2 | |
| 112 | 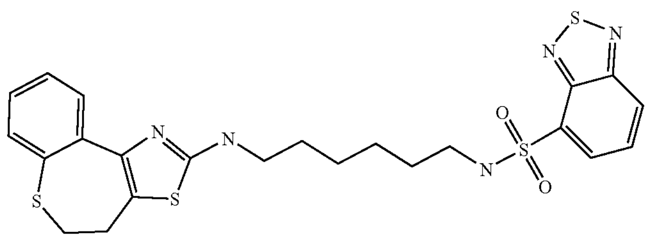 | 4.4 | |
| 113 | 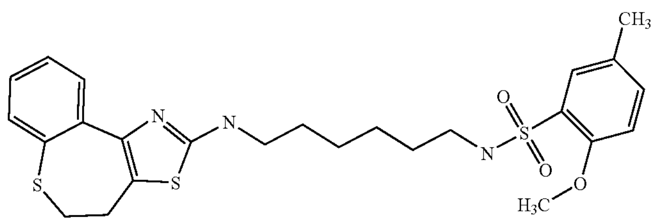 | 5.4 | |
| 114 | 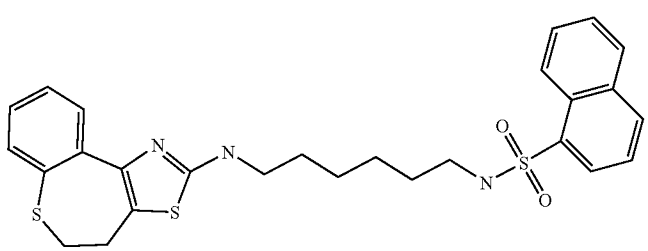 | 16.6 | |
| 115 | 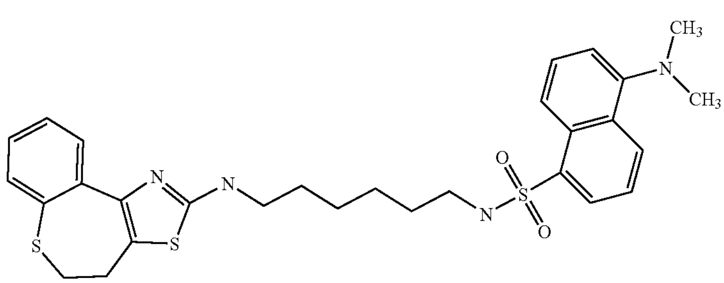 | 71 | |

TABLE 6-continued
| EXAMPLE No. | STRUCTURE | $K_i$, nM hNPY-5 | $K_i$, nM hNPY-1,2,4 |
|---|---|---|---|
| 116 | 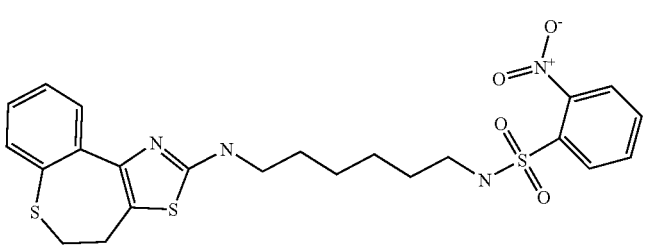 | 7.1 | |
| 117 | 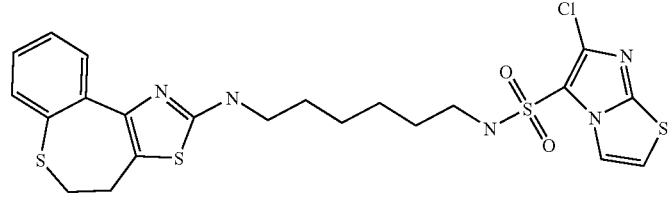 | 6.6 | |
| 118 | 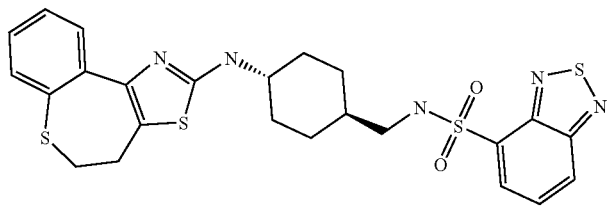 | 2.4 | >10000 |
| 119 | 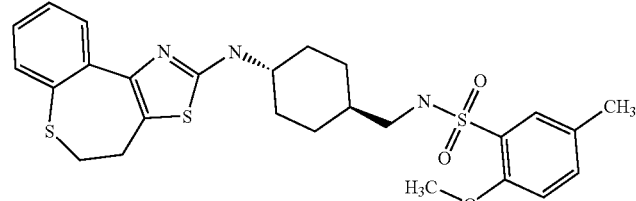 | 14.1 | |
| 120 | 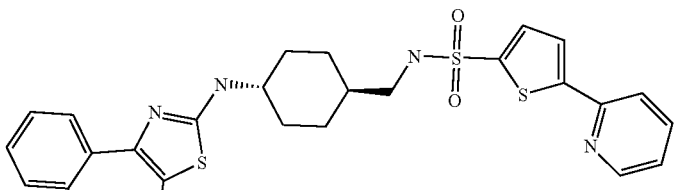 | 54 | |
| 121 | 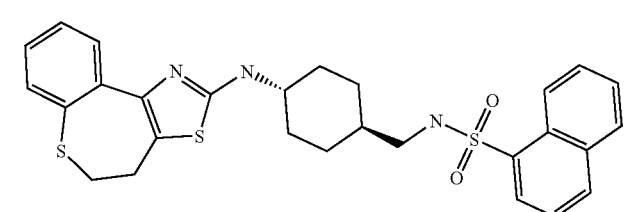 | 18.4 | |

TABLE 6-continued

| EXAMPLE No. | STRUCTURE | K$_i$, nM hNPY-5 | K$_i$, nM hNPY-1,2,4 |
|---|---|---|---|
| 122 | 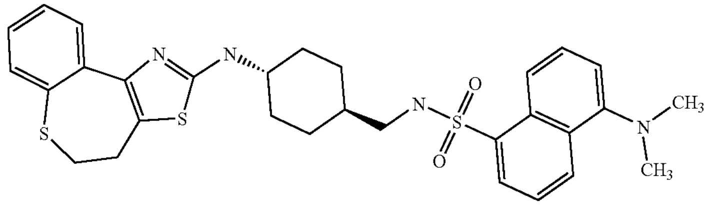 | 27 | |
| 123 | 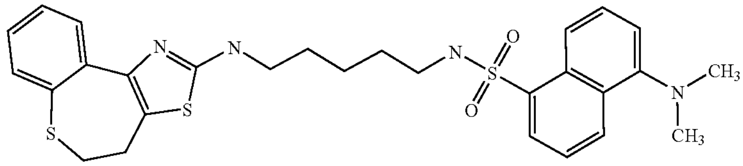 | 161 | |
| 124 | 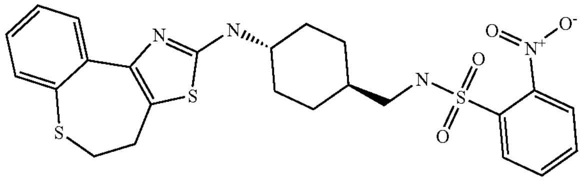 | 11.5 | |
| 125 | 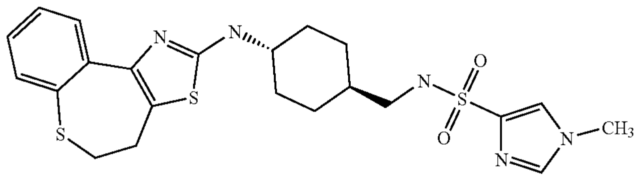 | 33 | |
| 126 | 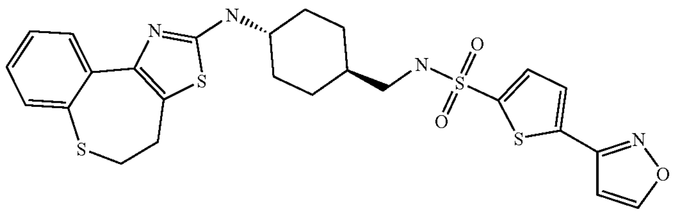 | 34 | |
| 127 | 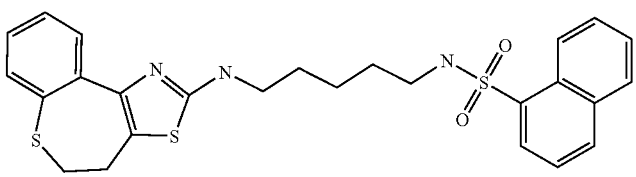 | 17.2 | |
| 128 | 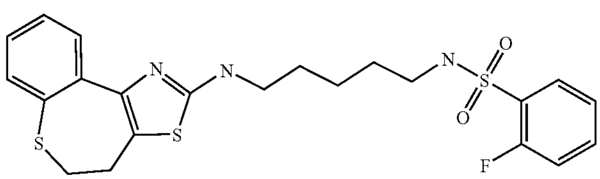 | 3.7 | |
| 129 | 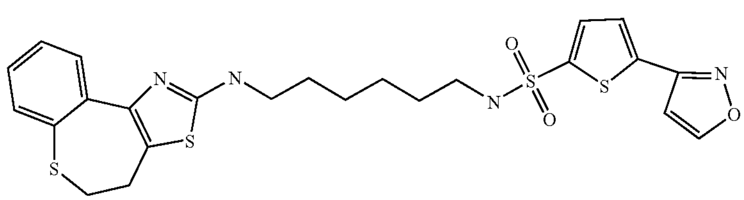 | 29 | |

TABLE 6-continued

| EXAMPLE No. | STRUCTURE | $K_i$, nM hNPY-5 | $K_i$, nM hNPY-1,2,4 |
|---|---|---|---|
| 130 | 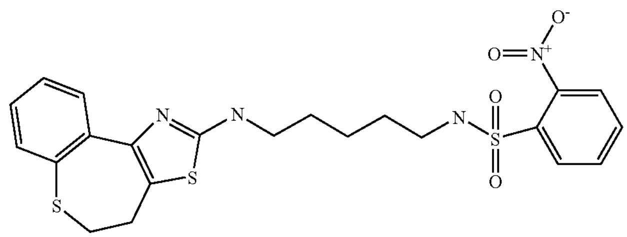 | 5.2 | |
| 131 | 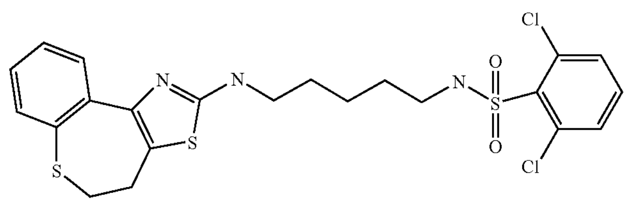 | 71 | |
| 132 | 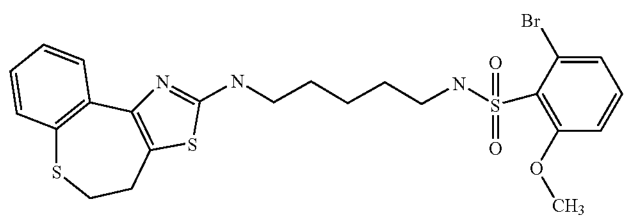 | 9.7 | |
| 133 | 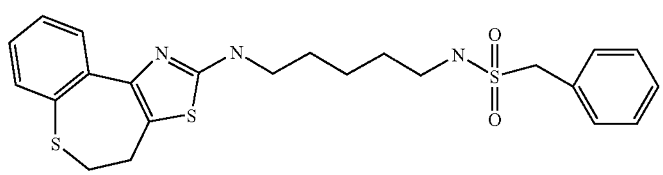 | 38 | |
| 134 | 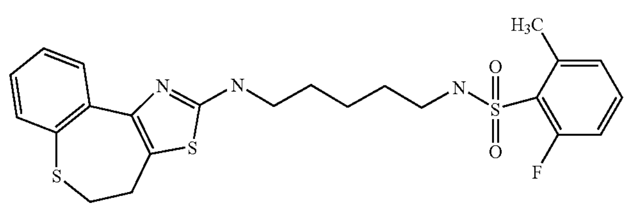 | 8.3 | |
| 135 | 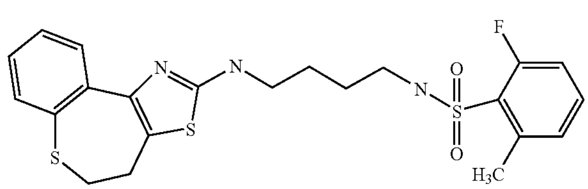 | 110 | |
| 136 | 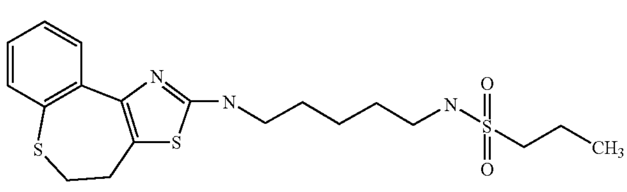 | 24 | |

TABLE 6-continued

| EXAMPLE No. | STRUCTURE | $K_i$, nM hNPY-5 | $K_i$, nM hNPY-1,2,4 |
|---|---|---|---|
| 137 | 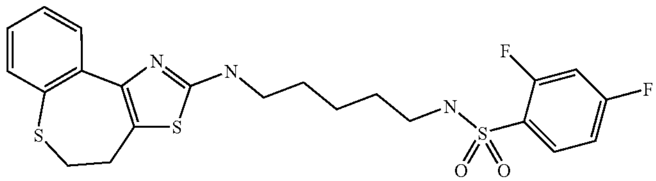 | 6.5 | |
| 138 | 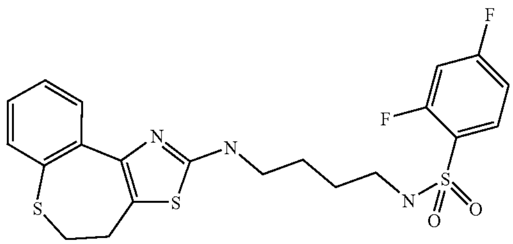 | 119 | |
| 139 | 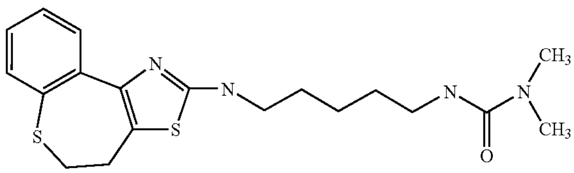 | 122 | |
| 140 | 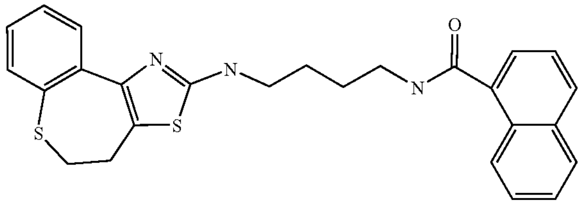 | 123 | |
| 141 | 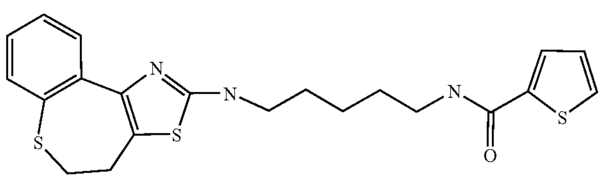 | 84 | |
| 142 | 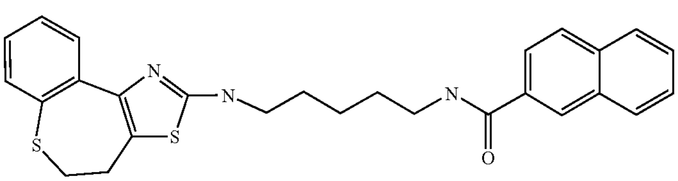 | 100 | |
| 143 | 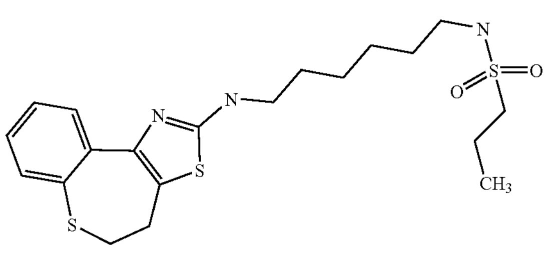 | 3.6 | |

TABLE 6-continued

| EXAMPLE No. | STRUCTURE | $K_i$, nM hNPY-5 | $K_i$, nM hNPY-1,2,4 |
|---|---|---|---|
| 144 | 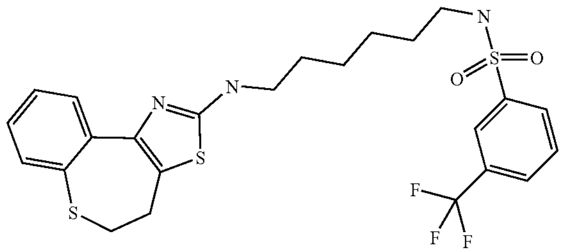 | 22.4 | |
| 145 | 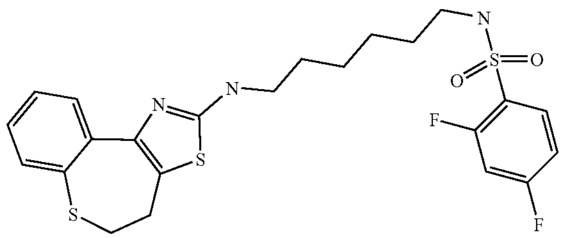 | 4.1 | |
| 146 | 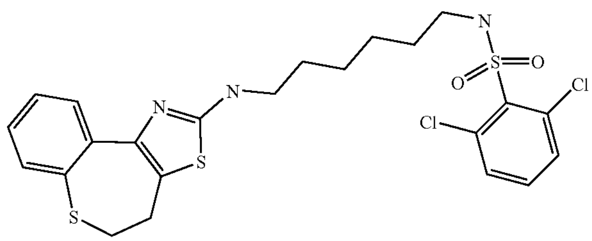 | 25 | |
| 147 | 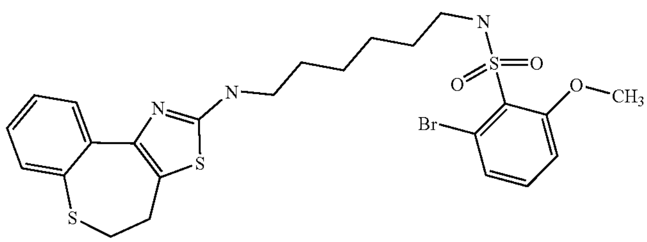 | 7.9 | |
| 148 | 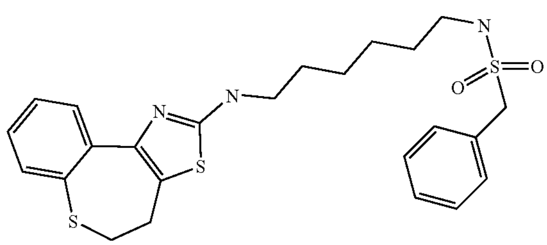 | 10.5 | |
| 149 | 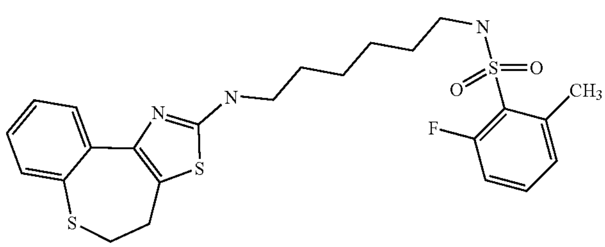 | 4 | |

TABLE 6-continued

| EXAMPLE No. | STRUCTURE | $K_i$, nM hNPY-5 | $K_i$, nM hNPY-1,2,4 |
|---|---|---|---|
| 150 | 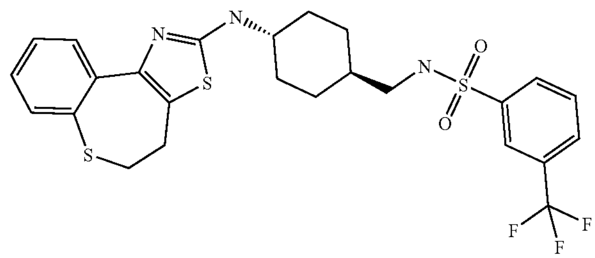 | 21 | |
| 151 | 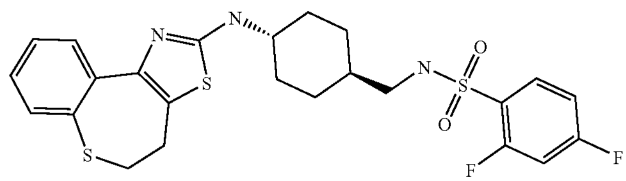 | 7.9 | |
| 152 | 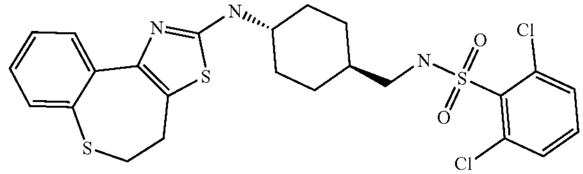 | 17.4 | |
| 153 | 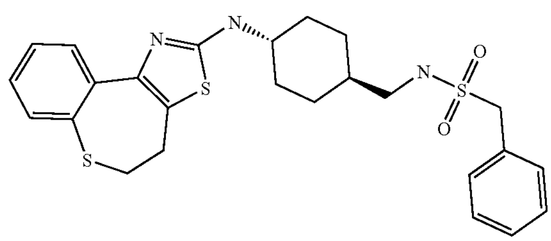 | 8.9 | |
| 154 | 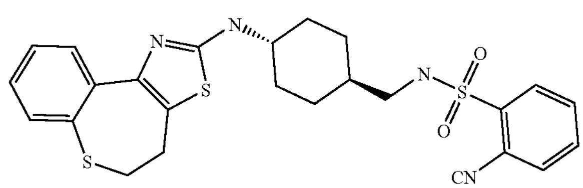 | 69 | |
| 155 | 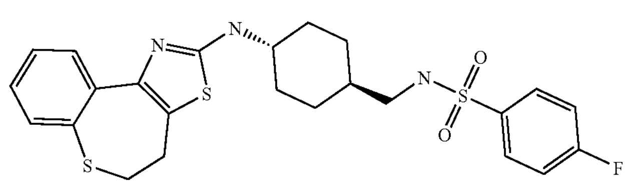 | 9.1 | |
| 156 | 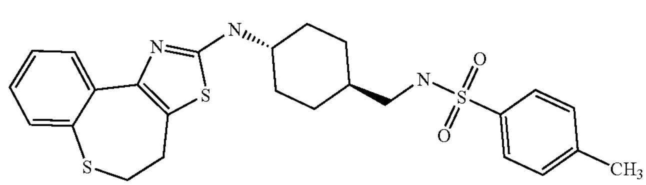 | 6.6 | |

TABLE 6-continued

| EXAMPLE No. | STRUCTURE | K$_i$, nM hNPY-5 | K$_i$, nM hNPY-1,2,4 |
|---|---|---|---|
| 157 | 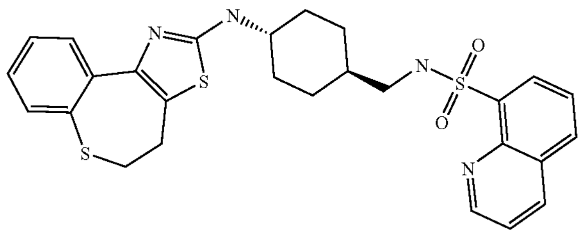 | 5.7 | |
| 158 | 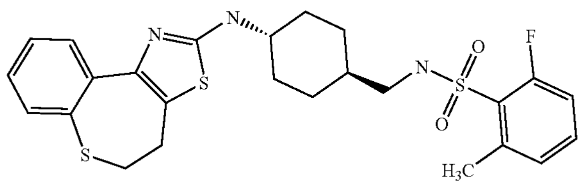 | 8.2 | >10000 |
| 159 | 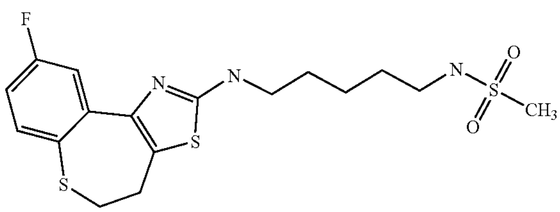 | 6.1 | >10000 |
| 160 | 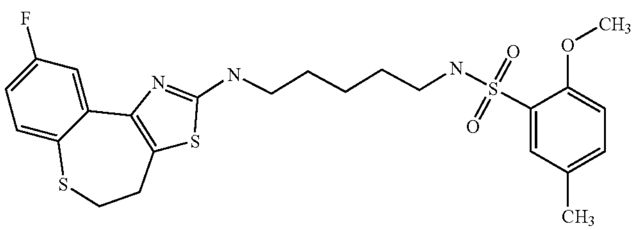 | 2.8 | >10000 |
| 161 | 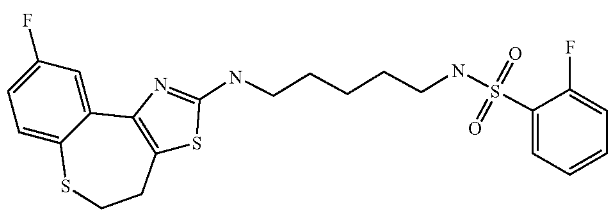 | 4.9 | >10000 |
| 162 | 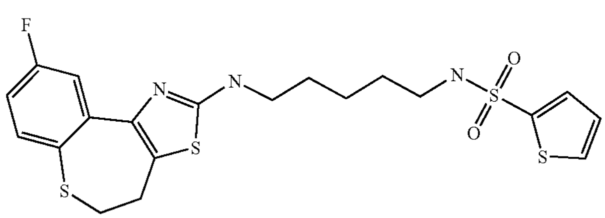 | 4.8 | >10000 |
| 163 | 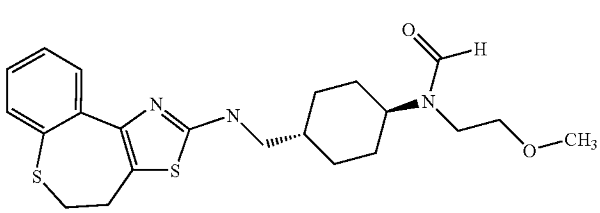 | 12.3 | |

TABLE 6-continued

| EXAMPLE No. | STRUCTURE | $K_i$, nM hNPY-5 | $K_i$, nM hNPY-1,2,4 |
|---|---|---|---|
| 164 | 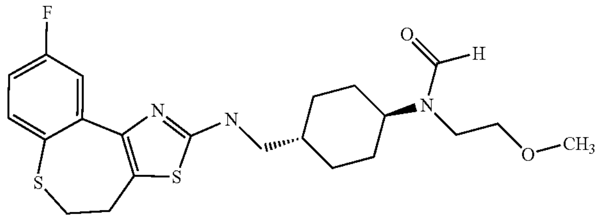 | 13 | |
| 165 | 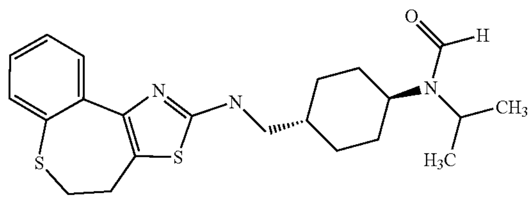 | 4.8 | |
| 166 | 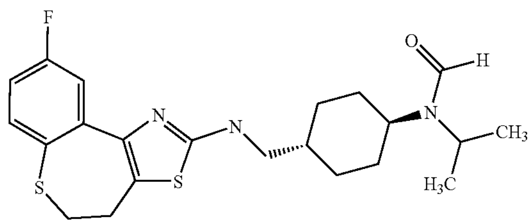 | 6 | |

Functional Assay Results

The functional in vitro activity of several compounds was characterized using a radioimmunoassay of cAMP, the results of which are summarized in Table 7.

TABLE 7

Functional Antagonism Data

| Example # | $K_i$ (h NPY-5), nM | $pK_b$ |
|---|---|---|
| 1 | 13 | 6.7 |
| 37 | 55 | 6.8 |
| 49 | 138 | 6.0 |
| 65 | 2.7 | 7.8 |
| 98 | 1.5 | 8.4 |
| 104 | 6.8 | 8.6 |
| 157 | 5.7 | 7.7 | i) $BOC_2O$, $CH_2Cl_2$, DIEA; ii) $R_{16}SO_2Cl$, DIEA;

iii) TFA, $CH_2Cl_2$; iv) $R_{16}SO_2Cl$, DIEA $R_{14}$, $R_{15}$, $R_{16}$, X, m, p, and s are described herein

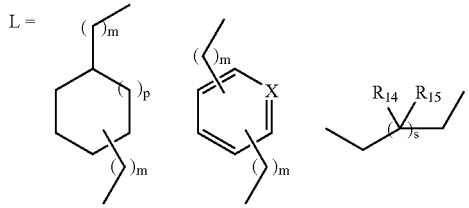

Scheme 1A. Synthesis of Side Chains

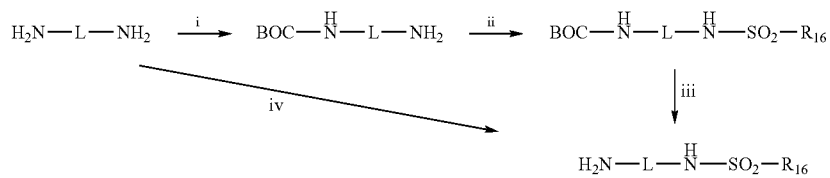

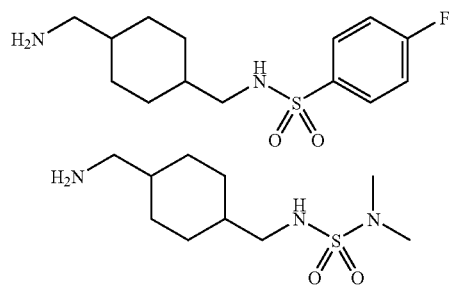
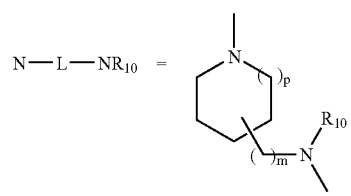
Scheme 1B. Synthesis of Side Chains
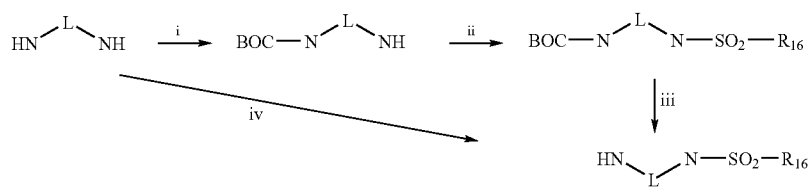
i) BOC$_2$O, CH$_2$Cl$_2$, DIEA; ii) R$_{16}$SO$_2$Cl, DIEA;
iii) TFA, CH$_2$Cl$_2$; iv) R$_{16}$SO$_2$Cl, DIEA
R$_{16}$, q, and r are described herein
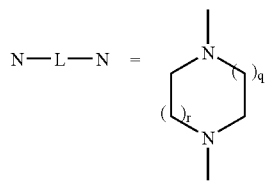
Scheme 1C. Synthesis of Side Chains
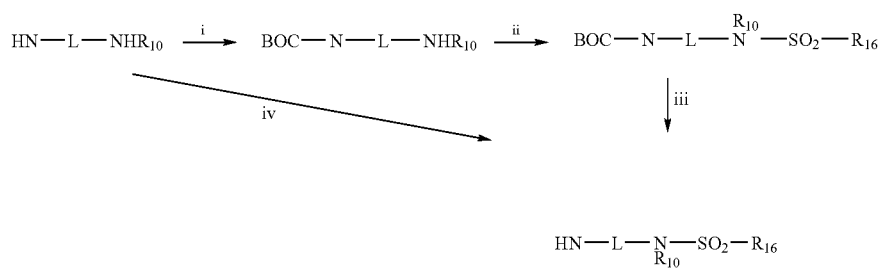
i) BOC$_2$O, CH$_2$Cl$_2$, DIEA; ii) R$_{16}$SO$_2$Cl, DIEA;
iii) TFA, CH$_2$Cl$_2$; iv) R$_{16}$SO$_2$Cl, DIEA
R$_{16}$, R$_{10}$, m, and p are described herein Scheme 1D. Synthesis of Side Chains

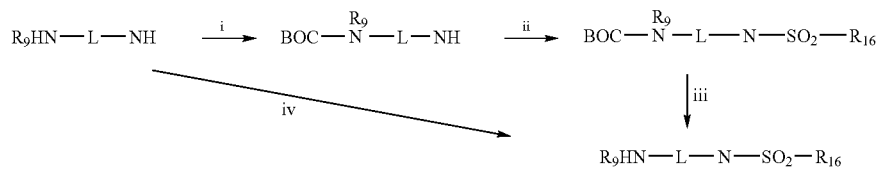

i) BOC$_2$O, CH$_2$Cl$_2$, DIEA; ii) R$_{16}$SO$_2$Cl, DIEA;
iii) TFA, CH$_2$Cl$_2$; iv) R$_{16}$SO$_2$Cl, DIEA R$_{16}$, R$_9$, p, and m are described herein

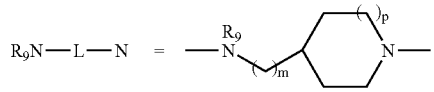

Scheme 1E. Synthesis of Side Chains

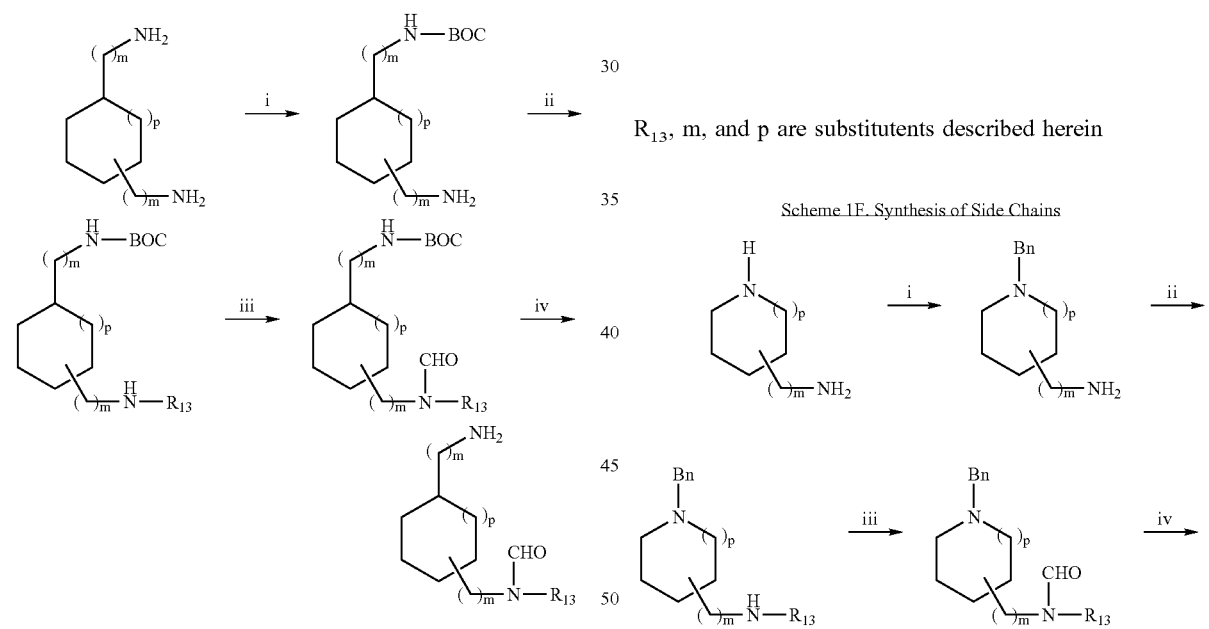

i) BOC$_2$O, CH$_2$Cl$_2$, DIEA; ii) acid chloride followed by reduction with B$_2$H$_6$; DIEA; iii) A formylating agent such as 1H-benzotriazole-1-carboxaldehyde; iv) TFA, CH$_2$Cl$_2$ -continued

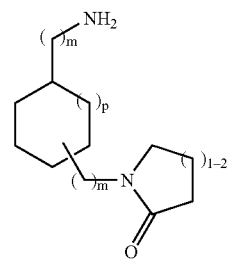

R$_{13}$, m, and p are substitutents described herein

Scheme 1F. Synthesis of Side Chains

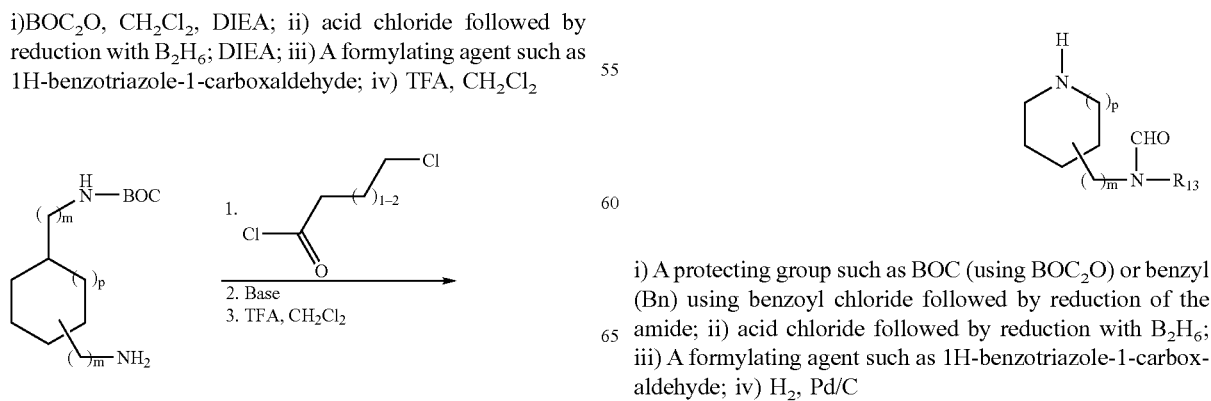

i) A protecting group such as BOC (using BOC$_2$O) or benzyl (Bn) using benzoyl chloride followed by reduction of the amide; ii) acid chloride followed by reduction with B$_2$H$_6$; iii) A formylating agent such as 1H-benzotriazole-1-carboxaldehyde; iv) H$_2$, Pd/C

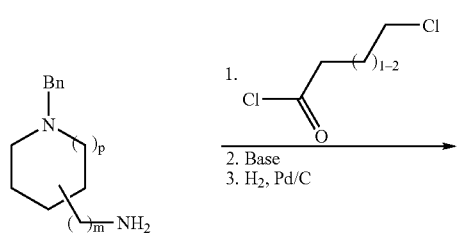

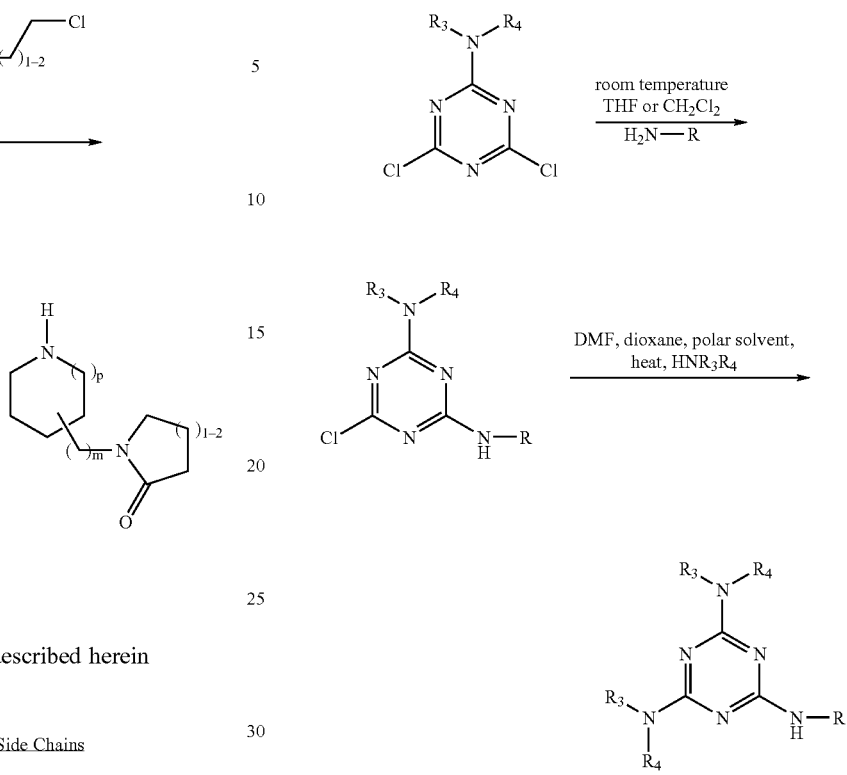

-continued room temperature THF or CH$_2$Cl$_2$
H$_2$N—R

DMF, dioxane, polar solvent, heat, HNR$_3$R$_4$

R$_{13}$, m, and p are substitutents described herein

Scheme 1G. Synthesis of Side Chains

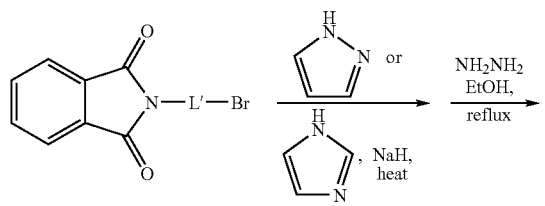

R$_6$ and R$_4$ are substituents described herein

—FHR is a subset of the substituent R$_8$ described herein

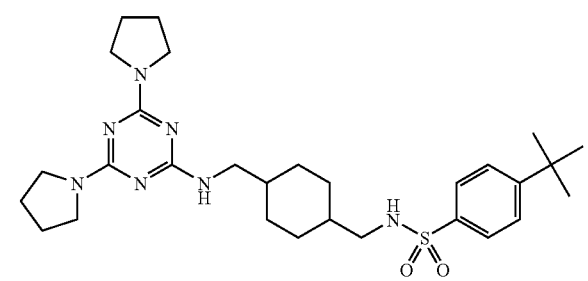

H$_2$N—L'—R

L' = (CH$_2$)$_{2-6}$
R = pyrazole or imidazole

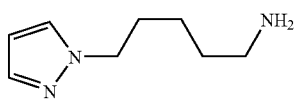

Scheme 2. Synthesis of Triaminotriazines

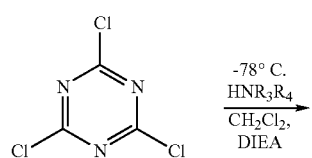

-78° C.
HNR$_3$R$_4$
CH$_2$Cl$_2$,
DIEA

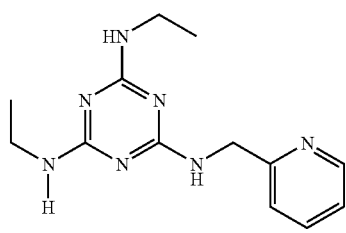

Scheme 3. Synthesis of Triaminotriazines
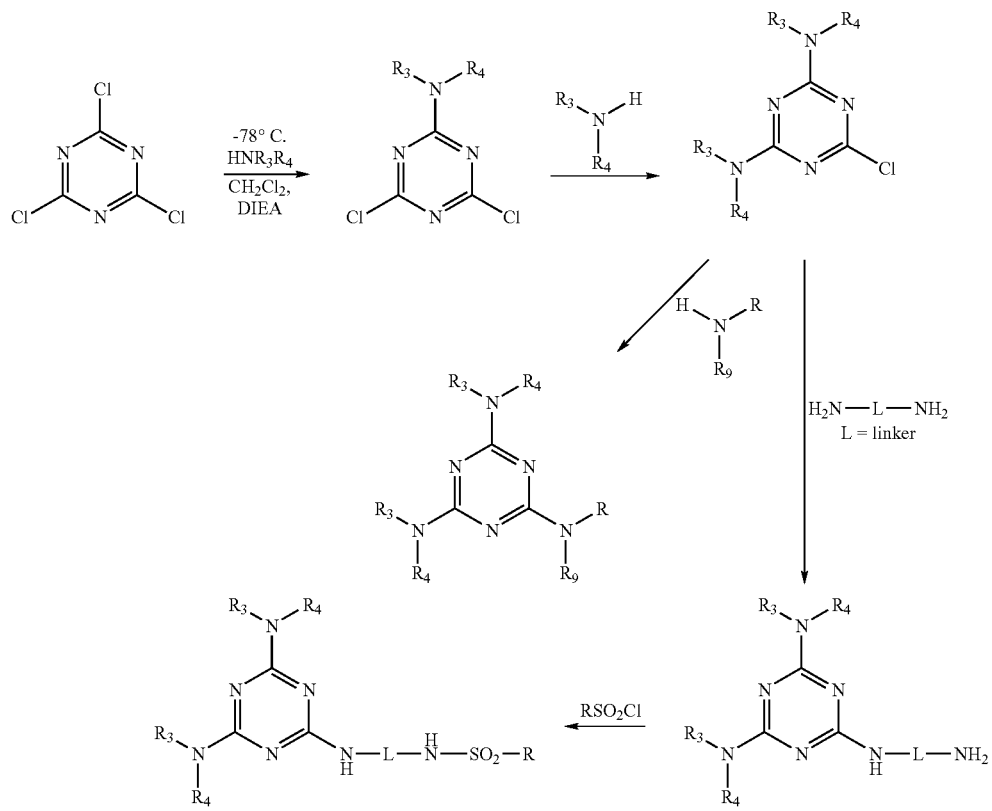
$R_3$ and $R_4$ are substituents described herein
—$N(R_9)R$ and —NH—L—NHSO$_2$—R are independently subsets of the substituent $R_8$ described herein
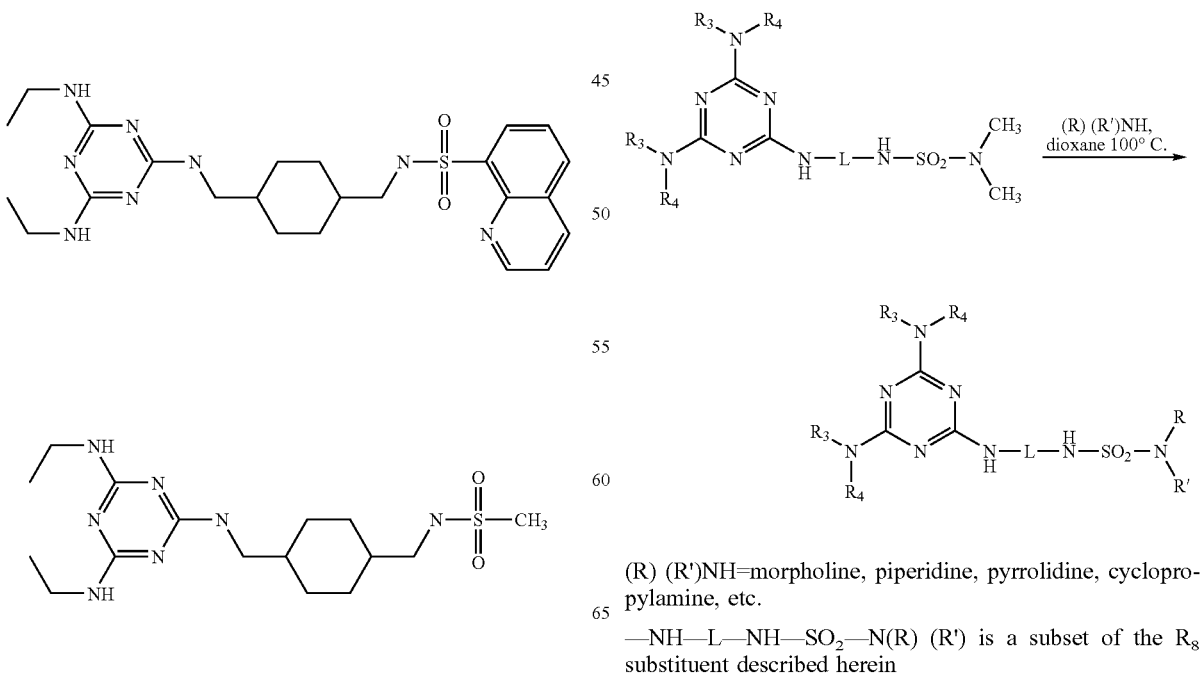
(R) (R')NH=morpholine, piperidine, pyrrolidine, cyclopropylamine, etc.
—NH—L—NH—SO$_2$—N(R) (R') is a subset of the $R_8$ substituent described herein Scheme 4B. Synthesis of Triazine Derivatives

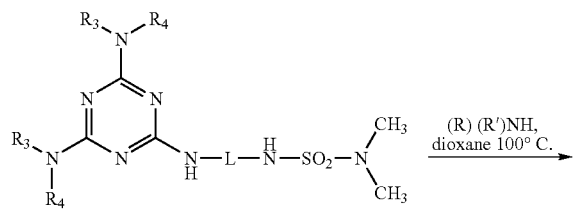

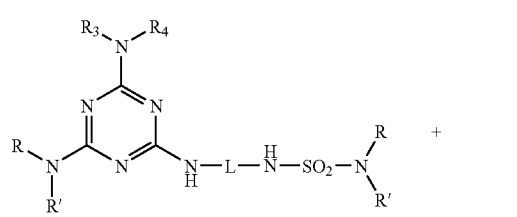

+

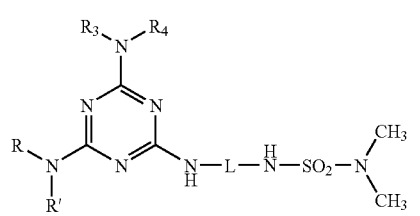

$R_3$ and $R_4$ are substituents described herein (R)(R')NH=morpholine, piperidine, pyrrolidine, cyclopropylamine, etc.

(R)(R')N—=morpholinyl, piperidinyl, pyrrolidinyl, cyclopropylamine, etc.

—NH—L—NH—SO$_2$—N(R) (R') and —NH—L—NH—SO$_2$—N(CH$_3$)$_2$ are independently subsets of the $R_8$ substituent described herein Scheme 4C. Synthesis of Triazine Derivatives

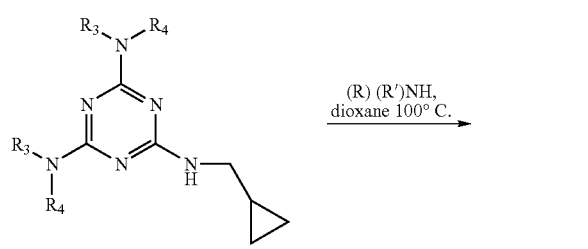

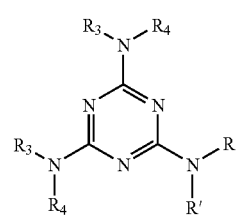

Scheme 4D. Synthesis of Triazine Derivatives

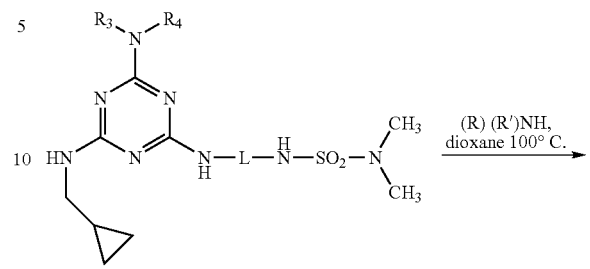

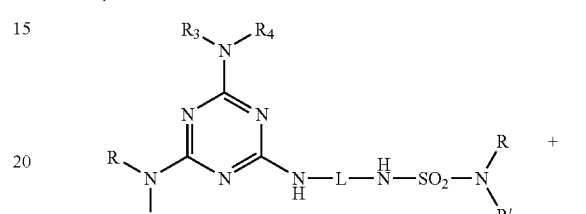

+

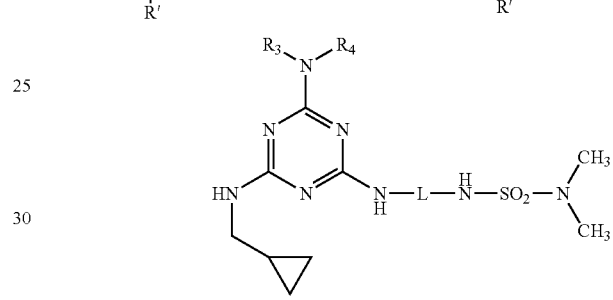

$R_3$ and $R_4$ are substituents described herein (R) (R')NH=morpholine, piperidine, pyrrolidine, cyclopropylamine, etc.

—N(R)(R'), —NH—L—NHSO$_2$NR(R'), and —NH—L—NH—SO$_2$N(CH$_3$)$_2$ are subsets of the $R_8$ substituent described herein Scheme 5. Synthesis of Diamino-1,3,5-triazines

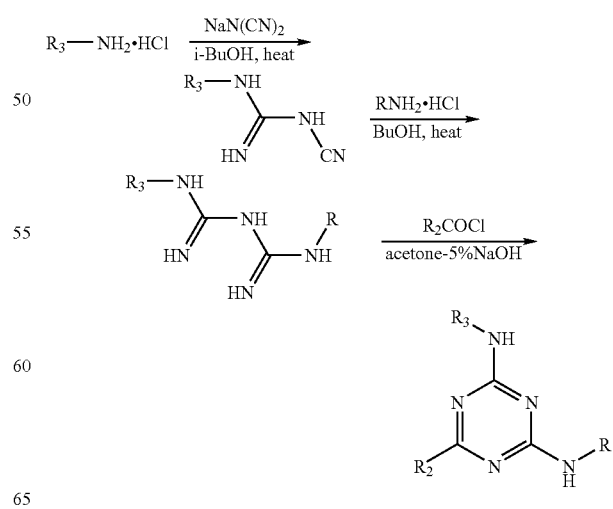

$R_2$ and $R_3$ are substituents described herein

—NH—R is a subset of the $R_8$ substituent described herein

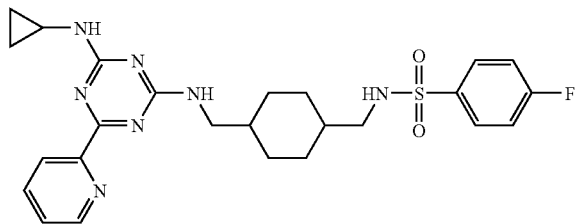

Scheme 6A. Synthesis of Thioureas

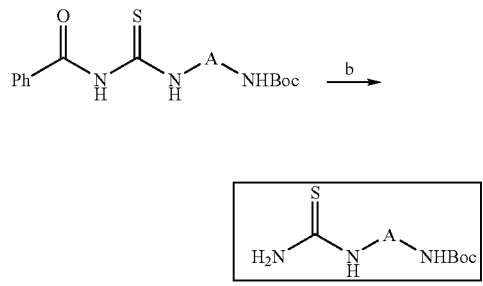

a. benzoylisothiocyanate
b. $K_2CO_3$, MeOH

Scheme 6B. Synthesis of Thioureas

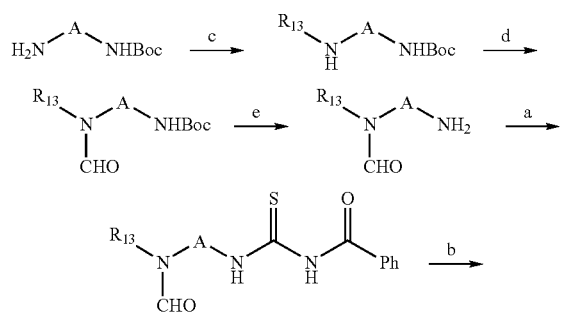

-continued a. benzoylisothiocyanate
b. $K_2CO_3$, MeOH
c. alkyl halide or acyl halide followed by borane reduction
d. formylating agent such as 1H-benzotriazole-1-carboxaldehyde
e. HCl or TFA a. benzoylisothiocyanate b. $K_2CO_3$, MeOH c. alkyl halide or acyl halide followed by borane reduction d. formylating agent such as 1H-benzotriazole-1-carboxaldehyde e. HCl or TFA

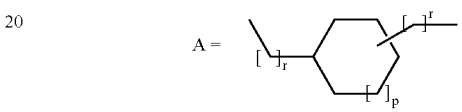

Scheme 6B. Synthesis of Thioureas

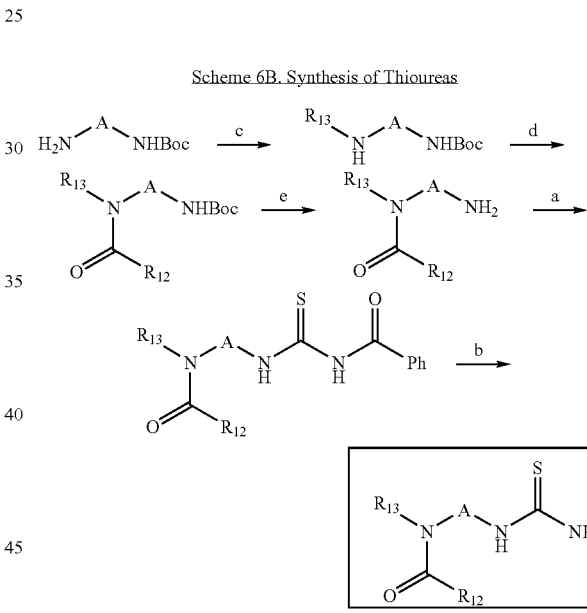

a. benzoylisothiocyanate
b. $K_2CO_3$, MeOH
c. alkyl halide or acyl halide followed by borane reduction
d. $R_{12}$COCl
e. HCl or TFA a. benzoylisothiocyanate b. $K_2CO_3$, MeOH c. alkyl halide or acyl halide followed by borane reduction d. $R_{12}$COCl e. HCl or TFA

Scheme 7A. Synthesis of Bromoketones
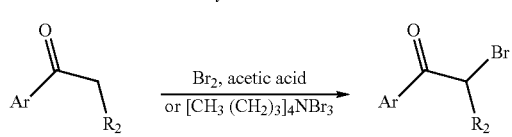
Scheme 7B. Synthesis of Chloroketones
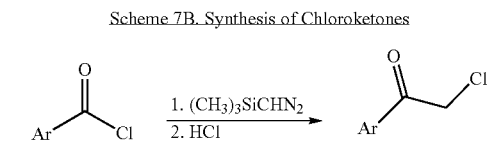
Scheme 8A. Synthesis of Bicycles
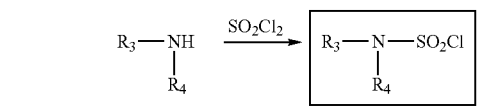
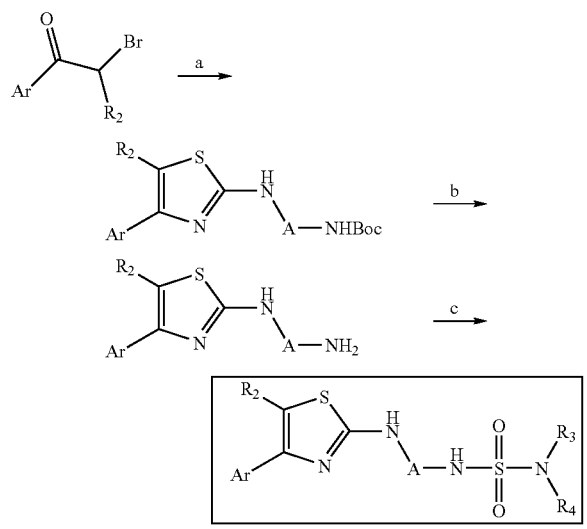
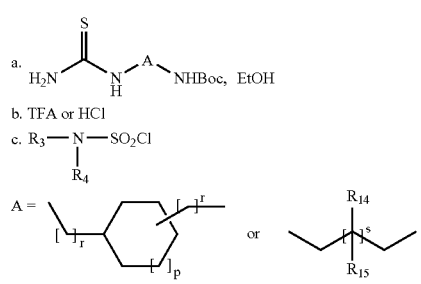
Scheme 8B. Synthesis of Bicycles
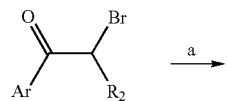
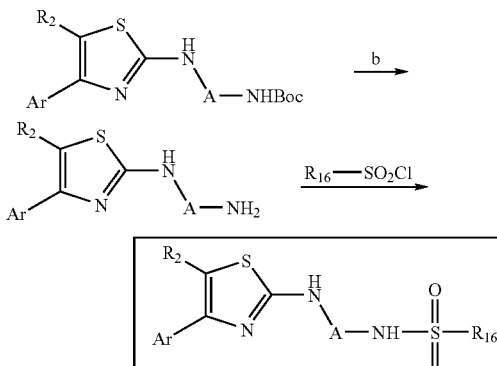
Scheme 8C. Synthesis of Bicycles
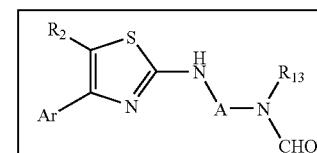
Scheme 8D. Synthesis of Bicycles -continued
Scheme 8E. Synthesis of Bicycles
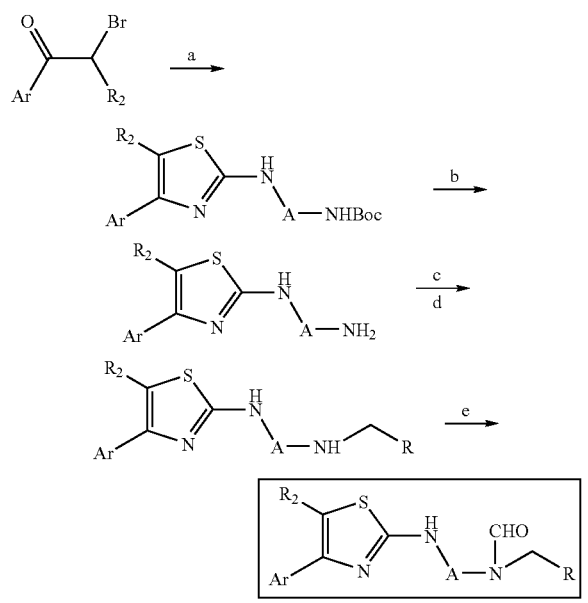
Scheme 8F. Synthesis of Bicycles
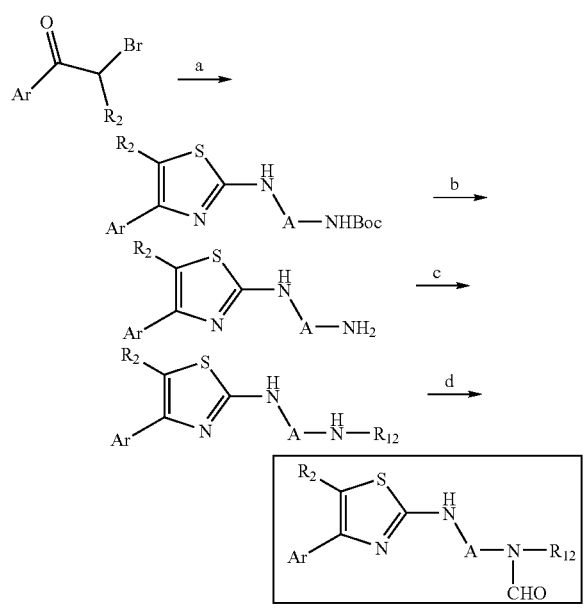
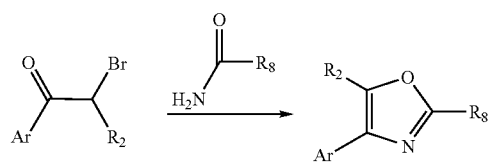
Scheme 9A. Synthesis of Bicycles
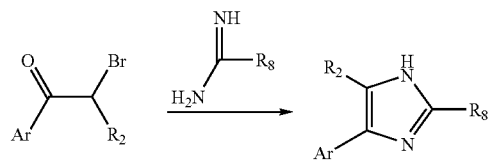
Scheme 9B. Synthesis of Bicycles
Scheme 10: Synthesis of Side Chains
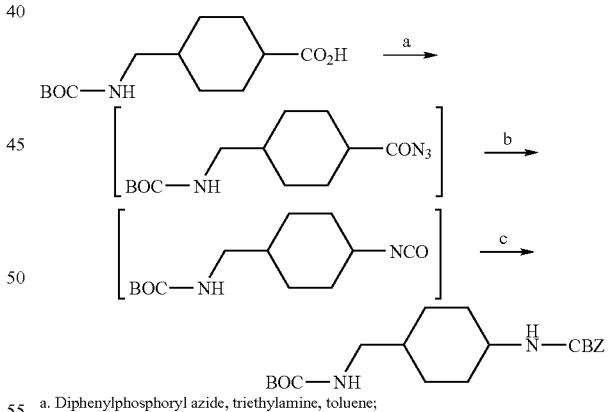
a. Diphenylphosphoryl azide, triethylamine, toluene;
b. heat; c. HOCH$_2$Ph
Scheme 11A. Synthesis of Thioureas
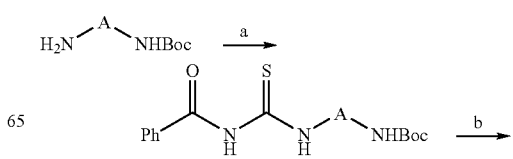

-continued

a. benzoylisothiocyanate
b. K$_2$CO$_3$, MeOH

A = 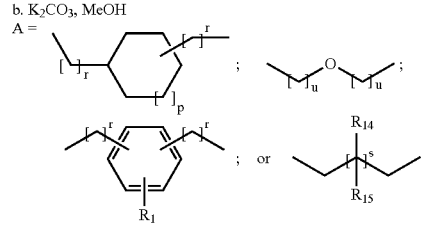

Scheme 11B. Synthesis of Thioureas

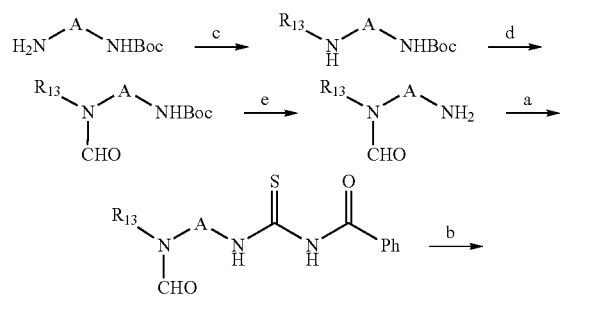

a. Benzoylisothiocyanate
b. K$_2$CO$_3$, MeOH
c. alkyl halide or acyl halide followed by borane reduction
d. formylating agent such as 1H-benzotriazole-1-carboxaldehyde
e. HCl or TFA A = 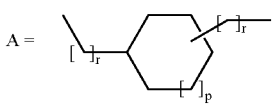

Scheme 11C. Synthesis of Thioureas

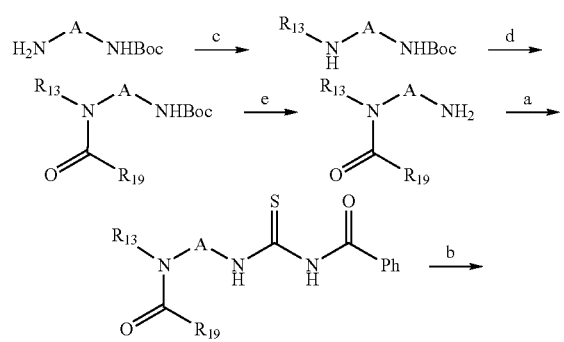

-continued

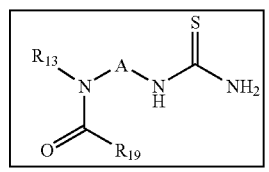

a. Benzoylisothiocyanate
b. K$_2$CO$_3$, MeOH
c. alkyl halide or acyl halide followed by borane reduction
d. R$_{19}$COCl
e. HCl or TFA A = 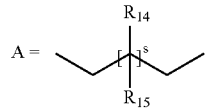

Scheme 11D. Synthesis of Thioureas

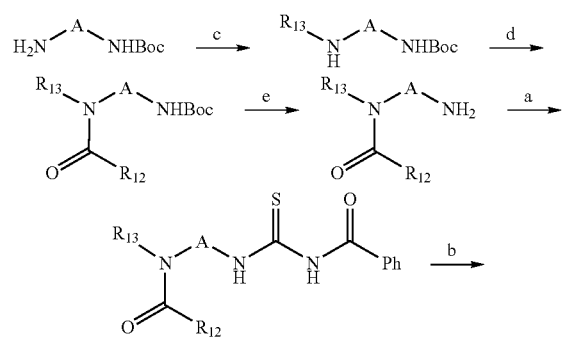

a. Benzoylisothiocyanate
b. K$_2$CO$_3$, MeOH
c. alkyl halide or acyl halide followed by borane reduction
d. R$_{12}$COCl
e. HCl or TFA A = 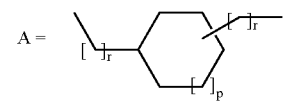

Scheme 12. Synthesis of Bromoketones

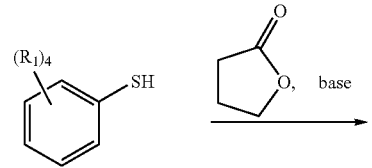

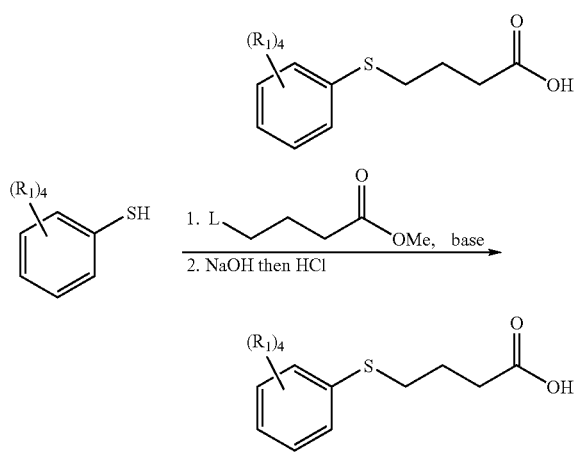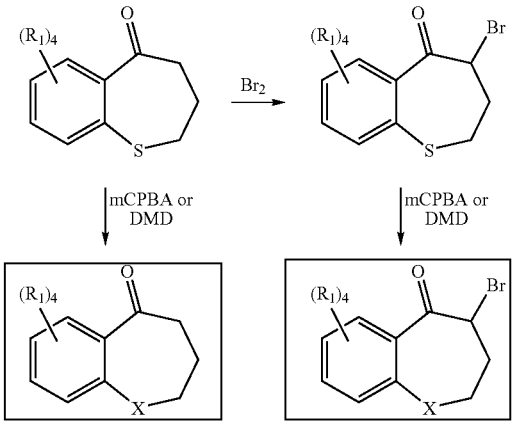
L = leaving group such as Br
X = S, SO, SO$_2$
DMD = dimethyldioxirane
mCPBA = m-chloroperbenzoic acid
Scheme 13A. Synthesis of the Tricycles
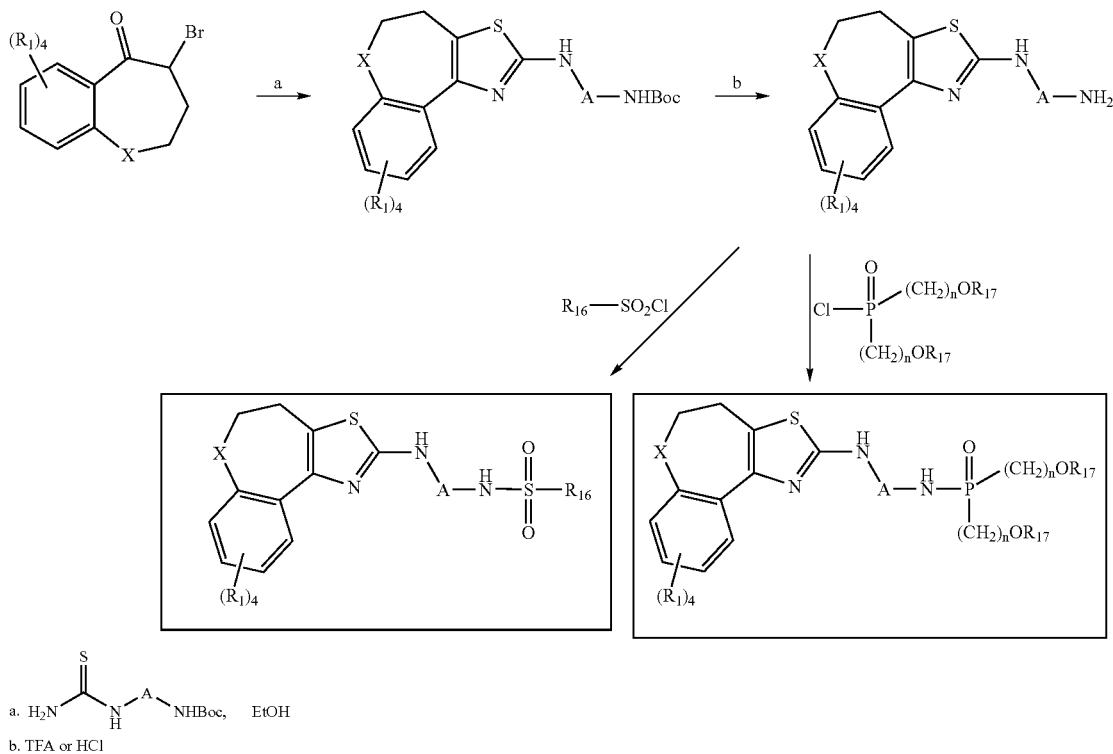
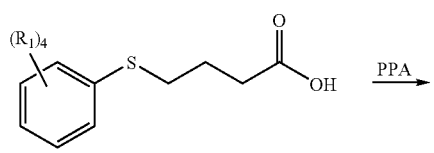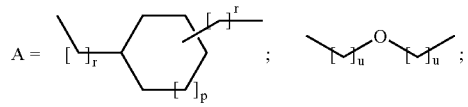

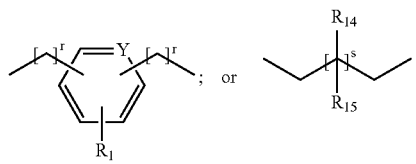 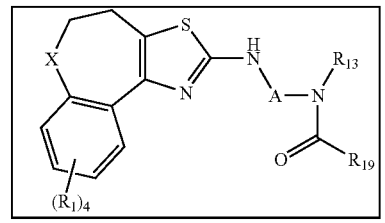
Scheme 13B. Synthesis of the Tricycles
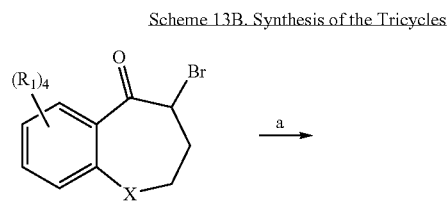
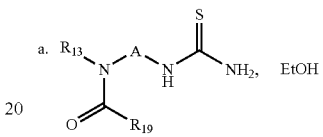
a. 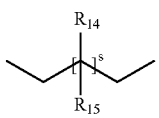
Scheme 13D. Synthesis of the Tricycles
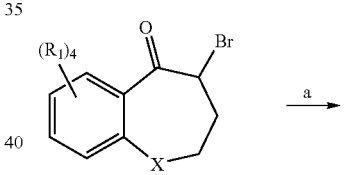
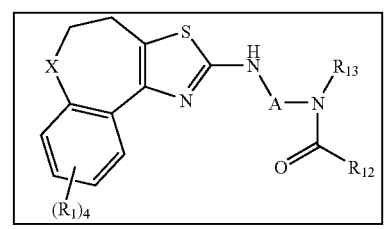
a. 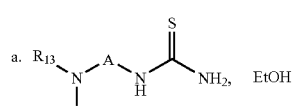
A = 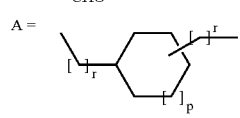
Scheme 13C. Synthesis of the Tricycles
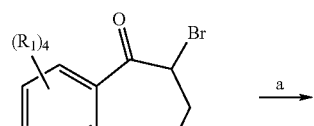
a. 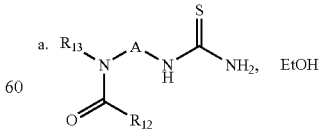
A = 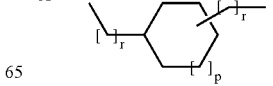

Scheme 13E. Synthesis of the Tricycles
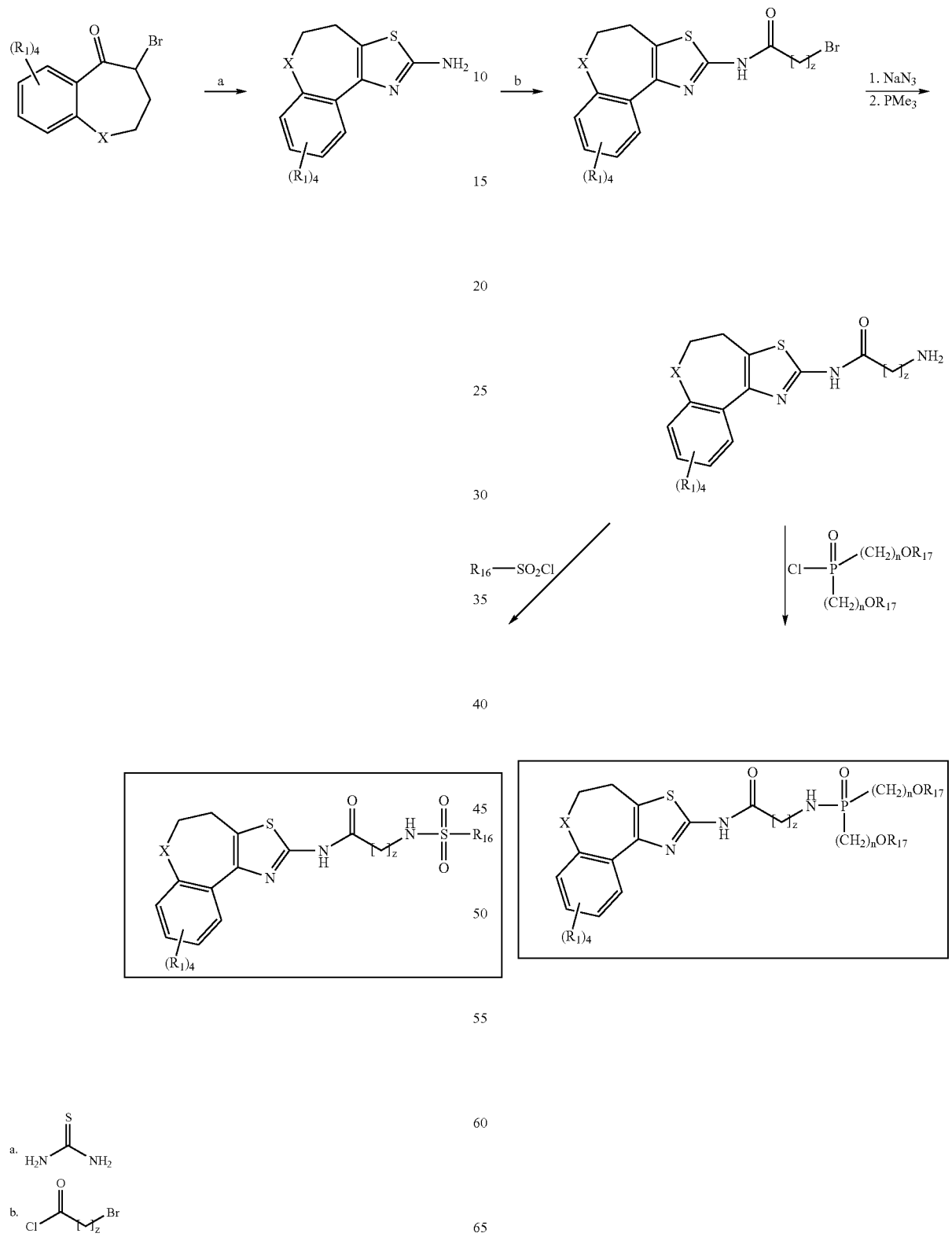

Scheme 14A. Synthesis of Tricycles

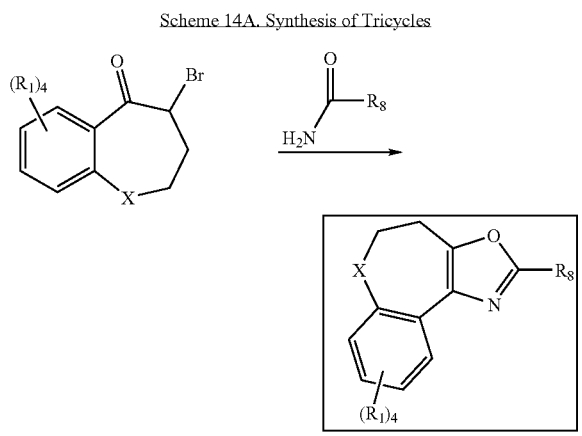

Scheme 14B. Synthesis of Tricycles

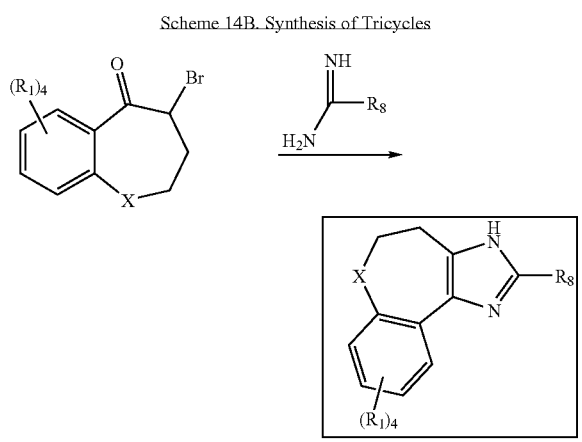

Scheme 15: Synthesis of Side Chains

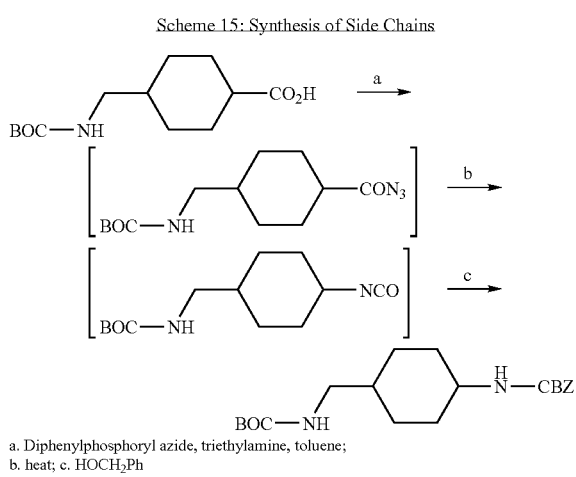

a. Diphenylphosphoryl azide, triethylamine, toluene;
b. heat; c. HOCH$_2$Ph

REFERENCES

Balasubramaniam, A., Sheriff, S., Johnson, M. E., Prabhakaran, M., Huang, Y., Fischer, J. E., and Chance, W. T. (1994). [D-Trp$^{32}$]Neuropeptide Y: A competitive antagonist of NPY in rat hypothalamus. *J. Med. Chem,* 37: 311–815.

Bradford, M. M. (1976). A rapid and sensitive method for the quantitation of microgram quantities of protein utilizing the principle of protein-dye binding. *Anal. Biochem.* 72: 248–254.

Campbell, J. R., Hatton, R. E. (1961). Unsymmetrically Substituted Melamines. *J. Org. Chem,* 26: 2786.

Chabaka, L. M., et al., "Facile Synthesis of 2-Furyl-, 2-Pyrrolyl-, 2-Imidazolyl- and Pyrrolo-Azoles from 2-Substituted Methylazoles." *Pol. J. Chem.* (1994) 68(7): 1317–1325.

Clark, J. T., Kalra, P. S., Crowley, W. R., and Kalra, S. P. (1984). Neuropeptide Y and human pancreatic polypeptide stimulate feeding behavior in rats. *Endocrinology* 115: 427–429.

Crangk, G. and Foulis, M. J., " Oxazoles from ureas" *J. Med. Chem.* (1971) 14: 1075.

Criscione, L., Rigollier, P., Batzl-Hartmann, C., Rueger, H., Stricker-Krongrad, A., Wyss, P., Brunner, L., Whitebread, S., Yamaguchi, Y., Gerald, C., Heurich, R. O., Walker, M. W., Chiesi, M., Schilling, W., Hofbauer, K. G., Levens, N. (1998) Food intake in free-feeding and energy-deprived lean rats is mediated by the neuropeptide Y5 receptor. *J. Clin. Invest.* 102(12): 2136–45.

Critcher, D. J. and Pattenden, G., "Synthetic Studies Towards Pateamine, a Novel Thiazole-Based 19-Membered Bis-lactone from Mycale sp." *Tetrahedron. Lett.* (1996) 37(50): 9107–9110.

Cullen, B. (1987). Use of eurkaryotic expression technology in the functional analysis of cloned genes. *Methods Enzymol.* 152: 685–704.

Curd, F. H. S., Hendry, J. A., Kenny, A. G., Murray, A. G., and Rose, F. L. (1948). Synthetic Antimalarials. Part XXVIII. An Alternative Route to N$^1$-Aryl-N$^5$-alkyl-diguanides. *J. Chem. Soc.* 1630–1636.

Curd, F. H. S. and Rose, F. L. (1946). Synthetic Antimalarials. Part X. Some Aryl-diguanide ("-biguanide") Derivatives. *J. Chem. Soc.* 729–737.

De Kimpe, N., et al., "Synthesis of 2-Imino-4-thiazolines, 2-Imino-4-alkoxythiazolidines, Thiazoles, and 4-Imidazolin-2-ones from alpha-Halomethyl Ketimines.", *J. Heterocycl. Chem.* (1996) 33(4): 1179–1183.

Demchenko, A. M., et al., " Preparation and Application of alpha-Bromomono- and -bisdifluoromethoxyacetophenones in the Course of Synthesis of Polymethyleneimidazoles Containing a Bridge Nitrogen Atom", *Khim. Geterotsikl. Soedin.* (1997) 10: 1371–1376.

Di Fabio, R. and Pentassuglia, G., "Novel Synthesis of Ethyl 3-(Bromoacetyl)-4,6-dichloro-1H-indole-2-carboxylate as Useful Intermediate in the Preparation of Potential Glycine Site Antagonists", *Synth. Commun.* (1998) 28(1): 51–60.

Dryden, S., Frankish, H., Wang, Q., and Williams, G. (1994). Neuropeptide Y and energy balance: one way ahead for the treatment of obesity? *Eur. J. Clin. Invest.* 24: 293–308.

Dumont, Y., Martel, J.-C., Fournier, A., St-Pierre, S., and Quirion, R. (1992). Neuropeptide Y and neuropeptide Y receptor subtypes in brain and peripheral tissues. *Progress in Neurobiology* 38: 125–167.

Eva, C., Oberto, A., Sprengel, R. and Genazzani, E. (1992). The murine NPY-1 receptor gene: structure and delineation of tissue specific expression. *FEBS lett.* 314: 285–288.

Eva, C., Keinanen, K., Monyer, H., Seeburg, P., and Sprengel, R. (1990). Molecular cloning of a novel G protein-coupled receptor that may belong to the neuropeptide receptor family. *FEBS Lett.* 271: 80–84.

Friedman, B. S., et al., "Thiazoles from thioamides", *J. Am. Chem. Soc.* (1937) 59: 2262.

Furukawa, M., Seto, Y., and Toyoshima, S. (1961). *Chem. Pharm. Bull.* 9: 914.

Hammar, W. J. and Rustad, M. A., "Oxazoles from alpha-bromoketones" *J. Heterocycl. Chem.* (1981) 18: 885.

Herzog, H., Hort, Y. J., Ball, H. J., Hayes, G., Shine, J., and Selbie, L. (1992). Cloned human neuropeptide Y receptor couples to two different second messenger systems. *Proc. Natl. Acad. Sci. USA* 89: 5794–5798.

Kalra, S. P., Dube, M. G., Fournier, A., and Kalra, P. S. (1991). Structure-function analysis of stimulation of food intake by neuropeptide Y: Effects of receptor agonists. *Physiology & Behavior* 50: 5–9.

Kearney, P. C., et al., "Solid-Phase Synthesis of 2-Aminothiazoles", *J. Org. Chem.* (1998) 63(1): 196–200.

Koshelev, V. N., Kelarev, V. I., Karakhanov, R. A., and Shalkarov, S. I. (1995) Synthesis of N-substituted 2,4-diamino-1,3,5-triazines containing pyridyl groups. *Zh. Org. Khim.* 31(2): 291–294.

Kreutzberger, A., Langner, P., and Stratmann, J. (1991). Antineoplastics 17. Analysis of mono- and disubstituted 2,4-dichloro-5-diethylamino-1,3,5-triazines. *Arch. Pharm. (Weinheim. Ger.)* 324(3): 173–176.

Larhammar, D., Blomqvist, A. G., Yee, F., Jazin, E., Yoo, H., and Wahlestedt, C. (1992). Cloning and functional expression of a human neuropeptide Y/peptide YY receptor of the Y1 type. *J. Biol. Chem.* 267: 10935–10938.

Levine, A. S., and Morley, J. E. (1984). Neuropeptide Y: A potent inducer of consummatory behavior in rats. *Peptides* 5: 1025–1029.

Little, T. L. and Webber, S. E., "A Simple and Practical Synthesis of 2-Aminoimidazoles" *J. Org. Chem.* (1994) 59(24): 7299–7305.

Marchetti, E., et al., "Oxazoles from ureas" *J. Med. Chem.* (1968) 11: 1092.

May, E. L. (1947) Attempts to find new antimalarials. XXII. Biguanide derivatives of phenanthrene. *J. Org. Chem.* 12: 443–445.

Michel, M. C. (1991). Receptors for neuropeptide Y: multiple subtypes and multiple second messengers. *Trends Pharmacol.* 12: 389–394.

Nagao, Y., et al., "Novel Nonprostanoid Prostacyclin (PGI2) Mimetics with Heterocyclic Moiety", *Heterocycles* (1996) 42(2): 517–523.

Nagasaka, H., Ishikawa, E., Odo, K. (1967). *Yuki Gosei Kagaku Kyokaishi* 25: 1048 (Chem Abstr [CHABA8], 68 (105164)).

Neelakantan, L. (1957). Preparation of some 1,5-diaryl biguanides. *J. Org. Chem.* 22: 1587–1588.

Nestler, H. and Furst, H. J. (1963). *Prakt. Chem.* 22: 173.

Novikova, A. P., et al., "Synthesis and Properties of 1,3,4-Thiadiazine Derivatives. Part 1. Condensation of Substituted Phenacyl Bromides and Bromoacetylpyridines with Thiosemicarbazide", *Khim. Geterotsikl. Soedin.* (1991) (6): 843–846.

Pathak, V. N., et al., "Synthesis of Some New Fluorine Containing Oxazoles, Oxadiazoles, Thiadiazoles and Triazines"; *J. Indian Chem. Soc.* (1993) 70(6): 539–542.

Plazzi, P. V., et al., " Heteroarylaminoethyl and Heteroarylthioethylimidazoles. Synthesis and H3-Receptor Affinity", *Eur. J. Med. Chem.* (1995) 30(11): 881–889.

Sahu, A., and Kalra, S. P. (1993). Neuropeptidergic regulation of feeding behavior (neuropeptide Y). *Trends Endocrinol. Metab.* 4: 217–224.

Shaw, J. T. and Gross, F. J. (1959). The Preparation of Certain Amino-Substituted Perfluoroalkyl-s-Triazines. *J. Org. Chem.* 24: 1809–1811.

Stanley, B. G., and Leibowitz, S. F. (1984). Neuropeptide Y: Stimulation of feeding and drinking by injection into the paraventricular nucleus. *Life Sci.* 35: 2635–2642.

Stanley, B. G., Magdalin, W., Seirafi, A., Nguyen, M. M., and Leibowitz, S. F. (1992). Evidence for neuropeptide Y mediation of eating produced by food deprivation and for a variant of the $Y_1$ receptor mediating this peptide's effect. *Peptides* 13: 581–587.

Tsitsa, P., Antoniadou-Vyza, E., Hamodrakas, S. J., Eliopoulos, E. E., Tsantili-Kakoulidou, A., Lada-Hytriroglou, E., Roussakis, C., Chinou, I., Hempel, A., Camerman, N., Ottensmeyer, F. P., and Vanden Berghe, D. A. (1993). Synthesis, crystal structure, and biological properties of a new series of lipophilic s-triazines, dihydrofolate reductase inhibitors. *Eur. J. Med. Chem.* 28(2): 149–158.

Vanderhoek, R., Allen, G., and Settepani, J. A. (1973). Bis(dimethylamino)-s-triazinyl antiinflammatory agents. *J. Med. Chem.* 16: 1305.

Wahlestedt, C., Edvinsson, L., Ekblad, E., and Hakanson, R. Effects of neuropeptide Y at sympathetic neuroeffector junctions: Existence of $Y_1$ and $Y_2$ receptors. In: *Neuronal messengers in vascular function*, Fernstrom Symp. No 10., pp. 231–242. Eds A. Nobin and C. H. Owman. Elsevier: Amsterdam (1987).

Wahlestedt, C., and Reis, D. J. (1993). Neuropeptide Y-Related Peptides and Their Receptors—Are the Receptors Potential Therapeutic Targets? *Ann. Rev. Pharmacol. Tox.* 32: 309–352.

Zhao, Z., et al., "Synthesis of trans-4-Alkenyloxazoles" *Tetrahedron. Lett.* (1991) 32(13): 1609–1612.

What is claimed is:

1. A compound having the structure:

wherein $R_1$ is F; Cl; Br; I; $NR_3R_4$, phenyl or heteroaryl, wherein the phenyl or heteroaryl may be substituted with one or more of F, Cl, Br, I, —CN, —$NO_2$, —$NR_5R_6$, —$SO_2R_5$, —$(CH_2)_nC(Y)R_7$, —$(CH_2)_nYR_5$, —$(CH_2)_nC(Y)NR_5R_6$, —$(CH_2)_nNR_5C(Y)R_5$, —$(CH_2)_n$ $CO_2R_5$, —$(CH_2)_nSO_2NR_5R_6$, straight chained or branched $C_1$–$C_7$ alkyl, monofluoroalkyl, polyfluoroalkyl, aminoalkyl, $C_2$–$C_7$ alkenyl or $C_2$–$C_7$ alkynyl, or $C_3$–$C_7$ cycloalkyl or cycloalkenyl;

wherein $R_3$ is independently H; or straight chained or branched $C_1$–$C_7$ alkyl;

wherein $R_4$ is independently straight chained or branched $C_1$–$C_7$ alkyl;

or $R_3$ and $R_4$ taken together with the nitrogen atom to which they are attached are 1-azetidinyl, 1-pyrrolidinyl, 1-piperidinyl, or 1H-azepanyl, wherein the 1-azetidinyl, 1-pyrrolidinyl, 1-piperidinyl, or 1H-azepanyl is substituted with one or more of F, —CN, —$(CH_2)_n$ $NR_5R_6$, —$SO_2R_5$, —$(CH_2)_nC(Y)R_7$, —$(CH_2)_nYR_5$, —$(CH_2)_nC(Y)NR_5R_6$, —$(CH_2)_nNR_5C(Y)R_5$, —$(CH_2)_n$ $CO_2R_5$, straight chained or branched $C_1$–$C_7$ alkyl, monofluoroalkyl, polyfluoroalkyl, aminoalkyl, $C_2$–$C_7$ alkenyl or $C_2$–$C_7$ alkynyl, $C_3$–$C_7$ cycloalkyl or cycloalkenyl, phenyl or heteroaryl; wherein if —$(CH_2)_n NR_5R_6$, —$(CH_2)_n YR_5$, or —$(CH_2)_n NR_5C(Y)R_5$ are in the 2-position, then n is not 0; wherein the phenyl or heteroaryl may be substituted with one or more of F, Cl, Br, I, —CN, —$NO_2$, —$NR_5R_6$, —$SO_2R_5$, —$(CH_2)_n C(Y)R_7$, —$(CH_2)_n YR_5$, —$(CH_2)_n C(Y)NR_5R_6$, —$(CH_2)_n NR_5C(Y)R_5$, —$(CH_2)_n CO_2R_5$, —$(CH_2)_n SO_2NR_5R_6$, straight chained or branched $C_1$–$C_7$ alkyl, monofluoroalkyl, polyfluoroalkyl, aminoalkyl, $C_2$–$C_7$ alkenyl or $C_2$–$C_7$ alkynyl, or $C_3$–$C_7$ cycloalkyl or cycloalkenyl;

or $R_3$ and $R_4$ taken together with the nitrogen atom to which they are attached are morpholinyl, thiomorpholinyl, [1,4]oxazepanyl, [1,4]thiazepanyl, piperazinyl, or [1,4]diazepanyl, wherein the morpholinyl, thiomorpholinyl, [1,4]oxazepanyl, [1,4]thiazepanyl, piperazinyl, or [1,4]diazepanyl is substituted with one or more straight chained or branched $C_1$–$C_7$ alkyl or $C_1$–$C_7$ phenylalkyl; and wherein the nitrogen atom of the piperazinyl or [1,4]diazepanyl ring is substituted with —$(CH_2)_u YR_5$; —$(CH_2)_t C(Y)NR_5R_6$; —$(CH_2)_u NR_5 C(Y)R_5$; —$(CH_2)_t C(Y)R_7$; —$(CH_2)_t CO_2R_5$; —$(CH_2)_u NR_5R_6$; —$(CH_2)_u CN$; —$C(Y)R_5$; —$C(Y)NR_5R_6$; —$CO_2R_5$; straight chained or branched $C_1$–$C_7$ alkyl, $C_2$–$C_7$ alkenyl, $C_2$–$C_7$ alkynyl; $C_3$–$C_7$ cycloalkyl or cycloalkenyl; phenyl, $C_1$–$C_6$ phenylalkyl; or $C_1$–$C_6$ heteroarylalkyl; wherein the phenyl, $C_1$–$C_6$ phenylalkyl; or $C_1$–$C_6$ heteroarylalkyl may be substituted with one or more of F, Cl, Br, I, —CN, —$NO_2$, —$NR_5R_6$, —$SO_2R_5$, —$(CH_2)_n C(Y)R_7$, —$(CH_2)_n YR_5$, —$(CH_2)_n C(Y)NR_5R_6$, —$(CH_2)_n NR_5C(Y)R_5$, —$(CH_2)_n CO_2R_5$, —$(CH_2)_n SO_2NR_5R_6$, straight chained or branched $C_1$–$C_7$ alkyl, monofluoroalkyl, polyfluoroalkyl, aminoalkyl, $C_2$–$C_7$ alkenyl or $C_2$–$C_7$ alkynyl, or $C_3$–$C_7$ cycloalkyl or cycloalkenyl;

wherein each of $R_5$, $R_6$, and $R_7$ is independently H; or straight chained or branched $C_1$–$C_7$ alkyl;

wherein each n independently is an integer from 0 to 6 inclusive;

wherein each t independently is an integer from 1 to 4 inclusive;

wherein each u independently is an integer from 2 to 4 inclusive;

wherein Y is O or S;

wherein $R_8$ is

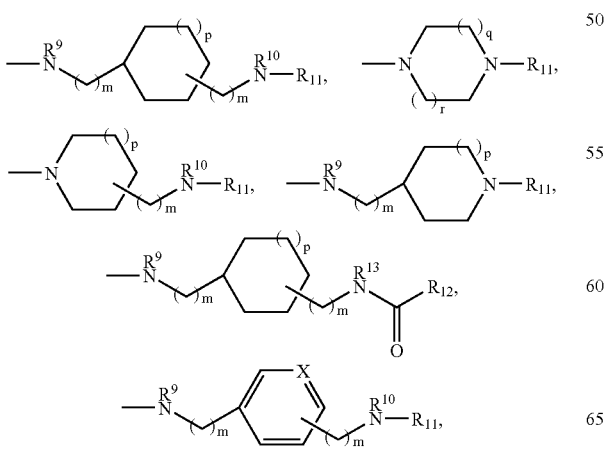

provided that if $R_8$ contains a piperidinyl group and m is 0, then the compound is not an α-aminal-containing compound;

wherein each of $R_9$ and $R_{10}$ is independently H; straight chained or branched $C_1$–$C_4$ alkyl;

wherein $R_{11}$ is

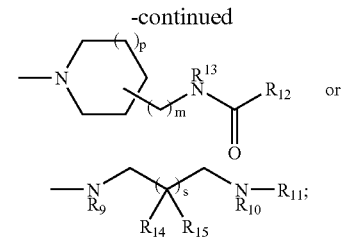

wherein $R_{12}$ is H;

wherein $R_{13}$ is independently H; —$(CH_2)_u YR_5$; —$(CH_2)_t C(Y)NR_5R_6$; —$(CH_2)_u NR_5C(Y)R_5$; —$(CH_2)_t C(Y)R_7$; —$(CH_2)_t CO_2R_5$; —$(CH_2)_u NR_5R_6$; —$(CH_2)_u CN$; —$C(Y)R_5$; —$C(Y)NR_5R_6$; —$CO_2R_5$; straight chained or branched $C_1$–$C_7$ alkyl; $C_1$–$C_7$ alkyl substituted with one or more F or Cl; $C_3$–$C_7$ cycloalkyl-$C_1$–$C_7$ alkyl; straight chained or branched $C_2$–$C_7$ alkenyl or alkynyl; or $C_3$–$C_7$ cycloalkyl or cycloalkenyl; phenyl or $C_1$–$C_6$ phenylalkyl; wherein the phenyl or $C_1$–$C_6$ phenylalkyl may be substituted with one or more of F, Cl, —CN, —$NO_2$, —$NR_5R_6$, —$SO_2R_5$, —$(CH_2)_n C(Y)R_7$, —$(CH_2)_n YR_5$, —$(CH_2)_n C(Y)NR_5R_6$, —$(CH_2)_n NR_5C(Y)R_5$, —$(CH_2)_n CO_2R_5$, —$(CH_2)_n SO_2NR_5R_6$, straight chained or branched $C_1$–$C_7$ alkyl, monofluoroalkyl, polyfluoroalkyl, aminoalkyl, $C_2$–$C_7$ alkenyl or $C_2$–$C_7$ alkynyl, or $C_3$–$C_7$ cycloalkyl or cycloalkenyl;

or $R_{12}$ and $R_{13}$ together with the amide linkage to which they are attached are pyrrolidinonyl or piperidonyl;

wherein $R_{14}$ is H; straight chained or branched $C_1$–$C_7$ alkyl; F; or —$(CH_2)_n OR_5$;

wherein $R_{15}$ is H, straight chained or branched $C_1$–$C_7$ alkyl, or F;

wherein $R_{16}$ is $NR_3R_4$, unsubstituted straight chained or branched $C_2$–$C_7$ alkyl, substituted straight chained or branched $C_1$–$C_7$ alkyl, wherein the $C_1$–$C_7$ alkyl may be substituted with one or more of F, Cl, —CN, —$NR_5R_6$, —$SO_2R_5$, —$(CH_2)_n C(Y)R_7$, —$(CH_2)_n YR_5$, —$(CH_2)_n C(Y)NR_5R_6$, —$(CH_2)_n NR_5C(Y)R_5$, —$(CH_2)_n CO_2R_5$, —$(CH_2)_n OCF_3$, monofluoroalkyl, polyfluoroalkyl, or aminoalkyl, straight chained or branched $C_2$–$C_7$ alkenyl or $C_2$–$C_7$ alkynyl, or $C_3$–$C_7$ cycloalkyl or cycloalkenyl, phenyl, heteroaryl, or $C_1$–$C_7$ phenylalkyl, wherein the phenyl, heteroaryl, or $C_1$–$C_7$ phenylalkyl may be substituted with one or more of F, Cl, Br, I, —CN, —$NO_2$, —$NR_5R_6$, —$(CH_2)_n NR_5C(Y)R_5$, —$SO_2R_5$, —$(CH_2)_n C(Y)R_7$, —$(CH_2)_n YR_5$, —$(CH_2)_n C(Y)NR_5R_6$, —$(CH_2)_n CO_2R_5$, —$(CH_2)_n SO_2NR_5R_6$, ethylenedioxy, methylenedioxy, straight chained or branched $C_1$–$C_7$ alkyl, monofluoroalkyl, polyfluoroalkyl, or aminoalkyl, straight chained or branched $C_2$–$C_7$ alkenyl or alkynyl, $C_3$–$C_7$ cycloalkyl or cycloalkenyl; quinolinyl, 1-naphthyl, 2-naphthyl, or 2,1,3-benzothiadiazolyl; with the provisos that when $R_1$ is F, Cl, Br, or I, then $R_{16}$ is 1-naphthyl; and when $R_1$ and $R_2$ are morpholinyl, then $R_{16}$ is not $NR_3R_4$;

wherein each m independently is an integer from 0 to 3 inclusive;

wherein each s independently is an integer from 1 to 6 inclusive;

wherein each p independently is an integer from 0 to 2 inclusive;

wherein each q independently is an integer from 1 to 2 inclusive;

wherein each r independently is an integer from 1 to 2 inclusive; and wherein X is N or C;

or a pharmaceutically acceptable salt thereof.

2. The compound of claim 1, wherein the compound is the (+) enantiomer.

3. The compound of claim 1, wherein the compound is the (−) enantiomer.

4. The compound of claim 1, wherein $R_8$ is

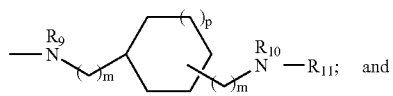

wherein each m is 1 or 2.

5. The compound of claim 4, wherein $R_{16}$ is 1-napthyl.

6. The compound of claim 5, wherein $R_3$ is H.

7. The compound of claim 5, wherein $R_3$ and $R_4$ taken together with the nitrogen atom to which they are attached are 1-azetidinyl, 1-pyrrolidinyl, 1-piperidinyl, or 1H-azepanyl, wherein the 1-azetidinyl, 1-pyrrolidinyl, 1-piperidinyl, or 1H-azepanyl is substituted with one or more of F, —CN, —$(CH_2)_nNR_5R_6$, —$SO_2R_5$, —$(CH_2)_nC(Y)R_7$, —$(CH_2)_nYR_5$, —$(CH_2)_nC(Y)NR_5R_6$, —$(CH_2)_nNR_5C(Y)R_5$, —$(CH_2)_nCO_2R_5$, straight chained or branched $C_1$–$C_7$ alkyl, monofluoroalkyl, polyfluoroalkyl, aminoalkyl, $C_2$–$C_7$ alkenyl or $C_2$–$C_7$ alkynyl, or $C_3$–$C_7$ cycloalkyl or cycloalkenyl; or $R_3$ and $R_4$ taken together with the nitrogen atom to which they are attached are morpholinyl, thiomorpholinyl, [1,4]oxazepanyl, [1,4]thiazepanyl, piperizinyl, or [1,4]diazepanyl, wherein the morpholinyl, thiomorpholinyl, [1,4]oxazepanyl, [1,4]thiazepanyl, piperazinyl, or [1,4]diazepanyl is substituted with one or more straight chained or branched $C_1$–$C_7$ alkyl or $C_1$–$C_7$ phenylalkyl; and wherein the nitrogen atom of the piperazinyl or [1,4]diazepanyl ring is substituted with —$(CH_2)_uYR_5$; —$(CH_2)_tC(Y)NR_5R_6$; —$(CH_2)_uNR_5C(Y)R_5$; —$(CH_2)_tC(Y)R_7$; —$(CH_2)_tCO_2R_5$; —$(CH_2)_uNR_5R_6$; —$(CH_2)_u$CN; —$C(Y)R_5$; —$C(Y)NR_5R_6$; —$CO_2R_5$; straight chained or branched $C_1$–$C_7$ alkyl, $C_2$–$C_7$ alkenyl, or $C_2$–$C_7$ alkynyl; or $C_3$–$C_7$ cycloalkyl or cycloalkenyl.

8. The compound of claim 7, wherein $R_3$ and $R_4$ taken together with the nitrogen atom to which they are attached are 1-azetidinyl, 1-pyrrolidinyl, or 1-piperidinyl.

9. The compound of claim 7, wherein $R_3$ and $R_4$ taken together with the nitrogen atom to which they are attached are morpholinyl or piperizinyl.

10. The compound of claim 8, wherein the compound is

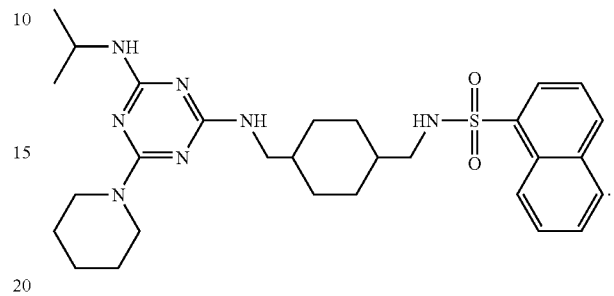

11. The compound of claim 9, wherein the compound is

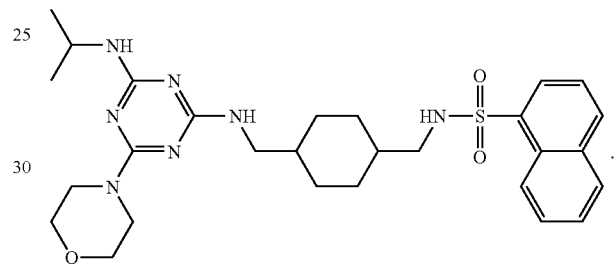

12. A pharmaceutical composition comprising a therapeutically effective amount of a compound of claim 1 and a pharmaceutically acceptable carrier.

13. A method of treating a subject suffering from obesity, which comprises administering to the subject a therapeutically effective amount of a compound of claim 1 to treat the subject's obesity.

14. A method of treating an abnormal condition, wherein the abnormality is an eating disorder, obesity or bulimia nervosa which comprises administering to the subject a therapeutically effective amount of the compound of claim 1.

15. A method of treating a subject suffering from depression, which comprises administering to the subject a therapeutically effective amount of a compound of claim 1 to treat the subject's depression.

16. A method of treating a subject suffering from a sleep disturbance, which comprises administering to the subject a therapeutically effective amount of a compound of claim 1 to treat the subject's sleep disturbance.

* * * * *